United States Patent [19]
Fujimoto et al.

[11] Patent Number: 6,030,546
[45] Date of Patent: *Feb. 29, 2000

[54] TRANS-OLEFIN COMPOUNDS, METHOD FOR PRODUCTION THEREOF, LIQUID CRYSTAL COMPOSITION CONTAINING THE SAME AS ACTIVE INGREDIENT, AND LIQUID CRYSTAL ELEMENT USING SAID COMPOSITION

[75] Inventors: Yukari Fujimoto; Naoyuki Takano, both of Takatsuki; Takayuki Higashii, Yokohama; Masayoshi Minai, Moriyama; Chizu Sekine, Tsukuba; Kayoko Ueda, Tsukuba; Koichi Fujisawa, Tsukuba; Kyoko Endo, Ibaraki-ken; Takeshi Tani, Tsukuba, all of Japan

[73] Assignee: Sumitomo Chemical Company, Limited, Osaka, Japan

[*] Notice: This patent is subject to a terminal disclaimer.

[21] Appl. No.: 08/832,972

[22] Filed: Apr. 4, 1997

Related U.S. Application Data

[62] Division of application No. 08/282,024, Jul. 29, 1994, Pat. No. 5,707,547.

[30] Foreign Application Priority Data

| Aug. 3, 1993 | [JP] | Japan | 5-192381 |
| Dec. 27, 1993 | [JP] | Japan | 5-351210 |
| Jan. 24, 1994 | [JP] | Japan | 6-006015 |
| Mar. 8, 1994 | [JP] | Japan | 6-036832 |
| Mar. 9, 1994 | [JP] | Japan | 6-066723 |
| Mar. 18, 1994 | [JP] | Japan | 6-048990 |

[51] Int. Cl.[7] .......... C09K 19/06; C09K 19/12; C09K 19/34; C07C 69/76
[52] U.S. Cl. .......... 252/299.6; 252/299.61; 252/299.66; 560/102; 560/108; 560/65; 568/626; 568/647; 544/298; 546/152
[58] Field of Search .......... 252/299.61, 299.66, 252/299.6, 299.62; 560/102, 108, 65; 568/626, 647; 544/298; 546/152

[56] References Cited

U.S. PATENT DOCUMENTS

| 4,565,425 | 1/1986 | Petizilka | 359/103 X |
| 4,676,604 | 6/1987 | Petizilka | 359/103 X |
| 4,834,904 | 5/1989 | Krause et al. | 252/299.61 |
| 5,013,478 | 5/1991 | Petizilka et al. | 252/299.63 |
| 5,087,769 | 2/1992 | Aslam et al. | 568/736 |
| 5,209,866 | 5/1993 | Reiffenrath et al. | 252/299.61 |
| 5,232,624 | 8/1993 | Reiffenrath et al. | 252/299.61 |
| 5,238,602 | 8/1993 | Petrzilka et al. | 252/299.65 |

FOREIGN PATENT DOCUMENTS

| 0122389 | 10/1984 | European Pat. Off. . |
| 168683 | 1/1986 | European Pat. Off. . |
| 0168683 | 1/1986 | European Pat. Off. . |
| 0332024 | 9/1989 | European Pat. Off. . |
| 0427957 | 5/1991 | European Pat. Off. . |

(List continued on next page.)

*Primary Examiner*—C. H. Kelly
*Attorney, Agent, or Firm*—Stevens, Davis, Miller & Mosher, L.L.P.

[57] ABSTRACT

The present invention relates to trans-olefin compounds represented by the general formula (1) useful as an ingredient of liquid crystal composition, trans-olefin compounds useful as intermediate of pesticides, medical drugs, liquid crystal materials and the like, a process for producing those trans-olefin compounds, a liquid crystal composition containing the trans-olefin compound as an active ingredient, and a liquid crystal element using the liquid crystal composition.

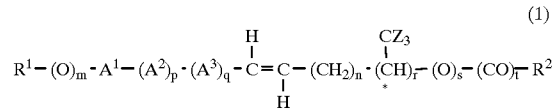

(In the general formula (1), $R^1$, $A^1$, $A^2$, $A^3$, $Z$ and $R^2$ are same as defined in the specification. Also, m, p, q, n, r, s and t are each an integer as defined in the specification.)

14 Claims, 3 Drawing Sheets

U.S. PATENT DOCUMENTS

| | | |
|---|---|---|
| 61-83136 | 4/1986 | Japan . |
| 62-502620 | 10/1987 | Japan . |
| 2503434 | 10/1990 | Japan . |
| 4128267 | 4/1992 | Japan . |
| 4178369 | 6/1992 | Japan . |
| 86 06373 | 11/1986 | WIPO . |
| 87 04426 | 7/1987 | WIPO . |

τ-V CHARACTERISTICS OF FERROELECTRIC COMPOSITION (4-a) AT 25°C
(EXAMPLE 171)

τ-V CHARACTERISTICS OF EXAMPLE 172

τ-V CHARACTERISTICS OF EXAMPLE 173

TRANS-OLEFIN COMPOUNDS, METHOD FOR PRODUCTION THEREOF, LIQUID CRYSTAL COMPOSITION CONTAINING THE SAME AS ACTIVE INGREDIENT, AND LIQUID CRYSTAL ELEMENT USING SAID COMPOSITION

This is a division of application Ser. No. 08/282,024 filed Jul. 29, 1994, U.S. Pat. No. 5,707,547.

BACKGROUND OF THE INVENTION

1. Field of the Invention

The present invention relates to trans-olefin compounds useful as an ingredient of liquid crystal composition, trans-olefin compounds useful as intermediate of pesticides, medical drugs, liquid crystal materials and the like, a process for producing those trans-olefin compounds, a liquid crystal composition containing the trans-olefin compound as an active ingredient, and a liquid crystal element using said liquid crystal composition.

2. Related Art Statement

With the recent progress in information society, a variety of display devices are getting an increasing importance as one of machine interfaces. Of such displays, planar displays and particularly liquid crystal displays (LCD) have rapidly been distributed because of their small thickness, lightness in weight, low driving voltage, and small consumption of electric power.

Among the liquid crystal elements represented by liquid crystal display, the matrix type liquid crystal elements large in the amount of information are classified into active matrix type and simple matrix type from the viewpoint of method of driving.

In the active matrix type, thin-film transistors or diodes made of polysilicon, amorphous silicon or the like are set as non-linear elements by every image element. However, the active matrix type is complicated in the process of production and low in product yield, so that it is inferior from the viewpoint of enlargement of area, reduction of cost and enhancement of density. Thus, at the present time, the simple matrix type is advantageous over the active matrix type so far as price and productivity are taken into account.

As the liquid crystal element of simple matrix type which is in practical use currently, those using TN type and STN type liquid crystals are predominant. The optical response of these elements utilizes orientation of the average liquid crystal molecular axis in a particular direction in an electric field, which is based on the dielectric anisotropy of liquid crystal molecules. Accordingly, the limit of optical response speed of these elements is of milli-second order, which is insufficient in the light of the increasing amount of information of the current time. Although a variety of driving methods have so far been proposed with the aim of overcoming this difficulty, none of those proposals can give an essential solution to the problem, so that enlargement of capacity and enhancement of density are difficult to realize by those proposals. Further, these liquid crystals are so restricted in the angle of visual field and in the quality of display as to present another important difficulty.

In 1980, N. A. Clark and S. T. Lagerwall [Applied Phys. Lett., 36, 899 (1980)] proposed a liquid crystal element utilizing a bistable liquid crystal with the aim of solving the above-mentioned essential problem of liquid crystal element. As such bistable liquid crystal, ferroelectric liquid crystals exhibiting a chiral-smectic C phase are predominantly used.

The ferroelectric liquid crystal element is essentially characterized in that (1) it shows two optically stable states, and the optically stable states are maintained as they are even after removal of electric field (bistability) and (2) the optically stable states can be switched in micro-second order (high-speed response property). Further, the ferroelectric liquid crystal element is characterized also in that (3) the liquid crystal molecules respond in a plane parallel to substrate and the cell has a small thickness, so that the visual field angle-dependence of display is small (wide angle of visual field). Accordingly, the ferroelectric liquid crystal element requires no use of expensive non-linear element unlike active matrix type, and is expected as a high-quality large-sized display which can achieve a high display capacity and a high display quality by a simple matrix method.

Recently, M. F. Bone (U.S. Pat. No. 5,047,757; JP-A-3-20715) has reported an address method of matrix array type liquid crystal cell (inverse mode or $\tau$-Vmin mode) using a liquid crystal material so controlled that response time of the liquid crystal takes a minimum value at a particular voltage. In such address method, a liquid crystal element is driven by using the positive gradient region of the voltage-dependence of response time, on the basis of the fact that response time of liquid crystal takes a minimum value at a particular voltage. The use of such a driving method expectedly gives a non-flickering good image.

A liquid crystal material which can be used in such inverse mode must have a negative dielectric anisotropy at least over the high frequency number range of 1–40 kHz, in addition to the characteristic properties conventionally required of ferroelectric liquid crystal materials, namely a phase series necessary for obtaining a good state of orientation or, in other words, a phase series changing, when slowly cooled, from isotropic phase via cholesteric phase and smectic A phase into chiral smectic C phase, and a low viscosity and a high-speed response property.

Although a number of liquid crystal materials have so far been reported either on paper or verbally, all these techniques have had some unsolved problem. One of the problems is to develop a liquid crystal material exhibiting chiral smectic C phase in a sufficiently wide temperature range and showing a minimum response time at a particular electric field.

Many properties are required of a ferroelectric liquid crystal material used in an actual ferroelectric liquid crystal element, whatever driving method is adopted. At the present stage, any single compound cannot fulfil all of such requirements, but a ferroelectric liquid crystal composition prepared by mixing together a plurality of liquid crystal compounds or non-liquid crystal compounds must be used. Up to today, however, there has been discovered no liquid crystal material simultaneously satisfying these practical requirements.

Although some aspects of the present invention may be involved in the conceptions of U.S. Pat. No. 4,834,904 (Japanese patent Kohyo 62-502620) and U.S. Pat. No. 5,209,866 (Japanese Patent Kohyo 2-503434) if the factors in the general formulas presented therein are favorably combined, the compounds of the present invention are by no means mentioned concretely in these prior patents.

OBJECT AND SUMMARY OF THE INVENTION

The object of the present invention is to provide a compound having excellent properties as a liquid crystal compound, an industrial process for advantageously producing said compound, a liquid crystal composition containing said compound, and a liquid crystal element using said composition.

After extensive studies for development of excellent liquid crystal compound and liquid crystal composition, the present inventors invented trans-olefin compounds represented by the general formula (1) and liquid crystal compositions containing said trans-olefin compounds. The compounds of the present invention are quite excellent in properties in that:

when the compound of the present invention is an optically active compound, it exhibits a ferroelectric Sc* phase; and even when the compound of the invention is not optically active, the compound of the present invention exhibits Sc phase having a low viscosity and a broad temperature range; and in both the cases, the liquid crystal developing temperature is higher than that of the corresponding saturated compound. Thus, if the compound of the present invention is used as a composition, it is effective for enhancing the upper limit temperature of Sc* phase, and exhibiting Sc* phase in a broad temperature range. Further, a liquid crystal composition containing said trans-olefin compound is quite useful as a ferroelectric liquid crystal material in that it readily undergoes a spontaneous polarization and exhibits a large tilt angle and a high-speed response property.

Some of the compounds of the present invention are useful as a liquid crystal element using nematic phase.

Further, the present inventors have found out a process for producing the trans-olefin compounds of the present invention in a high selectivity by using a compound prepared by adding a boron compound to the trans position of an acetylene compound.

Thus, the present invention provides a trans-olefin compound represented by general formula (1):

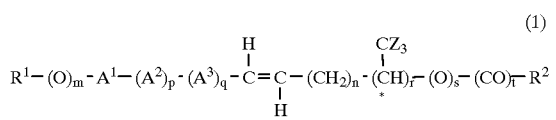

wherein $R^1$ is saturated or unsaturated alkyl group having 1–20 carbon atoms, saturated or unsaturated alkoxyalkyl group having 2–20 carbon atoms or hydrogen atoms, provided that when m=1, $R^1$ may be a protecting group for hydroxyl group, and when r=0, s=0 and t=0, $R^1$ cannot be an unsaturated alkyl group; $R^2$ is hydrogen atom or saturated or unsaturated alkyl group having 1–20 carbon atoms which may optionally be substituted by halogen atom or saturated or unsaturated alkoxyalkyl group having 2–20 carbon atoms which may optionally be substituted by halogen atom, provided that when s=1 and t=0, $R^2$ may be a protecting group for hydroxyl group; $A^1$, $A^2$ and $A^3$ each represents one of the following groups:

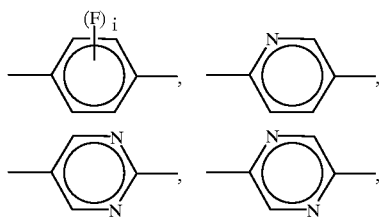

-continued

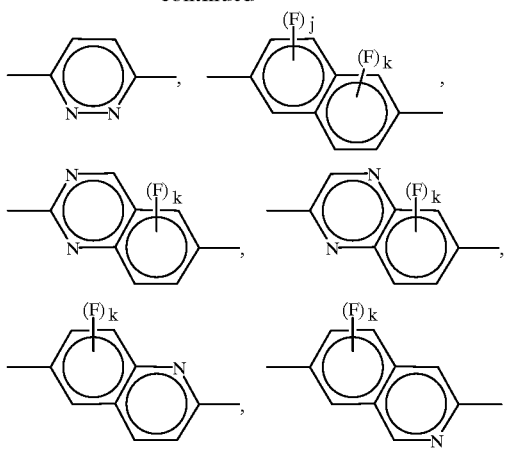

in which i is an integer of 0–4 and j and k are each an integer of 0–3; p and q are 0 or 1, provided that when $A^1$ is a fused ring, p+q=0 or 1 and $A^2$ and $A^3$ are single rings and when $A^1$ is a single ring, p+q=1 or 2, provided that when p+q=2, $A^2$ and $A^3$ are both single rings; Z is hydrogen atom or fluorine atom; n is an integer of 0–10; and m, r, s and t each represents 0 or 1; a process for producing said trans-olefin compound; a liquid crystal composition containing said trans-olefin compound as at least one of its active ingredients; and a liquid crystal element using said liquid crystal composition.

Further, the present invention provides a ferroelectric liquid crystal composition containing at least one trans-olefin compound represented by the general formula (1) and at least one compound represented by the following general formula (A):

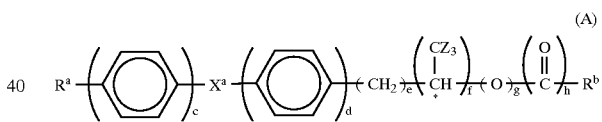

wherein $R^a$ represents alkyl, alkoxy or alkoxyalkyl group having 5–15 carbon atoms, and $R^b$ represents an alkyl or alkoxy group having 1–10 carbon atoms which may optionally be substituted by halogen atom or an alkoxyalkyl group having 2–10 carbon atoms which may optionally be substituted by halogen atom, provided that when the consecutive methylene chains $R^a$ and $R^b$ may optionally be substituted by double bond or triple bond, c and d independently represent an integer of 1 or greater, provided that c+d is equal to 3, e is an integer of 0–10, f, g and h are independently 0 or 1, $X^a$ is —COO— or —OCO—, the hydrogen atoms of the benzene rings may optionally be substituted by fluorine atom, the mark * signifies an asymmetric carbon atoms, and Z represents hydrogen atom or fluorine atom, as indispensable ingredients; provided that, when none of the compounds of general formula (1) and general formula (A) is optically active, said ferroelectric liquid crystal composition contains other optically active compound.

BRIEF DESCRIPTION OF THE DRAWING

FIG. 1 is an outlined view illustrating one example of the display device using the ferroelectric liquid crystal of the present invention, wherein:

1—polarizing plate,

2—glass substrate,
3—transparent electrode,
4—insulating oriented film,
5—ferroelectric liquid crystal layer, and
6—spacer.

Figure 2:
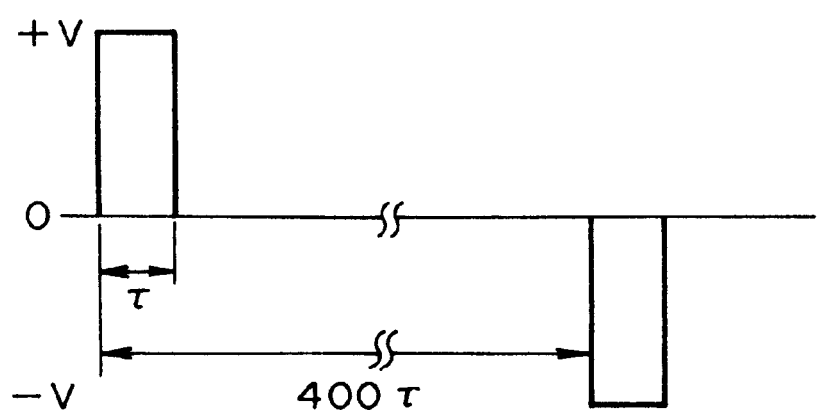

FIG. 2 shows a pulse applied to a liquid crystal element for evaluating a τ-V characteristic of a ferroelectric liquid crystal composition.

Figure 3:
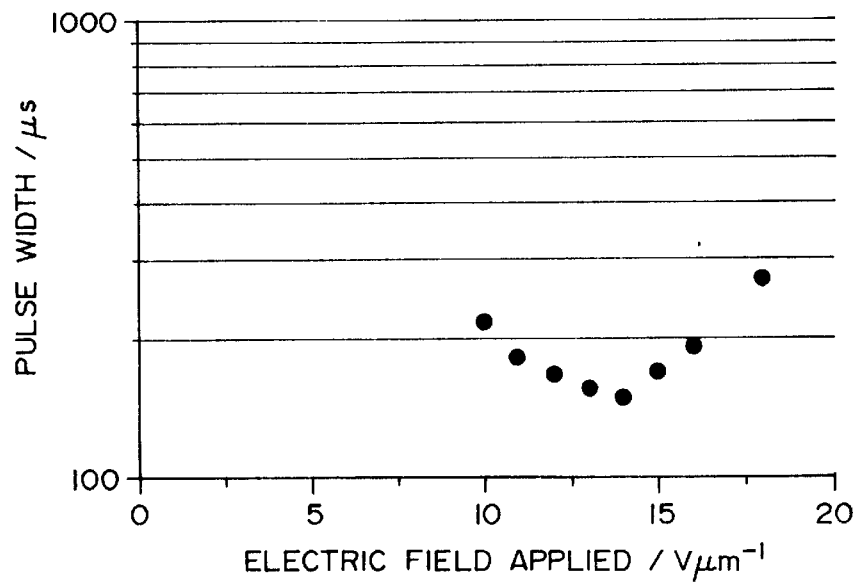

FIG. 3 shows the τ-V characteristic of a ferroelectric liquid crystal composition (4-a) of Example 171 at 25° C.

Figure 4:
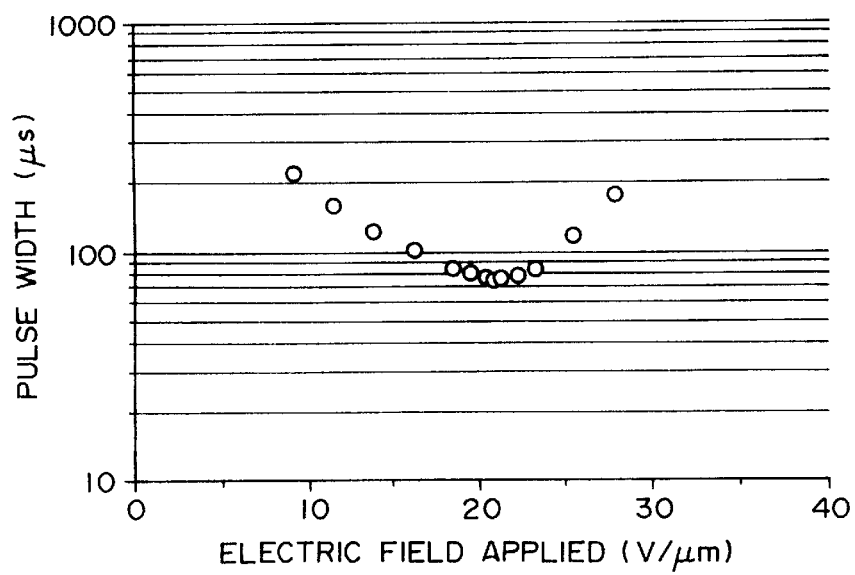

FIG. 4 shows the τ-V characteristic of a ferroelectric liquid crystal composition 5 of Example 172.

Figure 5:
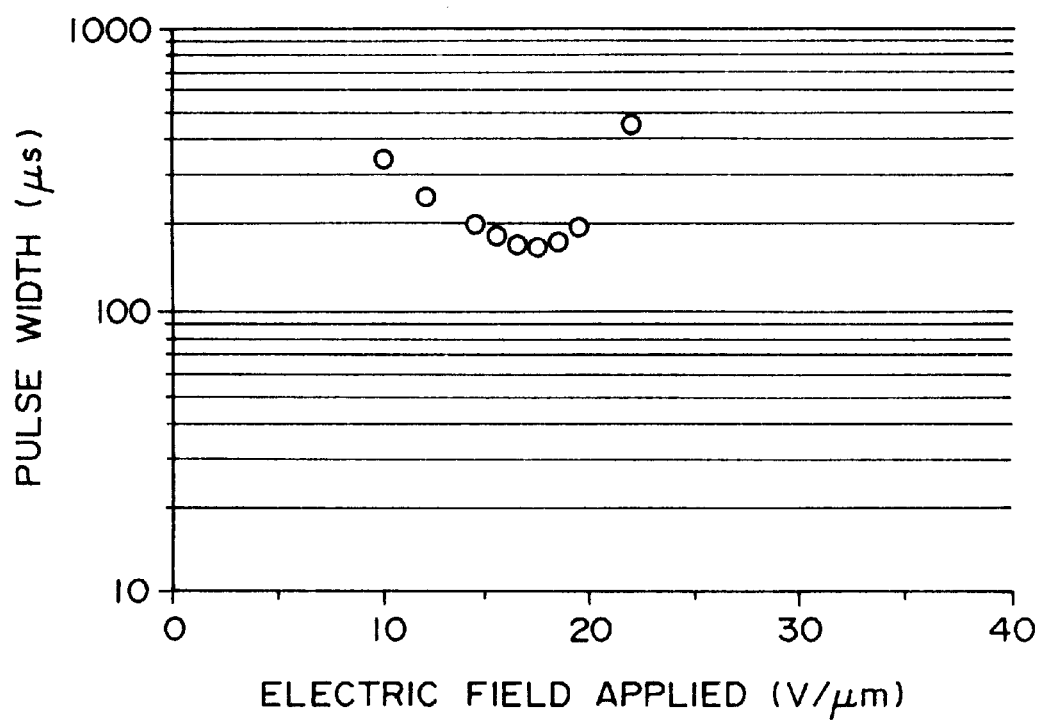

FIG. 5 shows the τ-V characteristic of a ferroelectric liquid crystal composition 6 of Example 173.

DETAILED DESCRIPTION OF THE INVENTION

The present invention is explained below in more detail.

The trans-olefin compound (1) can be obtained by reacting a boron compound represented by the general formula (2):

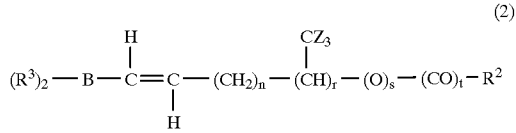

(2)

wherein $R^2$, Z, n, r, s and t are as defined above and $R^3$ represents hydroxyl group, a straight chain, branched chain or cyclic alkyl group or a straight chain, branched chain or cyclic alkoxy group, provided that the two $R^3$ may be combined with each other to form one ring or $(R^3)_2$ taken conjointly may represent as a whole an optionally substituted benzodioxy group, with a compound represented by the general formula (3):

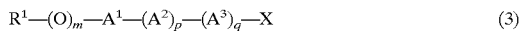

(3)

wherein $R^1$, $A^1$, $A^2$, $A^3$, m, p and q are as defined above and X represents halogen atom or —$OSO_2R'$ in which R' is a lower alkyl group which may optionally be substituted by fluorine atom or an optionally substituted phenyl group, in the presence of a palladium catalyst and a basic substance.

The compound represented by the general formula (3) can be produced by the following method:

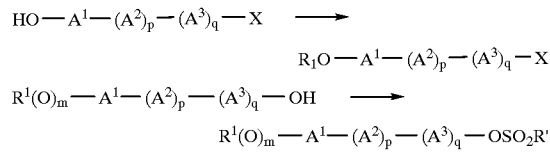

wherein $R^1$, $A^1$, $A^2$, $A^3$, R', m, p and q are as defined above.

In the boron compound represented by the general formula (2), $R^3$ represents a straight chain, branched chain or cyclic alkoxy group, provided that the two $R^3$ groups may be combined with each other to form one ring. When $(R^3)_2$ taken conjointly represents an optionally substituted benzodioxy group, such a compound (2) can be obtained by reacting an acetylene compound represented by the general formula (6):

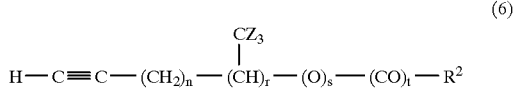

(6)

wherein $R^2$, Z, n, r, s and t are as defined above, with a boron compound represented by the general formula (7):

$(R^{3'})_2BH$  (7)

wherein $R^{3'}$ represents a straight chain, branched chain or cyclic alkyl group or a straight chain, branched chain or cyclic alkoxy group, provided that the two $R^{3'}$ groups may be combined with each other to form one ring or $(R^{3'})_2$ taken conjointly may represent an optionally substituted benzodioxy group.

Some of the acetylene compound (6) are optically active, and these optically active compounds can be synthesized from a racemic alcohol or an optically active alcohol. Said optically active alcohol can be prepared by an enzymatic resolution of a racemic alcohol, for example in the following manner. If desired, $R^2$ can further be introduced thereinto.

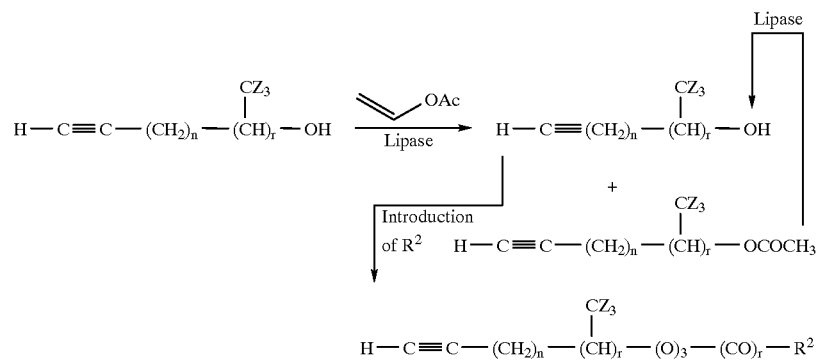

wherein $R^2$ represents a saturated or unsaturated alkyl group having 1–20 carbon atoms which may optionally be substituted by halogen atom or a saturated or unsaturated alkoxyalkyl group having 2–20 carbon atoms which may optionally be substituted by halogen atom, provided that, when s=1 and t=0, $R^2$ may be a protecting group for hydroxyl group, Z represents hydrogen atom or fluorine atom, and n is an integer of 0–10.

As examples of the boron compound (7), dialkyl-boranes such as dicyclohexylborane, dicyamylborane, diisopinocamphenylborane, 9-borabicyclo[3,3,1]nonane and the like and dialkoxyboranes such as catecholborane, diisopropyloxyborane, dimethoxyborane and the like can be referred to.

In the above-mentioned reaction between acetylene compound (6) and boron compound (7) for obtaining boron compound (2), the amount of boron compound (7) is 0.5–10 equivalents and preferably 0.5–2 equivalents per equivalent of acetylene compound (6). When a reaction solvent is used, tetrahydrofuran, diethyl ether, dioxane, dimethylformamide and the like can be used as the solvent. The amount of the reaction solvent is not particularly critical.

In this reaction, the reaction temperature is usually −20 to 150° C., and preferably 0 to 100° C.

The compounds represented by the general formula (2) wherein $R^3$ is a hydroxyl group can be obtained by reacting the above-mentioned acetylene compound (6) and boron compound (7) to obtain a boron compound (2), and then hydrolyzing the boron compound (2).

Compounds represented by general formula (2'):

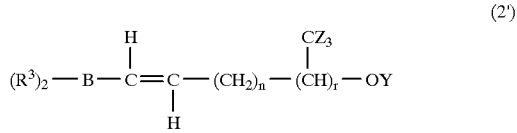

(2')

wherein $R^3$, Z, n and r are as defined above and Y represents hydrogen atom or $(R^3)_2B$, can be obtained by reacting an acetylene compound of the following formula:

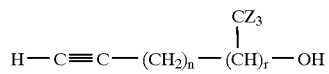

with a boron compound of the general formula (7). By hydrolyzing the compound thus obtained, there is obtained a compound represented by general formula (2') wherein $R^3$ is hydroxyl group and Y is hydrogen atom.

In the reactions between the boron compound represented by the general formulas (2) or (2') and the compound represented by the general formula (3) for obtaining a trans-olefin compound (1), the amount of the boron compound (2) or (2') is usually 0.9–10 equivalents and preferably 1–2 equivalents per equivalent of the compound (3).

As the metallic catalyst used in the above-mentioned reaction, palladium type catalysts such as palladium chloride, palladium acetate, palladium/carbon, triphenylphosphine-palladium complexes (for example, tetrakistriphenylphosphine-palladium and dichloro-ditriphenylphosphine-palladium) and the like can be referred to. Analogous catalysts of nickel type and rhodium type are also usable in the reaction.

These metallic catalysts are used in an amount of 0.001–0.1 equivalent per equivalent of the starting compound (3).

In the reaction mentioned above, it is sometimes desirable to use a trivalent phosphorus compound or a trivalent arsenic compound as a co-catalyst. These compounds are represented by the following general formula (8):

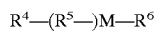

(8)

wherein M represents phosphorus atom or arsenic atom and $R^4$, $R^5$ and $R^6$, identical or different, each represents alkyl group, aryl group, alkoxy group, aryloxy group or halogen atom. Concrete examples of the phosphorus compound and arsenic compound include tri-n-butylphosphine, triphenylphosphine, tri-o-tolylphosphine, tri-o-tolyl phosphite, phosphorus trichloride, triphenylarsenic and the like.

The phosphorus compound and arsenic compound are used in an amount of 0.5–50 equivalents and preferably 10–30 equivalents per equivalent of the above-mentioned metallic catalyst.

As said basic substance, carbonates, carboxylates, alkoxides and hydroxides of alkali metals and organic bases such as triethylamine, diisopropylethylamine, tri-n-butylamine, tetramethylethylenediamine, dimethylaniline and the like can be used, among which hydroxides such as sodium hydroxide, potassium hydroxide and the like and alkoxides such as sodium ethoxide, sodium methoxide and the like are preferably.

The basic substance is used in an amount of 1–5 equivalents per equivalent of compound (3), usually. If desired, acetonitrile, tetrahydrofuran, dimethylformamide, hexamethylphosphorylamide, N-methylpyrrolidone, benzene, toluene or the like may be used as a reaction solvent.

The amount of the reaction solvent is not particularly critical.

In this reaction, the reaction temperature is usually from −20° C. to 190° C., and preferably from 40° C. to 150° C.

After the reaction, compound (1) can be isolated by conventional means such as extraction, distillation, recrystallization, column chromatography, etc.

When $R^2$ is hydrogen atom, s=1 and t=0, the trans-olefin compound (1) obtained by the above-mentioned reaction is represented by the following structural formula (1"):

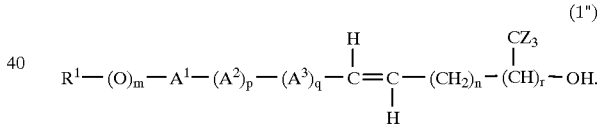

(1")

wherein $R^1$ represents a saturated or unsaturated alkyl group having 1–20 carbon atoms or a saturated or unsaturated alkoxyalkyl group having 2–20 carbon atoms and, when m=1, represents a protecting group for hydroxyl group, too, and $A^1$, $A^2$, $A^3$, Z, m, n, p, q and r are as defined above.

By reacting this compound with a carboxylic acid compound represented by the following general formula (4):

(4)

wherein $R^2$ represents a saturated or unsaturated alkyl group having 1–20 carbon atoms which may optionally be substituted by halogen atom or a saturated or unsaturated alkoxyalkyl group having 2–20 carbon atoms which may optionally be substituted by halogen atom and R" represents hydroxyl group, $OCOR^2$ or halogen atom, there can be obtained an ester compound represented by the general formula (1) wherein s and t are both equal to 1.

Apart from the above, an ether compound represented by the general formula (1) wherein s=1 and t=0 can be obtained by reacting the compound (1") with an alkylating agent represented by the general formula (5):

$$R^2\text{—}X \quad (5)$$

wherein $R^2$ and X are as defined above.

Next the reactions mentioned above will be explained in more detail.

In the reaction between trans-olefin compound (1") and carboxylic acid compound (4), as the carboxylic acid compound (4), carboxylic acids having an alkyl group represented by $R^2$, acid anhydrides thereof, and acid halides such as acid chlorides and acid bromides can be used. Said carboxylic acid compound may be any of racemic mixture and optically active isomers.

When a solvent is used in the above reaction, the solvents usable are those inert to the reaction such as ethers, ketones, aliphatic and aromatic hydrocarbons, halogenated hydrocarbons, aprotic polar solvents and the like. Concrete examples of the solvent include tetrahydrofuran, ethyl ether, acetone, methyl ethyl ketone, toluene, benzene, chlorobenzene, dichloromethane, dichlorethane, chloroform, carbon tetrachloride, dimethylformaide, hexane and the like. These solvents may be used either singly or in the form of mixture. The amount of the solvent is not particularly critical.

When an acid anhydride or an acid halide of aliphatic carboxylic acid is used in the above reaction, the amount of the acid anhydride or acid halide must be at least one equivalent per equivalent of the trans-olefin compound (1"). Although upper limit of its amount is not critical, the upper limit is preferably 1.1–4 equivalents.

As the catalyst, organic and inorganic basic substances such as dimethylaminopyridine, 4-pyrrolidinopyridine, triethylamine, tri-n-butylamine, pyridine, picoline, collidine, imidazole, sodium carbonate, sodium methylate, potassium hydrogen carbonate and the like can be used.

Further, organic and inorganic acids such as toluenesulfonic acid, methanesulfonic acid, sulfuric acid and the like are also usable as the catalyst.

When an acid halide of carboxylic acid is used as the starting compound, pyridine or triethylamine is preferably used as the catalyst.

Although the amount of the catalyst is dependent on the kind of the acid anhydride or acid halide of carboxylic acid and combination with catalyst and cannot be specified particularly, the amount of catalyst is, for example, at least one equivalent per equivalent of acid halide, when acid halide is used.

When a carboxylic acid is used in the above reaction, the carboxylic acid can be obtained also by carrying out a dehydrating condensation using 1–2 equivalents of carboxylic acid with one equivalent of trans-olefin compound (1") in the presence of a condensing agent.

As said condensing agent, carbodiimides such as N,N'-dicyclohexylcarbodiimide, N-cyclohexyl-N'-(4-diethylamino)-cyclohexylcarbodiimide and the like are preferred. If desired, an organic base such as 4-diethylaminopyridine, 4-pyrrolidinopyridine, pyridine, triethylamine and the like is also used in combination therewith.

The condensing agent is used in an amount of 1–1.5 equivalents per equivalent of carboxylic acid. When an organic base is used in combination, the amount of the organic base is 0.01–0.2 equivalent per equivalent of the condensing agent.

The reaction temperature is usually −30 to 100° C. and preferably 0 to 80° C.

The reaction time is not critical, and the point in time when the starting compound (1") has disappeared may be taken as end point of the reaction.

After the reaction, the trans-olefin compound (1) wherein s and t are 1 can be obtained in a high yield by conventional separating means such as extraction, phase separation, concentration and the like. If desired, the product may be purified by column chromatography, recrystallization or the like.

Next, the reaction between trans-olefin compound (1") and alkylating agent (5) for obtaining an ether compound represented by general formula (1) wherein s=1 and t=0 will be explained.

The term "alkylating agent" used herein means a halide or a sulfonic acid ester both having a substituent $R^2$, which can be produced from the corresponding alcohol according to well known methods.

The substituent $R^2$ in the alkylating agent may be an optically active residue.

This reaction is carried out usually in the presence of a basic substance. Although the alkylating agent may be used in an arbitrary amount so far as not smaller than one equivalent per equivalent of trans-olefin compound (1"), the amount is usually in the range of 1–5 equivalents.

The reaction is usually carried out in the presence of a solvent. The solvents usable are those inert to the reaction such as ethers, ketones, aliphatic and aromatic hydrocarbons, halogenated hydrocarbons, aprotic polar solvents and the like. These solvents may be used either singly or in the form of mixture. Concrete examples of the solvent include tetrahydrofuran, ethyl ether, acetone, methyl, ethyl ketone, toluene, benzene, chlorobenzene, dichloromethane, dichloroethane, chloroform, carbon tetrachloride, hexane, dimethylformamide, dimethyl sulfoxide, hexamethylphosphorylamide, N-methylpyrrolidone and the like. The amount of the solvent is not critical.

As the basic substance, for example, alkali metal hydrides such as sodium hydride, potassium hydride and the like, alkali metals such as lithium, sodium, potassium and the like, alkali metal alcoholates such as sodium ethylate, sodium methylate and the like, alkali metal carbonates such as sodium carbonate, potassium carbonate and the like, butyllithium, and the like can be used.

Said basic substance must be used in an amount of at least one equivalent per equivalent of trans-olefin compound (1"). Although upper limit of its amount is not critical, the upper limit is usually 1.1–5 equivalents.

The reaction temperature is usually −50 to 120° C., and preferably −30 to 100° C.

The reaction time is not particularly critical, and the point in time when the starting compound (1") has disappeared may be taken as end point of the reaction.

After the reaction, the objective trans-olefin compound of general formula (1) wherein s=1 and t=0 can be isolated from the reaction mixture by conventional separating means such as extraction, phase separation, concentration or the like. If desired, the product may be purified by column chromatography, recrystallization or the like.

In the alkylating reaction, when substituent X of the alkylating agent is an iodine atom, silver oxide may be used in place of the above-mentioned basic substance.

In this case, the silver oxide must be used in an amount of at least one equivalent per equivalent of trans-olefin compound (1"). Although the upper limit is not critical, it is preferably used in an amount of at least 3 equivalents.

When the alkylating reaction is carried out in the presence of silver oxide, the alkylating agent in which substituent X is iodine atom may be used in an arbitrary amount so far as not smaller than one equivalent per equivalent of starting compound (1"), and preferably in an amount of 2–10 equivalents.

As the reaction solvent, an excessive amount of alkylating agent in which the substituent is iodine atom can be used as the solvent. Apart from it, solvents inert to the reaction such as tetrahydrofuran, ethyl ether, dioxane, acetone, methyl ethyl ketone, benzene, toluene, hexane or the like may be used either singly or in the form of mixture.

The reaction temperature is usually 0–150° C., and preferably 20–100° C.

The reaction time is usually from one hour to 20 days.

From the reaction mixture, the trans-olefin compound (1) wherein s=1 and t=0 can be isolated by filtering off the silver salt and subjecting the filtrate to conventional after-treatments such as extraction, phase separation, concentration and the like.

If desired, the product may be purified by column chromatography or the like.

In the descriptions presented above, the method for obtaining trans-olefin compound (1) from compound (1") has been explained.

As examples of the substituent $R^2$ in the carboxylic acid compounds and alkylating agents used herein, the following can be referred to:

methyl, ethyl, propyl, isopropyl, butyl, isobutyl, pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, 2,2-dimethylcyclopropyl, cyclopentyl, cyclohexyl, propenyl, 2-butenyl, 3-butenyl, 2-pentenyl, 2-hexenyl, 3-hexenyl, 2-heptenyl, 2-octenyl, 2-nonenyl, 2-decenyl, 3-decenyl, 2-undecenyl, 2-dodecenyl, 2-tridecenyl, 2-tetradecenyl, 2-pentadecenyl, 2-hexadecenyl, 2-heptadecenyl, 2-octadecenyl, 2-nonadecenyl, 2-eicosenyl, 2-propynyl, 2-butynyl, 2-pentynyl, 2-hexynyl, 3-hexynyl, 2-heptynyl, 2-octynyl, 2-nonynyl, 2-decynyl, 2-undecynyl, 2-dodecynyl, 2-tridecynyl, 2-tetradecynyl, 2-pentadecynyl, 2-hexadecynyl, 2-heptadecynyl, 2-octadecynyl, 2-nonadecynyl, 2-eicosynyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxynonyl, propoxydecyl, butoxybutoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, heptyloxypentyl, heptyloxyhexyl, heptyloxyheptyl, heptyloxyoctyl, heptyloxynonyl, heptyloxydecyl, octyloxymethyl, octyloxyethyl, octyloxypropyl, octyloxybutyl, octyloxypentyl, octyloxyhexyl, octyloxyheptyl, octyloxynonyl, octyloxyoctyl, decyloxymethyl, decyloxyethyl, decyloxypropyl, decyloxybutyl, decyloxypentyl, decyloxyhexyl, decyloxyheptyl, 2-propenyloxymethyl, 2-butenyloxymethyl, 3-butenyloxymethyl, 2-pentenyloxymethyl, 2-hexenyloxymethyl, 3-hexenyloxymethyl, 2-heptenyloxymethyl, 2-octenyloxymethyl, 2-nonenyloxymethyl, 2-decenyloxymethyl, 3-decenyloxymethyl, 2-undecenyloxymethyl, 2-dodecenyloxymethyl, 2-tridecenyloxymethyl, 2-tetradecenyloxymethyl, 2-pentadecenyloxymethyl, 2-hexadecenyloxymethyl, 2-heptadecenyloxymethyl, 2-octadecenyloxymethyl, 2-nonadecenyloxymethyl, 2-eicosenyloxymethyl, 1-methylethyl, 1-methylpropyl, 1-methylbutyl, 1-methylpentyl, 1-methylhexyl, 1-methylheptyl, 1-methyloctyl, 1-methylnonyl, 1-methyldecyl, 2-methylpropyl, 2-methylbutyl, 2-methylpentyl, 2-methylhexyl, 2-methylheptyl, 2-methyloctyl, 2,3-dimethylbutyl, 2,3,3-trimethylbutyl, 3-methylpentyl, 2,3-dimethylpentyl, 2,4-dimethylpentyl, 2,3,3,4-tetramethylpentyl, 3-methylhexyl, 2,5-dimethylhexyl, 2-trifluoromethylpropyl, 2-trifluoromethylbutyl, 2-trifluoromethylpentyl, 2-trifluoromethylhexyl, 2-trifluoromethylheptyl, 2-fluoroethyl, 2-fluoropropyl, 3-fluoropropyl, 3-fluoro-2-methylpropyl, 2,3-difluoropropyl, 2-fluorobutyl, 3-fluorobutyl, 4-fluorobutyl, 2,3-difluorobutyl, 2,4-difluorobutyl, 3,4-difluorobutyl, 2-fluoro-3-methylbutyl, 2-fluoro-3,3-dimethylbutyl, 2-fluoropentyl, 3-fluoropentyl, 4-fluoropentyl, 5-fluoropentyl, 2,4-difluoropentyl, 2,5-difluoropentyl, 2-fluoro-3-methylpentyl, 2-fluoro-4-methylpentyl, 2-fluoro-3-monofluoromethyl-4-methylpentyl, 2-fluorohexyl, 3-fluorohexyl, 4-fluorohexyl, 5-fluorohexyl, 6-fluorohexyl, 2-fluoroheptyl, 2-fluorooctyl and the like, provided that, in the examples mentioned above, the expression "fluoro" may be read "chloro" and "bromo".

As for carboxylic acid compounds, fluoromethyl, 1-fluoroethyl, 1-fluoropropyl, 1-fluorobutyl, 1-fluoropentyl, 1-fluorohexyl, 1-fluoroheptyl, 1-fluorooctyl and the like can also be referred to in addition to the above-mentioned examples, provided that, in the above-mentioned examples, the expression "fluoro" may be read "chloro" and "bromo".

These alkyl groups and some of the alkoxyalkyl groups form a straight chain, a branched chain or a ring. In the case of branched chain and ring, they may be optically active.

Some of the optically active carboxylic acid compounds having substituent $R^2$ mentioned above are obtained by oxidation of the corresponding alcohol or a reductive de-amination of amino acid, and some of them can be derived from the optically active amino acids and optically active oxy acids mentioned below which are produced in the natural world or obtained by optical resolution.

Some of the optically active alkylating agents having substituent $R^2$ can easily be produced from the corresponding alcohols. Some of these alcohols can be obtained by an asymmetric reduction of the corresponding ketone using an asymmetric metallic catalyst or a microorganism or an enzyme. Further, some of them are produced in the natural world or can be derived from optically active amino acids or optically active oxy acids obtained by optical resolution, such as those mentioned below:

alanine, valine, leucine, isoleucine, phenylalanine, threonine, allothreonine, homoserine, alloisoleucine, tert-leucine, 2-aminobutyric acid, norvaline, norleucin, ornithine, lysine, hydroxylysine, phenylglycine, aspartic acid, glutamic acid, mandelic acid, tropic acid, 3-hydroxylbutyric acid, malic acid, tartaric acid, isopropylmalic acid and the like.

As examples of $R^1$, the following can be referred to:
methyl, ethyl, propyl, isopropyl, butyl, isobutyl, pentyl, isopentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, 2,2-dimethylcyclopropyl, cyclopentyl, cyclohexyl, propenyl, 2-butenyl, 3-butenyl, 2-pentenyl, 2-hexenyl, 3-hexenyl, 2-heptenyl, 2-octenyl, 2-nonenyl, 2-decenyl, 3-decenyl, 2-undecenyl, 2-dodecenyl, 2-tridecenyl, 2-tetradecenyl, 2-pentadecenyl, 2-hexadecenyl, 2-heptadecenyl, 2-octadecenyl, 2-nonadecenyl, 2-eicosenyl, 2-propynyl, 2-butynyl, 2-pentynyl, 2-hexynyl, 3-hexynyl, 2-heptynyl, 2-octynyl, 2-nonynyl, 2-decynyl, 2-undecynyl, 2-dodecynyl, 2-tridecynyl, 2-tetradecynyl, 2-pentadecynyl, 2-hexadecynyl, 2-heptadecynyl, 2-octadecynyl, 2-nonadecynyl, 2-eicosynyl, methoxymethyl, methoxyethyl, methoxypropyl, methoxybutyl, methoxypentyl, methoxyhexyl, methoxyheptyl, methoxyoctyl, methoxynonyl, methoxydecyl, ethoxymethyl, ethoxyethyl, ethoxypropyl, ethoxybutyl, ethoxypentyl, ethoxyhexyl, ethoxyheptyl, ethoxyoctyl, ethoxynonyl, ethoxydecyl, propoxymethyl, propoxyethyl, propoxypropyl, propoxybutyl, propoxypentyl, propoxyhexyl, propoxyheptyl, propoxyoctyl, propoxynonyl, propoxydecyl, butoxybutoxymethyl, butoxyethyl, butoxypropyl, butoxybutyl, butoxypentyl, butoxyhexyl, butoxyheptyl, butoxyoctyl, butoxynonyl, butoxydecyl, pentyloxymethyl, pentyloxyethyl, pentyloxypropyl, pentyloxybutyl, pentyloxypentyl, pentyloxyhexyl, pentyloxyoctyl, pentyloxynonyl, pentyloxydecyl, hexyloxymethyl, hexyloxyethyl, hexyloxypropyl, hexyloxybutyl, hexyloxypentyl, hexyloxyhexyl, hexyloxyheptyl, hexyloxyoctyl, hexyloxynonyl, hexyloxydecyl, heptyloxymethyl, heptyloxyethyl, heptyloxypropyl, heptyloxybutyl, hexyloxypentyl, heptyloxyhexyl, heptyloxyheptyl, heptyloxyoctyl, heptyloxynonyl, heptyloxydecyl, octyloxymethyl, octyloxyethyl, octyloxypropyl, octyloxybutyl, octyloxypentyl, octyloxyhexyl, octyloxyheptyl, octyloxynonyl, octyloxyoctyl, decyloxymethyl, decyloxyethyl, decyloxypropyl, decyloxybutyl, decyloxypentyl, decyloxyhexyl, decyloxyheptyl, 2-propenyloxymethyl, 2-butenyloxymethyl, 3-butenyloxymethyl, 2-pentenyloxymethyl, 2-hexenyloxymethyl, 3-hexenyloxymethyl, 2-heptenyloxymethyl, 2-octenyloxymethyl, 2-nonenyloxymethyl, 2-decenyloxymethyl, 3-decenyloxymethyl, 2-undecenyloxymethyl, 2-dodecenyloxymethyl, 2-tridecenyloxymethyl, 2-tetradecenyloxymethyl, 2-pentadecenyloxymethyl, 2-hexadecenyloxymethyl, 2-heptadecenyloxymethyl, 2-octadecenyloxymethyl, 2-nonadecenyloxymethyl, 2-eicosenyloxymethyl, 1-methylethyl, 1-methylpropyl, 1-methylbutyl, 1-methylpentyl, 1-methylhexyl, 1-methylheptyl, 1-methyloctyl, 1-methylnonyl, 1-methyldecyl, 2-methylpropyl, 2-methylbutyl, 2-methylpentyl, 2-methylhexyl, 2-methylheptyl, 2-methyloctyl, 2,3-dimethylbutyl, 2,3,3-trimethylbutyl, 3-methylpentyl, 2,3-dimethylpentyl, 2,4-dimethylpentyl, 2,3,3,4-tetramethylpentyl, 3-methylhexyl and 2,5-dimethylhexyl.

When $R^1$ and $R^2$ are protecting groups of hydroxyl group, the above-mentioned groups exemplifying $R^1$ and $R^2$ can be used as the protecting groups. In addition, those groups which are conventionally used for protection of hydroxyl group are also usable for the purpose. As examples of such protecting group, the following can be referred to:

aliphatic acyl groups such as acetyl, propionyl, butyryl and pentyryl which may optionally be substituted by halogen atom such as fluorine atom, chlorine atom and bromine atom or by alkoxy group such as methoxy, ethoxy, propoxy and butoxy;

benzoyl group which may optionally be substituted by halogen atom such as fluorine atom, chlorine atom and bromine atom, or by alkyl group such as methyl, ethyl, propyl and butyl, or by alkoxy group such as methoxy, ethoxy, propoxy and butoxy, or by nitro group, or by cyano group;

benzyl group which may optionally be substituted by halogen atom such as fluorine atom, chlorine atom and bromine atom, or by alkyl group such as methyl, ethyl, propyl and butyl, or by alkoxy group such as methoxy, ethoxy, propoxy and butoxy, or by nitro group, or by cyano group;

trialkylsilyl group, dialkylphenylsilyl group, alkyldiphenylsilyl group, triphenylsilyl group, aralkyldialkylsilyl group, diaralkylalkylsilyl group and triaralkylsilyl group such as trimethylsilyl, triethylsilyl, triisopropylsilyl, dimethylisopropylsilyl, diethylisopropylsilyl, dimethylhexylsilyl, dimethylphenylsilyl, dimethylbenzylsilyl, methyldibenzylsilyl, tribenzylsilyl, dimethylbutylsilyl, t-butylmethoxyphenylsilyl, methyldiphenylsilyl, t-butyldiphenylsilyl, triphenylsilyl and t-p-xylylsilyl, provided that the phenyl and aralkyl groups in the above-mentioned groups may optionally be substituted by halogen atom, alkyl group, alkoxy group or the like; and ether groups including tetrahydropyranyl group, tetrahydrofuranyl group and 1-(alkoxy)-alkyl groups such as methoxymethyl, ethoxyethyl and propoxyethyl, which may optionally be substituted by halogen atom or alkoxy group.

When the protecting group is $R^1$ or $R^2$, the de-protection can be effected in the following manner. The method of de-protection may be selected from a few ones depending on the kind of protecting group.

When $R^1$ is an ester-forming group such as aliphatic acyl group or benzoyl group, the de-protection can be effected by hydrolyzing the ester linkage with an inorganic or organic acid such as hydrochloric acid, nitric acid, sulfuric acid or toluenesulfonic acid or with an alkali such as caustic soda or caustic potash. The amount of the acid or alkali is as follows. Thus, when an alkali is used, it is used in an amount not smaller than 1–10 moles, and when an acid is used, it is used in an amount of 0.01–30 moles, per mole of the ester. As the solvent, alcohols such as methanol, ethanol and propanol, and polar solvents such as tetrahydrofuran, dioxane, water and dimethyl sulfoxide are used.

When $R^1O$ or $R^2O$ forms an ether linkage, acids such as acetic acid, trifluoroacetic acid, trichloroacetic acid, hydroiodic acid, hydrobromic acid and boron trifluoride can be used in addition to the acids mentioned above, although bases such as lithium hydroxide and the like are also usable. When $R^1$ and $R^2$ are benzyl groups, the de-protection can be effected by a reductive treatment in the case of some compounds.

When the protecting group is a silyl group, the same acids as mentioned above can be used, in addition to which fluoride anion-containing de-silylating agents such as tetrabutylammonium fluoride, cesium fluoride, potassium fluoride and the like can be used for deprotecting the hydroxyl group.

Among the present compounds represented by the general formula (1), the compounds wherein r, s and t are 0, the compounds wherein at least one of the rings $A^1$, $A^2$ and $A^3$ has a fluorine atom, the compounds wherein the rings $A^1$, $A_2$ and $A^3$ have no fluorine atom, the compounds wherein one of the rings $A^1$, $A^2$ and $A^3$ is 2,3-difluorophenylene group, and the compounds wherein one of the rings $A^1$, $A^2$ and $A^3$ is 2,3-difluorophenylene group and r, s and t are 0 or the like are preferable.

Further, the trans-olefin compounds represented by the general formula (1), wherein, when r=1, p+q=1 and $A^1$ is a pyrimidine-2,5-diyl group, $A^2$ and $A^3$ each represents one of the following groups:

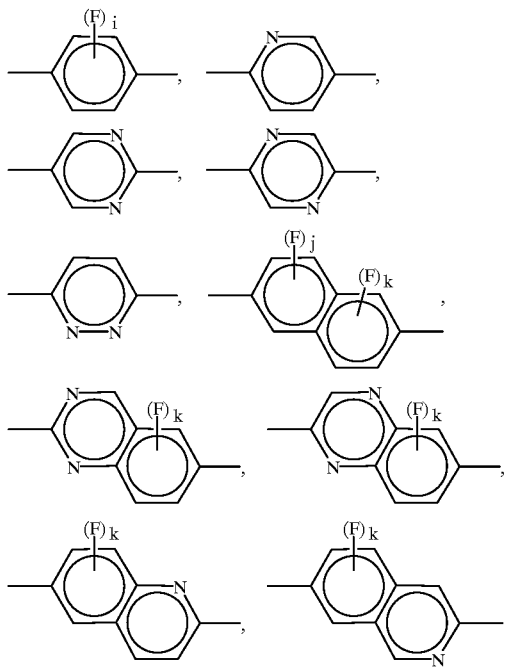

and i is an integer of 1–4 and j and k are each an integer of 0–3, and when r=1, p+q=1 and $A^2$ or $A^3$ represents pyrimidine-2,5-diyl group, $A^1$ represents one of the following groups:

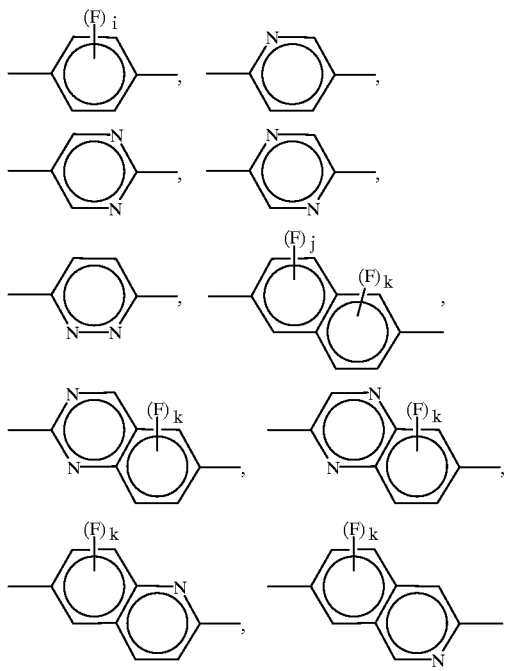

and i is an integer of 1–4 and j and k are each an integer of 0–3 are also preferable.

Among the compounds represented by the general formula (1), as a liquid crystal composition exhibiting smectic phase, preferred are those in which $R^1$ is a straight chain alkyl or alkoxyalkyl group having 3–12 carbon atoms. When the compound represented by the general formula (1) is optically active, $R^1$ may be the same ones as the above, in addition to which alkenyl, alkenyloxyalkyl and alkyloxyalkenyl groups having 3–12 carbon atoms are also usable.

Any one of $A^1$, $A^2$ and $A^3$ is preferably pyrimidin-2,5-diyl group, pyridin-1,4-diyl group, 1,4-phenylene 2,5-diyl group, pyridin-1,4-diyl group, 1,4-phenylene group, 2,3-difluophenyl-1,4-ene group, 2-fluorophenyl-1,4-ene group or 3-fluorophenyl-1,4-ene group, or form a naphthalene ring, a quinoxaline ring or a quinoline ring.

When r=0, the sum of carbon numbers of —$(CH_2)_n$— and $R^2$ is preferably from 3 to 10. When r=1, n is preferably from 1 to 7, and $R^2$ is preferably an alkyl group having 1–10 carbon atoms, an alkoxyalkyl group having 2–10 carbon atoms or a hydrogen atom.

Examples of the compound represented by the general formula (1) are mentioned below.

4'-alkyl-4-(1-trans-alkenyl)-biphenyl,
4'-alkyl-4-(6-hydroxy-1-trans-heptenyl)-biphenyl,
4'-alkyl-4-(6-alkoxy-1-trans-heptenyl)-biphenyl,
4'-alkyl-4-(6-acyloxy-1-trans-heptenyl)-biphenyl,
4'-alkyloxy-4-(1-trans-alkenyl)-biphenyl,
4'-alkyloxy-4-(6-hydroxy-1-trans-heptenyl)-biphenyl,
4'-alkyloxy-4-(6-alkoxy-1-trans-heptenyl)-biphenyl,
4'-alkyloxy-4-(6-acyloxy-1-trans-heptenyl)-biphenyl,
4"-alkyl-4-(1-trans-alkenyl)-p-terphenyl,
4"-alkyl-4-(6-hydroxy-1-trans-heptenyl)-p-terphenyl,
4"-alkyl-4-(6-alkoxy-1-trans-heptenyl)-p-terphenyl,
4"-alkyl-4-(6-acyloxy-1-trans-heptenyl)-p-terphenyl,
4"-alkyloxy-4-(1-trans-alkenyl)-p-terphenyl,
4"-alkyloxy-4-(6-hydroxy-1-trans-heptenyl)-p-terphenyl,
4"-alkyloxy-4-(6-alkoxy-1-trans-heptenyl)-p-terphenyl,
4"-alkyloxy-4-(6-acyloxy-1-trans-heptenyl)-p-terphenyl,
6-alkyl-2-{4-(1-trans-alkenyl)-phenyl}-naphthalene,
6-alkyl-2-{4-(6-hydroxy-trans-heptenyl)-phenyl}-naphthalene,
6-alkyl-2-{4-(6-alkoxy-1-trans-heptenyl)-phenyl}-naphthalene,
6-alkyl-2-{4-(6-acyloxy-1-trans-heptenyl)-phenyl}-naphthalene,
6-alkyloxy-2-{4-(1-trans-alkenyl)-phenyl}-naphthalene,
6-alkyloxy-2-{4-(6-hydroxy-1-trans-heptenyl)-phenyl}-naphthalene,
6-alkyloxy-2-{4-(6-alkoxy-1-trans-heptenyl)-phenyl}-naphthalene,
6-alkyloxy-2-{4-(6-acyloxy-1-trans-heptenyl)-phenyl}-naphthalene,
6-(4-alkylphenyl)-2-(1-trans-alkenyl)-naphthalene,
6-(4-alkylphenyl)-2-(6-hydroxy-1-trans-heptenyl)-naphthalene,
6-(4-alkylphenyl)-2-(6-alkoxy-1-trans-heptenyl)-naphthalene,
6-(4-alkylphenyl)-2-(6-acyloxy-1-trans-heptenyl)-naphthalene,
6-(4-alkyloxyphenyl)-2-(1-trans-alkenyl)-naphthalene,
6-(4-alkyloxyphenyl)-2-(6-hydroxy-1-trans-heptenyl) naphthalene,
6-(4-alkyloxyphenyl)-2-(6-alkoxy-1-trans-heptenyl)-naphthalene,
6-(4-alkyloxyphenyl)-2-(6-acyloxy-1-trans-heptenyl)-naphthalene,
5-alkyl-{4-(1-trans-alkenyl)-phenyl}-pyridine,
5-alkyl-{4-(6-hydroxy-trans-heptenyl)-phenyl}-pyridine,
5-alkyl-{4-(6-alkoxy-1-trans-heptenyl)-phenyl}-pyridine,
5-alkyl-{4-(6-acyloxy-1-trans-heptenyl)-phenyl}-pyridine, 5-alkyloxy-{4-(1-trans-alkenyl)-phenyl}-pyridine,
5-alkyloxy-{4-(6-hydroxy-trans-heptenyl)-phenyl}-pyridine,
5-alkyloxy-{4-(6-alkoxy-1-trans-heptenyl)-phenyl}-pyridine,
5-alkyloxy-{4-(6-acyloxy-1-trans-heptenyl-phenyl}-pyridine,
2-(4-alkylphenyl)-5-(1-trans-alkenyl)-pyridine,
2-(4-alkylphenyl)-5-(6-hydroxy-1-trans-heptenyl)-pyridine,
2-(4-alkylphenyl)-5-(6-alkoxy-1-trans-heptenyl)-pyridine,
2-(4-alkylphenyl)-5-(6-acyloxy-1-trans-heptenyl)-pyridine,
2-(4-alkyloxyphenyl)-5-(1-trans-alkenyl)-pyridine,
2-(4-alkyloxyphenyl)-5-(6-hydroxy-1-trans-heptenyl)-pyridine,
2-(4-alkyloxyphenyl)-5-(6-alkoxy-1-trans-heptenyl)-pyridine,
2-(4-alkyloxyphenyl)-5-(6-acyloxy-1-trans-heptenyl)-pyridine,
2-alkyl-5-{4-(1-trans-alkenyl)-phenyl}-pyridine,
2-alkyl-5-{4-(6-hydroxy-1-trans-heptenyl)-phenyl}-pyridine,
2-alkyl-5-{4-(6-alkoxy-1-trans-heptenyl)-phenyl}-pyridine,
2-alkyl-5-{4-(6-acyloxy-1-trans-heptenyl)-phenyl}-pyridine,
2-alkyloxy-5-{4-(1-trans-alkenyl)-phenyl}-pyridine,
2-alkyloxy-5-{4-(6-hydroxy-1-trans-heptenyl)-phenyl}-pyridine,
2-alkyloxy-5-{4-(6-alkoxy-1-trans-heptenyl)-phenyl}-pyridine,
2-alkyloxy-5-{4-(6-acyloxy-1-trans-heptenyl)-phenyl}-pyridine,
5-(4-alkylphenyl)-2-(1-trans-alkenyl)-pyridine,
5-(4-alkylphenyl)-2-(6-hydroxy-1-trans-heptenyl)-pyridine,
5-(4-alkylphenyl)-2-(6-alkoxy-1-trans-heptenyl)-pyridine,
5-(4-alkylphenyl)-2-(6-acyloxy-1-trans-heptenyl)-pyridine,
5-(4-alkyloxyphenyl)-2-(1-trans-alkenyl)-pyridine,
5-(4-alkyloxyphenyl)-2-(6-hydroxy-1-trans-heptenyl)-pyridine,
5-(4-alkyloxyphenyl)-2-(6-alkoxy-1-trans-heptenyl)-pyridine,
5-(4-alkyloxyphenyl)-2-(6-acyloxy-1-trans-heptenyl)-pyridine,
5-alkyl-2-{4'-(1-trans-alkenyl)-biphenyl-4-yl}-pyridine,
5-alkyl-2-{4'-(6-hydroxy-1-trans-heptenyl)-biphenyl-4-yl}-pyridine,
5-alkyl-2-{4'-(6-alkoxy-1-trans-heptenyl)-biphenyl- 4-yl}-pyridine,
5-alkyl-2-{4'-(6-acyloxy-1-trans-heptenyl)-biphenyl-4-yl}-pyridine,
5-alkyloxy-2-{4'-(1-trans-alkenyl)-biphenyl-4-yl}-pyridine,
5-alkyloxy-2-{4'-(6-hydroxy-1-trans-heptenyl)-biphenyl-4-yl}-pyridine,
5-alkyloxy-2-{4'-(6-alkoxy-1-trans-heptenyl)-biphenyl-4-yl}-pyridine,
5-alkyloxy-2-{4'-(6-acyloxy-1-trans-heptenyl)-biphenyl-4-yl}-pyridine,
2-(4'-alkyl-biphenyl-4-yl)-5-(1-trans-alkenyl)-pyridine,
2-(4'-alkyl-biphenyl-4-yl)-5-(6-hydroxy-1-trans-heptenyl)-pyridine,
2-(4'-alkyl-biphenyl-4-yl)-5-(6-alkoxy-1-trans-heptenyl)-pyridine,
2-(4'-alkyl-biphenyl-4-yl)-5-(6-acyloxy-1-trans-heptenyl)-pyridine,
2-(4'-alkyloxy-biphenyl-4-yl)-5-(1-trans-alkenyl)-pyridine,
2-(4'-alkyloxy-biphenyl-4-yl)-5-(6-hydroxy-1-trans-heptenyl)-pyridine,
2-(4'-alkyloxy-biphenyl-4-yl)-5-(6-alkoxy-1-trans-heptenyl)-pyridine,
2-(4'-alkyloxy-biphenyl-4-yl)-5-(6-acyloxy-1-trans-heptenyl)-pyridine,
5-(4-alkylphenyl)-2-{4-(1-trans-alkenyl)-phenyl}-pyridine,
5-(4-alkylphenyl)-2-{4-(6-hydroxy-1-trans-heptenyl)-phenyl}-pyridine,
5-(4-alkylphenyl)-2-{4-(6-alkoxy-1-trans-heptenyl)-phenyl}-pyridine,
5-(4-alkylphenyl)-2-{4-(6-acyloxy-1-trans-heptenyl)-phenyl}-pyridine,
5-(4-alkyloxyphenyl)-2-{4-(1-trans-alkenyl)-phenyl}-pyridine,
5-(4-alkyloxyphenyl)-2-{4-(6-hydroxy-1-trans-heptenyl)-phenyl}-pyridine,
5-(4-alkyloxyphenyl)-2-{4-(6-alkoxy-1-trans-heptenyl)-phenyl}-pyridine,
5-(4-alkyloxyphenyl)-2-{4-(6-acyloxy-1-trans-heptenyl)-phenyl}-pyridine,
2-(4-alkylphenyl)-5-{4-(1-trans-alkenyl)-phenyl}-pyridine,
2-(4-alkylphenyl)-5-{4-(6-hydroxy-1-trans-heptenyl)-phenyl}-pyridine,
2-(4-alkylphenyl)-5-{4-(6-alkoxy-1-trans-heptenyl)-phenyl}-pyridine,
2-(4-alkylphenyl)-5-{4-(6-acyloxy-1-trans-heptenyl)-phenyl}-pyridine,
2-(4-alkyloxyphenyl)-5-{4-(1-trans-alkenyl)-phenyl}-pyridine,
2-(4-alkyloxyphenyl)-5-{4-(6-hydroxy-1-trans-heptenyl)-phenyl}-pyridine,
2-(4-alkyloxyphenyl)-5-{4-(6-alkoxy-1-trans-heptenyl)-phenyl}-pyridine,
2-(4-alkyloxyphenyl)-5-{4-(6-acyloxy-1-trans-heptenyl)-phenyl}-pyridine,
2-alkyl-5-{4'-(1-trans-alkenyl)-biphenyl-4-yl}-pyridine,
2-alkyl-5-{4'-(6-hydroxy-1-trans-heptenyl)-biphenyl-4-yl}-pyridine,
2-alkyl-5-{4'-(6-alkoxy-1-trans-heptenyl)-biphenyl-4-yl}-pyridine,
2-alkyl-5-{4'-(6-acyloxy-1-trans-heptenyl)-biphenyl-4-yl}-pyridine,
2-alkyloxy-5-{4'-(1-trans-alkenyl)-biphenyl-4-yl}-pyridine,
2-alkyloxy-5-{4'-6-hydroxy-1-trans-heptenyl)-biphenyl-4-yl}-pyridine,
2-alkyloxy-5-{4'-(6-alkoxy-1-trans-heptenyl)-biphenyl-4-yl}-pyridine,
2-alkyloxy-5-{4'-(6-acyloxy-1-trans-heptenyl)-biphenyl-4-yl}-pyridine,
2-(1-trans-alkenyl)-5-{4'-alkyl-biphenyl-4-yl}-pyridine,
2-(6-hydroxy-1-trans-heptenyl)-5-{4'-alkyl-biphenyl-4-yl}-pyridine,
2-(6-alkoxy-1-trans-heptenyl)-5-{4'-alkyl-biphenyl-4-yl}-pyridine,
2-(6-acyloxy-1-trans-heptenyl)-5-{4'-alkyl-biphenyl-4-yl}-pyridine,
2-(1-trans-alkenyl)-5-{4'-alkyloxy-biphenyl-4-yl}-pyridine,
2-(6-hydroxy-1-trans-heptenyl)-5-{4'-alkyloxy-biphenyl-4-yl}-pyridine,
2-(6-alkoxy-1-trans-heptenyl)-5-{4'-alkyloxy-biphenyl-4-yl}-pyridine,
2-(6-acyloxy-1-trans-heptenyl)-5-{4'-alkyloxy-biphenyl-4-yl}-pyridine,
5-alkyl-2-{4-(1-trans-alkenyl)-phenyl}-pyrimidine,
5-alkyl-2-{4-(6-hydroxy-1-trans-heptenyl)-phenyl}-pyrimidine,
5-alkyl-2-{4-(6-alkoxy-1-trans-heptenyl)-phenyl}-pyrimidine,
5-alkyl-2-{4-(6-acyloxy-1-trans-heptenyl)-phenyl}-pyrimidine, 5-alkyloxy-2-{4-(1-trans-alkenyl)-phenyl}-pyrimidine,
5-alkyloxy-2-{4-(6-hydroxy-1-trans-heptenyl)-phenyl}-pyrimidine,
5-alkyloxy-2-{4-(6-alkoxy-1-trans-heptenyl)-phenyl}-pyrimidine,
5-alkyloxy-2-{4-(6-acyloxy-1-trans-heptenyl-phenyl}-pyrimidine,
2-(4-alkylphenyl)-5-(1-trans-alkenyl)-pyrimidine,
2-(4-alkylphenyl)-5-(6-hydroxy-1-trans-heptenyl)-pyrimidine,
2-(4-alkylphenyl)-5-(6-alkoxy-1-trans-heptenyl)-pyrimidine,
2-(4-alkylphenyl)-5-(6-acyloxy-1-trans-heptenyl)-pyrimidine,
2-(4-alkyloxyphenyl)-5-(1-trans-alkenyl)-pyrimidine,
2-(4-alkyloxyphenyl)-5-(6-hydroxy-1-trans-heptenyl)-pyrimidine,
2-(4-alkyloxyphenyl)-5-(6-alkoxy-1-trans-heptenyl)-pyrimidine,
2-(4-alkyloxyphenyl)-5-(6-acyloxy-1-trans-heptenyl)-pyrimidine,
2-alkyl-5-{4-(1-trans-alkenyl)-phenyl}-pyrimidine,
2-alkyl-5-{4-(6-hydroxy-1-trans-heptenyl)-phenyl}-pyrimidine,
2-alkyl-5-{4-(6-alkoxy-1-trans-heptenyl)-phenyl}-pyrimidine,
2-alkyl-5-{4-(6-acyloxy-1-trans-heptenyl)-phenyl}-pyrimidine,
2-alkyloxy-5-{4-(1-trans-alkenyl)-phenyl}-pyrimidine,
2-alkyloxy-5-{4-(6-hydroxy-1-trans-heptenyl)-phenyl}-pyrimidine,
2-alkyloxy-5-{4-(6-alkoxy-1-trans-heptenyl)-phenyl}-pyrimidine,
2-alkyloxy-5-{4-(6-acyloxy-1-trans-heptenyl-phenyl}-pyrimidine,
5-(4-alkylphenyl)-2-(1-trans-alkenyl)-pyrimidine,
5-(4-alkylphenyl)-2-(6-hydroxy-1-trans-heptenyl)-pyrimidine,
5-(4-alkylphenyl)-2-(6-alkoxy-1-trans-heptenyl)-pyrimidine,
5-(4-alkylphenyl)-2-(6-acyloxy-1-trans-heptenyl)-pyrimidine,
5-(4-alkyloxyphenyl)-2-(1-trans-alkenyl)-pyrimidine,
5-(4-alkyloxyphenyl)-2-(6-hydroxy-1-trans-heptenyl)-pyrimidine,
5-(4-alkyloxyphenyl)-2-(6-alkoxy-1-trans-heptenyl)-pyrimidine,
5-(4-alkyloxyphenyl)-2-(6-acyloxy-1-trans-heptenyl)-pyrimidine,
5-alkyl-2-{4'-(1-trans-alkenyl)-biphenyl-4-yl}-pyrimidine,
5-alkyl-2-{4'-(6-hydroxy-1-trans-heptenyl)-biphenyl-4-yl}-pyrimidine,
5-alkyl-2-{4'-(6-alkoxy-1-trans-heptenyl)-biphenyl-4-yl}-pyrimidine,
5-alkyl-2-{4'-(6-acyloxy-1-trans-heptenyl)-biphenyl-4-yl}-pyrimidine,
5-alkyloxy-2-{4'-(1-trans-alkenyl)-biphenyl-4-yl}-pyrimidine,
5-alkyloxy-2-{4'-(6-hydroxy-1-trans-heptenyl)-biphenyl-4-yl}-pyrimidine,
5-alkyloxy-2-{4'-(6-alkoxy-1-trans-heptenyl)-biphenyl-4-yl}-pyrimidine,
5-alkyloxy-2-{4'-(6-acyloxy-1-trans-heptenyl)-biphenyl-4-yl}-pyrimidine,
2-{4'-(1-trans-alkenyl)-biphenyl-4-yl}-5-alkyl-pyrimidine,
2-{4'-(6-hydroxy-1-trans-heptenyl)-biphenyl-4-yl}-5-alkyl-pyrimidine,
2-{4'-(6-alkoxy-1-trans-heptenyl)-biphenyl-4-yl}-5-alkyl-pyrimidine,
2-{4'-(6-acyloxy-1-trans-heptenyl)-biphenyl-4-yl}-5-alkyl-pyrimidine,
2-{4'-(1-trans-alkenyl)-biphenyl-4-yl}-5-alkyloxy-pyrimidine,
2-{4'-(6-hydroxy-1-trans-heptenyl)-biphenyl-4-yl}-5-alkyloxy-pyrimidine,
2-{4'-(6-alkoxy-1-trans-heptenyl)-biphenyl-4-yl}-5-alkyloxy-pyrimidine,
2-{4'-(6-acyloxy-1-trans-heptenyl)biphenyl-4-yl}-5-alkyloxy-pyrimidine,
5-(4-alkylphenyl)-2-{4-(1-trans-alkenyl)-phenyl}-pyrimidine,
5-(4-alkylphenyl)-2-{4-(6-hydroxy-1-trans-heptenyl)-phenyl}-pyrimidine,
5-(4-alkylphenyl)-2-{4-(6-alkoxy-1-trans-heptenyl)-phenyl}-pyrimidine,
5-(4-alkylphenyl)-2-{4-(6-acyloxy-1-trans-heptenyl)-phenyl}-pyrimidine,
5-(4-alkyloxyphenyl)-2-{4-(1-trans-alkenyl)-phenyl}-pyrimidine,
5-(4-alkyloxyphenyl)-2-{4-(6-hydroxy-1-trans-heptenyl)-phenyl}-pyrimidine,
5-(4-alkyloxyphenyl)-2-{4-(6-alkoxy-1-trans-heptenyl)-phenyl}-pyrimidine,
5-(4-alkyloxyphenyl)-2-{4-(6-acyloxy-1-trans-heptenyl)-phenyl}-pyrimidine,
2-(4-alkylphenyl)-5-{4-(1-trans-alkenyl)-phenyl}-pyrimidine,
2-(4-alkylphenyl)-5-{4-(6-hydroxy-1-trans-heptenyl)-phenyl}-pyrimidine,
2-(4-alkylphenyl)-5-{4-(6-alkoxy-1-trans-heptenyl)-phenyl}-pyrimidine,
2-(4-alkylphenyl)-5-{4-(6-acyloxy-1-trans-heptenyl)-phenyl}-pyrimidine,
2-(4-alkyloxyphenyl)-5-{4-(1-trans-alkenyl)-phenyl}-pyrimidine,
2-(4-alkyloxyphenyl)-5-{4-(6-hydroxy-1-trans-heptenyl)-phenyl}-pyrimidine,
2-(4-alkyloxyphenyl)-5-{4-(6-alkoxy-1-trans-heptenyl)-phenyl}-pyrimidine,
2-(4-alkyloxyphenyl)-5-{4-(6-acyloxy)-1-trans-heptenyl)-phenyl}-pyrimidine,
2-alkyl-5-{4'-(1-trans-alkenyl)-biphenyl-4-yl}-pyrimidine,
2-alkyl-5-{4'-(6-hydroxy-1-trans-heptenyl)-biphenyl-4-yl}-pyrimidine,
2-alkyl-5-{4'-(6-alkoxy-1-trans-heptenyl)-biphenyl-4-yl}-pyrimidine,
2-alkyl-5-{4'-(6-acyloxy-1-trans-heptenyl)-biphenyl-4-yl}-pyrimidine,
2-alkyloxy-5-{4'-(1-trans-alkenyl)-biphenyl-4-yl}-pyrimidine,
2-alkyloxy-5-{4'-(6-hydroxy-1-trans-heptenyl)-biphenyl-4-yl}-pyrimidine,
2-alkyloxy-5-{4'-(6-alkoxy-1-trans-heptenyl)-biphenyl-4-yl}-pyrimidine,
2-alkyloxy-5-{4'-(6-acyloxy-1-trans-heptenyl)-biphenyl-4-yl}-pyrimidine,
2-(1-trans-alkenyl)-5-{4'-alkyl-biphenyl-4-yl}-pyrimidine,
2-(6-hydroxy-1-trans-heptenyl)-5-{4'-alkyl-biphenyl-4-yl}-pyrimidine,
2-(6-alkoxy-1-trans-heptenyl)-5-{4'-alkyl-biphenyl-4-yl}-pyrimidine,
2-(6-acyloxy-1-trans-heptenyl)-5-{4'-alkyl-biphenyl-4-yl}-pyrimidine,
2-(1-trans-alkenyl)-5-{4'-alkyloxy-biphenyl-4-yl}-pyrimidine, 2-(6-hydroxy-1-trans-heptenyl)-5-{4'-alkyloxy-biphenyl-4-yl}-pyrimidine,
2-(6-alkoxy-1-trans-heptenyl)-5-{4'-alkyloxy-biphenyl-4-yl}-pyrimidine,
2-(6-acyloxy-1-trans-heptenyl)-5-{4'-alkyloxy-biphenyl-4-yl}-pyrimidine,
2-{5-(1-trans-alkenyl)-pyridin-2-yl}-5-(4-alkylphenyl)-pyrimidine,
2-{5-(6-hydroxy-1-trans-heptenyl)-pyridin-2-yl}-5-(4-alkylphenyl)-pyrimidine,
2-{5-(6-alkoxy-1-trans-heptenyl)-pyridin-2-yl}-5-(4-alkylphenyl)-pyrimidine,
2-{5-(6-acyloxy-1-trans-heptenyl)-pyridine-2-yl}-5-(4-alkylphenyl)-pyrimidine,
2-{5-(1-trans-alkenyl)-pyridin-2-yl}-5-(4-alkyloxyphenyl)-pyrimidine,
2-{5-(6-hydroxy-1-trans-heptenyl)-pyridin-2-yl}-5-(4-alkyloxyphenyl)-pyrimidine,
2-{5-(6-alkoxy-1-trans-heptenyl)-pyridin-2-yl}-5-(4-alkyloxyphenyl)-pyrimidine,
2-{5-(6-acyloxy-1-trans-heptenyl)-pyridin-2-yl}-5-(4-alkyloxyphenyl)-pyrimidine,
2-{5-alkyl-pyridin-2-yl}-5-{4-(1-trans-alkenyl)-phenyl}-pyrimidine,
2-{5-alkyl-pyridin-2-yl}-5-{4-(6-hydroxy-1-trans-heptenyl)-phenyl}-pyrimidine,
2-{5-alkyl-pyridin-2-yl}-5-{4-(6-alkoxy-1-trans-heptenyl)-phenyl}-pyrimidine,
2-{5-alkyl-pyridin-2-yl}-5-{4-(6-acyloxy-1-trans-heptenyl)-phenyl}-pyrimidine,
2-{5-alkyloxy-pyridin-2-yl}-5-{4-(1-trans-alkenyl)-phenyl}-pyrimidine,
2-{5-alkyloxy-pyridin-2-yl}-5-{4-(6-hydroxy-1-trans-heptenyl)-phenyl}-pyrimidine,
2-{5-alkyloxy-pyridin-2-yl}-5-{4-(6-alkoxy-1-trans-heptenyl)-phenyl}-pyrimidine,
2-{5-alkyloxy-pyridin-2-yl}-5-{4-(6-acyloxy-1-trans-heptenyl)-phenyl}-pyrimidine,
2-{4-(5-alkylpyrimidin-2-yl}-5-(1-trans-alkenyl)-pyrimidine,
2-{4-(5-alkylpyrimidin-2-yl)-phenyl}-5-(6-hydroxy-1-trans-heptenyl)-pyrimidine,
2-{4-(5-alkylpyrimidin-2-yl)-phenyl}-5-(6-alkoxy-1-trans-heptenyl)-pyrimidine,
2-{4-(5-alkylpyrimidin-2-yl)-phenyl}-5-(6-acyloxy-1-trans-heptenyl)-pyrimidine,
2-{4-(5-alkyloxypyrimidin-2-yl)-phenyl}-5-(1-trans-alkenyl)pyrimidine,
2-{4-(5-alkyloxypyrimidin-2-yl)-phenyl}-5-(6-hydroxy-1-trans-heptenyl)-pyrimidine,
2-{4-(5-alkyloxypyrimidin-2-yl)-phenyl}-5-(6-alkoxy-1-trans-heptenyl)-pyrimidine,
2-{4-(5-alkyloxypyrimidin-2-yl)-phenyl}-5-(6-acyloxy-1-trans-heptenyl)-pyrimidine,
2-alkyl-5-{4-(1-trans-alkenyl)-phenyl}-pyrazine,
2-alkyl-5-{4-(6-hydroxy-1-trans-heptenyl)-phenyl}-pyrazine,
2-alkyl-5-{4-(6-alkoxy-1-trans-heptenyl)-phenyl}-pyrazine,
2-alkyl-5-{4-(6-acyloxy-1-trans-heptenyl)-phenyl}-pyrazine,
2-alkyloxy-5-{4-(1-trans-alkenyl)-phenyl}-pyrazine,
2-alkyloxy-5-{4-(6-hydroxy-1-trans-heptenyl)-phenyl}-pyrazine,
2-alkyloxy-5-{4-(6-alkoxy-1-trans-heptenyl)-phenyl}-pyrazine,
2-alkyloxy-5-{4-(6-acyloxy-1-trans-heptenyl)-phenyl}-pyrazine,
2-(4-alkylphenyl)-5-(1-trans-alkenyl)-pyrazine,
2-(4-alkylphenyl)-5-(6-hydroxy-1-trans-heptenyl)-pyrazine,
2-(4-alkylphenyl)-5-(6-alkoxy-1-trans-heptenyl)-pyrazine,
2-(4-alkylphenyl)-5-(6-acyloxy-1-trans-heptenyl)-pyrazine,
2-(4-alkyloxyphenyl)-5-(1-trans-alkenyl)-pyrazine,
2-(4-alkyloxyphenyl)-5-(6-hydroxy-1-trans-heptenyl)-pyrazine,
2-(4-alkyloxyphenyl)-5-(6-alkoxy-1-trans-heptenyl)-pyrazine,
2-(4-alkyloxyphenyl)-5-(6-acyloxy-1-trans-heptenyl)-pyrazine,
6-alkyl-3-{4-(1-trans-alkenyl)-phenyl}-pyridazine,
6-alkyl-3-{4-(6-hydroxy-1-trans-heptenyl)-phenyl}-pyridazine,
6-alkyl-3-{4-(6-alkoxy-1-trans-heptenyl)-phenyl}-pyridazine,
6-alkyl-3-{4-(6-acyloxy-1-trans-heptenyl)-phenyl}-pyridazine,
6-alkyloxy-3-{4-(1-trans-alkenyl)-phenyl}-pyridazine,
6-alkyloxy-3-{4-(6-hydroxy-1-trans-heptenyl)-phenyl}-pyridazine,
6-alkyloxy-3-{4-(6-alkoxy-1-trans-heptenyl)-phenyl}-pyridazine,
6-alkyloxy-3-{4-(6-acyloxy-1-trans-heptenyl)-phenyl}-pyridazine,
6-(4-alkylphenyl-3-(1-trans-alkenyl)-pyridazine,
6-(4-alkylphenyl-3-(6-hydroxy-1-trans-heptenyl)-pyridazine,
6-(4-alkylphenyl-3-(6-alkoxy-1-trans-heptenyl)-pyridazine,
6-(4-alkylphenyl-3-(6-acyloxy-1-trans-heptenyl)-pyridazine,
6-(4-alkyloxyphenyl-3-(1-trans-alkenyl)-pyridazine,
6-(4-alkyloxyphenyl-3-(6-hydroxy-1-trans-heptenyl)-pyridazine,
6-(4-alkyloxyphenyl-3-(6-alkoxy-1-trans-heptenyl)-pyridazine,
6-(4-alkyloxyphenyl-3-(6-acyloxy-1-trans-heptenyl)-pyridazine,
5-(4-alkylphenyl)-2-{4-(1-trans-alkenyl)-phenyl}-pyridazine,
5-(4-alkylphenyl)-2-{4-(6-hydroxy-1-trans-heptenyl)-phenyl}-pyridazine,
5-(4-alkylphenyl)-2-{4-(6-alkenyl-1-trans-heptenyl)-phenyl}-pyridazine,
5-(4-alkylphenyl)-2-{4-(6-acyloxy-1-trans-heptenyl)-phenyl}-pyridazine,
5-(4-alkyloxyphenyl)-2-{4-(1-trans-alkenyl)-phenyl}-pyrazine,
5-(4-alkyloxyphenyl)-2-{4-(6-hydroxy-1-trans-heptenyl)-phenyl}-pyridazine,
5-(4-alkyloxyphenyl)-2-{4-(6-alkenyl-1-trans-heptenyl)-phenyl}-pyridazine,
5-(4-alkyloxyphenyl)-2-{4-(6-acyloxy-1-trans-heptenyl)-phenyl}-pyridazine,
6-(4-alkylphenyl-3-{4-(1-trans-alkenyl)-phenyl}-pyridazine,
6-(4-alkylphenyl-3-{4-(6-hydroxy-1-trans-heptenyl)-phenyl}-pyridazine,
6-(4-alkylphenyl-3-{4-(6-alkenyl-1-trans-heptenyl)-phenyl}-pyridazine,
6-(4-alkylphenyl-3-{4-(6-acyloxy-1-trans-heptenyl)-phenyl}-pyridazine,
6-(4-alkyloxyphenyl)-3-{4-(1-trans-alkenyl)-phenyl}-pyridazine,
6-(4-alkyloxyphenyl)-3-{4-(6-hydroxy-1-trans-heptenyl)-phenyl}-pyridazine,
6-(4-alkyloxyphenyl)-3-{4-(6-alkenyl-1-trans-heptenyl)-phenyl}-pyridazine, 6-(4-alkyloxyphenyl)-3-{4-(6-acyloxy-1-trans-heptenyl)-phenyl}-pyridazine,
2-alkyl-6-(1-trans-alkenyl)-naphthalene,
2-alkyl-6-(6-hydroxy-1-trans-heptenyl)-naphthalene,
2-alkyl-6-(6-alkoxy-1-trans-heptenyl)-naphthalene,
2-alkyl-6-(6-acyloxy-1-trans-heptenyl)-naphthalene,
2-alkyloxy-6-(1-trans-alkenyl)-naphthalene,
2-alkyloxy-6-(6-hydroxy-1-trans-heptenyl)-naphthalene,
2-alkyloxy-6-(6-(6-alkoxy-1-trans-heptenyl)-naphthalene,
2-alkyloxy-6-(6-acyloxy-1-trans-heptenyl)-naphthalene,
6-alkyl-2-(1-trans-alkenyl-quinoline,
6-alkyl-2-(6-hydroxy-1-trans-heptenyl)-quinoline,
6-alkyl-2-(6-alkoxy-1-trans-heptenyl)-quinoline,
6-alkyl-2-(6-acyloxy-1-trans-heptenyl)-quinoline,
6-alkyloxy-2-(1-trans-alkenyl)-quinoline,
6-alkyloxy-2-(6-hydroxy-1-trans-heptenyl)-quinoline,
6-alkyloxy-2-(6-alkoxy-1-trans-heptenyl)-quinoline,
6-alkyloxy-2-(6-acyloxy-1-trans-heptenyl)-quinoline,
2-alkyl-6-(1-trans-alkenyl)-quinoline,
2-alkyl-6-(6-hydroxy-1-trans-heptenyl)-quinoline,
2-alkyl-6-(6-alkoxy-1-trans-heptenyl)-quinoline,
2-alkyl-6-(6-acyloxy-1-trans-heptenyl)-quinoline,
2-alkyloxy-6-(1-trans-alkenyl)-quinoline,
2-alkyloxy-6-(6-hydroxy-1-trans-heptenyl)-quinoline,
2-alkyloxy-6-(6-alkoxy-1-trans-heptenyl)-quinoline,
2-alkyloxy-6-(6-acyloxy-1-trans-heptenyl)-quinoline,
7-alkyl-3-(1-trans-alkenyl)-isoquinoline,
7-alkyl-3-(6-hydroxy-1-trans-heptenyl)-isoquinoline,
7-alkyl-3-(6-alkoxy-1-trans-heptenyl)-isoquinoline,
7-alkyl-3-(6-acyloxy-1-trans-heptenyl)-isoquinoline,
7-alkyloxy-3-(1-trans-alkenyl)-isoquinoline,
7-alkyloxy-3-(6-hydroxy-1-trans-heptenyl)-isoquinoline,
7-alkyloxy-3-(6-alkoxy-1-trans-heptenyl)-isoquinoline,
7-alkyloxy-3-(6-acyloxy-1-trans-heptenyl)-isoquinoline,
3-alkyl-7-(1-trans-alkenyl)-isoquinoline,
3-alkyl-7-(6-hydroxy-1-trans-heptenyl)-isoquinoline,
3-alkyl-7-(6-alkoxy-1-trans-heptenyl)-isoquinoline,
3-alkyl-7-(6-acyloxy-1-trans-heptenyl)-isoquinoline,
3-alkyloxy-7-(1-trans-alkenyl)-isoquinoline,
3-alkyloxy-7-(6-hydroxy-1-trans-heptenyl)-isoquinoline,
3-alkyloxy-7-(6-alkoxy-1-trans-heptenyl)-isoquinoline,
3-alkyloxy-7-(6-acyloxy-1-trans-heptenyl)-isoquinoline,
2-alkyl-6-(1-trans-alkenyl)-quinazoline,
2-alkyl-6-(6-hydroxy-1-trans-heptenyl)-quinazoline,
2-alkyl-6-(6-alkoxy-1-trans-heptenyl)-quinazoline,
2-alkyl-6-(6-acyloxy-1-trans-heptenyl)-quinazoline,
2-alkyloxy-6-(1-trans-alkenyl)-quinazoline,
2-alkyloxy-6-(6-hydroxy-1-trans-heptenyl)-quinazoline,
2-alkyloxy-6-(6-alkoxy-1-trans-heptenyl)-quinazoline,
2-alkyloxy-6-(6-acyloxy-1-trans-heptenyl)-quinazoline,
6-alkyl-2-(1-trans-alkenyl)-quinazoline,
6-alkyl-2-(6-hydroxy-1-trans-heptenyl)-quinazoline,
6-alkyl-2-(6-alkoxy-1-trans-heptenyl)-quinazoline,
6-alkyl-2-(6-acyloxy-1-trans-heptenyl)-quinazoline,
6-alkyloxy-2-(1-trans-alkenyl)-quinazoline,
6-alkyloxy-2-(6-hydroxy-1-trans-heptenyl)-quinazoline,
6-alkyloxy-2-(6-alkoxy-1-trans-heptenyl)-quinazoline,
6-alkyloxy-2-(6-acyloxy-1-trans-heptenyl)-quinazoline,
2-alkyl-6-(1-trans-alkenyl)-quinoxaline,
2-alkyl-6-(6-hydroxy-1-trans-heptenyl)-quinaxoline,
2-alkyl-6-(6-alkoxy-1-trans-heptenyl)-quinoaxoline,
2-alkyl-6-(6-acyloxy-1-trans-heptenyl-quinoxaline
2-alkyloxy-6-(1-trans-alkenyl)-quinoxaline,
2-alkyloxy-6-(6-hydroxy-1-trans-heptenyl)-quinoxaline,
2-alkyloxy-6-(6-alkoxy-1-trans-heptenyl)-quinoxaline,
2-alkyloxy-6-(6-acyloxy-1-trans-heptenyl)-quinoxaline,
6-alkyl-2-(1-trans-alkenyl)-quinoxaline,
6-alkyl-2-(6-hydroxy-1-trans-heptenyl)-quinoxaline,
6-alkyl-2-(6-alkoxy-1-trans-heptenyl)-quinoxaline,
6-alkyl-2-(6-acyloxy-1-trans-heptenyl)-quinoxaline,
6-alkyloxy-2-(1-trans-alkenyl)-quinoxaline,
6-alkyloxy-2-(6-hydroxy-1-trans-heptenyl)-quinoxaline,
6-alkyloxy-2-(6-alkoxy-1-trans-heptenyl)-quinoxaline,
6-alkyloxy-2-(6-acyloxy-1-trans-heptenyl)-quinoxaline,
2-(6-alkyl-naphthalene-2-yl)-5-(1-trans-alkenyl)-pyridine,
2-(6-alkyl-naphthalene-2-yl)-5-(6-hydroxy-1-trans-heptenyl)-pyridine,
2-(6-alkyl-naphthalene-2-yl)-5-(6-alkoxy-1-trans-heptenyl)-pyridine,
2-(6-alkyl-naphthalene-2-yl)-5-(6-acyloxy-1-trans-heptenyl)-pyridine,
2-(6-alkyloxy-naphthalene-2-yl)-5-(1-trans-alkenyl)-pyridine,
2-(6-alkyloxy-naphthalene-2-yl)-5-(6-hydroxy-1-trans-heptenyl)-pyridine,
2-(6-alkyloxy-naphthalene-2-yl)-5-(6-alkoxy-1-trans-heptenyl)-pyridine,
2-(6-alkyloxy-naphthalene-2-yl)-5-(6-acyloxy-1-trans-heptenyl)-pyridine,
5-(6-alkyl-naphthalene-2-yl)-2-(1-trans-alkenyl)-pyridine,
5-(6-alkyl-naphthalene-2-yl)-2-(6-hydroxy-1-trans-heptenyl)-pyridine,
5-(6-alkyl-naphthalene-2-yl)-2-(6-alkoxy-1-trans-heptenyl)-pyridine,
5-(6-alkyl-naphthalene-2-yl)-2-(6-acyloxy-1-trans-heptenyl)pyridine,
5-(6-alkyloxy-naphthalene-2-yl)-2-(1-trans-alkenyl)-pyridine,
5-(6-alkyloxy-naphthalene-2-yl)-2-(6-hydroxy-1-trans-heptenyl)-pyridine,
5-(6-alkyloxy-naphthalene-2-yl)-2-(6-alkoxy-1-trans-heptenyl)-pyridine,
5-(6-alkyloxy-naphthalene-2-yl)-2-(6-acyloxy-1-trans-heptenyl)-pyridine,
2-alkyl-5-{6-(1-trans-alkenyl)-naphthalene-2-yl}-pyridine,
2-alkyl-5-{6-(6-hydroxy-1-trans-heptenyl)-naphthalene-2-yl}-pyridine,
2-alkyl-5-{6-(6-alkoxy-1-trans-heptenyl)-naphthalene-2-yl}-pyridine,
2-alkyl-5-{6-(6-acyloxy-1-trans-heptenyl)-naphthalene-2-yl}-pyridine,
2-alkyloxy-5-{6-(1-trans-alkenyl)-naphthalene-2-yl}-pyridine,
2-alkyloxy-5-{6-(6-hydroxy-1-trans-heptenyl)-naphthalene-2-yl}-pyridine,
2-alkyloxy-5-{6-(6-alkoxy-1-trans-heptenyl)-napthalene-2-yl}-pyridine,
2-alkyloxy-5-{6-(6-acyloxy-1-trans-heptenyl)-napthalene-2-yl}-pyridine,
5-alkyl-2-{6-(1-trans-alkenyl)-naphthalene-1-yl}-pyridine,
5-alkyl-2-{6-(6-hydroxy-1-trans-heptenyl)-naphthalene-1-yl}-pyridine,
5-alkyl-2-{6-(6-alkoxy-1-trans-heptenyl)-naphthalene-1-yl}-pyridine,
5-alkyl-2-{6-(6-acyloxy-1-trans-heptenyl)-naphthalene-1-yl}-pyridine,
5-alkyloxy-2-{6-(1-trans-alkenyl)-naphthalene-1-yl}-pyridine,
5-alkyloxy-2-{6-(6-hydroxy-1-trans-heptenyl)-naphthalene-1-yl}-pyridine,
5-alkyloxy-2-{6-(6-alkoxy-1-trans-heptenyl)-naphthalene-1-yl}-pyridine,
5-alkyloxy-2-{6-(6-acyloxy-1-trans-heptenyl)-naphthalene-1-yl}-pyridine, 7-alkyl-3-{4-(1-trans-alkenyl)-phenyl}-isoquinoline,
7-alkyl-3-{4-(6-hydroxy-1-trans-heptenyl)phenyl}-isoquinoline,
7-alkyl-3-{4-(6-alkoxy-1-trans-heptenyl)-phenyl}-isoquinoline,
7-alkyl-3-{4-(6-acyloxy-1-trans-heptenyl)-phenyl}-isoquinoline,
7-alkyloxy-3-{4-(1-trans-alkenyl)-phenyl}-isoquinoline,
7-alkyloxy-3-{4-(6-hydroxy-1-trans-heptenyl)-phenyl}-isoquinoline,
7-alkyloxy-3-{4-(6-alkoxy-1-trans-heptenyl)-phenyl}-isoquinoline,
7-alkyloxy-3-{4-(6-acyloxy-1-trans-heptenyl)-phenyl}-isoquinoline,
3-(4-alkyl-phenyl)-7-(1-trans-alkenyl)-isoquinoline,
3-(4-alkyl-phenyl)-7-(6-hydroxy-1-trans-heptenyl)-isoquinoline,
3-(4-alkyl-phenyl)-7-(6-alkoxy-1-trans-heptenyl)-isoquinoline,
3-(4-alkyl-phenyl)-7-(6-acyloxy-1-trans-heptenyl)-isoquinoline,
3-(4-alkyloxy-phenyl)-7-(1-trans-alkenyl)-isoquinoline,
3-(4-alkyloxy-phenyl)-7-(6-hydroxy-1-trans-heptenyl)-isoquinoline,
3-(4-alkyloxy-phenyl)-7-(6-alkoxy-1-trans-heptenyl)-isoquinoline,
3-(4-alkyloxy-phenyl)-7-(6-acyloxy-1-trans-heptenyl)-isoquinoline,
6-alkyl-2-{4-(1-trans-alkenyl)-phenyl}-quinoline,
6-alkyl-2-{4-(6-hydroxy-1-trans-heptenyl)-phenyl}-quinoline,
6-alkyl-2-{4-(6-alkoxy-1-trans-heptenyl)-phenyl}-quinoline,
6-alkyl-2-{4-(6-acyloxy-1-trans-heptenyl)-phenyl}-quinoline,
6-alkyloxy-2-{4-(1-trans-alkenyl)-phenyl}-quinoline,
6-alkyloxy-2-{4-(6-hydroxy-1-trans-heptenyl)-phenyl}-quinoline,
6-alkyloxy-2-{4-(6-alkoxy-1-trans-heptenyl)-phenyl}-quinoline,
6-alkyloxy-2-{4-(6-acyloxy-1-trans-heptenyl)-phenyl}-quinoline,
2-(4-alkyl-phenyl)-6-(1-trans-alkenyl)-quinoline,
2-(4-alkyl-phenyl)-6-(6-hydroxy-1-trans-heptenyl)-quinoline,
2-(4-alkyl-phenyl)-6-(6-alkoxy-1-trans-heptenyl)-quinoline,
2-(4-alkyl-phenyl)-6-(6-acyloxy-1-trans-heptenyl)-quinoline,
2-(4-alkyloxy-phenyl)-6-(1-trans-alkenyl)-quinoline,
2-(4-alkyloxy-phenyl)-6-(6-hydroxy-1-trans-heptenyl)-quinoline,
2-(4-alkyloxy-phenyl)-6-(6-alkoxy-1-trans-heptenyl)-quinoline,
2-(4-alkyloxy-phenyl)-6-(6-acyloxy-1-trans-heptenyl)-quinoline,
5-alkyl-5-{6-(1-trans-alkenyl)-naphthalene-2-yl}-pyrimidine,
5-alkyl-5-{6-(6-hydroxy-1-trans-heptenyl)-naphthalene-2-yl}-pyrimidine,
5-alkyl-5-{6-(6-alkoxy-1-trans-heptenyl)-naphthalene-2-yl}-pyrimidine,
5-alkyl-5-{6-(6-acyloxy-1-trans-heptenyl)-naphthalene-2-yl}-pyrimidine,
5-alkyloxy-5-{6-(1-trans-alkeny)-naphthalene-2-yl}-pyrimidine,
5-alkyloxy-5-{6-(6-hydroxy-1-trans-heptenyl)-naphthalene-2-yl}-pyrimidine,
5-alkyloxy-5-{6-(6-alkoxy-1-trans-heptenyl)-naphthalene-2-yl}-pyrimidine,
5-alkyloxy-5-{6-(6-acyloxy-1-trans-heptenyl)-napthalene-2-yl}-pyrimidine,
2-(6-alkyl-naphthalene-2-yl)-5-(1-trans-alkenyl)-pyrimidine,
2-(6-alkyl-naphthalene-2-yl)-5-(6-hydroxy-1-trans-heptenyl)-pyrimidine,
2-(6-alkyl-naphthalene-2-yl)-5-(6-alkoxy-1-trans-heptenyl)-pyrimidine,
2-(6-alkyl-naphthalene-2-yl)-5-(6-acyloxy-1-trans-heptenyl)-pyrimidine,
2-(6-alkyloxy-naphthalene-2-yl)-5-(1-trans-alkenyl)-pyrimidine,
2-(6-alkyloxy-naphthalene-2-yl)-5-(6-hydroxy-1-trans-heptenyl)-pyrimidine,
2-(6-alkyloxy-naphthalene-2-yl)-5-(6-alkoxy-1-trans-heptenyl)-pyrimidine,
2-(6-alkyloxy-naphthalene-2-yl)-5-(6-acyloxy-1-trans-heptenyl)pyrimidine,
3-alkyl-7-{4-(1-trans-alkenyl)-phenyl}-quinoxaline,
3-alkyl-7-{4-(6-hydroxy-1-trans-heptenyl)-phenyl}-quinoxaline,
3-alkyl-7-{4-(6-alkoxy-1-trans-heptenyl)-phenyl}-quinoxaline,
3-alkyl-7-{4-(6-acyloxy-1-trans-heptenyl)-phenyl}-quinoxaline,
3-alkyloxy-7-{4-(1-trans-alkenyl)-phenyl}-quinoxaline,
3-alkyloxy-7-{4-(6-hydroxy-1-trans-heptenyl)-phenyl}quinoxaline,
3-alkyloxy-7-{4-(6-alkoxy-1-trans-heptenyl)-phenyl}-quinoxaline,
3-alkyloxy-7-{4-(6-acyloxy-1-trans-heptenyl)-phenyl}-quinoxaline,
2-(1-trans-alkenyl)-6-(4-alkylphenyl)-quinoxaline,
2-(6-hydroxy-1-trans-heptenyl)-6-(4-alkylphenyl)-quinoxaline,
2-(6-alkoxy-1-trans-heptenyl)-6-(4-alkylphenyl)-quinoxaline,
2-(6-acyloxy-1-trans-heptenyl)-6-(4-alkylphenyl)-quinoxaline,
2-(1-trans-alkenyl)-6-(4-alkyloxyphenyl)-quinoxaline,
2-(6-hydroxy-1-trans-heptenyl)-6-(4-alkyloxyphenyl)-quinoxaline,
2-(6-alkoxy-1-trans-heptenyl)-6-(4-alkyloxyphenyl)-quinoxaline,
2-(6-acyloxy-1-trans-heptenyl)-6-(4-alkyloxyphenyl)-quinoxaline,
6-alkyl-2{-4-(1-trans-alkenyl)-phenyl}-quinoxaline,
6-alkyl-2{-4-(6-hydroxy-1-trans-heptenyl)-phenyl}-quinoxaline,
6-alkyl-2{-4-(6-alkoxy-1-trans-heptenyl)-phenyl}-quinoxaline,
6-alkyl-2{-4-(6-acyloxy-1-trans-heptenyl)-phenyl}-quinoxaline,
6-alkyloxy-2-{4-(1-trans-alkenyl)-phenyl}-quinoxaline,
6-alkyloxy-2-{4-(6-hydroxy-1-trans-heptenyl)-phenyl}-quinoxaline,
6-alkyloxy-2-{4-(6-alkoxy-1-trans-heptenyl)-phenyl}-quinoxaline,
6-alkyloxy-2-{4-(6-acyloxy-1-trans-heptenyl)-phenyl}-quinoxaline,
2-(4-alkylphenyl)-6-(1-trans-alkenyl)-quinoxaline,
2-(4-alkylphenyl)-6-(6-hydroxy-1-trans-heptenyl)-quinoxaline,
2-(4-alkylphenyl)-6-(6-alkoxy-1-trans-heptenyl)-quinoxaline, 2-(4-alkylphenyl)-6-(6-acyloxy-1-trans-heptenyl)-quinoxaline,
2-(4-alkyloxyphenyl)-6-(1-trans-alkenyl)-quinoxaline,
2-(4-alkyloxyphenyl)-6-(6-hydroxy-1-trans-heptenyl)-quinoxaline,
2-(4-alkyloxyphenyl)-6-(6-alkoxy-1-trans-heptenyl)-quinoxaline,
2-(4-alkyloxyphenyl)-6-(6-acyloxy-1-trans-heptenyl)-quinoxaline,
2-alkyl-6-{4-(1-trans-alkenyl)-phenyl}-quinazoline,
2-alkyl-6-{4-(6-hydroxy-1-trans-heptenyl)-phenyl}-quinazoline,
2-alkyl-6-{4-(6-alkoxy-1-trans-hetenyl)-phenyl}-quinazoline,
2-alkyl-6-{4-(6-acyloxy-1-trans-heptenyl)-phenyl}-quinazoline,
2-alkyloxy-6-{4-(1-trans-alkenyl)-phenyl}-quinazoline,
2-alkyloxy-6-{4-(6-hydroxy-1-trans-heptenyl)-phenyl}-quinazoline,
2-alkyloxy-6-{4-(6-alkoxy-1-trans-heptenyl)-phenyl}-quinazoline,
2-alkyloxy-6-{4-(6-acyloxy-1-trans-heptenyl)-phenyl}-quinazoline,
2-(1-trans-alkenyl)-6-(4-alkylphenyl)-quinazoline,
2-(6-hydroxy-1-trans-heptenyl)-6-(4-alkylphenyl)-quinazoline,
2-(6-alkoxy-1-trans-heptenyl)-6-(4-alkylphenyl)-quinazoline,
2-(6-acyloxy-1-trans-heptenyl)-6-(4-alkylphenyl)-quinazoline,
2-(1-trans-alkenyl)-6-(4-alkyloxyphenyl)-quinazoline,
2-(6-hydroxy-1-trans-heptenyl)-6-(4-alkyloxyphenyl)-quinazoline,
2-(6-alkoxy-1-trans-heptenyl)-6-(4-alkyloxyphenyl)-quinazoline,
2-(6-acyloxy-1-trans-heptenyl)-6-(4-alkyloxyphenyl)-quinazoline,
4'-alkyl-2-fluoro-4-(1-trans-alkenyl)-biphenyl,
4'-alkyl-2-fluoro-4-(6-hydroxy-1-trans-heptenyl)-biphenyl,
4'-alkyl-2-fluoro-4-(6-alkoxy-1-trans-heptenyl)-biphenyl,
4'-alkyl-2-fluoro-4-(6-acyloxy-1-trans-heptenyl)-biphenyl,
4'-alkyloxy-2-fluoro-4-(1-trans-alkenyl)-biphenyl,
4'-alkyloxy-2-fluoro-4-(6-hydroxy-1-trans-heptenyl)-biphenyl,
4'-alkyloxy-2-fluoro-4-(6-alkoxy-1-trans-heptenyl)-biphenyl,
4'-alkyloxy-2-fluoro-4-(6-acyloxy-1-trans-heptenyl)-biphenyl,
4'-alkyl-3-fluoro-4-(1-trans-alkenyl)-biphenyl,
4'-alkyl-3-fluoro-4-(6-hydroxy-1-trans-heptenyl)-biphenyl,
4'-alkyl-3-fluoro-4-(6-alkoxy-1-trans-heptenyl)-biphenyl,
4'-alkyl-3-fluoro-4-(6-acyloxy-1-trans-heptenyl)-biphenyl,
4'-alkyloxy-3-fluoro-4-(1-trans-alkenyl)-biphenyl,
4'-alkyloxy-3-fluoro-4-(6-hydroxy-1-trans-heptenyl)-biphenyl,
4'-alkyloxy-3-fluoro-4-(6-alkoxy-1-trans-heptenyl)-biphenyl,
4'-alkyloxy-3-fluoro-4-(6-acyloxy-1-trans-heptenyl)-biphenyl,
4-alkyl-2-fluoro-4'-(1-trans-alkenyl)-biphenyl,
4-alkyl-2-fluoro-4'-(6-hydroxy-1-trans-heptenyl)-biphenyl,
4-alkyl-2-fluoro-4'-(6-alkoxy-1-trans-heptenyl)-biphenyl,
4-alkyl-2-fluoro-4'-(6acyloxy-1-trans-heptenyl)-biphenyl,
4-alkyloxy-2-fluoro-4'-(1-trans-alkenyl)-biphenyl,
4-alkyloxy-2-fluoro-4'-(6-hydroxy-1-trans-heptenyl)-biphenyl,
4-alkyloxy-2-fluoro-4'-(6-alkoxy-1-trans-heptenyl)-biphenyl,
4-alkyloxy-2-fluoro-4'-(6-acyloxy-1-trans-heptenyl)-biphenyl,
4-alkyl-3-fluoro-4'-(1-trans-alkenyl)-biphenyl,
4-alkyl-3-fluoro-4'-(6-hydroxy-1-trans-heptenyl)-biphenyl,
4-alkyl-3-fluoro-4'-(6-alkoxy-1-trans-heptenyl)-biphenyl,
4-alkyl-3-fluoro-4'-(6-acyloxy-1-trans-heptenyl)-biphenyl,
4-alkyloxy-3-fluoro-4'-(1-trans-alkenyl)-biphenyl,
4-alkyloxy-3-fluoro-4'-(6-hydroxy-1-trans-heptenyl)-biphenyl,
4-alkyloxy-3-fluoro-4'-(6-alkoxy-1-trans-heptenyl)-biphenyl,
4-alkyloxy-3-fluoro-4'-(6-acyloxy-1-trans-heptenyl)-biphenyl,
2-alkyl-6-{4-(1-trans-alkenyl)-2-fluorophenyl}-naphthalene,
2-alkyl-6-{4-(6-hydroxy-1-trans-heptenyl)-2-fluorophenyl}-naphthalene,
2-alkyl-6-{4-(6-alkoxy-1-trans-heptenyl)-2-fluorophenyl}-naphthalene,
2-alkyl-6-{4-(6-acyloxy-1-trans-heptenyl)-2-fluorophenyl}-naphthalene,
2-alkyloxy-6-{4-(1-trans-alkenyl)-2-fluorophenyl}-naphthalene,
2-alkyloxy-6-{4-(6-hydroxy-1-trans-heptenyl)-2-fluorophenyl)}-naphthalene,
2-alkyloxy-6-{4-(6-alkoxy-1-trans-heptenyl)-2-fluorophenyl)}-naphthalene,
2-alkyloxy-6-{4-(6-acyloxy-1-trans-heptenyl)-2-fluorophenyl)}-naphthalene,
2-alkyl-6-{4-(1-trans-alkenyl)-3-fluorophenyl}-naphthalene,
2-alkyl-6-{4-(6-hydroxy-1-trans-heptenyl)-3-fluorophenyl}-naphthalene,
2-alkyl-6-{4-(6-alkoxy-1-trans-heptenyl)-3-fluorophenyl}-naphthalene,
2-alkyl-6-{4-(6-acyloxy-1-trans-heptenyl)-3-fluorophenyl}-naphthalene,
2-alkyloxy-6-{4-(1-trans-alkenyl)-3-fluorophenyl}-naphthalene,
2-alkyloxy-6-{4-(6-hydroxy-1-trans-heptenyl)-3-fluorophenyl}-naphthalene,
2-alkyloxy-6-{4-(6-alkoxy-1-trans-heptenyl)-3-fluorophenyl}-naphthalene,
2-alkyloxy-6-{4-(6-acyloxy-1-trans-heptenyl)-3-fluorophenyl}-naphthalene,
2-(4-alkyl-2-fluorophenyl)-6-(1-trans-alkenyl)-naphthalene,
2-{4-alkyl-2-fluorophenyl}-6-(6-hydroxy-1-trans-heptenyl)-naphthalene,
2-{4-alkyl-2-fluorophenyl}-6-(6-alkoxy-1-trans-heptenyl)-naphthalene,
2-{4-alkyl-2-fluorophenyl}-6-(6-acyloxy-1-trans-heptenyl)-naphthalene,
2-{4-alkyloxy-2-fluorophenyl}-6-(1-trans-alkenyl)-naphthalene,
2-{4-alkyloxy-2-fluorophenyl}-6-(6-hydroxy-1-trans-heptenyl)-naphthalene,
2-{4-alkyloxy-2-fluorophenyl}-6-(6-alkoxy-1-trans-heptenyl)-naphthalene,
2-{4-alkyloxy-2-fluorophenyl}-6-(6-acyloxy-1-trans-heptenyl)-napthalene,
2-{4-alkyl-3-fluorophenyl}-6-(1-trans-alkenyl)-naphthalene,
2-{4-alkyl-3-fluorophenyl}-6-(6-hydroxy-1-trans-heptenyl)-naphthalene,
2-{4-alkyl-3-fluorophenyl}-6-(6-alkoxy-1-trans-heptenyl)-naphthalene,
2-{4-alkyl-3-fluorophenyl}-6-(6-acyloxy-1-trans-heptenyl)-naphthalene, 2-{4-alkyloxy-3-fluorophenyl}-6-(1-trans-alkenyl)-naphthalene,
2-{4-alkyloxy-3-fluorophenyl}-6-(6-hydroxy-1-trans-heptenyl)-naphthalene,
2-{4-alkyloxy-3-fluorophenyl}-6-(6-alkoxy-1-trans-heptenyl)-naphthalene,
2-{4-alkyloxy-3-fluorophenyl}-6-(6-acyloxy-1-trans-heptenyl)-naphthalene,
4"-alkyl-2-fluoro-4-(1-trans-alkenyl)-p-terphenyl,
4"-alkyl-2-fluoro-4-(6-hydroxy-1-trans-heptenyl)-p-terphenyl,
4"-alkyl-2-fluoro-4-(6-alkoxy-1-trans-heptenyl)-p-terphenyl,
4"-alkyl-2-fluoro-4-(6-acyloxy-1-trans-heptenyl)-p-terphenyl,
4"-alkyloxy-2-fluoro-4-(1-trans-alkenyl)-p-terphenyl,
4"-alkyloxy-2-fluoro-4-(6-hydroxy-1-trans-heptenyl)-p-terphenyl,
4"-alkyloxy-2-fluoro-4-(6-alkoxy-1-trans-heptenyl)-p-terphenyl,
4"-alkyloxy-2-fluoro-4-(6-acyloxy-1-trans-heptenyl)-p-terphenyl,
4"-alkyl-3-fluoro-4-(1-trans-alkenyl)-p-terphenyl,
4"-alkyl-3-fluoro-4-(6-hydroxy-1-trans-heptenyl)-p-terphenyl,
4"-alkyl-3-fluoro-4-(6-alkoxy-1-trans-heptenyl)-p-terphenyl,
4"-alkyl-3-fluoro-4-(6-acyloxy-1-trans-heptenyl)-p-terphenyl,
4"-alkyloxy-3-fluoro-4-(1-trans-alkenyl)-p-terphenyl,
4"-alkyloxy-3-fluoro-4-(6-hydroxy-1-trans-heptenyl)-p-terphenyl,
4"-alkyloxy-3-fluoro-4-(6-alkoxy-1-trans-heptenyl)-p-terphenyl,
4"-alkyloxy-3-fluoro-4-(6-acyloxy-1-trans-heptenyl)-p-terphenyl,
4-alkyl-2-fluoro-4"-(1-trans-alkenyl)-p-terphenyl,
4-alkyl-2-fluoro-4"-(6-hydroxy-1-trans-heptenyl)-p-terphenyl,
4-alkyl-2-fluoro-4"-(6-alkoxy-1-trans-heptenyl)-p-terphenyl,
4-alkyl-2-fluoro-4"-(6-acyloxy-1-trans-heptenyl)-p-terphenyl,
4-alkyloxy-2-fluoro-4"-(1-trans-alkenyl)-p-terphenyl,
4-alkyloxy-2-fluoro-4"-(6-hydroxy-1-trans-heptenyl)-p-terphenyl,
4-alkyloxy-2-fluoro-4"-(6-alkoxy-1-trans-heptenyl)-p-terphenyl,
4-alkyloxy-2-fluoro-4"-(6-acyloxy-1-trans-heptenyl)-p-terphenyl,
4-alkyl-3-fluoro-4"-(1-trans-alkenyl)-p-terphenyl,
4-alkyl-3-fluoro-4"-(6-hydroxy-1-trans-heptenyl)-p-terphenyl,
4-alkyl-3-fluoro-4"-(6-alkoxy-1-trans-heptenyl)-p-terphenyl,
4-alkyl-3-fluoro-4"-(6-acyloxy-1-trans-heptenyl)-p-terphenyl,
4-alkyloxy-3-fluoro-4"-(1-trans-alkenyl)-p-terphenyl,
4-alkyloxy-3-fluoro-4"-(6-hydroxy-1-trans-heptenyl)-p-terphenyl,
4-alkyloxy-3-fluoro-4"-(6-alkoxy-1-trans-heptenyl)-p-terphenyl,
4-alkyloxy-3-flluoro-4"-(6-acyloxy-1-trans-heptenyl)-p-terphenyl,
4"-alkyl-2'-fluoro-4-(1-trans-alkenyl)-p-terphenyl,
4"-alkyl-2'-fluoro-4-(6-hydroxy-1-trans-heptenyl)-p-terphenyl,
4"-alkyl-2'-fluoro-4-(6-alkoxy-1-trans-heptenyl)-p-terphenyl,
4"-alkyl-2'-fluoro-4-(6-acyloxy-1-trans-heptenyl)-p-terphenyl,
4"-alkyloxy-2'-fluoro-4-(1-trans-alkenyl)-p-terphenyl,
4"-alkyloxy-2'-fluoro-4-(6-hydroxy-1-trans-heptenyl)-p-terphenyl,
4"-alkyloxy-2'-fluoro-4-(6-alkoxy-1-trans-heptenyl)-p-terphenyl,
4"-alkyloxy-2'-fluoro-4-(6-acyloxy-1-trans-heptenyl)-p-terphenyl,
4"-alkyl-3'-fluoro-4-(1-trans-alkenyl)-p-terphenyl,
4"-alkyl-3'-fluoro-4-(6-hydroxy-1-trans-heptenyl)-p-terphenyl,
4"-alkyl-3'-fluoro-4-(6-alkoxy-1-trans-heptenyl)-p-terphenyl,
4"-alkyl-3'-fluoro-4-(6-acyloxy-1-trans-heptenyl)-p-terphenyl,
4"-alkyloxy-3'-fluoro-4-(1-trans-alkenyl)-p-terphenyl,
4"-alkyloxy-3'-fluoro-4-(6-hydroxy-1-trans-heptenyl)-p-terphenyl,
4"-alkyloxy-3'-fluoro-4-(6-alkoxy-1-trans-heptenyl)-p-terphenyl,
4"-alkyloxy-3'-fluoro-4-(6-acyloxy-1-trans-heptenyl)-p-terphenyl,
5-alkyl-2-{4-(1-trans-alkenyl)-2-fluorophenyl}-pyridine,
5-alkyl-2-{4-(6-hydroxy-1-trans-heptenyl)-2-fluorophenyl}-pyridine,
5-alkyl-2-{4-(6-alkoxy-1-trans-heptenyl)-2-fluorophenyl}-pyridine,
5-alkyl-2-{4-(6-acyloxy-1-trans-heptenyl)-2-fluorophenyl}-pyridine,
5-alkyloxy-2-{4-(1-trans-alkenyl)-2-fluorophenyl}-pyridine,
5-alkyloxy-2-{4-(6-hydroxy-1-trans-heptenyl)-2-fluorophenyl}-pyridine,
5-alkyloxy-2-{4-(6-alkoxy-1-trans-heptenyl)-2-fluorophenyl}-pyridine,
5-alkyloxy-2-{4-(6-acyloxy-1-trans-heptenyl)-2-fluorophenyl}-pyridine,
2-(4-alkyl-2-fluorophenyl)-5-(1-trans-alkenyl)-pyridine,
2-(4-alkyl-2-fluorophenyl)-5-(6-hydroxy-1-trans-heptenyl)-pyridine,
2-(4-alkyl-2-fluorophenyl)-5-(6-alkoxy-1-trans-heptenyl)-pyridine,
2-(4-alkyl-2-fluorophenyl)-5-(6-acyloxy-1-trans-heptenyl)-pyridine,
2-(4-alkyloxy-2-fluorophenyl)-5-(1-trans-alkenyl)-pyridine,
2-(4-alkyloxy-2-fluorophenyl)-5-(6-hydroxy-1-trans-heptenyl)-pyridine,
2-(4-alkyloxy-2-fluorophenyl)-5-(6-alkoxy-1-trans-heptenyl)-pyridine,
2-(4-alkyloxy-2-fluorophenyl)-5-(6-acyloxy-1-trans-heptenyl)-pyridine,
2-alkyl-5-{4-(1-trans-alkenyl)-2-fluorophenyl}-pyridine,
2-alkyl-5-{4-(6-hydroxy-1-trans-heptenyl)-2-fluorophenyl}-pyridine,
2-alkyl-5-{4-(6-alkoxy-1-trans-heptenyl)-2-fluorophenyl}-pyridine,
2-alkyl-5-{4-(6-acyloxy-1-trans-heptenyl)-2-fluorophenyl}-pyridine,
2-alkyloxy-5-{4-(1-trans-alkenyl)-2-fluorophenyl}-pyridine,
2-alkyloxy-5-{4-(6-hydroxy-1-trans-heptenyl)-2-fluorophenyl}-pyridine,
2-alkyloxy-5-{4-(6-alkoxy-1-trans-heptenyl)-2-fluorophenyl}-pyridine, 2-alkyloxy-5-{4-(6-acyloxy-1-trans-heptenyl)-2-fluorophenyl}-pyridine,
5-(4-alkyl-2-fluorophenyl)-2-(1-trans-alkenyl)-pyridine,
5-(4-alkyl-2-fluorophenyl)-2-(6-hydroxy-1-trans-heptenyl)-pyridine,
5-(4-alkyl-2-fluorophenyl)-2-(6-alkoxy-1-trans-heptenyl)-pyridine,
5-(4-alkyl-2-fluorophenyl)-2-(6-acyloxy-1-trans-heptenyl)-pyridine,
5-(4-alkyloxy-2-fluorophenyl)-2-(1-trans-alkenyl)-pyridine,
5-(4-alkyloxy-2-fluorophenyl)-2-(6-hydroxy-1-trans-heptenyl)-pyridine,
5-(4-alkyloxy-2-fluorophenyl)-2-(6-alkoxy-1-trans-heptenyl)-pyridine,
5-(4-alkyloxy-2-fluorophenyl)-2-(6-acyloxy-1-trans-heptenyl)-pyridine,
2-alkyl-5-{4'-(1-trans-alkenyl)-2'-fluorobiphenyl-4-yl}-pyridine,
2-alkyl-5-{4'-(6-hydroxy-1-trans-alkenyl)-2'-fluorobiphenyl-4-yl}-pyridine,
2-alkyl-5-{4'-(6-alkoxy-1-trans-alkenyl)-2'-fluorobiphenyl-4-yl}-pyridine,
2-alkyl-5-{4'-(6-acyloxy-1-trans-heptenyl)-2'-fluorobiphenyl-4-yl}-pyridine,
2-alkyloxy-5-{4'-(1-trans-alkenyl)-2'-fluorobiphenyl-4-yl}-pyridine,
2-alkyloxy-5-{4'-(6-hydroxy-1-trans-alkenyl)-2'-fluorobiphenyl-4-yl}-pyridine,
2-alkyloxy-5-{4'-(6-alkoxy-1-trans-alkenyl)-2'-fluorobiphenyl-4-yl}-pyridine,
2-alkyloxy-5-{4'-(6-acyloxy-1-trans-heptenyl)-2'-fluorobiphenyl-4-yl}-pyridine,
5-(4'-alkyl-2'-fluorobiphenyl-4-yl)-2-(1-trans-alkenyl)-pyridine,
5-(4'-alkyl-2'-fluorobiphenyl-4-yl)-2-(6-hydroxy-1-trans-heptenyl)-pyridine,
5-(4'-alkyl-2'-fluorobiphenyl-4-yl)-2-(6-alkoxy-1-trans-heptenyl)-pyridine,
5-(4'-alkyl-2'-fluorobiphenyl-4-yl)-2-(6-acyloxy-1-trans-heptenyl)-pyridine,
5-(4'-alkyloxy-2'-fluorobiphenyl-4-yl)-2-(1-trans-alkenyl)-pyridine,
5-(4'-alkyloxy-2'-fluorobiphenyl-4-yl)-2-(6-hydroxy-1-trans-heptenyl)-pyridine,
5-(4'-alkyloxy-2'-fluorobiphenyl-4-yl)-2-(6-alkoxy-1-trans-heptenyl)-pyridine,
5-(4'-alkyloxy-2'-fluorobiphenyl-4-yl)-2-(6-acyloxy-1-trans-heptenyl)-pyridine,
5-alkyl-2-{4'-(1-trans-alkenyl)-2'-fluorobiphenyl-4-yl}-pyridine,
5-alkyl-2-{4'-(6-hydroxy-1-trans-heptenyl)-2'-fluorobiphenyl-4-yl}-pyridine,
5-alkyl-2-{4'-(6-alkoxy-1-trans-heptenyl)-2'-fluorobiphenyl-4-yl}-pyridine,
5-alkyl-2-{4'-(6-acyloxy-1-trans-heptenyl)-2'-fluorobiphenyl-4-yl}-pyridine,
5-alkyloxy-2-{4'-(1-trans-alkenyl)-2'-fluorobiphenyl-4-yl}-pyridine,
5-alkyloxy-2-{4'-(6-hydroxy-1-trans-heptenyl)-2'-fluorobiphenyl-4-yl}-pyridine,
5-alkyloxy-2-{4'-(6-alkoxy-1-trans-heptenyl)-2'-fluorobiphenyl-4-yl}-pyridine,
5-alkyloxy-2-{4'-(6-acyloxy-1-trans-heptenyl)-2'-fluorobiphenyl-4-yl}-pyridine,
2-(4'-alkyl-2'-fluorobiphenyl-4-yl)-5-(1-trans-alkenyl)-pyridine,
2-(4'-alkyl-2'-fluorobiphenyl-4-yl)-5-(6-hydroxy-1-trans-heptenyl)-pyridine,
2-(4'-alkyl-2'-fluorobiphenyl-4-yl)-5-(6-alkoxy-1-trans-heptenyl)-pyridine,
2-(4'-alkyl-2'-fluorobiphenyl-4-yl)-5-(6-acyloxy-1-trans-heptenyl)-pyridine,
2-(4'-alkyloxy-2'-fluorobiphenyl-4-yl)-5-(1-trans-alkenyl)-pyridine,
2-(4'-alkyloxy-2'-fluorobiphenyl-4-yl)-5-(6-hydroxy-1-trans-heptenyl)-pyridine,
2-(4'-alkyloxy-2'-fluorobiphenyl-4-yl)-5-(6-alkoxy-1-trans-heptenyl)-pyridine,
2-(4'-alkyloxy-2'-fluorobiphenyl-4-yl)-5-(6-acyloxy-1-trans-heptenyl)-pyridine,
5-(4-alkyl-2-fuorophenyl)-2-{4-(1-trans-alkenyl)-phenyl}-pyridine,
5-(4-alkyl-2-fluorophenyl)-2-{4-(6-hydroxy-1-trans-heptenyl)-phenyl}-pyridine,
5-(4-alkyl-2-fluorophenyl)-2-{4-(6-alkoxy-1-trans-heptenyl)-phenyl}-pyridine,
5-(4-alkyl-2-fluorophenyl)-2-{4-(6-acyloxy-1-trans-heptenyl)-phenyl}-pyridine,
5-(4-alkyloxy-2-fluorophenyl)-2-{4-(1-trans-alkenyl)-phenyl}-pyridine,
5-(4-alkyloxy-2-fluorophenyl)-2-{4-(6-hydroxy-1-trans-heptenyl)-phenyl}-pyridine,
5-(4-alkyloxy-2-fluorophenyl)-2-{4-(6-alkoxy-1-trans-heptenyl)-phenyl}-pyridine,
5-(4-alkyloxy-2-fluorophenyl)-2-{4-(6-acyloxy-1-trans-heptenyl)-phenyl}-pyridine,
2-(4-alkyl-2-fluorophenyl)-5-{4-(1-trans-alkenyl)-phenyl}-pyridine,
2-(4-alkyl-2-fluorophenyl)-5-{4-(6-hydroxy-1-trans-heptenyl)-phenyl}-pyridine,
2-(4-alkyl-2-fluorophenyl)-5-{4-(6-alkoxy-1-trans-heptenyl)-phenyl}-pyridine,
2-(4-alkyl-2-fluorophenyl)-5-{4-(6-acyloxy-1-trans-heptenyl)-phenyl}-pyridine,
2-(4-alkyloxy-2-fluorophenyl)-5-{4-(1-trans-alkenyl)-phenyl}-pyridine,
2-(4-alkyloxy-2-fluorophenyl)-5-{4-(6-hydroxy-1-trans-heptenyl)-phenyl}-pyridine,
2-(4-alkyloxy-2-fluorophenyl)-5-{4-(6-alkoxy-1-trans-heptenyl)-phenyl}-pyridine,
2-(4-alkyloxy-2-fluorophenyl)-5-{4-(6-acyloxy-1-trans-heptenyl)-phenyl}-pyridine,
5-(4-alkylphenyl)-2-{4-(1-trans-alkenyl)-2-fluorophenyl}-pyridine,
5-(4-alkylphenyl)-2-{4-(6-hydroxy-1-trans-heptenyl)-2-fluorophenyl}-pyridine,
5-(4-alkylphenyl)-2-{4-(6-alkoxy-1-trans-heptenyl)-2-fluorophenyl}-pyridine,
5-(4-alkylphenyl)-2-{4-(6-acyloxy-1-trans-heptenyl)-2-fluorophenyl}-pyridine,
5-(4-alkyloxyphenyl)-2-{4-(1-trans-alkenyl)-2-fluorophenyl}-pyridine,
5-(4-alkyloxyphenyl)-2-{4-(6-hydroxy-1-trans-heptenyl)-2-fluorophenyl}-pyridine,
5-(4-alkyloxyphenyl)-2-{4-(6-alkoxy-1-trans-heptenyl)-2-fluorophenyl}-pyridine,
5-(4-alkyloxyphenyl)-2-{4-(6-acyloxy-1-trans-heptenyl)-2-fluorophenyl}-pyridine,
2-(4-alkylphenyl)-5-{4-(1-trans-alkenyl)-2-fluorophenyl}-pyridine,
2-(4-alkylphenyl)-5-{4-(6-hydroxy-1-trans-heptenyl)-2-fluorophenyl}-pyridine,
2-(4-alkylphenyl)-5-{4-(6-alkoxy-1-trans-heptenyl)-2-fluorophenyl}-pyridine,
2-(4-alkylphenyl)-5-{4-(6-acyloxy-1-trans-heptenyl)-2-fluorophenyl}-pyridine, 2-(4-alkyloxyphenyl)-5-{4-(1-trans-alkenyl)-2-fluorophenyl}-pyridine,
2-(4-alkyloxyphenyl)-5-{4-(6-hydroxy-1-trans-heptenyl)-2-fluorophenyl}-pyridine,
2-(4-alkyloxyphenyl)-5-{4-(6-alkoxy-1-trans-heptenyl)-2-fluorophenyl}-pyridine,
2-(4-alkyloxyphenyl)-5-{4-(6-acyloxy-1-trans-heptenyl)-2-fluorophenyl}-pyridine,
5-alkyl-2-{4-(1-trans-alkenyl)-3-fluorophenyl}-pyridine,
5-alkyl-2-{4-(6-hydroxy-1-trans-heptenyl)-3-fluorophenyl}-pyridine,
5-alkyl-2-{4-(6-alkoxy-1-trans-hepteny)-3-fluorophenyl}-pyridine,
5-alkyl-2-{4-(6-acyloxy-1-trans-heptenyl)-3-fluorophenyl}-pyridine,
5-alkyloxy-2-{4-(1-trans-alkenyl)-3-fluorophenyl}-pyridine,
5-alkyloxy-2-{4-(6-hydroxy-1-trans-heptenyl)-3-fluorophenyl}-pyridine,
5-alkyloxy-2-{4-(6-alkoxy-1-trans-heptenyl)-3-fluorophenyl}-pyridine,
5-alkyloxy-2-{4-(6-acyloxy-1-trans-heptenyl)-3-fluorophenyl}-pyridine,
2-(4-alkyl-3-fluorophenyl)-5-(1-trans-alkenyl)-pyridine,
2-(4-alkyl-3-fluorophenyl)-5-(6-hydroxy-1-trans-heptenyl)-pyridine,
2-(4-alkyl-3-fluorophenyl)-5-(6-alkoxy-1-trans-heptenyl)-pyridine,
2-(4-alkyl-3-fluorophenyl)-5-(6-acyloxy-1-trans-heptenyl)-pyridine,
2-(4-alkyloxy-3-fluorophenyl)-5-(1-trans-alkenyl)-pyridine,
2-(4-alkyloxy-3-fluorophenyl)-5-(6-hydroxy-1-trans-heptenyl)-pyridine,
2-(4-alkyloxy-3-fluorophenyl)-5-(6-alkoxy-1-trans-heptenyl)-pyridine,
2-(4-alkyloxy-3-fluorophenyl)-5-(6-acyloxy-1-trans-heptenyl)-pyridine,
2-alkyl-5-{4-(1-trans-alkenyl)-3-fluorophenyl}-pyridine,
2-alkyl-5-{4-(6-hydroxy-1-trans-heptenyl)-3-fluorophenyl}-pyridine,
2-alkyl-5-{4-(6-alkoxy-1-trans-heptenyl)-3-fluorophenyl}-pyridine,
2-alkyl-5-{4-(6-acyloxy-1-trans-heptenyl)-3-fluorophenyl}-pyridine,
2-alkyloxy-5-{4-(1-trans-alkenyl)-3-fluorophenyl}-pyridine,
2-alkyloxy-5-{4-(6-hydroxy-1-trans-heptenyl)-3-fluorophenyl}-pyridine,
2-alkyloxy-5-{4-(6-alkoxy-1-trans-heptenyl)-3-fluorophenyl}-pyridine,
2-alkyloxy-5-{4-(6-acyloxy-1-trans-heptenyl)-3-fluorophenyl}-pyridine,
5-(4-alkyl-3-fluorophenyl)-2-(1-trans-alkenyl)-pyridine,
5-(4-alkyl-3-fluorophenyl)-2-(6-hydroxy-1-trans-heptenyl)-pyridine,
5-(4-alkyl-3-fluorophenyl)-2-(6-alkoxy-1-trans-heptenyl)-pyridine,
5-(4-alkyl-3-fluorophenyl)-2-(6-acyloxy-1-trans-heptenyl)-pyridine,
5-(4-alkyloxy-3-fluorophenyl)-2-(1-trans-alkenyl)-pyridine,
5-(4-alkyloxy-3-fluorophenyl)-2-(6-hydroxy-1-trans-heptenyl)-pyridine,
5-(4-alkyloxy-3-fluorophenyl)-2-(6-alkoxy-1-trans-heptenyl)-pyridine,
5-(4-alkyloxy-3-fluorophenyl)-2-(6-acyloxy-1-trans-heptenyl)-pyridine,
2-alkyl-5-{4'-(1-trans-alkenyl)-3'-fluorobiphenyl-4-yl}-pyridine,
2-alkyl-5-{4'-(6-hydroxy-1-trans-heptenyl)-3'-fluorobiphenyl-4-yl}-pyridine,
2-alkyl-5-{4'-(6-alkoxy-1-trans-heptenyl)-3'-fluorobiphenyl-4-yl}-pyridine,
2-alkyl-5-{4'-(6-acyloxy-1-trans-heptenyl)-3'-fluorobiphenyl-4-yl}-pyridine,
2-alkyloxy-5-{4'-(1-trans-alkenyl)-3'-fluorobiphenyl-4-yl}-pyridine,
2-alkyloxy-5-{4'-(6-hydroxy-1-trans-heptenyl)-3'-fluorobiphenyl-4-yl}-pyridine,
2-alkyloxy-5-{4'-(6-alkoxy-1-trans-heptenyl)-3'-fluorobiphenyl-4-yl}-pyridine,
2-alkyloxy-5-{4'-(6-acyloxy-1-trans-heptenyl)-3'-fluorobiphenyl-4-yl}-pyridine,
5-(4'-alkyl-3'-fluorobiphenyl-4-yl)-2-(1-trans-alkenyl)-pyridine,
5-(4'-alkyl-3'-fluorobiphenyl-4-yl)-2-(6-hydroxy-1-trans-heptenyl)-pyridine,
5-(4'-alkyl-3'-fluorobiphenyl-4-yl)-2-(6-alkoxy-1-trans-heptenyl)-pyridine,
5-(4'-alkyl-3'-fluorobiphenyl-4-yl)-2-(6-acyloxy-1-trans-heptenyl)-pyridine,
5-(4'-alkyloxy-3'-fluorobiphenyl-4-yl)-2-(1-trans-alkenyl)-pyridine,
5-(4'-alkyloxy-3'-fluorobiphenyl-4-yl)-2-(6-hydroxy-1-trans-heptenyl)-pyridine,
5-(4'-alkyloxy-3'-fluorobiphenyl-4-yl)-2-(6-alkoxy-1-trans-heptenyl)-pyridine,
5-(4'-alkyloxy-3'-fluorobiphenyl-4-yl)-2-(6-acyloxy-1-trans-heptenyl)-pyridine,
5-alkyl-2-{4'-(1-trans-alkenyl)-3'-fluorobiphenyl-4-yl}-pyridine,
5-alkyl-2-{4'-(6-hydroxy-1-trans-heptenyl)-3'-fluorobiphenyl-4-yl}-pyridine,
5-alkyl-2-{4'-(6-alkoxy-1-trans-heptenyl)-3'-fluorobiphenyl-4-yl}-pyridine,
5-alkyl-2-{4'-(6-acyloxy-1-trans-heptenyl)-3'-fluorobiphenyl-4-yl}-pyridine,
5-alkyloxy-2-{4'-(1-trans-alkenyl)-3'-fluorobiphenyl-4-yl}-pyridine,
5-alkyloxy-2-{4'-(6-hydroxy-1-trans-heptenyl)-3'-fluorobiphenyl-4-yl}-pyridine,
5-alkyloxy-2-{4'-(6-alkoxy-1-trans-heptenyl)-3'-fluorobiphenyl-4-yl}-pyridine,
5-alkyloxy-2-{4'-(6-acyloxy-1-trans-heptenyl)-3'-fluorobiphenyl-4-yl}-pyridine,
2-(4'-alkyl-3'-fluorobiphenyl-4-yl)-5-(1-trans-alkenyl)-pyridine,
2-(4'-alkyl-3'-fluorobiphenyl-4-yl)-5-(6-hydroxy-1-trans-heptenyl)-pyridine,
2-(4'-alkyl-3'-fluorobiphenyl-4-yl)-5-(6-alkoxy-1-trans-heptenyl)-pyridine,
2-(4'-alkyl-3'-fluorobiphenyl-4-yl)-5-(6-acyloxy-1-trans-heptenyl)-pyridine,
2-(4'-alkyloxy-3'-fluorobiphenyl-4-yl)-5-(1-trans-alkenyl)-pyridine,
2-(4'-alkyloxy-3'-fluorobiphenyl-4-yl)-5-(6-hydroxy-1-trans-heptenyl)-pyridine,
2-(4'-alkyloxy-3'-fluorobiphenyl-4-yl)-5-(6-alkoxy-1-trans-heptenyl)-pyridine,
2-(4'-alkyloxy-3'-fluorobiphenyl-4-yl)-5-(6-acyloxy-1-trans-heptenyl)-pyridine,
5-(4-alkyl-3-fluorophenyl)-2-{4-(1-trans-alkenyl)-phenyl}-pyridine,
5-(4-alkyl-3-fluorophenyl)-2-{4-(6-hydroxy-1-trans-heptenyl)-phenyl}-pyridine,
5-(4-alkyl-3-fluorophenyl)-2-{4-(6-alkoxy-1-trans-heptenyl)-phenyl}-pyridine, 5-(4-alkyl-3-fluorophenyl)-2-{4-(6-acyloxy-1-trans-heptenyl)-phenyl}-pyridine,
5-(4-alkyloxy-3-fluorophenyl)-2-{4-(1-trans-alkenyl)-phenyl}-pyridine,
5-(4-alkyloxy-3-fluorophenyl)-2-{4-(6-hydroxy-1-trans-heptenyl)-phenyl}-pyridine,
5-(4-alkyloxy-3-fluorophenyl)-2-{4-(6-alkoxy-1-trans-heptenyl)-phenyl}-pyridine,
5-(4-alkyloxy-3-fluorophenyl)-2-{4-(6-acyloxy-1-trans-heptenyl)-phenyl}-pyridine,
2-(4-alkyl-3-fluorophenyl)-5-{4-(1-trans-alkenyl)-phenyl}-pyridine,
2-(4-alkyl-3-fluorophenyl)-5-{4-(6-hydroxy-1-trans-heptenyl)-phenyl}-pyridine,
2-(4-alkyl-3-fluorophenyl)-5-{4-(6-alkoxy-1-trans-heptenyl)-phenyl}-pyridine,
2-(4-alkyl-3-fluorophenyl)-5-{4-(6-acyloxy-1-trans-heptenyl)-phenyl}-pyridine,
2-(4-alkyloxy-3-fluorophenyl)-5-{4-(1-trans-alkenyl)-phenyl}-pyridine,
2-(4-alkyloxy-3-fluorophenyl)-5-{4-(6-hydroxy-1-trans-heptenyl)-phenyl}-pyridine,
2-(4-alkyloxy-3-fluorophenyl)-5-{4-(6-alkoxy-1-trans-heptenyl)-phenyl}-pyridine,
2-(4-alkyloxy-3-fluorophenyl)-5-{4-(6-acyloxy-1-trans-heptenyl)-phenyl}-pyridine,
5-(4-alkylphenyl)-2-{4-(1-trans-alkenyl)-3-fluorophenyl}-pyridine,
5-(4-alkylphenyl)-2-{4-(6-hydroxy-1-trans-heptenyl)-3-fluorophenyl}-pyridine,
5-(4-alkylphenyl)-2-{4-(6-alkoxy-1-trans-heptenyl)-3-fluorophenyl}-pyridine,
5-(4-alkylphenyl)-2-{4-(6-acyloxy-1-trans-heptenyl)-3-fluorophenyl}-pyridine,
5-(4-alkyloxyphenyl)-2-{4-(1-trans-alkenyl)-3-fluorophenyl}-pyridine,
5-(4-alkyloxyphenyl)-2-{4-(6-hydroxy-1-trans-heptenyl)-3-fluorophenyl}-pyridine,
5-(4-alkyloxyphenyl)-2-{4-(6-alkoxy-1-trans-heptenyl)-3-fluorophenyl}-pyridine,
5-(4-alkyloxyphenyl)-2-{4-(6-acyloxy-1-trans-heptenyl)-3-fluorophenyl}-pyridine,
2-(4-alkylphenyl)-5-{4-(1-trans-alkenyl)-3-fluorophenyl}-pyridine,
2-(4-alkylphenyl)-5-{4-(6-hydroxy-1-trans-heptenyl)-3-fluorophenyl}-pyridine,
2-(4-alkylphenyl)-5-{4-(6-alkoxy-1-trans-heptenyl)-3-fluorophenyl}-pyridine,
2-(4-alkylphenyl)-5-{4-(6-acyloxy-1-trans-heptenyl)-3-fuorophenyl}-pyridine,
2-(4-alkyloxyphenyl)-5-{4-(1-trans-alkenyl)-3-fluorophenyl}-pyridine,
2-(4-alkyloxyphenyl)-5-{4-(6-hydroxy-1-trans-heptenyl)-3-fluorophenyl}-pyridine,
2-(4-alkyloxyphenyl)-5-{4-(6-alkoxy-1-trans-heptenyl)-3-fluorophenyl}-pyridine,
2-(4-alkyloxyphenyl)-5-{4-(6-acyloxy-1-trans-heptenyl)-3-fluorophenyl}-pyridine,
5-alkyl-2-{4-(1-trans-alkenyl)-2-fluorophenyl}-pyrimidine,
5-alkyl-2-{4-(6-hydroxy-1-trans-heptenyl)-2-fluorophenyl}-pyrimidine,
5-alkyl-2-{4-(6-alkoxy-1-trans-heptenyl)-2-fluorophenyl}-pyrimidine,
5-alkyl-2-{4-(6-acyloxy-1-trans-heptenyl)-2-fluorophenyl}-pyrimidine,
5-alkyloxy-2-{4-(1-trans-alkenyl)-2-fluorophenyl}-pyrimidine,
5-alkyloxy-2-{4-(6-hydroxy-1-trans-heptenyl)-2-fluorophenyl}-pyrimidine,
5-alkyloxy-2-{4-(6-alkoxy-1-trans-heptenyl)-2-fluorophenyl}-pyrimidine,
5-alkyloxy-2-{4-(6-acyloxy-1-trans-heptenyl)-2-fluorophenyl}-pyrimidine,
5-alkyl-2-{4-(1-trans-alkenyl)-3-fluorophenyl}-pyrimidine,
5-alkyl-2-{4-(6-hydroxy-1-trans-heptenyl)-3-fluorophenyl}-pyrimidine,
5-alkyl-2-{4-(6-alkoxy-1-trans-heptenyl)-3-fluorophenyl}-pyrimidine,
5-alkyl-2-{4-(6-acyloxy-1-trans-heptenyl)-3-fluorophenyl}-pyrimidine,
5-alkyloxy-2-{4-(1-trans-alkenyl)-3-fluorophenyl}-pyrimidine,
5-alkyloxy-2-{4-(6-hydroxy-1-trans-heptenyl)-3-fluorophenyl}-pyrimidine,
5-alkyloxy-2-{4-(6-alkoxy-1-trans-heptenyl)-3-fluorophenyl}-pyrimidine,
5-alkyloxy-2-{4-(6-acyloxy-1-trans-heptenyl)-3-fluorophenyl}-pyrimidine,
2-(4-alkyl-2-fuorophenyl)-5-(1-trans-alkenyl)-pyrimidine,
2-(4-alkyl-2-fuorophenyl)-5-(6-hydroxy-1-trans-heptenyl)-pyrimidine,
2-(4-alkyl-2-fuorophenyl)-5-(6-alkoxy-1-trans-heptenyl)-pyrimidine,
2-(4-alkyl-2-fuorophenyl)-5-(6-acyloxy-1-trans-heptenyl)-pyrimidine,
2-(4-alkyloxy-2-fluorophenyl)-5-(1-trans-alkenyl)-pyrimidine,
2-(4-alkyloxy-2-fluorophenyl)-5-(6-hydroxy-1-trans-heptenyl)-pyrimidine,
2-(4-alkyloxy-2-fluorophenyl)-5-(6-alkoxy-1-trans-heptenyl)-pyrimidine,
2-(4-alkyloxy-2-fluorophenyl)-5-(6-acyloxy-1-trans-heptenyl)-pyrimidine,
2-(4-alkyl-3-fluorophenyl)-5-(1-trans-alkenyl)-pyrimidine,
2-(4-alkyl-3-fluorophenyl)-5-(6-hydroxy-1-trans-heptenyl)-pyrimidine,
2-(4-alkyl-3-fluorophenyl)-5-(6-alkoxy-1-trans-heptenyl)-pyrimidine,
2-(4-alkyl-3-fluorophenyl)-5-(6-acyloxy-1-trans-heptenyl)-pyrimidine,
2-(4-alkyloxy-3-fluorophenyl)-5-(1-trans-alkenyl)-pyrimidine,
2-(4-alkyloxy-3-fluorophenyl)-5-(6-hydroxy-1-trans-heptenyl)-pyrimidine,
2-(4-alkyloxy-3-fluorophenyl)-5-(6-alkoxy-1-trans-heptenyl)-pyrimidine,
2-(4-alkyloxy-3-fluorophenyl)-5-(6-acyloxy-1-trans-heptenyl)-pyrimidine,
2-alkyl-5-{4-(1-trans-alkenyl)-2-fluorophenyl}-pyrimidine,
2-alkyl-5-{4-(6-hydroxy-1-trans-heptenyl)-2-fluorophenyl}-pyrimidine,
2-alkyl-5-{4-(6-alkoxy-1-trans-heptenyl)-2-fluorophenyl}-pyrimidine,
2-alkyl-5-{4-(6-acyloxy-1-trans-heptenyl)-2-fluorophenyl}-pyrimidine,
2-alkyloxy-5-{4-(1-trans-alkenyl)-2-fluorophenyl}-pyrimidine,
2-alkyloxy-5-{4-(6-hydroxy-1-trans-heptenyl)-2-fluorophenyl}-pyrimidine,
2-alkyloxy-5-{4-(6-alkoxy-1-trans-heptenyl)-2-fluorophenyl}-pyrimidine,
2-alkyloxy-5-{4-(6-acyloxy-1-trans-heptenyl)-2-fluorophenyl}-pyrimidine,
2-alkyl-5-{4-(1-trans-alkenyl)-3-fluorophenyl}-pyrimidine, 2-alkyl-5-{4-(6-hydroxy-1-trans-heptenyl)-3-fluorophenyl}-pyrimidine,
2-alkyl-5-{4-(6-alkoxy-1-trans-heptenyl)-3-fluorophenyl}-pyrimidine,
2-alkyl-5-{4-(6-acyloxy-1-trans-heptenyl)-3-fluorophenyl}-pyrimidine,
2-alkyloxy-5-{4-(1-trans-alkenyl)-3-fluorophenyl}-pyrimidine,
2-alkyloxy-5-{4-(6-hydroxy-1-trans-heptenyl)-3-fluorophenyl}-pyrimidine,
2-alkyloxy-5-{4-(6-alkoxy-1-trans-heptenyl)-3-fluorophenyl}-pyrimidine,
2-alkyloxy-5-{4-(6-acyloxy-1-trans-heptenyl)-3-fluorophenyl}-pyrimidine,
5-(4-alkyl-2-fluorophenyl)-2-(1-trans-alkenyl)-pyrimidine,
5-(4-alkyl-2-fluorophenyl)-2-(6-hydroxy-1-trans-heptenyl)-pyrimidine,
5-(4-alkyl-2-fluorophenyl)-2-(6-alkoxy-1-trans-heptenyl)-pyrimidine,
5-(4-alkyl-2-fluorophenyl)-2-(6-acyloxy-1-trans-heptenyl)-pyrimidine,
5-(4-alkyloxy-2-fluorophenyl)-2-(1-trans-alkenyl)-pyrimidine,
5-(4-alkyloxy-2-fluorophenyl)-2-(6-hydroxy-1-trans-heptenyl)-pyrimidine,
5-(4-alkyloxy-2-fluorophenyl)-2-(6-alkoxy-1-trans-heptenyl)-pyrimidine,
5-(4-alkyloxy-2-fluorophenyl)-2-(6-acyloxy-1-trans-heptenyl)-pyrimidine,
5-(4-alkyl-3-fluorophenyl)-2-(1-trans-alkenyl)-pyrimidine,
5-(4-alkyl-3-fluorophenyl)-2-(6-hydroxy-1-trans-heptenyl)-pyrimidine,
5-(4-alkyl-3-fluorophenyl)-2-(6-alkoxy-1-trans-heptenyl)-pyrimidine,
5-(4-alkyl-3-fluorophenyl)-2-(6-acyloxy-1-trans-heptenyl)-pyrimidine,
5-(4-alkyloxy-3-fluorophenyl)-2-(1-trans-alkenyl)-pyrimidine,
5-(4-alkyloxy-3-fluorophenyl)-2-(6-hydroxy-1-trans-heptenyl)-pyrimidine,
5-(4-alkyloxy-3-fluorophenyl)-2-(6-alkoxy-1-trans-heptenyl)-pyrimidine,
5-(4-alkyloxy-3-fluorophenyl)-2-(6-acyloxy-1-trans-heptenyl)-pyrimidine,
6-alkyl-3-{4-(1-trans-alkenyl)-2-fluorophenyl}-pyridazine,
6-alkyl-3-{4-(6-hydroxy-1-trans-heptenyl)-2-fluorophenyl}-pyridazine,
6-alkyl-3-{4-(6-alkoxy-1-trans-heptenyl)-2-fluorophenyl}-pyridazine,
6-alkyl-3-{4-(6-acyloxy-1-trans-heptenyl)-2-fluorophenyl}-pyridazine,
6-alkyloxy-3-{4-(1-trans-alkenyl)-2-fluorophenyl}-pyridazine,
6-alkyloxy-3-{4-(6-hydroxy-1-trans-heptenyl)-2-fluorophenyl}-pyridazine,
6-alkyloxy-3-{4-(6-alkoxy-1-trans-heptenyl)-2-fluorophenyl}-pyridazine,
6-alkyloxy-3-{4-(6-acyloxy-1-trans-heptenyl)-2-fluorophenyl}-pyridazine,
6-(4-alky-2-fluorophenyl)-3-(1-trans-alkenyl)-pyridazine,
6-(4-alky-2-fluorophenyl)-3-(6-hydroxy-1-trans-heptenyl)-pyridazine,
6-(4-alky-2-fluorophenyl)-3-(6-alkoxy-1-trans-heptenyl)-pyridazine,
6-(4-alky-2-fluorophenyl)-3-(6-acyloxy-1-trans-heptenyl)-pyridazine,
6-(4-alkyloxy-2-fluorophenyl)-3-(1-trans-alkenyl)-pyridazine,
6-(4-alkyloxy-2-fluorophenyl)-3-(6-hydroxy-1-trans-heptenyl)-pyridazine,
6-(4-alkyloxy-2-fluorophenyl)-3-(6-alkoxy-1-trans-heptenyl)-pyridazine,
6-(4-alkyloxy-2-fluorophenyl)-3-(6-acyloxy-1-trans-heptenyl)-pyridazine,
6-alkyl-3-{4-(1-trans-alkenyl)-3-fluorophenyl}-pyridazine,
6-alkyl-3-{4-(6-hydroxy-1-trans-heptenyl)-3-fluorophenyl}-pyridazine,
6-alkyl-3-{4-(6-alkoxy-1-trans-heptenyl)-3-fluorophenyl}-pyridazine,
6-alkyl-3-{4-(6-acyloxy-1-trans-heptenyl)-3-fluorophenyl}-pyridazine,
6-alkyloxy-3-{4-(1-trans-alkenyl)-3-fluorophenyl}-pyridazine,
6-alkyloxy-3-{4-(6-hydroxy-1-trans-heptenyl)-3-fluorophenyl}-pyridazine,
6-alkyloxy-3-{4-(6-alkoxy-1-trans-heptenyl)-3-fluorophenyl}-pyridazine,
6-alkyloxy-3-{4-(6-acyloxy-1-trans-heptenyl)-3-fluorophenyl}-pyridazine,
6-(4-alkyl-3-fluorophenyl)-3-(1-trans-alkenyl)-pyridazine,
6-(4-alkyl-3-fluorophenyl)-3-(6-hydroxy-1-trans-heptenyl)-pyridazine,
6-(4-alkyl-3-fluorophenyl)-3-(6-alkoxy-1-trans-heptenyl)-pyridazine,
6-(4-alkyl-3-fluorophenyl)-3-(6-acyloxy-1-trans-heptenyl)-pyridazine,
6-(4-alkyloxy-3-fluorophenyl)-3-(1-trans-alkenyl)-pyridazine,
6-(4-alkyloxy-3-fluorophenyl)-3-(6-hydroxy-1-trans-heptenyl)-pyridazine,
6-(4-alkyloxy-3-fluorophenyl)-3-(6-alkoxy-1-trans-heptenyl)-pyridazine,
6-(4-alkyloxy-3-fluorophenyl)-3-(6-acyloxy-1-trans-heptenyl)-pyridazine,
5-alkyl-2-{4'-(1-trans-alkenyl)-2'-fluorobiphenyl-4-yl}-pyrimidine,
5-alkyl-2-{4'-(6-hydroxy-1-trans-heptenyl)-2'-fluorobiphenyl-4-yl}-pyrimidine,
5-alkyl-2-{4'-(6-alkoxy-1-trans-heptenyl)-2'-fluorobiphenyl-4-yl}-pyrimidine,
5-alkyl-2-{4'-(6-acyloxy-1-trans-heptenyl)-2'-fluorobiphenyl-4-yl}-pyrimidine,
5-alkyloxy-2-{4'-(1-trans-alkenyl)-2'-fluorobiphenyl-4-yl}-pyrimidine,
5-alkyloxy-2-{4'-(6-hydroxy-1-trans-heptenyl)-2'-fluorobiphenyl-4-yl}-pyrimidine,
5-alkyloxy-2-{4'-(6-alkoxy-1-trans-heptenyl)-2'-fluorobiphenyl-4-yl}-pyrimidine,
5-alkyloxy-2-{4'-(6-acyloxy-1-trans-heptenyl)-2'-fluorobiphenyl-4-yl}-pyrimidine,
2-(4'-alkyl-2'-fluorobiphenyl-4-yl)-5-(1-trans-alkenyl)-pyrimidine,
2-(4'-alkyl-2'-fluorobiphenyl-4-yl)-5-(6-hydroxy-1-trans-heptenyl)-pyrimidine,
2-(4'-alkyl-2'-fluorobiphenyl-4-yl)-5-(6-alkoxy-1-trans-heptenyl)-pyrimidine,
2-(4'-alkyl-2'-fluorobiphenyl-4-yl)-5-(6-acyloxy-1-trans-heptenyl)-pyrimidine,
2-(4'-alkyloxy-2'-fluorobiphenyl-4-yl)-5-(1-trans-alkenyl)-pyrimidine,
2-(4'-alkyloxy-2'-fluorobiphenyl-4-yl)-5-(6-hydroxy-1-trans-heptenyl)-pyrimidine,
2-(4'-alkyloxy-2'-fluorobiphenyl-4-yl)-5-(6-alkoxy-1-trans-heptenyl)-pyrimidine,
2-(4'-alkyloxy-2'-fluorobiphenyl-4-yl)-5-(6-acyloxy-1-trans-heptenyl)-pyrimidine, 2-alkyl-5-{4'-(1-trans-alkenyl)-2'-fluorobiphenyl-4-yl}-pyrimidine,
2-alkyl-5-{4'-(6-hydroxy-1-trans-heptenyl)-2'-fluorobiphenyl-4-yl}-pyrimidine,
2-alkyl-5-{4'-(6-alkoxy-1-trans-heptenyl)-2'-fluorobiphenyl-4-yl}-pyrimidine,
2-alkyl-5-{4'-(6-acyloxy-1-trans-heptenyl)-2'-fluorobiphenyl-4-yl}-pyrimidine,
2-alkyloxy-5-{4'-(1-trans-alkenyl)-2'-fluorobiphenyl-4-yl}-pyrimidine,
2-alkyloxy-5-{4'-(6-hydroxy-1-trans-heptenyl)-2'-fluorobiphenyl-4-yl}-pyrimidine,
2-alkyloxy-5-{4'-(6-alkoxy-1-trans-heptenyl)-2'-fluorobiphenyl-4-yl}-pyrimidine,
2-alkyloxy-5-{4'-(6-acyloxy-1-trans-heptenyl)-2'-fluorobiphenyl-4-yl}-pyrimidine,
5-(4'-alkyl-2'-fluorobiphenyl-4-yl)-2-(1-trans-alkenyl)-pyrimidine,
5-(4'-alkyl-2'-fluorobiphenyl-4-yl)-2-(6-hydroxy-1-trans-heptenyl)-pyrimidine,
5-(4'-alkyl-2'-fluorobiphenyl-4-yl)-2-(6-alkoxy-1-trans-heptenyl)-pyrimidine,
5-(4'-alkyl-2'-fluorobiphenyl-4-yl)-2-(6-acyloxy-1-trans-heptenyl)-pyrimidine,
5-(4'-alkyloxy-2'-fluorobiphenyl-4-yl)-2-(1-trans-alkenyl)-pyrimidine,
5-(4'-alkyloxy-2'-fluorobiphenyl-4-yl)-2-(6-hydroxy-1-trans-heptenyl)-pyrimidine,
5-(4'-alkyloxy-2'-fluorobiphenyl-4-yl)-2-(6-alkoxy-1-trans-heptenyl)-pyrimidine,
5-(4'-alkyloxy-2'-fluorobiphenyl-4-yl)-2-(6-acyloxy-1-trans-heptenyl)-pyrimidine,
5-(4-alkyl-2-fluorophenyl)-2-{4-(1-trans-alkenyl)-phenyl}-pyrimidine,
5-(4-alkyl-2-fluorophenyl)-2-{4-(6-hydroxy-1-trans-heptenyl)-phenyl}-pyrimidine,
5-(4-alkyl-2-fluorophenyl)-2-{4-(6-alkoxy-1-trans-heptenyl)-phenyl}-pyrimidine,
5-(4-alkyl-2-fluorophenyl)-2-{4-(6-acyloxy-1-trans-heptenyl)-phenyl}-pyrimidine,
5-(4-alkyloxy-2-fluorophenyl)-2-{4-(1-trans-alkenyl)-phenyl}-pyrimidine,
5-(4-alkyloxy-2-fluorophenyl)-2-{4-(6-hydroxy-1-trans-heptenyl)-phenyl}-pyrimidine,
5-(4-alkyloxy-2-fluorophenyl)-2-{4-(6-alkoxy-1-trans-heptenyl)-phenyl}-pyrimidine,
5-(4-alkyloxy-2-fluorophenyl)-2-{4-(6-acyloxy-1-trans-heptenyl)-phenyl}-pyrimidine,
2-(4-alkyl-2-fluorophenyl)-5-{4-(1-trans-alkenyl)-phenyl}-pyrimidine,
2-(4-alkyl-2-fluorophenyl)-5-{4-(6-hydroxy-1-trans-heptenyl)-phenyl}-pyrimidine,
2-(4-alkyl-2-fluorophenyl)-5-{4-(6-alkoxy-1-trans-heptenyl)-phenyl}-pyrimidine,
2-(4-alkyl-2-fluorophenyl)-5-{4-(6-acyloxy-1-trans-heptenyl)-phenyl}-pyrimidine,
2-(4-alkyloxy-2-fluorophenyl)-5-{4-(1-trans-alkenyl)-phenyl}-pyrimidine,
2-(4-alkyloxy-2-fluorophenyl)-5-{4-(6-hydroxy-1-trans-heptenyl)-phenyl}-pyrimidine,
2-(4-alkyloxy-2-fluorophenyl)-5-{4-(6-alkoxy-1-trans-heptenyl)-phenyl}-pyrimidine,
2-(4-alkyloxy-2-fluorophenyl)-5-{4-(6-acyloxy-1-trans-heptenyl)-phenyl}-pyrimidine,
5-(4-alkylphenyl)-2-{4-(1-trans-alkenyl)-2-fluorophenyl}-pyrimidine,
5-(4-alkylphenyl)-2-{4-(6-hydroxy-1-trans-heptenyl)-2-fluorophenyl}-pyrimidine,
5-(4-alkylphenyl)-2-{4-(6-alkoxy-1-trans-heptenyl)-2-fluorophenyl}-pyrimidine,
5-(4-alkylphenyl)-2-{4-(6-acyloxy-1-trans-heptenyl)-2-fluorophenyl}-pyrimidine,
5-(4-alkyloxyphenyl)-2-{4-(1-trans-alkenyl)-2-fluorophenyl}-pyrimidine,
5-(4-alkyloxyphenyl)-2-{4-(6-hydroxy-1-trans-heptenyl)-2-fluorophenyl}-pyrimidine,
5-(4-alkyloxyphenyl)-2-{4-(6-alkoxy-1-trans-heptenyl)-2-fluorophenyl}-pyrimidine,
5-(4-alkyloxyphenyl)-2-{4-(6-acyloxy-1-trans-heptenyl)-2-fluorophenyl}-pyrimidine,
2-(4-alkylphenyl)-5-{4-(1-trans-alkenyl)-2-fluorophenyl}-pyrimidine,
2-(4-alkylphenyl)-5-{4-(6-hydroxy-1-trans-heptenyl-2-fluorophenyl}-pyrimidine,
2-(4-alkylphenyl)-5-{4-(6-alkoxy-1-trans-heptenyl)-2-fluorophenyl}-pyrimidine,
2-(4-alkylphenyl)-5-{4-(6-acyloxy-1-trans-heptenyl)-2-fluorophenyl}-pyrimidine,
2-(4-alkyloxyphenyl)-5-{4-(1-trans-alkenyl)-2-fluorophenyl}-pyrimidine,
2-(4-alkyloxyphenyl)-5-{4-(6-hydroxy-1-trans-heptenyl-2-fluorophenyl}-pyrimidine,
2-(4-alkyloxyphenyl)-5-{4-(6-alkoxy-1-trans-heptenyl)-2-fluorophenyl}-pyrimidine,
2-(4-alkyloxyphenyl)-5-{4-(6-acyloxy-1-trans-heptenyl)-2-fluorophenyl}-pyrimidine,
5-alkyl-2-{4'-(1-trans-alkenyl)-3'-fluorobiphenyl-4-yl}-pyrimidine,
5-alkyl-2-{4'-(6-hydroxy-1-trans-heptenyl)-3'-fluorobiphenyl-4-yl}-pyrimidine,
5-alkyl-2-{4'-(6-alkoxy-1-trans-heptenyl)-3'-fluorobiphenyl-4-yl}-pyrimidine,
5-alkyl-2-{4'-(6-acyloxy-1-trans-heptenyl)-3'-fluorobiphenyl-4-yl}-pyrimidine,
5-alkyloxy-2-{4'-(1-trans-alkenyl)-3'-fluorobiphenyl-4-yl}-pyrimidine,
5-alkyloxy-2-{4'-(6-hydroxy-1-trans-heptenyl)-3'-fluorobiphenyl-4-yl}-pyrimidine,
5-alkyloxy-2-{4'-(6-alkoxy-1-trans-heptenyl)-3'-fluorobiphenyl-4-yl}-pyrimidine,
5-alkyloxy-2-{4'-(6-acyloxy-1-trans-heptenyl)-3'-fluorobiphenyl-4-yl}-pyrimidine,
2-(4'-alkyl-3'-fluorobiphenyl-4-yl)-5-(1-trans-alkenyl)-pyrimidine,
2-(4'-alkyl-3'-fluorobiphenyl-4-yl)-5-(6-hydroxy-1-trans-heptenyl)-pyrimidine,
2-(4'-alkyl-3'-fluorobiphenyl-4-yl)-5-(6-alkoxy-1-trans-heptenyl)-pyrimidine,
2-(4'-alkyl-3'-fluorobiphenyl-4-yl)-5-(6-acyloxy-1-trans-heptenyl)-pyrimidine,
2-(4'-alkyloxy-3'-fluorobiphenyl-4-yl)-5-(1-trans-alkenyl)-pyrimidine,
2-(4'-alkyloxy-3'-fluorobiphenyl-4-yl)-5-(6-hydroxy-1-trans-heptenyl)-pyrimidine,
2-(4'-alkyloxy-3'-fluorobiphenyl-4-yl)-5-(6-alkoxy-1-trans-heptenyl)-pyrimidine,
2-(4'-alkyloxy-3'-fluorobiphenyl-4-yl)-5-(6-acyloxy-1-trans-heptenyl)-pyrimidine,
2-alkyl-5-{4'-(1-trans-alkenyl)-3'-fluorobiphenyl-4-yl}-pyrimidine,
2-alkyl-5-{4'-(6-hydroxy-1-trans-heptenyl)-3'-fluorobiphenyl-4-yl}-pyrimidine,
2-alkyl-5-{4'-(6-alkoxy-1-trans-heptenyl)-3'-fluorobiphenyl-4-yl}-pyrimidine,
2-alkyl-5-{4'-(6-acyloxy-1-trans-heptenyl)-3'-fluorobiphenyl-4-yl}-pyrimidine, 2-alkyloxy-5-{4'-(1-trans-alkenyl)-3'-fluorobiphenyl-4-yl}-pyrimidine,
2-alkyloxy-5-{4'-(6-hydroxy-1-trans-heptenyl)-3'-fluorobiphenyl-4-yl}-pyrimidine,
2-alkyloxy-5-{4'-(6-alkoxy-1-trans-heptenyl)-3'-fluorobiphenyl-4-yl}-pyrimidine,
2-alkyloxy-5-{4'-(6-acyloxy-1-trans-heptenyl)-3'-fluorobiphenyl-4-yl}-pyrimidine,
5-(4'-alkyl-3'-fluorobiphenyl-4-yl)-2-(1-trans-alkenyl)-pyrimidine,
5-(4'-alkyl-3'-fluorobiphenyl-4-yl)-2-(6-hydroxy-1-trans-heptenyl)-pyrimidine,
5-(4'-alkyl-3'-fluorobiphenyl-4-yl)-2-(6-alkoxy-1-trans-heptenyl)-pyrimidine,
5-(4'-alkyl-3'-fluorobiphenyl-4-yl)-2-(6-acyloxy-1-trans-heptenyl)-pyrimidine,
5-(4'-alkyloxy-3'-fluorobiphenyl-4-yl)-2-(1-trans-alkenyl)-pyrimidine,
5-(4'-alkyloxy-3'-fluorobiphenyl-4-yl)-2-(6-hydroxy-1-trans-heptenyl)-pyrimidine,
5-(4'-alkyloxy-3'-fluorobiphenyl-4-yl)-2-(6-alkoxy-1-trans-heptenyl)-pyrimidine,
5-(4'-alkyloxy-3'-fluorobiphenyl-4-yl)-2-(6-acyloxy-1-trans-heptenyl)-pyrimidine,
5-(4-alkyl-3-fluorophenyl)-2-{4-(1-trans-alkenyl)-phenyl}-pyrimidine,
5-(4-alkyl-3-fluorophenyl)-2-{4-(6-hydroxy-1-trans-heptenyl)-phenyl}-pyrimidine,
5-(4-alkyl-3-fluorophenyl)-2-{4-(6-alkoxy-1-trans-heptenyl)-phenyl}-pyrimidine,
5-(4-alkyl-3-fluorophenyl)-2-{4-(6-acyloxy-1-trans-heptenyl)-phenyl}-pyrimidine,
5-(4-alkyloxy-3-fluorophenyl)-2-{4-(1-trans-alkenyl)-phenyl}-pyrimidine,
5-(4-alkyloxy-3-fluorophenyl)-2-{4-(6-hydroxy-1-trans-heptenyl)-phenyl}-pyrimidine,
5-(4-alkyloxy-3-fluorophenyl)-2-{4-(6-alkoxy-1-trans-heptenyl)-phenyl}-pyrimidine,
5-(4-alkyloxy-3-fluorophenyl)-2-{4-(6-acyloxy-1-trans-heptenyl)-phenyl}-pyrimidine,
2-(4-alkyl-3-fluorophenyl)-5-{4-(1-trans-alkenyl)-phenyl}-pyrimidine,
2-(4-alkyl-3-fluorophenyl)-5-{4-(6-hydroxy-1-trans-heptenyl)-phenyl}-pyrimidine,
2-(4-alkyl-3-fluorophenyl)-5-{4-(6-alkoxy-1-trans-heptenyl)-phenyl}-pyrimidine,
2-(4-alkyl-3-fluorophenyl)-5-{4-(6-acyloxy-1-trans-heptenyl)-phenyl}-pyrimidine,
2-(4-alkyloxy-3-fluorophenyl)-5-{4-(1-trans-alkenyl)-phenyl}-pyrimidine,
2-(4-alkyloxy-3-fluorophenyl)-5-{4-(6-hydroxy-1-trans-heptenyl)-phenyl}-pyrimidine,
2-(4-alkyloxy-3-fluorophenyl)-5-{4-(6-alkoxy-1-trans-heptenyl)-phenyl}-pyrimidine,
2-(4-alkyloxy-3-fluorophenyl)-5-{4-(6-acyloxy-1-trans-heptenyl)-phenyl}-pyrimidine,
5-(4-alkylphenyl)-2-{4-(1-trans-alkenyl)-3-fluorophenyl}-pyrimidine,
5-(4-alkylphenyl)-2-{4-(6-hydroxy-1-trans-heptenyl)-3-fluorophenyl}-pyrimidine,
5-(4-alkylphenyl)-2-{4-(6-alkoxy-1-trans-heptenyl)-3-fluorophenyl}-pyrimidine,
5-(4-alkylphenyl)-2-{4-(6-acyloxy-1-trans-heptenyl)-3-fluorophenyl}-pyrimidine,
5-(4-alkyloxyphenyl)-2-{4-(1-trans-alkenyl)-3-fluorophenyl}-pyrimidine,
5-(4-alkyloxyphenyl)-2-{4-(6-hydroxy-1-trans-heptenyl)-3-fluorophenyl}-pyrimidine,
5-(4-alkyloxyphenyl)-2-{4-(6-alkoxy-1-trans-heptenyl)-3-fluorophenyl}-pyrimidine,
5-(4-alkyloxyphenyl)-2-{4-(6-acyloxy-1-trans-heptenyl)-3-fluorophenyl}-pyrimidine,
2-(4-alkylphenyl)-5-{4-(1-trans-alkenyl)-2-fluorophenyl}-pyrimidine,
2-(4-alkylphenyl)-5-{4-(6-hydroxy-1-trans-heptenyl)-2-fluorophenyl}-pyrimidine,
2-(4-alkylphenyl)-5-{4-(6-alkoxy-1-trans-heptenyl)-2-fluorophenyl}-pyrimidine,
2-(4-alkylphenyl)-5-{4-(6-acyloxy-1-trans-heptenyl)-2-fluorophenyl}-pyrimidine,
2-(4-alkyloxyphenyl)-5-{4-(1-trans-alkenyl)-2-fluorophenyl}-pyrimidine,
2-(4-alkyloxyphenyl)-5-{4-(6-hydroxy-1-trans-heptenyl)-2-fluorophenyl}-pyrimidine,
2-(4-alkyloxyphenyl)-5-{4-(6-alkoxy-1-trans-heptenyl)-2-fluorophenyl}-pyrimidine,
2-(4-alkyloxyphenyl)-5-{4-(6-acyloxy-1-trans-heptenyl)-2-fluorophenyl}-pyrimidine,
7-alkyl-3-{4-(1-trans-alkenyl)-2-fluorophenyl}-isoquinoline,
7-alkyl-3-{4-(6-hydroxy-1-trans-heptenyl)-2-fluorophenyl}-isoquinoline,
7-alkyl-3-{4-(6-alkoxy-1-trans-heptenyl)-2-fluorophenyl}-isoquinoline,
7-alkyl-3-{4-(6-acyloxy-1-trans-heptenyl)-2-fluorophenyl}-isoquinoline,
7-alkyloxy-3-{4-(1-trans-alkenyl)-2-fluorophenyl}-isoquinoline,
7-alkyloxy-3-{4-(6-hydroxy-1-trans-heptenyl)-2-fluorophenyl}-isoquinoline,
7-alkyloxy-3-{4-(6-alkoxy-1-trans-heptenyl)-2-fluorophenyl}-isoquinoline,
7-alkyloxy-3-{4-(6-acyloxy-1-trans-heptenyl)-2-fluorophenyl}-isoquinoline,
3-(4-alkyl-2-fluorophenyl)-7-(1-trans-alkenyl)-isoquinoline,
3-(4-alkyl-2-fluorophenyl)-7-(6-hydroxy-1-trans-heptenyl)-isoquinoline,
3-(4-alkyl-2-fluorophenyl)-7-(6-alkoxy-1-trans-heptenyl)-isoquinoline,
3-(4-alkyl-2-fluorophenyl)-7-(6-acyloxy-1-trans-heptenyl)-isoquinoline,
3-(4-alkyloxy-2-fluorophenyl)-7-(1-trans-alkenyl)-isoquinoline,
3-(4-alkyloxy-2-fluorophenyl)-7-(6-hydroxy-1-trans-heptenyl)-isoquinoline,
3-(4-alkyloxy-2-fluorophenyl)-7-(6-alkoxy-1-trans-heptenyl)-isoquinoline,
3-(4-alkyloxy-2-fluorophenyl)-7-(6-acyloxy-1-trans-heptenyl)-isoquinoline,
7-alkyl-3-{4-(1-trans-alkenyl)-3-fluorophenyl}-isoquinoline,
7-alkyl-3-{4-(6-hydroxy-1-trans-heptenyl)-3-fluorophenyl}-isoquinoline,
7-alkyl-3-{4-(6-alkoxy-1-trans-heptenyl)-3-fluorophenyl}-isoquinoline,
7-alkyl-3-{4-(6-acyloxy-1-trans-heptenyl)-3-fluorophenyl}-isoquinoline,
7-alkyloxy-3-{4-(1-trans-alkenyl)-3-fluorophenyl}-isoquinoline,
7-alkyloxy-3-{4-(6-hydroxy-1-trans-heptenyl)-3-fluorophenyl}-isoquinoline,
7-alkyloxy-3-{4-(6-alkoxy-1-trans-heptenyl)-3-fluorophenyl}-isoquinoline,
7-alkyloxy-3-{4-(6-acyloxy-1-trans-heptenyl)-3-fluorophenyl}-isoquinoline, 3-(4-alkyl-3-fluorophenyl)-7-(1-trans-alkenyl)-isoquinoline,
3-(4-alkyl-3-fluorophenyl)-7-(6-hydroxy-1-trans-heptenyl)-isoquinoline,
3-(4-alkyl-3-fluorophenyl)-7-(6-alkoxy-1-trans-heptenyl)-isoquinoline,
3-(4-alkyl-3-fluorophenyl)-7-(6-acyloxy-1-trans-heptenyl)-isoquinoline,
3-(4-alkyloxy-3-fluorophenyl)-7-(1-trans-alkenyl)-isoquinoline,
3-(4-alkyloxy-3-fluorophenyl)-7-(6-hydroxy-1-trans-heptenyl)-isoquinoline,
3-(4-alkyloxy-3-fluorophenyl)-7-(6-alkoxy-1-trans-heptenyl)-isoquinoline,
3-(4-alkyloxy-3-fluorophenyl)-7-(6-acyloxy-1-trans-heptenyl)-isoquinoline,
6-alkyl-2-{4-(1-trans-alkenyl)-2-fluorophenyl}-quinoline,
6-alkyl-2-{4-(6-hydroxy-1-trans-heptenyl)-2-fluorophenyl}-quinoline,
6-alkyl-2-{4-(6-alkoxy-1-trans-heptenyl)-2-fluorophenyl}-quinoline,
6-alkyl-2-{4-(6-acyloxy-1-trans-heptenyl)-2-fluorophenyl}-quinoline,
6-alkyloxy-2-{4-(1-trans-alkenyl)-2-fluorophenyl}-quinoline,
6-alkyloxy-2-{4-(6-hydroxy-1-trans-heptenyl)-2-fluorophenyl}-quinoline,
6-alkyloxy-2-{4-(6-alkoxy-1-trans-heptenyl)-2-fluorophenyl}-quinoline,
6-alkyloxy-2-{4-(6-acyloxy-1-trans-heptenyl)-2-fluorophenyl}-quinoline,
2-(4-alkyl-2-fluorophenyl)-6-(1-trans-alkenyl)-quinoline,
2-(4-alkyl-2-fluorophenyl)-6-(6-hydroxy-1-trans-heptenyl)-quinoline,
2-(4-alkyl-2-fluorophenyl)-6-(6-alkoxy-1-trans-heptenyl)-quinoline,
2-(4-alkyl-2-fluorophenyl)-6-(6-acyloxy-1-trans-heptenyl)-quinoline,
2-(4-alkyloxy-2-fluorophenyl)-6-(1-trans-alkenyl)-quinoline,
2-(4-alkyloxy-2-fluorophenyl)-6-(6-hydroxy-1-trans-heptenyl)-quinoline,
2-(4-alkyloxy-2-fluorophenyl)-6-(6-alkoxy-1-trans-heptenyl)-quinoline,
2-(4-alkyloxy-2-fluorophenyl)-6-(6-acyloxy-1-trans-heptenyl)-quinoline,
6-alkyl-2-{4-(1-trans-alkenyl)-3-fluorophenyl}-quinoline,
6-alkyl-2-{4-(6-hydroxy-1-trans-heptenyl)-3-fluorophenyl}-quinoline,
6-alkyl-2-{4-(6-alkoxy-1-trans-heptenyl)-3-fluorophenyl}-quinoline,
6-alkyl-2-{4-(6-acyloxy-1-trans-heptenyl)-3-fluorophenyl}-quinoline,
6-alkyloxy-2-{4-(1-trans-alkenyl)-3-fluorophenyl}-quinoline,
6-alkyloxy-2-{4-(6-hydroxy-1-trans-heptenyl)-3-fluorophenyl}-quinoline,
6-alkyloxy-2-{4-(6-alkoxy-1-trans-heptenyl)-3-fluorophenyl}-quinoline,
6-alkyloxy-2-{4-(6-acyloxy-1-trans-heptenyl)-3-fluorophenyl}-quinoline,
2-(4-alkyl-3-fluorophenyl)-6-(1-trans-alkenyl)-quinoline,
2-(4-alkyl-3-fluorophenyl)-6-(6-hydroxy-1-trans-heptenyl)-quinoline,
2-(4-alkyl-3-fluorophenyl)-6-(6-alkoxy-1-trans-heptenyl)-quinoline,
2-(4-alkyl-3-fluorophenyl)-6-(6-acyloxy-1-trans-heptenyl)-quinoline,
2-(4-alkyloxy-3-fluorophenyl)-6-(1-trans-alkenyl)-quinoline,
2-(4-alkyloxy-3-fluorophenyl)-6-(6-hydroxy-1-trans-heptenyl)-quinoline,
2-(4-alkyloxy-3-fluorophenyl)-6-(6-alkoxy-1-trans-heptenyl)-quinoline,
2-(4-alkyloxy-3-fluorophenyl)-6-(6-acyloxy-1-trans-heptenyl)-quinoline,
2-alkyl-6-{4-(1-trans-alkenyl)-2-fluorophenyl}-quinoxaline,
2-alkyl-6-{4-(6-hydroxy-1-trans-heptenyl)-2-fluorophenyl}-quinoxaline,
2-alkyl-6-{4-(6-alkoxy-1-trans-heptenyl)-2-fluorophenyl}-quinoxaline,
2-alkyl-6-{4-(6-acyloxy-1-trans-heptenyl)-2-fluorophenyl}-quinoxaline,
2-alkyloxy-6-{4-(1-trans-alkenyl)-2-fluorophenyl}-quinoxaline,
2-alkyloxy-6-{4-(6-hydroxy-1-trans-heptenyl)-2-fluorophenyl}-quinoxaline,
2-alkyloxy-6-{4-(6-alkoxy-1-trans-heptenyl)-2-fluorophenyl}-quinoxaline,
2-alkyloxy-6-{4-(6-acyloxy-1-trans-heptenyl)-2-fluorophenyl}-quinoxaline,
2-(1-trans-alkenyl)-6-(4-alkyl-2-fluorophenyl)-quinoxaline,
2-(6-hydroxy-1-trans-heptenyl)-6-(4-alkyl-2-fluorophenyl)-quinoxaline,
2-(6-alkoxy-1-trans-heptenyl)-6-(4-alkyl-2-fluorophenyl)-quinoxaline,
2-(6-acyloxy-1-trans-heptenyl)-6-(4-alkyl-2-fluorophenyl)-quinoxaline,
2-(1-trans-alkenyl)-6-(4-alkyloxy-2-fluorophenyl)-quinoxaline,
2-(6-hydroxy-1-trans-heptenyl)-6-(4-alkyloxy-2-fluorophenyl)-quinoxaline,
2-(6-alkoxy-1-trans-heptenyl)-6-(4-alkyloxy-2-fluorophenyl)-quinoxaline,
2-(6-acyloxy-1-trans-heptenyl)-6-(4-alkyloxy-2-fluorophenyl)-quinoxaline,
6-alkyl-2-{4-(1-trans-alkenyl)-2-fluorophenyl}-quinoxaline,
6-alkyl-2-{4-(6-hydroxy-1-trans-heptenyl)-2-fluorophenyl}-quinoxaline,
6-alkyl-2-{4-(6-alkoxy-1-trans-heptenyl)-2-fluorophenyl}-quinoxaline,
6-alkyl-2-{4-(6-acyloxy-1-trans-heptenyl)-2-fluorophenyl}-quinoxaline,
6-alkyloxy-2-{4-(1-trans-alkenyl)-2-fluorophenyl}-quinoxaline,
6-alkyloxy-2-{4-(6-hydroxy-1-trans-heptenyl)-2-fluorophenyl}-quinoxaline,
6-alkyloxy-2-{4-(6-alkoxy-1-trans-heptenyl)-2-fluorophenyl}-quinoxaline,
6-alkyloxy-2-{4-(6-acyloxy-1-trans-heptenyl)-2-fluorophenyl}-quinoxaline,
2-(4-alkyl-2-fluorophenyl)-6-(1-trans-alkenyl)-quinoxaline,
2-(4-alkyl-2-fluorophenyl)-6-(6-hydroxy-1-trans-heptenyl-quinoxaline,
2-(4-alkyl-2-fluorophenyl)-6-(6-alkoxy-1-trans-heptenyl)-quinoxaline,
2-(4-alkyl-2-fluorophenyl)-6-(6-acyloxy-1-trans-heptenyl)-quinoxaline,
2-(4-alkyloxy-2-fluorophenyl)-6-(1-trans-alkenyl)-quinoxaline,
2-(4-alkyloxy-2-fluorophenyl)-6-(6-hydroxy-1-trans-heptenyl-quinoxaline,
2-(4-alkyloxy-2-fluorophenyl)-6-(6-alkoxy-1-trans-heptenyl)-quinoxaline, 2-(4-alkyloxy-2-fluorophenyl)-6-(6-acyloxy-1-trans-heptenyl)-quinoxaline,
2-alkyl-6-{4-(1-trans-alkenyl)-3-fluorophenyl}-quinoxaline,
2-alkyl-6-{4-(6-hydroxy-1-trans-heptenyl)-3-fluorophenyl}-quinoxaline,
2-alkyl-6-{4-(6-alkoxy-1-trans-heptenyl)-3-fluorophenyl}-quinoxaline,
2-alkyl-6-{4-(6-acyloxy-1-trans-heptenyl)-3-fluorophenyl}-quinoxaline,
2-alkyloxy-6-{4-(1-trans-alkenyl)-3-fluorophenyl}-quinoxaline,
2-alkyloxy-6-{4-(6-hydroxy-1-trans-heptenyl)-3-fluorophenyl}-quinoxaline,
2-alkyloxy-6-{4-(6-alkoxy-1-trans-heptenyl)-3-fluorophenyl}-quinoxaline,
2-alkyloxy-6-{4-(6-acyloxy-1-trans-heptenyl)-3-fluorophenyl}-quinoxaline,
2-(1-trans-alkenyl-6-(4-alkyl-3-fluorophenyl)-quinoxaline,
2-(6-hydroxy-1-trans-heptenyl)-6-(4-alkyl-3-fluorophenyl)-quinoxaline,
2-(6-alkoxy-1-trans-heptenyl)-6-(4-alkyl-3-fluorophenyl)-quinoxaline,
2-(6-acyloxy-1-trans-heptenyl)-6-(4-alkyl-3-fluorophenyl)-quinoxaline,
2-(1-trans-alkenyl)-6-(4-alkyloxy-3-fluorophenyl)-quinoxaline,
2-(6-hydroxy-1-trans-heptenyl)-6-(4-alkyloxy-3-fluorophenyl)-quinoxaline,
2-(6-alkoxy-1-trans-heptenyl)-6-(4-alkyloxy-3-fluorophenyl)-quinoxaline,
2-(6-acyloxy-1-trans-heptenyl)-6-(4-alkyloxy-3-fluorophenyl)-quinoxaline,
6-alkyl-2-{4-(1-trans-alkenyl)-3-fluorophenyl}-quinoxaline,
6-alkyl-2-{4-(6-hydroxy-1-trans-heptenyl)-3-fluorophenyl}-quinoxaline,
6-alkyl-2-{4-(6-alkoxy-1-trans-heptenyl)-3-fluorophenyl}-quinoxaline,
6-alkyl-2-{4-(6-acyloxy-1-trans-heptenyl)-3-fluorophenyl}-quinoxaline,
6-alkyloxy-2-{4-(1-trans-alkenyl)-3-fluorophenyl}-quinoxaline,
6-alkyloxy-2-{4-(6-hydroxy-1-trans-heptenyl)-3-fluorophenyl}-quinoxaline,
6-alkyloxy-2-{4-(6-alkoxy-1-trans-heptenyl)-3-fluorophenyl}-quinoxaline,
6-alkyloxy-2-{4-(6-acyloxy-1-trans-heptenyl)-3-fluorophenyl}-quinoxaline,
2-(4-alkyl-3-fluorophenyl)-6-(1-trans-alkenyl)-quinoxaline,
2-(4-alkyl-3-fluorophenyl)-6-(6-hydroxy-1-trans-heptenyl)-quinoxaline,
2-(4-alkyl-3-fluorophenyl)-6-(6-alkoxy-1-trans-heptenyl)-quinoxaline,
2-(4-alkyl-3-fluorophenyl)-6-(6-acyloxy-1-trans-heptenyl)-quinoxaline,
2-(4-alkyloxy-3-fluorophenyl)-6-(1-trans-alkenyl)-quinoxaline,
2-(4-alkyloxy-3-fluorophenyl)-6-(6-hydroxy-1-trans-heptenyl)-quinoxaline,
2-(4-alkyloxy-3-fluorophenyl)-6-(6-alkoxy-1-trans-heptenyl)-quinoxaline,
2-(4-alkyloxy-3-fluorophenyl)-6-(6-acyloxy-1-trans-heptenyl)-quinoxaline,
2-alkyl-6-{4-(1-trans-alkenyl)-2-fluorophenyl}-quinazoline,
2-alkyl-6-{4-(6-hydroxy-1-trans-heptenyl)-2-fluorophenyl}-quinazoline,
2-alkyl-6-{4-(6-alkoxy-1-trans-heptenyl)-2-fluorophenyl}-quinazoline,
2-alkyl-6-{4-(6-acyloxy-1-trans-heptenyl)-2-fluorophenyl}-quinazoline,
2-alkyloxy-6-{4-(1-trans-alkenyl)-2-fluorophenyl}-quinazoline,
2-alkyloxy-6-{4-(6-hydroxy-1-trans-heptenyl)-2-fluorophenyl}-quinazoline,
2-alkyloxy-6-{4-(6-alkoxy-1-trans-heptenyl)-2-fluorophenyl}-quinazoline,
2-alkyloxy-6-{4-(6-acyloxy-1-trans-heptenyl)-2-fluorophenyl}-quinazoline,
2-(1-trans-alkenyl)-6-(4-alkyl-2-fluorophenyl)-quinazoline,
2-(6-hydroxy-1-trans-heptenyl)-6-(4-alkyl-2-fluorophenyl)-quinazoline,
2-(6-alkoxy-1-trans-heptenyl)-6-(4-alkyl-2-fluorophenyl)-quinazoline,
2-(6-acyloxy-1-trans-heptenyl)-6-(4-alkyl-2-fluorophenyl)-quinazoline,
2-(1-trans-alkenyl)-6-(4-alkyloxy-2-fluorophenyl)-quinazoline,
2-(6-hydroxy-1-trans-heptenyl)-6-(4-alkyloxy-2-fluorophenyl)-quinazoline,
2-(6-alkoxy-1-trans-heptenyl)-6-(4-alkyloxy-2-fluorophenyl)-quinazoline,
2-(6-acyloxy-1-trans-heptenyl)-6-(4-alkyloxy-2-fluorophenyl)-quinazoline,
2-alkyl-6-{4-(1-trans-alkenyl)-3-fluorophenyl}-quinazoline,
2-alkyl-6-{4-(6-hydroxy-1-trans-heptenyl)-3-fluorophenyl}-quinazoline,
2-alkyl-6-{4-(6-alkoxy-1-trans-heptenyl)-3-fluorophenyl}-quinazoline,
2-alkyl-6-{4-(6-acyloxy-1-trans-heptenyl)-3-fluorophenyl}-quinazoline,
2-alkyloxy-6-{4-(1-trans-alkenyl)-3-fluorophenyl}-quinazoline,
2-alkyloxy-6-{4-(6-hydroxy-1-trans-heptenyl)-3-fluorophenyl}-quinazoline,
2-alkyloxy-6-{4-(6-alkoxy-1-trans-heptenyl)-3-fluorophenyl}-quinazoline,
2-alkyloxy-6-{4-(6-acyloxy-1-trans-heptenyl)-3-fluorophenyl}-quinazoline,
2-(1-trans-alkenyl)-6-(4-alkyl-3-fluorophenyl)-quinazoline,
2-(6-hydroxy-1-trans-heptenyl)-6-(4-alkyl-3-fluorophenyl)-quinazoline,
2-(6-alkoxy-1-trans-heptenyl)-6-(4-alkyl-3-fluorophenyl)-quinazoline,
2-(6-acyloxy-1-trans-heptenyl)-6-(4-alkyl-3-fluorophenyl)-quinazoline,
2-(1-trans-alkenyl)-6-(4-alkyloxy-3-fluorophenyl)-quinazoline,
2-(6-hydroxy-1-trans-heptenyl)-6-(4-alkyloxy-3-fluorophenyl)-quinazoline,
2-(6-alkoxy-1-trans-heptenyl)-6-(4-alkyloxy-3-fluorophenyl)-quinazoline,
2-(6-acyloxy-1-trans-heptenyl)-6-(4-alkyloxy-3-fluorophenyl)-quinazoline,
4"-alkyl-2,3-difluoro-4-(1-trans-alkenyl)-biphenyl,
4"-alkyl-2,3-difluoro-4-(6-hydroxy-1-trans-heptenyl)-biphenyl,
4"-alkyl-2,3-difluoro-4-(6-alkoxy-1-trans-heptenyl)-biphenyl,
4"-alkyl-2,3-difluoro-4-(6-acyloxy-1-trans-heptenyl)-biphenyl,
4"-alkyloxy-2,3-difluoro-4-(1-trans-alkenyl)-biphenyl,
4"-alkyloxy-2,3-difluoro-4-(6-hydroxy-1-trans-heptenyl)-biphenyl, 4"-alkyloxy-2,3-difluoro-4-(6-alkoxy-1-trans-heptenyl)-biphenyl,
4"-alkyloxy-2,3-difluoro-4-(6-acyloxy-1-trans-heptenyl)-biphenyl,
4-alkyl-2,3-difluoro-4'-(1-trans-alkenyl)-biphenyl,
4-alkyl-2,3-difluoro-4'-(6-hydroxy-1-trans-heptenyl)-biphenyl,
4-alkyl-2,3-difluoro-4'-(6-alkoxy-1-trans-heptenyl)-biphenyl,
4-alkyl-2,3-difluoro-4'-(6-acyloxy-1-trans-heptenyl)-biphenyl,
4-alkyloxy-2,3-difluoro-4'-(1-trans-alkenyl)-biphenyl,
4-alkyloxy-2,3-difluoro-4'-(6-hydroxy-1-trans-heptenyl)-biphenyl,
4-alkyloxy-2,3-difluoro-4'-(6-alkoxy-1-trans-heptenyl)-biphenyl,
4-alkyloxy-2,3-difluoro-4'-(6-acyloxy-1-trans-heptenyl)-biphenyl,
2-alkyl-6-{4-(1-trans-alkenyl)-2,3-difluorophenyl}-naphthalene,
2-alkyl-6-{4-(6-hydroxy-1-trans-heptenyl)-2,3-difluorophenyl}-naphthalene,
2-alkyl-6-{4-(6-alkoxy-1-trans-heptenyl)-2,3-difluorophenyl}-naphthalene,
2-alkyl-6-{4-(6-acyloxy-1-trans-heptenyl)-2,3-difluorophenyl}-naphthalene,
2-alkyloxy-6-{4-(1-trans-alkenyl)-2,3-difluorophenyl}-naphthalene,
2-alkyloxy-6-{4-(6-hydroxy-1-trans-heptenyl)-2,3-difluorophenyl}-naphthalene,
2-alkyloxy-6-{4-(6-alkoxy-1-trans-heptenyl)-2,3-difluorophenyl}-naphthalene,
2-alkyloxy-6-{4-(6-acyloxy-1-trans-heptenyl)-2,3-difluorophenyl}-naphthalene,
2-{4-alkyl-2,3-difluorophenyl}-6-(1-trans-alkenyl)-naphthalene,
2-{4-alkyl-2,3-difluorophenyl}-6-(6-hydroxy-1-trans-heptenyl)-naphthalene,
2-{4-alkyl-2,3-difluorophenyl}-6-(6-alkoxy-1-trans-heptenyl)-naphthalene,
2-{4-alkyl-2,3-difluorophenyl}-6-(6-acyloxy-1-trans-heptenyl)-naphthalene,
2-{4-alkyloxy-2,3-difluorophenyl}-6-(1-trans-alkenyl)-naphthalene,
2-{4-alkyloxy-2,3-difluorophenyl}-6-(6-hydroxy-1-trans-heptenyl)-naphthalene,
2-{4-alkyloxy-2,3-difluorophenyl}-6-(6-alkoxy-1-trans-heptenyl)-naphthalene,
2-{4-alkyloxy-2,3-difluorophenyl}-6-(6-acyloxy-1-trans-heptenyl)-naphthalene,
4"-alkyl-2,3-difluoro-4-(1-trans-alkenyl)-p-terphenyl,
4"-alkyl-2,3-difluoro-4-(6-hydroxy-1-trans-heptenyl)-p-terphenyl,
4"-alkyl-2,3-difluoro-4-(6-alkoxy-1-trans-heptenyl)-p-terphenyl,
4"-alkyl-2,3-difluoro-4-(6-acyloxy-1-trans-heptenyl)-p-terphenyl,
4"-alkyloxy-2,3-difluoro-4-(1-trans-alkenyl)-p-terphenyl,
4"-alkyloxy-2,3-difluoro-4-(6-hydroxy-1-trans-heptenyl)-p-terphenyl,
4"-alkyloxy-2,3-difluoro-4-(6-alkoxy-1-trans-heptenyl)-p-terphenyl,
4"-alkyloxy-2,3-difluoro-4-(6-acyloxy-1-trans-heptenyl)-p-terphenyl,
4-alkyl-2,3-difluoro-4"-(1-trans-alkenyl)-p-terphenyl,
4-alkyl-2,3-difluoro-4"-(6-hydroxy-1-trans-heptenyl)-p-terphenyl,
4-alkyl-2,3-difluoro-4"-(6-alkoxy-1-trans-heptenyl)-p-terphenyl,
4-alkyl-2,3-difluoro-4"-(6-acyloxy-1-trans-heptenyl)-p-terphenyl,
4-alkyloxy-2,3-difluoro-4"-(1-trans-alkenyl)-p-terphenyl,
4-alkyloxy-2,3-difluoro-4"-(6-hydroxy-1-trans-heptenyl)-p-terphenyl,
4-alkyloxy-2,3-difluoro-4"-(6-alkoxy-1-trans-heptenyl)-p-terphenyl,
4-alkyloxy-2,3-difluoro-4"-(6-acyloxy-1-trans-heptenyl)-p-terphenyl,
4"-alkyl-2',3'-difluoro-4-(1-trans-alkenyl)-p-terphenyl,
4"-alkyl-2',3'-difluoro-4-(6-hydroxy-1-trans-heptenyl)-p-terphenyl,
4"-alkyl-2',3'-difluoro-4-(6-alkoxy-1-trans-heptenyl)-p-terphenyl,
4"-alkyl-2',3'-difluoro-4-(6-acyloxy-1-trans-heptenyl)-p-terphenyl,
4"-alkyloxy-2',3'-difluoro-4-(1-trans-alkenyl)-p-terphenyl,
4"-alkyloxy-2',3'-difluoro-4-(6-hydroxy-1-trans-heptenyl)-p-terphenyl,
4"-alkyloxy-2',3'-difluoro-4-(6-alkoxy-1-trans-heptenyl)-p-terphenyl,
4"-alkyloxy-2',3'-difluoro-4-(6-acyloxy-1-trans-heptenyl)-p-terphenyl,
5-alkyl-2-{4-(1-trans-alkenyl)-2,3-difluorophenyl}-pyridine,
5-alkyl-2-{4-(6-hydroxy-1-trans-heptenyl)-2,3-difluorophenyl}-pyridine,
5-alkyl-2-{4-(6-alkoxy-1-trans-heptenyl)-2,3-difluorophenyl}-pyridine,
5-alkyl-2-{4-(6-acyloxy-1-trans-heptenyl)-2,3-difluorophenyl}-pyridine,
5-alkyloxy-2-{4-(1-trans-alkenyl)-2,3-difluorophenyl}-pyridine,
5-alkyloxy-2-{4-(6-hydroxy-1-trans-heptenyl)-2,3-difluorophenyl}-pyridine,
5-alkyloxy-2-{4-(6-alkoxy-1-trans-heptenyl)-2,3-difluorophenyl}-pyridine,
5-alkyloxy-2-{4-(6-acyloxy-1-trans-heptenyl)-2,3-difluorophenyl}-pyridine,
2-(4-alkyl-2,3-difluorophenyl)-5-(1-trans-alkenyl)-pyridine,
2-(4-alkyl-2,3-difluorophenyl)-5-(6-hydroxy-1-trans-heptenyl)-pyridine,
2-(4-alkyl-2,3-difluorophenyl)-5-(6-alkoxy-1-trans-heptenyl)-pyridine,
2-(4-alkyl-2,3-difluorophenyl)-5-(6-acyloxy-1-trans-heptenyl)-pyridine,
2-(4-alkyloxy-2,3-difluorophenyl)-5-(1-trans-alkenyl)-pyridine,
2-(4-alkyloxy-2,3-difluorophenyl)-5-(6-hydroxy-1-trans-heptenyl)-pyridine,
2-(4-alkyloxy-2,3-difluorophenyl)-5-(6-alkoxy-1-trans-heptenyl)-pyridine,
2-(4-alkyloxy-2,3-difluorophenyl)-5-(6-acyloxy-1-trans-heptenyl)-pyridine,
2-alkyl-5-{4-(1-trans-alkenyl)-2,3-difluorophenyl}-pyridine,
2-alkyl-5-{4-(6-hydroxy-1-trans-heptenyl)-2,3-difluorophenyl}-pyridine,
2-alkyl-5-{4-(6-alkoxy-1-trans-heptenyl)-2,3-difluorophenyl}-pyridine,
2-alkyl-5-{4-(6-acyloxy-1-trans-heptenyl)-2,3-difluorophenyl}-pyridine,
2-alkyloxy-5-{4-(1-trans-alkenyl)-2,3-difluorophenyl}-pyridine,
2-alkyloxy-5-{4-(6-hydroxy-1-trans-heptenyl)-2,3-difluorophenyl}-pyridine, 2-alkyloxy-5-{4-(6-alkoxy-1-trans-heptenyl)-2,3-difluorophenyl}-pyridine,
2-alkyloxy-5-{4-(6-acyloxy-1-trans-heptenyl)-2,3-difluorophenyl}-pyridine,
5-(4-alkyl-2,3-difluorophenyl)-2-(1-trans-alkenyl)-pyridine,
5-(4-alkyl-2,3-difluorophenyl)-2-(6-hydroxy-1-trans-heptenyl)-pyridine,
5-(4-alkyl-2,3-difluorophenyl)-2-(6-alkoxy-1-trans-heptenyl)-pyridine,
5-(4-alkyl-2,3-difluorophenyl)-2-(6-acyloxy-1-trans-heptenyl)-pyridine,
5-(4-alkyloxy-2,3-difluorophenyl)-2-(1-trans-alkenyl)-pyridine,
5-(4-alkyloxy-2,3-difluorophenyl)-2-(6-hydroxy-1-trans-heptenyl)-pyridine,
5-(4-alkyloxy-2,3-difluorophenyl)-2-(6-alkoxy-1-trans-heptenyl)-pyridine,
5-(4-alkyloxy-2,3-difluorophenyl)-2-(6-acyloxy-1-trans-heptenyl)-pyridine,
2-alkyl-5-{4'-(1-trans-alkenyl)-2',3'-difluorobiphenyl-4-yl}-pyridine,
2-alkyl-5-{4'-(6-hydroxy-1-trans-heptenyl)-2',3'-difluorobiphenyl-4-yl}-pyridine,
2-alkyl-5-{4'-(6-alkoxy-1-trans-heptenyl)-2',3'-difluorobiphenyl-4-yl}-pyridine,
2-alkyl-5-{4'-(6-acyloxy-1-trans-heptenyl)-2',3'-difluorobiphenyl-4-yl}-pyridine,
2-alkyloxy-5-{4'-(1-trans-alkenyl)-2',3'-difluorobiphenyl-4-yl}-pyridine,
2-alkyloxy-5-{4'-(6-hydroxy-1-trans-heptenyl)-2',3'-difluorobiphenyl-4-yl}-pyridine,
2-alkyloxy-5-{4'-(6-alkoxy-1-trans-heptenyl)-2',3'-difluorobiphenyl-4-yl}-pyridine,
2-alkyloxy-5-{4'-(6-acyloxy-1-trans-heptenyl)-2',3'-difluorobiphenyl-4-yl}-pyridine,
5-(4'-alkyl-2',3'-difluorobiphenyl-4-yl)-2-(1-trans-alkenyl)-pyridine,
5-(4'-alkyl-2',3'-difluorobiphenyl-4-yl)-2-(6-hydroxy-1-trans-heptenyl)-pyridine,
5-(4'-alkyl-2',3'-difluorobiphenyl-4-yl)-2-(6-alkoxy-1-trans-heptenyl)-pyridine,
5-(4'-alkyl-2',3'-difluorobiphenyl-4-yl)-2-(6-acyloxy-1-trans-heptenyl)-pyridine,
5-(4'-alkyloxy-2',3'-difluorobiphenyl-4-yl)-2-(1-trans-alkenyl)-pyridine,
5-(4'-alkyloxy-2',3'-difluorobiphenyl-4-yl)-2-(6-hydroxy-1-trans-heptenyl)-pyridine,
5-(4'-alkyloxy-2',3'-difluorobiphenyl-4-yl)-2-(6-alkoxy-1-trans-heptenyl)-pyridine,
5-(4'-alkyloxy-2',3'-difluorobiphenyl-4-yl)-2-(6-acyloxy-1-trans-heptenyl)-pyridine,
5-alkyl-2-{4'-(1-trans-alkenyl)-2',3'-difluorobiphenyl-4-yl}-pyridine,
5-alkyl-2-{4'-(6-hydroxy-1-trans-heptenyl)-2',3'-difluorobiphenyl-4-yl}-pyridine,
5-alkyl-2-{4'-(6-alkoxy-1-trans-heptenyl)-2',3'-difluorobiphenyl-4-yl}-pyridine,
5-alkyl-2-{4'-(6-acyloxy-1-trans-heptenyl)-2',3'-difluorobiphenyl-4-yl}-pyridine,
5-alkyloxy-2-{4'-(1-trans-alkenyl)-2',3'-difluorobiphenyl-4-yl}-pyridine,
5-alkyloxy-2-{4'-(6-hydroxy-1-trans-heptenyl)-2',3'-difluorobiphenyl-4-yl}-pyridine,
5-alkyloxy-2-{4'-(6-alkoxy-1-trans-heptenyl)-2',3'-difluorobiphenyl-4-yl}-pyridine,
5-alkyloxy-2-{4'-(6-acyloxy-1-trans-heptenyl)-2',3'-difluorobiphenyl-4-yl}-pyridine,
2-(4'-alkyl-2',3'-difluorobiphenyl-4-yl)-5-(1-trans-alkenyl)-pyridine,
2-(4'-alkyl-2',3'-difluorobiphenyl-4-yl)-5-(6-hydroxy-1-trans-heptenyl)-pyridine,
2-(4'-alkyl-2',3'-difluorobiphenyl-4-yl)-5-(6-alkoxy-1-trans-heptenyl)-pyridine,
2-(4'-alkyl-2',3'-difluorobiphenyl-4-yl)-5-(6-acyloxy-1-trans-heptenyl)-pyridine,
2-(4'-alkyloxy-2',3'-difluorobiphenyl-4-yl)-5-(1-trans-alkenyl)-pyridine,
2-(4'-alkyloxy-2',3'-difluorobiphenyl-4-yl)-5-(6-hydroxy-1-trans-heptenyl)-pyridine,
2-(4'-alkyloxy-2',3'-difluorobiphenyl-4-yl)-5-(6-alkoxy-1-trans-heptenyl)-pyridine,
2-(4'-alkyloxy-2',3'-difluorobiphenyl-4-yl)-5-(6-acyloxy-1-trans-heptenyl)-pyridine,
5-(4-alkyl-2,3-difluorophenyl)-2-{4-(1-trans-alkenyl)-phenyl}-pyridine,
5-(4-alkyl-2,3-difluorophenyl)-2-{4-(6-hydroxy-1-trans-heptenyl)-phenyl}-pyridine,
5-(4-alkyl-2,3-difluorophenyl)-2-{4-(6-alkoxy-1-trans-heptenyl)-phenyl}-pyridine,
5-(4-alkyl-2,3-difluorophenyl)-2-{4-(6-acyloxy-1-trans-heptenyl)-phenyl}-pyridine,
5-(4-alkyloxy-2,3-difluorophenyl)-2-{4-(1-trans-alkenyl)-phenyl}-pyridine,
5-(4-alkyloxy-2,3-difluorophenyl)-2-{4-(6-hydroxy-1-trans-heptenyl)-phenyl}-pyridine,
5-(4-alkyloxy-2,3-difluorophenyl)-2-{4-(6-alkoxy-1-trans-heptenyl)-phenyl}-pyridine,
5-(4-alkyloxy-2,3-difluorophenyl)-2-{4-(6-acyloxy-1-trans-heptenyl)-phenyl}-pyridine,
2-(4-alkyl-2,3-difluorophenyl)-5-{4-(1-trans-alkenyl)-phenyl}-pyridine,
2-(4-alkyl-2,3-difluorophenyl)-5-{4-(6-hydroxy-1-trans-heptenyl)-phenyl}-pyridine,
2-(4-alkyl-2,3-difluorophenyl)-5-{4-(6-alkoxy-1-trans-heptenyl)-phenyl}-pyridine,
2-(4-alkyl-2,3-difluorophenyl)-5-{4-(6-acyloxy-1-trans-heptenyl)-phenyl}-pyridine,
2-(4-alkyloxy-2,3-difluorophenyl)-5-{4-(1-trans-alkenyl)-phenyl}-pyridine,
2-(4-alkyloxy-2,3-difluorophenyl)-5-{4-(6-hydroxy-1-trans-heptenyl)-phenyl}-pyridine,
2-(4-alkyloxy-2,3-difluorophenyl)-5-{4-(6-alkoxy-1-trans-heptenyl)-phenyl}-pyridine,
2-(4-alkyloxy-2,3-difluorophenyl)-5-{4-(6-acyloxy-1-trans-heptenyl)-phenyl}-pyridine,
5-(4-alkylphenyl)-2-{4-(1-trans-alkenyl)-2,3-difluorophenyl}-pyridine,
5-(4-alkylphenyl)-2-{4-(6-hydroxy-1-trans-heptenyl)-2,3-difluorophenyl}-pyridine,
5-(4-alkylphenyl)-2-{4-(6-alkoxy-1-trans-heptenyl)-2,3-difluorophenyl}-pyridine,
5-(4-alkylphenyl)-2-{4-(6-acyloxy-1-trans-heptenyl)-2,3-difluorophenyl}-pyridine,
5-(4-alkyloxyphenyl)-2-{4-(1-trans-alkenyl)-2,3-difluorophenyl}-pyridine,
5-(4-alkyloxyphenyl)-2-{4-(6-hydroxy-1-trans-heptenyl)-2,3-difluorophenyl}-pyridine,
5-(4-alkyloxyphenyl)-2-{4-(6-alkoxy-1-trans-heptenyl)-2,3-difluorophenyl}-pyridine,
5-(4-alkyloxyphenyl)-2-{4-(6-acyloxy-1-trans-heptenyl)-2,3-difluorophenyl}-pyridine,
2-(4-alkylphenyl)-5-{4-(1-trans-alkenyl)-2,3-difluorophenyl}-pyridine,
2-(4-alkylphenyl)-5-{4-(6-hydroxy-1-trans-heptenyl)-2,3-difluorophenyl}-pyridine, 2-(4-alkylphenyl)-5-{4-(6-alkoxy-1-trans-heptenyl)-2,3-difluorophenyl}-pyridine,
2-(4-alkylphenyl)-5-{4-(6-acyloxy-1-trans-heptenyl)-2,3-difluorophenyl}-pyridine,
2-(4-alkyloxyphenyl)-5-{4-(1-trans-alkenyl)-2,3-difluorophenyl}-pyridine,
2-(4-alkyloxyphenyl)-5-{4-(6-hydroxy-1-trans-heptenyl)-2,3-difluorophenyl}-pyridine,
2-(4-alkyloxyphenyl)-5-{4-(6-alkoxy-1-trans-heptenyl)-2,3-difluorophenyl}-pyridine,
2-(4-alkyloxyphenyl)-5-{4-(6-acyloxy-1-trans-heptenyl)-2,3-difluorophenyl}-pyridine,
5-alkyl-2-{2,3-difluoro-4-(1-trans-alkenyl)-phenyl}-pyrimidine,
5-alkyl-2-{2,3-difluoro-4-(6-hydroxy-1-trans-heptenyl)-phenyl}-pyrimidine,
5-alkyl-2-{2,3-difluoro-4-(6-alkoxy-1-trans-heptenyl)-phenyl}-pyrimidine,
5-alkyl-2-{2,3-difluoro-4-(6-acyloxy-1-trans-heptenyl)-phenyl}-pyrimidine,
5-alkyloxy-2-{2,3-difluoro-4-(1-trans-alkenyl)-phenyl}-pyrimidine,
5-alkyloxy-2-{2,3-difluoro-4-(6-hydroxy-1-trans-heptenyl)-phenyl}-pyrimidine,
5-alkyloxy-2-{2,3-difluoro-4-(6-alkoxy-1-trans-heptenyl)-phenyl}-pyrimidine,
5-alkyloxy-2-{2,3-difluoro-4-(6-acyloxy-1-trans-heptenyl)-phenyl}-pyrimidine,
2-(2,3-difluoro-4-alkylphenyl)-5-(1-trans-alkenyl)-pyrimidine,
2-(2,3-difluoro-4-alkylphenyl)-5-(6-hydroxy-1-trans-heptenyl)-pyrimidine,
2-(2,3-difluoro-4-alkylphenyl)-5-(6-alkoxy-1-trans-heptenyl)-pyrimidine,
2-(2,3-difluoro-4-alkylphenyl)-5-(6-acyloxy-1-trans-heptenyl)-pyrimidine,
2-(2,3-difluoro-4-alkyloxyphenyl)-5-(1-trans-alkenyl)-pyrimidine,
2-(2,3-difluoro-4-alkyloxyphenyl)-5-(6-hydroxy-1-trans-heptenyl)-pyrimidine,
2-(2,3-difluoro-4-alkyloxyphenyl)-5-(6-alkoxy-1-trans-heptenyl)-pyrimidine,
2-(2,3-difluoro-4-alkyloxyphenyl)-5-(6-acyloxy-1-trans-heptenyl)-pyrimidine,
2-alkyl-5-{4-(1-trans-alkenyl)-2,3-difluorophenyl}-pyrimidine,
2-alkyl-5-{4-(6-hydroxy-1-trans-heptenyl)-2,3-difluorophenyl}-pyrimidine,
2-alkyl-5-{4-(6-alkoxy-1-trans-heptenyl)-2,3-difluorophenyl}-pyrimidine,
2-alkyl-5-{4-(6-acyloxy-1-trans-heptenyl)-2,3-difluorophenyl}-pyrimidine,
2-alkyloxy-5-{4-(1-trans-alkenyl)-2,3-difluorophenyl}-pyrimidine,
2-alkyloxy-5-{4-(6-hydroxy-1-trans-heptenyl)-2,3-difluorophenyl}-pyrimidine,
2-alkyloxy-5-{4-(6-alkoxy-1-trans-heptenyl)-2,3-difluorophenyl}-pyrimidine,
2-alkyloxy-5-{4-(6-acyloxy-1-trans-heptenyl)-2,3-difluorophenyl}-pyrimidine,
5-(4-alkyl-2,3-difluorophenyl)-2-(1-trans-alkenyl)-pyrimidine,
5-(4-alkyl-2,3-difluorophenyl)-2-(6-hydroxy-1-trans-heptenyl)-pyrimidine,
5-(4-alkyl-2,3-difluorophenyl)-2-(6-alkoxy-1-trans-heptenyl)-pyrimidine,
5-(4-alkyl-2,3-difluorophenyl)-2-(6-acyloxy-1-trans-heptenyl)-pyrimidine,
5-(4-alkyloxy-2,3-difluorophenyl)-2-(1-trans-alkenyl)-pyrimidine,
5-(4-alkyloxy-2,3-difluorophenyl)-2-(6-hydroxy-1-trans-heptenyl)-pyrimidine,
5-(4-alkyloxy-2,3-difluorophenyl)-2-(6-alkoxy-1-trans-heptenyl)-pyrimidine,
5-(4-alkyloxy-2,3-difluorophenyl)-2-(6-acyloxy-1-trans-heptenyl)-pyrimidine,
5-alkyl-2-{4-(1-trans-alkenyl)-2',3'-difluorobiphenyl-4-yl}-pyrimidine,
5-alkyl-2-{4-(6-hydroxy-1-trans-heptenyl)-2',3'-difluorobiphenyl-4-yl}-pyrimidine,
5-alkyl-2-{4-(6-alkoxy-1-trans-heptenyl)-2',3'-difluorobiphenyl-4-yl}-pyrimidine,
5-alkyl-2-{4-(6-acyloxy-1-trans-heptenyl)-2',3'-difluorobiphenyl-4-yl}-pyrimidine,
5-alkyloxy-2-{4-(1-trans-alkenyl)-2',3'-difluorobiphenyl-4-yl}-pyrimidine,
5-alkyloxy-2-{4-(6-hydroxy-1-trans-heptenyl)-2',3'-difluorobiphenyl-4-yl}-pyrimidine,
5-alkyloxy-2-{4-(6-alkoxy-1-trans-heptenyl)-2',3'-difluorobiphenyl-4-yl}-pyrimidine,
5-alkyloxy-2-{4-(6-acyloxy-1-trans-heptenyl)-2',3'-difluorobiphenyl-4-yl}-pyrimidine,
2-(4'-alkyl-2',3'-difluorobiphenyl-4-yl)-5-(1-trans-alkenyl)-pyrimidine,
2-(4'-alkyl-2',3'-difluorobiphenyl-4-yl)-5-(6-hydroxy-1-trans-heptenyl)-pyrimidine,
2-(4'-alkyl-2',3'-difluorobiphenyl-4-yl)-5-(6-alkoxy-1-trans-heptenyl)-pyrimidine,
2-(4'-alkyl-2',3'-difluorobiphenyl-4-yl)-5-(6-acyloxy-1-trans-heptenyl)-pyrimidine,
2-(4'-alkyloxy-2',3'-difluorobiphenyl-4-yl)-5-(1-trans-alkenyl)-pyrimidine,
2-(4'-alkyloxy-2',3'-difluorobiphenyl-4-yl)-5-(6-hydroxy-1-trans-heptenyl)-pyrimidine,
2-(4'-alkyloxy-2',3'-difluorobiphenyl-4-yl)-5-(6-alkoxy-1-trans-heptenyl)-pyrimidine,
2-(4'-alkyloxy-2',3'-difluorobiphenyl-4-yl)-5-(6-acyloxy-1-trans-heptenyl)-pyrimidine,
2-alkyl-5-{4'-(1-trans-alkenyl)-2',3'-difluorobiphenyl-4-yl}-pyrimidine,
2-alkyl-5-{4'-(6-hydroxy-1-trans-heptenyl)-2',3'-difluorobiphenyl-4-yl}-pyrimidine,
2-alkyl-5-{4'-(6-alkoxy-1-trans-heptenyl)-2',3'-difluorobiphenyl-4-yl}-pyrimidine,
2-alkyl-5-{4'-(6-acyloxy-1-trans-heptenyl)-2',3'-difluorobiphenyl-4-yl}-pyrimidine,
2-alkyloxy-5-{4'-(1-trans-alkenyl)-2',3'-difluorobiphenyl-4-yl}-pyrimidine,
2-alkyloxy-5-{4'-(6-hydroxy-1-trans-heptenyl)-2',3'-difluorobiphenyl-4-yl}-pyrimidine,
2-alkyloxy-5-{4'-(6-alkoxy-1-trans-heptenyl)-2',3'-difluorobiphenyl-4-yl}-pyrimidine,
2-alkyloxy-5-{4'-(6-acyloxy-1-trans-heptenyl)-2',3'-difluorobiphenyl-4-yl}-pyrimidine,
5-(4'-alkyl-2',3'-difluorobiphenyl-4-yl)-2-(1-trans-alkenyl)-pyrimidine,
5-(4'-alkyl-2',3'-difluorobiphenyl-4-yl)-2-(6-hydroxy-1-trans-heptenyl)-pyrimidine,
5-(4'-alkyl-2',3'-difluorobiphenyl-4-yl)-2-(6-alkoxy-1-trans-heptenyl)-pyrimidine,
5-(4'-alkyl-2',3'-difluorobiphenyl-4-yl)-2-(6-acyloxy-1-trans-heptenyl)-pyrimidine,
5-(4'-alkyloxy-2',3'-difluorobiphenyl-4-yl)-2-(1-trans-alkenyl)-pyrimidine,
5-(4'-alkyloxy-2',3'-difluorobiphenyl-4-yl)-2-(6-hydroxy-1-trans-heptenyl)-pyrimidine, 5-(4'-alkyloxy-2',3'-difluorobiphenyl-4-yl)-2-(6-alkoxy-1-trans-heptenyl)-pyrimidine,
5-(4'-alkyloxy-2',3'-difluorobiphenyl-4-yl)-2-(6-acyloxy-1-trans-heptenyl)-pyrimidine,
5-(4-alkyl-2,3-difluorophenyl)-2-{4-(1-trans-alkenyl)-phenyl}-pyrimidine,
5-(4-alkyl-2,3-difluorophenyl)-2-{4-(6-hydroxy-1-trans-heptenyl)-phenyl}-pyrimidine,
5-(4-alkyl-2,3-difluorophenyl)-2-{4-(6-alkoxy-1-trans-heptenyl)-phenyl}-pyrimidine,
5-(4-alkyl-2,3-difluorophenyl)-2-{4-(6-acyloxy-1-trans-heptenyl)-phenyl}-pyrimidine,
5-(4-alkyloxy-2,3-difluorophenyl)-2-{4-(1-trans-alkenyl)-phenyl}-pyrimidine,
5-(4-alkyloxy-2,3-difluorophenyl)-2-{4-(6-hydroxy-1-trans-heptenyl)-phenyl}-pyrimidine,
5-(4-alkyloxy-2,3-difluorophenyl)-2-{4-(6-alkoxy-1-trans-heptenyl)-phenyl}-pyrimidine,
5-(4-alkyloxy-2,3-difluorophenyl)-2-{4-(6-acyloxy-1-trans-heptenyl)-phenyl}-pyrimidine,
2-(4-alkyl-2,3-difluorophenyl)-5-{4-(1-trans-alkenyl)-phenyl}-pyrimidine,
2-(4-alkyl-2,3-difluorophenyl)-5-{4-(6-hydroxy-1-trans-heptenyl)-phenyl}-pyrimidine,
2-(4-alkyl-2,3-difluorophenyl)-5-{4-(6-alkoxy-1-trans-heptenyl)-phenyl}-pyrimidine,
2-(4-alkyl-2,3-difluorophenyl)-5-{4-(6-acyloxy-1-trans-heptenyl)-phenyl}-pyrimidine,
2-(4-alkyloxy-2,3-difluorophenyl)-5-{4-(1-trans-alkenyl)-phenyl}-pyrimidine,
2-(4-alkyloxy-2,3-difluorophenyl)-5-{4-(6-hydroxy-1-trans-heptenyl)-phenyl}-pyrimidine,
2-(4-alkyloxy-2,3-difluorophenyl)-5-{4-(6-alkoxy-1-trans-heptenyl)-phenyl}-pyrimidine,
2-(4-alkyloxy-2,3-difluorophenyl)-5-{4-(6-acyloxy-1-trans-heptenyl)-phenyl}-pyrimidine,
5-(4-alkylphenyl)-2-{4-(1-trans-alkenyl)-2,3-difluorophenyl}-pyrimidine,
5-(4-alkylphenyl)-2-{4-(6-hydroxy-1-trans-heptenyl)-2,3-difluorophenyl}-pyrimidine,
5-(4-alkylphenyl)-2-{4-(6-alkoxy-1-trans-heptenyl)-2,3-difluorophenyl}-pyrimidine,
5-(4-alkylphenyl)-2-{4-(6-acyloxy-1-trans-heptenyl)-2,3-difluorophenyl}-pyrimidine,
5-(4-alkyloxyphenyl)-2-{4-(1-trans-alkenyl)-2,3-difluorophenyl}-pyrimidine,
5-(4-alkyloxyphenyl)-2-{4-(6-hydroxy-1-trans-heptenyl)-2,3-difluorophenyl}-pyrimidine,
5-(4-alkyloxyphenyl)-2-{4-(6-alkoxy-1-trans-heptenyl)-2,3-difluorophenyl}-pyrimidine,
5-(4-alkyloxyphenyl)-2-{4-(6-acyloxy-1-trans-heptenyl)-2,3-difluorophenyl}-pyrimidine,
2-(4-alkylphenyl)-5-{4-(1-trans-alkenyl)-2,3-difluorophenyl}-pyrimidine,
2-(4-alkylphenyl)-5-{4-(6-hydroxy-1-trans-heptenyl)-2,3-difluorophenyl}-pyrimidine,
2-(4-alkylphenyl)-5-{4-(6-alkoxy-1-trans-heptenyl)-2,3-difluorophenyl}-pyrimidine,
2-(4-alkylphenyl)-5-{4-(6-acyloxy-1-trans-heptenyl)-2,3-difluorophenyl}-pyrimidine,
2-(4-alkyloxyphenyl)-5-{4-(1-trans-alkenyl)-2,3-difluorophenyl}-pyrimidine,
2-(4-alkyloxyphenyl)-5-{4-(6-hydroxy-1-trans-heptenyl)-2,3-difluorophenyl}-pyrimidine,
2-(4-alkyloxyphenyl)-5-{4-(6-alkoxy-1-trans-heptenyl)-2,3-difluorophenyl}-pyrimidine,
2-(4-alkyloxyphenyl)-5-{4-(6-acyloxy-1-trans-heptenyl)-2,3-difluorophenyl}-pyrimidine,
6-alkyl-3-{4-(1-trans-alkenyl)-2,3-difluorophenyl}-pyridazine,
6-alkyl-3-{4-(6-hydroxy-1-trans-heptenyl)-2,3-difluorophenyl}-pyridazine,
6-alkyl-3-{4-(6-alkoxy-1-trans-heptenyl)-2,3-difluorophenyl}-pyridazine,
6-alkyl-3-{4-(6-acyloxy-1-trans-heptenyl)-2,3-difluorophenyl}-pyridazine,
6-alkyloxy-3-{4-(1-trans-alkenyl)-2,3-difluorophenyl}-pyridazine,
6-alkyloxy-3-{4-(6-hydroxy-1-trans-heptenyl)-2,3-difluorophenyl}-pyridazine,
6-alkyloxy-3-{4-(6-alkoxy-1-trans-heptenyl)-2,3-difluorophenyl}-pyridazine,
6-alkyloxy-3-{4-(6-acyloxy-1-trans-heptenyl)-2,3-difluorophenyl}-pyridazine,
6-(4-alkyl-2,3-difluorophenyl)-3-(1-trans-alkenyl)-pyridazine,
6-(4-alkyl-2,3-difluorophenyl)-3-(6-hydroxy-1-trans-heptenyl)-pyridazine,
6-(4-alkyl-2,3-difluorophenyl)-3-(6-alkoxy-1-trans-heptenyl)-pyridazine,
6-(4-alkyl-2,3-difluorophenyl)-3-(6-acyloxy-1-trans-heptenyl)-pyridazine,
6-(4-alkyloxy-2,3-difluorophenyl)-3-(1-trans-alkenyl)-pyridazine,
6-(4-alkyloxy-2,3-difluorophenyl)-3-(6-hydroxy-1-trans-heptenyl)-pyridazine,
6-(4-alkyloxy-2,3-difluorophenyl)-3-(6-alkoxy-1-trans-heptenyl)-pyridazine,
6-(4-alkyloxy-2,3-difluorophenyl)-3-(6-acyloxy-1-trans-heptenyl)-pyridazine,
7-alkyl-3-{4-(1-trans-alkenyl)-2,3-difluorophenyl}-isoquinoline,
7-alkyl-3-{4-(6-hydroxy-1-trans-heptenyl)-2,3-difluorophenyl}-isoquinoline,
7-alkyl-3-{4-(6-alkoxy-1-trans-heptenyl)-2,3-difluorophenyl}-isoquinoline,
7-alkyl-3-{4-(6-acyloxy-1-trans-heptenyl)-2,3-difluorophenyl}-isoquinoline,
7-alkyloxy-3-{4-(1-trans-alkenyl)-2,3-difluorophenyl}-isoquinoline,
7-alkyloxy-3-{4-(6-hydroxy-1-trans-heptenyl)-2,3-difluorophenyl}-isoquinoline,
7-alkyloxy-3-{4-(6-alkoxy-1-trans-heptenyl)-2,3-difluorophenyl}-isoquinoline,
7-alkyloxy-3-{4-(6-acyloxy-1-trans-heptenyl)-2,3-difluorophenyl}-isoquinoline,
3-(4-alkyl-2,3-difluorophenyl)-7-(1-trans-alkenyl)-isoquinoline,
3-(4-alkyl-2,3-difluorophenyl)-7-(6-hydroxy-1-trans-heptenyl)-isoquinoline,
3-(4-alkyl-2,3-difluorophenyl)-7-(6-alkoxy-1-trans-heptenyl)-isoquinoline,
3-(4-alkyl-2,3-difluorophenyl)-7-(6-acyloxy-1-trans-heptenyl)-isoquinoline,
3-(4-alkyloxy-2,3-difluorophenyl)-7-(1-trans-alkenyl)-isoquinoline,
3-(4-alkyloxy-2,3-difluorophenyl)-7-(6-hydroxy-1-trans-heptenyl)-isoquinoline,
3-(4-alkyloxy-2,3-difluorophenyl)-7-(6-alkoxy-1-trans-heptenyl)-isoquinoline,
3-(4-alkyloxy-2,3-difluorophenyl)-7-(6-acyloxy-1-trans-heptenyl)-isoquinoline,
6-alkyl-2-{4-(1-trans-alkenyl)-2,3-difluorophenyl}-quinoline,
6-alkyl-2-{4-(6-hydroxy-1-trans-heptenyl)-2,3-difluorophenyl}-quinoline, 6-alkyl-2-{4-(6-alkoxy-1-trans-heptenyl)-2,3-difluorophenyl}-quinoline,
6-alkyl-2-{4-(6-acyloxy-1-trans-heptenyl)-2,3-difluorophenyl}-quinoline,
6-alkyloxy-2-{4-(1-trans-alkenyl)-2,3-difluorophenyl}-quinoline,
6-alkyloxy-2-{4-(6-hydroxy-1-trans-heptenyl)-2,3-difluorophenyl}-quinoline,
6-alkyloxy-2-{4-(6-alkoxy-1-trans-heptenyl)-2,3-difluorophenyl}-quinoline,
6-alkyloxy-2-{4-(6-acyloxy-1-trans-heptenyl)-2,3-difluorophenyl}-quinoline,
2-(4-alkyl-2,3-difluorophenyl)-6-(1-trans-alkenyl)-quinoline,
2-(4-alkyl-2,3-difluorophenyl)-6-(6-hydroxy-1-trans-heptenyl)-quinoline,
2-(4-alkyl-2,3-difluorophenyl)-6-(6-alkoxy-1-trans-heptenyl)-quinoline,
2-(4-alkyl-2,3-difluorophenyl)-6-(6-acyloxy-1-trans-heptenyl)-quinoline,
2-(4-alkyloxy-2,3-difluorophenyl)-6-(1-trans-alkenyl)-quinoline,
2-(4-alkyloxy-2,3-difluorophenyl)-6-(6-hydroxy-1-trans-heptenyl)-quinoline,
2-(4-alkyloxy-2,3-difluorophenyl)-6-(6-alkoxy-1-trans-heptenyl)-quinoline,
2-(4-alkyloxy-2,3-difluorophenyl)-6-(6-acyloxy-1-trans-heptenyl)-quinoline,
2-alkyl-6-{4-(1-trans-alkenyl)-2,3-difluorophenyl}-quinoxaline,
2-alkyl-6-{4-(6-hydroxy-1-trans-heptenyl)-2,3-difluorophenyl}-quinoxaline,
2-alkyl-6-{4-(6-alkoxy-1-trans-heptenyl)-2,3-difluorophenyl}-quinoxaline,
2-alkyl-6-{4-(6-acyloxy-1-trans-heptenyl)-2,3-difluorophenyl}-quinoxaline,
2-alkyloxy-6-{4-(1-trans-alkenyl)-2,3-difluorophenyl}-quinoxaline,
2-alkyloxy-6-{4-(6-hydroxy-1-trans-heptenyl)-2,3-difluorophenyl}-quinoxaline,
2-alkyloxy-6-{4-(6-alkoxy-1-trans-heptenyl)-2,3-difluorophenyl}-quinoxaline,
2-alkyloxy-6-{4-(6-acyloxy-1-trans-heptenyl)-2,3-difluorophenyl}-quinoxaline,
2-(1-trans-alkenyl)-6-(4-alkyl-2,3-difluorophenyl)-quinoxaline,
2-(6-hydroxy-1-trans-heptenyl)-6-(4-alkyl-2,3-difluorophenyl)-quinoxaline,
2-(6-alkoxy-1-trans-heptenyl)-6-(4-alkyl-2,3-difluorophenyl)-quinoxaline,
2-(6-acyloxy-1-trans-heptenyl)-6-(4-alkyl-2,3-difluorophenyl)-quinoxaline,
2-(1-trans-alkenyl)-6-(4-alkyloxy-2,3-difluorophenyl)-quinoxaline,
2-(6-hydroxy-1-trans-heptenyl)-6-(4-alkyloxy-2,3-difluorophenyl)-quinoxaline,
2-(6-alkoxy-1-trans-heptenyl)-6-(4-alkyloxy-2,3-difluorophenyl)-quinoxaline,
2-(6-acyloxy-1-trans-heptenyl)-6-(4-alkyloxy-2,3-difluorophenyl)-quinoxaline,
6-alkyl-2-{4-(1-trans-alkenyl)-2,3-difluorophenyl}-quinoxaline,
6-alkyl-2-{4-(6-hydroxy-1-trans-heptenyl)-2,3-difluorophenyl}-quinoxaline,
6-alkyl-2-{4-(6-alkoxy-1-trans-heptenyl)-2,3-difluorophenyl}-quinoxaline,
6-alkyl-2-{4-(6-acyloxy-1-trans-heptenyl)-2,3-difluorophenyl}-quinoxaline,
6-alkyloxy-2-{4-(1-trans-alkenyl)-2,3-difluorophenyl}-quinoxaline,
6-alkyloxy-2-{4-(6-hydroxy-1-trans-heptenyl)-2,3-difluorophenyl}-quinoxaline,
6-alkyloxy-2-{4-(6-alkoxy-1-trans-heptenyl)-2,3-difluorophenyl}-quinoxaline,
6-alkyloxy-2-{4-(6-acyloxy-1-trans-heptenyl)-2,3-difluorophenyl}-quinoxaline,
2-(4-alkyl-2,3-difluorophenyl)-6-(1-trans-alkenyl)-quinoxaline,
2-(4-alkyl-2,3-difluorophenyl)-6-(6-hydroxy-1-trans-heptenyl)-quinoxaline,
2-(4-alkyl-2,3-difluorophenyl)-6-(6-alkoxy-1-trans-heptenyl)-quinoxaline,
2-(4-alkyl-2,3-difluorophenyl)-6-(6-acyloxy-1-trans-heptenyl)-quinoxaline,
2-(4-alkyloxy-2,3-difluorophenyl)-6-(1-trans-alkenyl)-quinoxaline,
2-(4-alkyloxy-2,3-difluorophenyl)-6-(6-hydroxy-1-trans-heptenyl)-quinoxaline,
2-(4-alkyloxy-2,3-difluorophenyl)-6-(6-alkoxy-1-trans-heptenyl)-quinoxaline,
2-(4-alkyloxy-2,3-difluorophenyl)-6-(6-acyloxy-1-trans-heptenyl)-quinoxaline,
2-alkyl-6-{4-(1-trans-alkenyl)-2,3-difluorophenyl}-quinazoline,
2-alkyl-6-{4-(6-hydroxy-1-trans-heptenyl)-2,3-difluorophenyl}-quinazoline,
2-alkyl-6-{4-(6-alkoxy-1-trans-heptenyl)-2,3-difluorophenyl}-quinazoline,
2-alkyl-6-{4-(6-acyloxy-1-trans-heptenyl)-2,3-difluorophenyl}-quinazoline,
2-alkyloxy-6-{4-(1-trans-alkenyl)-2,3-difluorophenyl}-quinazoline,
2-alkyloxy-6-{4-(6-hydroxy-1-trans-heptenyl)-2,3-difluorophenyl}-quinazoline,
2-alkyloxy-6-{4-(6-alkoxy-1-trans-heptenyl)-2,3-difluorophenyl}-quinazoline,
2-alkyloxy-6-{4-(6-acyloxy-1-trans-heptenyl)-2,3-difluorophenyl}-quinazoline,
2-(1-trans-alkenyl)-6-(4-alkyl-2,3-difluorophenyl)-quinazoline,
2-(6-hydroxy-1-trans-heptenyl)-6-(4-alkyl-2,3-difluorophenyl)-quinazoline,
2-(6-alkoxy-1-trans-heptenyl)-6-(4-alkyl-2,3-difluorophenyl)-quinazoline,
2-(6-acyloxy-1-trans-heptenyl)-6-(4-alkyl-2,3-difluorophenyl)-quinazoline,
2-(1-trans-alkenyl)-6-(4-alkyloxy-2,3-difluorophenyl)-quinazoline,
2-(6-hydroxy-1-trans-heptenyl)-6-(4-alkyloxy-2,3-difluorophenyl)-quinazoline,
2-(6-alkoxy-1-trans-heptenyl)-6-(4-alkyloxy-2,3-difluorophenyl)-quinazoline,
2-(6-acyloxy-1-trans-heptenyl)-6-(4-alkyloxy-2,3-difluorophenyl)-quinazoline,
4'-hydroxy-4-(1-trans-alkenyl)-biphenyl,
4'-hydroxy-4-(6-hydroxy-1-trans-heptenyl)-biphenyl,
4'-hydroxy-4-(6-alkoxy-1-trans-heptenyl)-biphenyl,
4'-hydroxy-4-(6-acyloxy-1-trans-heptenyl)-biphenyl,
4"-hydroxy-4-(1-trans-alkenyl)-p-terphenyl,
4"-hydroxy-4-(6-hydroxy-1-trans-heptenyl)-p-terphenyl,
4"-hydroxy-4-(6-alkoxy-1-trans-heptenyl)-p-terphenyl,
4"-hydroxy-4-(6-acyloxy-1-trans-heptenyl)p--terphenyl,
6-hydroxy-2-{4-(1-trans-alkenyl)-p-phenyl}-naphthalene,
6-hydroxy-2-{4-(6-hydroxy-1-trans-heptenyl)-phenyl}-naphthalene, 6-hydroxy-2-{4-(6-alkoxy-1-trans-heptenyl)-phenyl}-naphthalene,
6-hydroxy-2-{4-(6-acyloxy-1-trans-heptenyl)-phenyl}-naphthalene,
6-(4-hydroxyphenyl)-2-(1-trans-alkenyl)-naphthalene,
6-(4-hydroxyphenyl)-2-(6-hydroxy-1-trans-heptenyl)-naphthalene,
6-(4-hydroxyphenyl)-2-(6-alkoxy-1-trans-heptenyl)-naphthalene,
6-(4-hydroxyphenyl)-2-(6-acyloxy-1-trans-heptenyl)-naphthalene,
5-hydroxy-{4-(1-trans-alkenyl)-p-phenyl}-pyridine,
5-hydroxy-{4-(6-hydroxy-1-trans-heptenyl)-phenyl}-pyridine,
5-hydroxy-{4-(6-alkoxy-1-trans-heptenyl)-phenyl}-pyridine,
5-hydroxy-{4-(6-acyloxy-1-trans-heptenyl)-phenyl}-pyridine,
2-(4-hydroxyphenyl)-5-(1-trans-alkenyl)-pyridine,
2-(4-hydroxyphenyl)-5-(6-hydroxy-1-trans-heptenyl)-pyridine,
2-(4-hydroxyphenyl)-5-(6-alkoxy-1-trans-heptenyl)-pyridine,
2-(4-hydroxyphenyl)-5-(6-acyloxy-1-trans-heptenyl)-p-pyridine,
2-hydroxy-5-{4-(1-trans-alkenyl)-phenyl}-pyridine,
2-hydroxy-5-{4-(6-hydroxy-1-trans-heptenyl)-phenyl}-pyridine,
2-hydroxy-5-{4-(6-alkoxy-1-trans-heptenyl)-phenyl}-pyridine,
2-hydroxy-5-{4-(6-acyloxy-1-trans-heptenyl)-phenyl}-pyridine,
5-(4-hydroxyphenyl)-2-(1-trans-alkenyl)-pyridine,
5-(4-hydroxyphenyl)-2-(6-hydroxy-1-trans-heptenyl)-pyridine,
5-(4-hydroxyphenyl)-2-(6-alkoxy-1-trans-heptenyl)-pyridine,
5-(4-hydroxyphenyl)-2-(6-acyloxy-1-trans-heptenyl)-pyridine,
5-hydroxy-2-{4'-(1-trans-alkenyl)-biphenyl-4-yl}-pyridine,
5-hydroxy-2-{4'-(6-hydroxy-1-trans-heptenyl)-biphenyl-4-yl}-pyridine,
5-hydroxy-2-{4'-(6-alkoxy-1-trans-heptenyl)-biphenyl-4-yl}-pyridine,
5-hydroxy-2-{4'-(6-acyloxy-1-trans-heptenyl)-p-biphenyl-4-yl}-pyridine,
2-(4'-hydroxy-biphenyl-4-yl)-5-(1-trans-alkenyl)-pyridine,
2-(4'-hydroxy-biphenyl-4-yl)-5-(6-hydroxy-1-trans-heptenyl)-pyridine,
2-(4'-hydroxy-biphenyl-4-yl)-5-(6-alkoxy-1-trans-heptenyl)-pyridine,
2-(4'-hydroxy-biphenyl-4-yl)-5-(6-acyloxy-1-trans-heptenyl)-pyridine,
5-(4-hydroxyphenyl)-2-{4-(1-trans-alkenyl)-phenyl}-pyridine,
5-(4-hydroxyphenyl)-2-{4-(6-hydroxy-1-trans-heptenyl)-phenyl}-pyridine,
5-(4-hydroxyphenyl)-2-{4-(6-alkoxy-1-trans-heptenyl)-phenyl}-pyridine,
5-(4-hydroxyphenyl)-2-{4-(6-acyloxy-1-trans-heptenyl)-phenyl}-pyridine,
2-(4-hydroxyphenyl)-5-{4-(1-trans-alkenyl)-phenyl}-pyridine,
2-(4-hydroxyphenyl)-5-{4-(6-hydroxy-1-trans-heptenyl)-phenyl}-pyridine,
2-(4-hydroxyphenyl)-5-{4-(6-alkoxy-1-trans-heptenyl)-phenyl}-pyridine,
2-(4-hydroxyphenyl)-5-{4-(6-acyloxy-1-trans-heptenyl)-phenyl}-pyridine,
2-hydroxy-5-{4'-(1-trans-alkenyl)-biphenyl-4-yl}-pyridine,
2-hydroxy-5-{4'-(6-hydroxy-1-trans-heptenyl)-biphenyl-4-yl}-pyridine,
2-hydroxy-5-{4'-(6-alkoxy-1-trans-heptenyl)-biphenyl-4-yl}-pyridine,
2-hydroxy-5-{4'-(6-acyloxy-1-trans-heptenyl)-biphenyl-4-yl}-pyridine,
2-(1-trans-alkenyl)-5-{4'-hydroxy-biphenyl-4-yl}-pyridine,
2-(6-hydroxy-1-trans-heptenyl)-5-{4'-hydroxy-biphenyl-4-yl}-pyridine,
2-(6-alkoxy-1-trans-heptenyl)-5-{4'-hydroxy-biphenyl-4-yl}-pyridine,
2-(6-acyloxy-1-trans-heptenyl)-5-{4'-hydroxy-biphenyl-4-yl}-pyridine,
2-(1-trans-alkenyl)-5-{4'-hydroxy-biphenyl-4-yl}-pyridine,
5-hydroxy-2-{4-(1-trans-alkenyl)-phenyl}-pyridine,
5-hydroxy-2-{4-(6-hydroxy-1-trans-heptenyl)-phenyl}-pyrimidine,
5-hydroxy-2-{4-(6-alkoxy-1-trans-heptenyl)-phenyl}-pyrimidine,
5-hydroxy-2-{4-(6-acyloxy-1-trans-heptenyl)-phenyl}-pyrimidine,
2-(4-hydroxyphenyl)-5-(1-trans-alkenyl)-pyrimidine,
2-(4-hydroxyphenyl)-5-(6-hydroxy-1-trans-heptenyl)-pyrimidine,
2-(4-hydroxyphenyl)-5-(6-alkoxy-1-trans-heptenyl)-pyrimidine,
2-(4-hydroxyphenyl)-5-(6-acyloxy-1-trans-heptenyl)-pyrimidine,
2-hydroxy-5-{4-(1-trans-alkenyl)-phenyl}-pyrimidine,
2-hydroxy-5-{4-(6-hydroxy-1-trans-heptenyl)-phenyl}-pyrimidine,
2-hydroxy-5-{4-(6-alkoxy-1-trans-heptenyl)-phenyl}-pyrimidine,
2-hydroxy-5-{4-(6-acyloxy-1-trans-heptenyl)-phenyl}-pyrimidine,
5-(4-hydroxyphenyl)-2-(1-trans-alkenyl)-pyrimidine,
5-(4-hydroxyphenyl)-2-(6-hydroxy-1-trans-heptenyl)-pyrimidine,
5-(4-hydroxyphenyl)-2-(6-alkoxy-1-trans-heptenyl)-pyrimidine,
5-(4-hydroxyphenyl)-2-(6-acyloxy-1-trans-heptenyl)-pyrimidine,
5-hydroxy-2-{4'-(1-trans-alkenyl)-biphenyl-4-yl}-pyrimidine,
5-hydroxy-2-{4'-(6-hydroxy-1-trans-heptenyl)-biphenyl-4-yl}-pyrimidine,
5-hydroxy-2-{4'-(6-alkoxy-1-trans-heptenyl)-biphenyl-4-yl}-pyrimidine,
5-hydroxy-2-{4'-(6-acyloxy-1-trans-heptenyl)-biphenyl-4-yl}-pyrimidine,
2-{4'-(1-trans-alkenyl)-biphenyl-4-yl}-5-hydroxy-pyrimidine,
2-{4'-(6-hydroxy-1-trans-heptenyl)-biphenyl-4-yl}-5-hydroxy-pyrimidine,
2-{4'-(6-alkoxy-1-trans-heptenyl)-biphenyl-4-yl}-5-hydroxy-pyrimidine,
2-{4'-(6-acyloxy-1-trans-heptenyl)-biphenyl-4-yl}-5-hydroxy-pyrimidine,
5-(4-hydroxyphenyl)-2-{4-(1-trans-alkenyl)-phenyl}-pyrimidine,
5-(4-hydroxyphenyl)-2-{4-(6-hydroxy-1-trans-heptenyl)-phenyl}-pyrimidine,
5-(4-hydroxyphenyl)-2-{4-(6-alkoxy-1-trans-heptenyl)-phenyl}-pyrimidine, 5-(4-hydroxyphenyl)-2-{4-(6-acyloxy-1-trans-heptenyl)-phenyl}-pyrimidine,
2-(4-hydroxyphenyl)-5-{4-(1-trans-alkenyl)-phenyl}-pyrimidine,
2-(4-hydroxyphenyl)-5-{4-(6-hydroxy-1-trans-heptenyl)-phenyl}-pyrimidine,
2-(4-hydroxyphenyl)-5-{4-(6-alkoxy-1-trans-heptenyl)-phenyl}-pyrimidine,
2-(4-hydroxyphenyl)-5-{4-(6-acyloxy-1-trans-heptenyl)-phenyl}-pyrimidine,
2-hydroxy-5-{4'-(1-trans-alkenyl)-biphenyl-4-yl}-pyrimidine,
2-hydroxy-5-{4'-(6-hydroxy-1-trans-heptenyl)-biphenyl-4-yl}-pyrimidine,
2-hydroxy-5-{4'-(6-alkoxy-1-trans-heptenyl)-biphenyl-4-yl}-pyrimidine,
2-hydroxy-5-{4'-(6-acyloxy-1-trans-heptenyl)-biphenyl-4-yl}-pyrimidine,
2-(1-trans-alkenyl)-5-{4'-hydroxy-biphenyl-4-yl}-pyrimidine,
2-(6-hydroxy-1-trans-heptenyl)-5-{4'-hydroxy-biphenyl-4-yl}-pyrimidine,
2-(6-alkoxy-1-trans-heptenyl)-5-{4'-hydroxy-biphenyl-4-yl}-pyrimidine,
2-(6-acyloxy-1-trans-heptenyl)-5-{4'-hydroxy-biphenyl-4-yl}-pyrimidine,
2-{5-(1-trans-alkenyl)-pyridin-2-yl}-5-(4-hydroxyphenyl)-pyrimidine,
2-{4-(5-hydroxy-1-trans-heptenyl)-pyridin-2-yl}-5-(4-hydroxyphenyl)-pyrimidine,
2-{5-(6-alkoxy-1-trans-heptenyl)-pyridin-2-yl}-5-(4-hydroxyphenyl)-pyrimidine,
2-{5-(6-acyloxy-1-trans-heptenyl)-pyridin-2-yl}-5-(4-hydroxyphenyl)-pyrimidine,
2-{5-hydroxy--pyridin-2-yl}-5-{4-(1-trans-alkenyl)-phenyl}-pyrimidine,
2-{5-hydroxy-pyridin-2-yl}-5-{4-(6-hydroxy-1-trans-heptenyl)-phenyl}-pyrimidine,
2-{5-hydroxy-pyridin-2-yl}-5-{4-(6-alkoxy-1-trans-heptenyl)-phenyl}-pyrimidine,
2-{5-hydroxy-pyridin-2-yl}-5-{4-(6-acyloxy-1-trans-heptenyl)-phenyl}-pyrimidine,
2-{4-(5-hydroxypyrimidin-2-yl)-phenyl}-5-(1-trans-alkenyl)-pyrimidine,
2-{4-(5-hydroxypyrimidin-2-yl)-phenyl}-5-(6-hydroxy-1-trans-heptenyl)-pyrimidine,
2-{4-(5-hydroxypyrimidin-2-yl)-phenyl}-5-(6-alkoxy-1-trans-heptenyl)-pyrimidine,
2-{4-(5-hydroxypyrimidin-2-yl)-phenyl}-5-(6-acyloxy-1-trans-heptenyl)pyrimidine,
2-hydroxy-5-{4-(1-trans-alkenyl)-phenyl}-pyrazine,
2-hydroxy-5-{4-(6-hydroxy-1-trans-heptenyl)-phenyl}-pyrazine,
2-hydroxy-5-{4-(6-alkoxy-1-trans-heptenyl)-phenyl}-pyrazine,
2-hydroxy-5-{4-(6-acyloxy-1-trans-heptenyl)-phenyl}-pyrazine,
2-(4-hydroxyphenyl)-5-(1-trans-alkenyl)-pyrazine,
2-(4-hydroxyphenyl)-5-(6-hydroxy-1-trans-heptenyl)-pyrazine,
2-(4-hydroxyphenyl)-5-(6-alkoxy-1-trans-heptenyl)-pyrazine,
2-(4-hydroxyphenyl)-5-(6-acyloxy-1-trans-heptenyl)-pyrazine,
6-hydroxy-3-{4-(1-trans-alkenyl)-phenyl}-pyridazine,
6-hydroxy-3-{4-(6-hydroxy-1-trans-heptenyl)-phenyl}-pyridazine,
6-hydroxy-3-{4-(6-alkoxy-1-trans-heptenyl)-phenyl}-pyridazine,
6-hydroxy-3-{4-(6-acyloxy-1-trans-heptenyl)-phenyl}-pyridazine,
6-(4-hydroxyphenyl)-3-(1-trans-alkenyl)-pyridazine,
6-(4-hydroxyphenyl)-3-(6-hydroxy-1-trans-heptenyl)-pyridazine,
6-(4-hydroxyphenyl)-3-(6-alkoxy-1-trans-heptenyl)-pyridazine,
6-(4-hydroxyphenyl)-3-(6-acyloxy-1-trans-heptenyl)-pyridazine,
5-(4-hydroxyphenyl)-2-{4-(1-trans-alkenyl)-phenyl-pyrazine,
5-(4-hydroxyphenyl)-2-{4-(6-hydroxy-1-trans-heptenyl)-phenyl}-pyrazine,
5-(5-hydroxyphenyl)-2-{4-(6-alkoxy-1-trans-heptenyl)-phenyl}-pyrazine,
5-(4-hydroxyphenyl)-2-{4-(6-acyloxy-1-trans-heptenyl)-phenyl}-pyrazine,
6-(4-hydroxyphenyl)-3-{4-(1-trans-alkenyl)-phenyl}-pyridazine,
6-(4-hydroxyphenyl)-3-{4-(6-hydroxy-1-trans-heptenyl)-phenyl}-pyridazine,
6-(4-hydroxyphenyl)-3-{4-(6-alkoxy-1-trans-heptenyl)-phenyl}-pyridazine,
6-(4-hydroxyphenyl)-3-{4-(6-acyloxy-1-trans-heptenyl)-phenyl}-pyridazine,
2-hydroxy-6-(1-trans-alkenyl)-naphthalene,
2-hydroxy-6-(6-hydroxy-1-trans-heptenyl)-naphthalene,
2-hydroxy-6-(6-alkoxy-1-trans-heptenyl)-naphthalene,
2-hydroxy-6-(6-acyloxy-1-trans-heptenyl)-naphthalene,
6-hydroxy-2-(1-trans-alkenyl)-quinoline,
6-hydroxy-2-(6-hydroxy-1-trans-heptenyl)-quinoline,
6-hydroxy-2-(6-alkoxy-1-trans-heptenyl)-quinoline,
6-hydroxy-2-(6-acyloxy-1-trans-heptenyl)-quinoline,
2-hydroxy-6-(1-trans-alkenyl)-quinoline,
2-hydroxy-6-(6-hydroxy-1-trans-heptenyl)-quinoline,
2-hydroxy-6-(6-alkoxy-1-trans-heptenyl)-quinoline,
2-hydroxy-6-(6-acyloxy-1-trans-heptenyl)-quinoline,
7-hydroxy-3-(1-trans-alkenyl)-isoquinoline,
7-hydroxy-3-(6-hydroxy-1-trans-heptenyl)-isoquinoline,
7-hydroxy-3-(6-alkoxy-1-trans-heptenyl)-isoquinoline,
7-hydroxy-3-(6-acyloxy-1-trans-heptenyl)-isoquinoline,
3-hydroxy-7-(1-trans-alkenyl)-isoquinoline,
3-hydroxy-7-(6-hydroxy-1-trans-heptenyl)-isoquinoline,
3-hydroxy-7-(6-alkoxy-1-trans-heptenyl)-isoquinoline,
3-hydroxy-7-(6-acyloxy-1-trans-heptenyl)-isoquinoline,
2-hydroxy-6-(1-trans-alkenyl)-quinazoline,
2-hydroxy-6-(6-hydroxy-1-trans-heptenyl)-quinazoline,
2-hydroxy-6-(6-alkoxy-1-trans-heptenyl)-quinazoline,
2-hydroxy-6-(6-acyloxy-1-trans-heptenyl)-quinazoline,
6-hydroxy-2-(1-trans-alkenyl)-quinazoline,
6-hydroxy-2-(6-hydroxy-1-trans-heptenyl)-quinazoline,
6-hydroxy-2-(6-alkoxy-1-trans-heptenyl)-quinazoline,
6-hydroxy-2-(6-acyloxy-1-trans-heptenyl)-quinazoline,
2-hydroxy-6-(1-trans-alkenyl)-quinoxaline,
2-hydroxy-6-(6-hydroxy-1-trans-heptenyl)-quinoxaline,
2-hydroxy-6-(6-alkoxy-1-trans-heptenyl)-quinoxaline,
2-hydroxy-6-(6-acyloxy-1-trans-heptenyl)-quinoxaline,
6-hydroxy-2-(1-trans-alkenyl)-quinoxaline,
6-hydroxy-2-(6-hydroxy-1-trans-heptenyl)-quinoxaline,
6-hydroxy-2-(6-alkoxy-1-trans-heptenyl)-quinoxaline,
6-hydroxy-2-(6-acyloxy-1-trans-heptenyl)-quinoxaline,
2-(6-hydroxy-naphthalene-2-yl)-5-(1-trans-alkenyl)-pyridine,
2-(6-hydroxy-naphthalene-2-yl)-5-(6-hydroxy-1-trans-heptenyl)-pyridine, 2-(6-hydroxy-naphthalene-2-yl)-5-(6-alkoxy-1-trans-heptenyl)-pyridine,
2(6-hydroxy-naphthalene-2-yl)-5-(6-acyloxy-1-trans-heptenyl)-pyridine,
5-(6-hydroxy-naphthalene-2-yl)-2-(1-trans-alkenyl)-pyridine,
5-(6-hydroxy-naphthalene-2-yl)-2-(6-hydroxy-1-trans-heptenyl)-pyridine,
5-(6-hydroxy-naphthalene-2-yl)-2-(6-alkoxy-1-trans-heptenyl)-pyridine,
5-(6-hydroxy-naphthalene-2-yl)-2-(6-acyloxy-1-trans-heptenyl)-pyridine,
2-hydroxy-5-{6-(1-trans-alkenyl)-naphthalene-2-yl}-pyridine,
2-hydroxy-5-{6-(6-hydroxy-1-trans-heptenyl)-naphthalene-2-yl}-pyridine,
2-hydroxy-5-{6-(6-alkoxy-1-trans-heptenyl)-naphthalene-2-yl}-pyridine,
2-hydroxy-5-{6-(6-acyloxy-1-trans-heptenyl)-naphthalene-2-yl}-pyridine,
5-hydroxy-2-{6-(1-trans-alkenyl)-naphthalene-1-yl}-pyridine,
5-hydroxy-2-{6-(6-hydroxy-1-trans-heptenyl)-naphthalene-1-yl}-pyridine,
5-hydroxy-2-{6-(6-alkoxy-1-trans-heptenyl)-naphthalene-1-yl}-pyridine,
5-hydroxy-2-{6-(6-acyloxy-1-trans-heptenyl)-naphthalene-1-yl}-pyridine,
7-hydroxy-3-{4-(1-trans-alkenyl)-phenyl}-isoquinoline,
7-hydroxy-3-{4-(6-hydroxy-1-trans-heptenyl)-phenyl}-isoquinoline,
7-hydroxy-3-{4-(6-alkoxy-1-trans-heptenyl)-phenyl}-isoquinoline,
7-hydroxy-3-{4-(6-acyloxy-1-trans-heptenyl)-phenyl}-isoquinoline,
3-(4-hydroxy-phenyl)-7-(1-trans-alkenyl)-isoquinoline,
3(4-hydroxy-phenyl)-7-(6-hydroxy-1-trans-heptenyl)-isoquinoline,
3-(4-hydroxy-phenyl)-7-(6-alkoxy1-trans-heptenyl)-isoquinoline,
3-(4-hydroxy-phenyl)-7-(6-acyloxy-1-trans-heptenyl)-isoquinoline,
6-hydroxy-2-{4-(1-trans-alkenyl)-phenyl}-quinoline,
6-hydroxy-2-{4-(6-hydroxy-1-trans-heptenyl)-phenyl}-quinoline,
6-hydroxy-2-{4-(6-alkoxy-1-trans-heptenyl)-phenyl}-quinoline,
6-hydroxy-2-{4-(6-acyloxy-1-trans-heptenyl)-phenyl}-quinoline,
2-(4-hydroxy-phenyl)-6-(1-trans-alkenyl)-quinoline,
2-(4-hydroxy-phenyl)-6-(6-hydroxy-1-trans-heptenyl)-quinoline,
2-(4-hydroxy-phenyl)-6-(6-alkoxy-1-trans-heptenyl)-quinoline,
2-(4-hydroxy-phenyl)-6-(6-acyloxy-1-trans-heptenyl)-quinoline,
5-hydroxy-5-{6-(1-trans-alkenyl)-naphthalene-2-yl}-pyrimidine,
5-hydroxy-5-{6-(6-hydroxy-1-trans-heptenyl)-naphthalene-2-yl}-pyrimidine,
5-hydroxy-5-{6-(6-alkoxy-1-trans-heptenyl)-naphthalene-2-yl}-pyrimidine,
5-hydroxy-5-{6-(6-acyloxy-1-trans-heptenyl)-naphthalene-2-yl}-pyrimidine,
2-(6-hydroxy-naphthalene-2-yl)-5-(1-trans-alkenyl)-pyrimidine,
2-(6-hydroxy-naphthalene-2-yl)-5-(6-hydroxy-1-trans-heptenyl)-pyrimidine,
2-(6-hydroxy-naphthalene-2-yl)-5-(6-alkoxy-1-trans-heptenyl)-pyrimidine,
2-(6-hydroxy-naphthalene-2-yl)-5-(6-acyloxy-1-trans-heptenyl)-pyrimidine,
3-hydroxy-7-{4-(1-trans-alkenyl)-phenyl}-quinoxaline,
3-hydroxy-7-{4-(6-hydroxy-1-trans-heptenyl)-phenyl}-quinoxaline,
3-hydroxy-7-{4-(6-alkoxy-1-trans-heptenyl)-phenyl}-quinoxaline,
3-hydroxy-7-{4-(6-acyloxy-1-trans-heptenyl)-phenyl}-quinoxaline,
2-(1-trans-alkenyl)-6-(4-hydroxyphenyl)-quinoxaline,
2-(6-hydroxy-1-trans-heptenyl)-6-(4-hydroxyphenyl)-quinoxaline,
2-(6-alkoxy-1-trans-heptenyl)-6-(4-hydroxyphenyl)-quinoxaline,
2-(6-acyloxy-1-trans-heptenyl)-6-(4-hydroxyphenyl)-quinoxaline,
6-hydroxy-2-{4-(1-trans-alkenyl)-phenyl}-quinoxaline,
6-hydroxy-2-{4-(6-hydroxy-1-trans-heptenyl)-phenyl}-quinoxaline,
6-hydroxy-2-{4-(6-alkoxy-1-trans-heptenyl)-phenyl}-quinoxaline,
6-hydroxy-2-{4-(6-acyloxy-1-trans-heptenyl)-phenyl}-quinoxaline,
2-(4-hydroxyphenyl)-6-(1-trans-alkenyl)-quinoxaline,
2-(4-hydroxyphenyl)-6-(6-hydroxy-1-trans-heptenyl)-quinoxaline,
2-(4-hydroxyphenyl)-6-(6-alkoxy-1-trans-heptenyl)-quinoxaline,
2-(4-hydroxyphenyl)-6-(6-acyloxy-1-trans-heptenyl)-quinoxaline,
2-hydroxy-6-{4-(1-trans-alkenyl)-phenyl}-quinazoline,
2-hydroxy-6-{4-(6-hydroxy-1-trans-heptenyl)-phenyl}-quinazoline,
2-hydroxy-6-{4-(6-alkoxy-1-trans-heptenyl)-phenyl}-quinazoline,
2-hydroxy-6-{4-(6-acyloxy-1-trans-heptenyl)-phenyl}-quinazoline,
2-(1-trans-alkenyl)-6-(4-hydroxyphenyl)-quinazoline,
2-(6-hydroxy-1-trans-heptenyl)-6-(4-hydroxyphenyl)-quinazoline,
2-(6-alkoxy-1-trans-heptenyl)-6-(4-hydroxyphenyl)-quinazoline,
2-(6-acyloxy-1-trans-heptenyl)-6-(4-hydroxyphenyl)-quinazoline,
4'-hydroxy-2-fluoro-4-(1-trans-alkenyl)-biphenyl,
4'-hydroxy-2-fluoro-4-(6-hydroxy-1-trans-heptenyl)-biphenyl,
4'-hydroxy-2-fluoro-4-(6-alkoxy-1-trans-heptenyl)-biphenyl,
4'-hydroxy-2-fluoro-4-(6-acyloxy-1-trans-heptenyl)-biphenyl,
4'-hydroxy-3-fluoro-4-(1-trans-alkenyl)-biphenyl,
4'-hydroxy-3-fluoro-4-(6-hydroxy-1-trans-heptenyl)-biphenyl,
4'-hydroxy-3-fluoro-4-(6-alkoxy-1-trans-heptenyl)-biphenyl,
4'-hydroxy-3-fluoro-4-(6-acyloxy-1-trans-heptenyl)-biphenyl,
4-hydroxy-2-fluoro-4'-(1-trans-alkenyl)-biphenyl,
4-hydroxy-2-fluoro-4'-(6-hydroxy-1-trans-heptenyl)-biphenyl,
4-hydroxy-2-fluoro-4'-(6-alkoxy-1-trans-heptenyl)-biphenyl,
4-hydroxy-2-fluoro-4'-(6-acyloxy-1-trans-heptenyl)-biphenyl, 4-hydroxy-3-fluoro-4'-(1-trans-alkenyl)-biphenyl,
4-hydroxy-3-fluoro-4'-(6-hydroxy-1-trans-heptenyl)-biphenyl,
4-hydroxy-3-fluoro-4'-(6-alkoxy-1-trans-heptenyl)-biphenyl,
4-hydroxy-3-fluoro-4'-(6-acyloxy-1-trans-heptenyl)-biphenyl,
2-hydroxy-6-{4-(1-trans-alkenyl)-2-fluorophenyl}-naphthalene,
2-hydroxy-6-{4-(6-hydroxy-1-trans-heptenyl)-2-fluorophenyl}-naphthalene,
2-hydroxy-6-{4-(6-alkoxy-1-trans-heptenyl)-2-fluorophenyl}-naphthalene,
2-hydroxy-6-{4-(6-acyloxy-1-trans-heptenyl)-2-fluorophenyl}-naphthalene,
2-hydroxy-6-{4-(1-trans-alkenyl)-3-fluorophenyl}-naphthalene,
2-hydroxy-6-{4-(6-hydroxy-1-trans-heptenyl)-3-fluorophenyl}-naphthalene,
2-hydroxy-6-{4-(6-alkoxy-1-trans-heptenyl)-3-fluorophenyl}-naphthalene,
2-hydroxy-6-{4-(6-acyloxy-1-trans-heptenyl)-3-fluorophenyl}-naphthalene,
2-{4-hydroxy-2-fluorophenyl}-6-(1-trans-alkenyl)-naphthalene,
2-{4-hydroxy-2-fluorophenyl}-6-(6-hydroxy-1-trans-heptenyl)-naphthalene,
2-{4-hydroxy-2-fluorophenyl}-6-(6-alkoxy-1-trans-heptenyl)-naphthalene,
2-{4-hydroxy-2-fluorophenyl}-6-(6-acyloxy-1-trans-heptenyl)-naphthalene,
2-{4-hydroxy-3-fluorophenyl}-6-(1-trans-alkenyl)-naphthalene,
2-{4-hydroxy-3-fluorophenyl}-6-(6-hydroxy-1-trans-heptenyl)-naphthalene,
2-{4-hydroxy-3-fluorophenyl}-6-(6-alkoxy-1-trans-heptenyl)-naphthalene,
2-{4-hydroxy-3-fluorophenyl}-6-(6-acyloxy-1-trans-heptenyl)-naphthalene,
4"-hydroxy-2-fluoro-4-(1-trans-alkenyl)-p-terphenyl,
4"-hydroxy-2-fluoro-4-(6-hydroxy-1-trans-heptenyl)-p-terphenyl,
4"-hydroxy-2-fluoro-4-(6-alkoxy-1-trans-heptenyl)-p-terphenyl,
4"-hydroxy-2-fluoro-4-(6-acyloxy-1-trans-heptenyl)-p-terphenyl,
4"-hydroxy-3-fluoro-4-(1-trans-alkenyl)-p-terphenyl,
4"-hydroxy-3-fluoro-4-(6-hydroxy-1-trans-heptenyl)-p-terphenyl,
4"-hydroxy-3-fluoro-4-(6-alkoxy-1-trans-heptenyl)-p-terphenyl,
4"-hydroxy-3-fluoro-4-(6-acyloxy-1-trans-heptenyl)-p-terphenyl,
4-hydroxy-2-fluoro-4"-(1-trans-alkenyl)-p-terphenyl,
4-hydroxy-2-fluoro-4"-(6-hydroxy-1-trans-heptenyl)-p-terphenyl,
4-hydroxy-2-fluoro-4"-(6-acyloxy-1-trans-heptenyl)-p-terphenyl,
4-hydroxy-2-fluoro-4"-(6-alkoxy-1-trans-heptenyl)-p-terphenyl,
4-hydroxy-3-fluoro-4"-(1-trans-alkenyl)-p-terphenyl,
4-hydroxy-3-fluoro-4"-(6-hydroxy-1-trans-heptenyl)-p-terphenyl,
4-hydroxy-3-fluoro-4"-(6-alkoxy-1-trans-heptenyl)-p-terphenyl,
4-hydroxy-3-fluoro-4"-(6-acyloxy-1-trans-heptenyl)-p-terphenyl,
4"-hydroxy-2'-fluoro-4-(1-trans-alkenyl)-p-terphenyl,
4"-hydroxy-2'-fluoro-4-(6-hydroxy-1-trans-heptenyl)-p-terphenyl,
4"-hydroxy-2'-fluoro-4-(6-alkoxy-1-trans-heptenyl)-p-terphenyl,
4"-hydroxy-2'-fluoro-4-(6-acyloxy-1-trans-heptenyl)-p-terphenyl,
4"-hydroxy-3'-fluoro-4-(1-trans-alkenyl)-p-terphenyl,
4"-hydroxy-3'-fluoro-4-(6-hydroxy-1-trans-heptenyl)-p-terphenyl,
4"-hydroxy-3'-fluoro-4-(6-alkoxy-1-trans-heptenyl)-p-terphenyl,
4"-hydroxy-3'-fluoro-4-(6-acyloxy-1-trans-heptenyl)-p-terphenyl,
5-hydroxy-2-{4-(1-trans-alkenyl)-2-fluorophenyl}-pyridine,
5-hydroxy-2-{4-(6-hydroxy-1-trans-heptenyl)-2-fluorophenyl}-pyridine,
5-hydroxy-2-{4-(6-alkoxy-1-trans-heptenyl)-2-fluorophenyl}-pyridine,
5-hydroxy-2-{4-(6-acyloxy-1-trans-heptenyl)-2-fluorophenyl}-pyridine,
5-hydroxy-2-{4-(1-trans-alkenyl)-2-fluorophenyl}-pyridine,
2-(4-hydroxy-2-fluorophenyl)-5-(1-trans-alkenyl)-pyridine,
2-(4-hydroxy-2-fluorophenyl)-5-(6-hydroxy-1-trans-heptenyl)-pyridine,
2-(4-hydroxy-2-fluorophenyl)-5-(6-alkoxy-1-trans-heptenyl)-pyridine,
2-(4-hydroxy-2-fluorophenyl)-5-(6-acyloxy-1-trans-heptenyl)-pyridine,
2-hydroxy-5-{4-(1-trans-alkenyl)-2-fluorophenyl}-pyridine,
2-hydroxy-5-{4-(6-hydroxy-1-trans-heptenyl)-2-fluorophenyl}-pyridine,
2-hydroxy-5-{4-(6-alkoxy-1-trans-heptenyl)-2-fluorophenyl}-pyridine,
2-hydroxy-5-{4-(6-acyloxy-1-trans-heptenyl)-2-fluorophenyl}-pyridine,
5-(4-hydroxy-2-fluorophenyl)-2-(1-trans-alkenyl)-pyridine,
5-(4-hydroxy-2-fluorophenyl)-2-(6-hydroxy-1-trans-heptenyl)-pyridine,
5-(4-hydroxy-2-fluorophenyl)-2-(6-alkoxy-1-trans-heptenyl)-pyridine,
5-(4-hydroxy-2-fluorophenyl)-2-(6-acyloxy-1-trans-heptenyl)-pyridine,
2-hydroxy-5-{4'-(1-trans-alkenyl)-2'-fluorobiphenyl-4-yl}-pyridine,
2-hydroxy-5-{4'-(6-hydroxy-1-trans-heptenyl)-2'-fluorobiphenyl-4-yl}-pyridine,
2-hydroxy-5-{4'-(6-alkoxy-1-trans-heptenyl)-2'-fluorobiphenyl-4-yl}-pyridine,
2-hydroxy-5-{4'-(6-acyloxy-1-trans-heptenyl)-2'-fluorobiphenyl-4-yl}-pyridine,
5-(4'-hydroxy-2'-fluorobiphenyl-4-yl)-2-(1-trans-alkenyl)-pyridine,
5-(4'-hydroxy-2'-fluorobiphenyl-4-yl)-2-(6-hydroxy-1-trans-heptenyl)-pyridine,
5-(4'-hydroxy-2'-fluorobiphenyl-4-yl)-2-(6-alkoxy-1-trans-heptenyl)-pyridine,
4-(4'-hydroxy-2'-fluorobiphenyl-4-yl)-2-(6-acyloxy-1-trans-heptenyl)-pyridine,
5-hydroxy-2-{4'-(1-trans-alkenyl)-2'-fluorobiphenyl-4-yl}-pyridine,
5-hydroxy-2-{4'-(6-hydroxy-1-trans-heptenyl)-2'-fluorobiphenyl-4-yl}-pyridine,
5-hydroxy-2-{4'-(6-alkoxy-1-trans-heptenyl)-2'-fluorobiphenyl-4-yl}-pyridine, 5-hydroxy-2-{4'-(6-acyloxy-1-trans-heptenyl)-2'-fluorobiphenyl-4-yl}-pyridine,
2-(4'-hydroxy-2'-fluorobiphenyl-4-yl)-5-(1-trans-alkenyl)-pyridine,
2-(4'-hydroxy-2'-fluorobiphenyl-4-yl)-5-(6-hydroxy-1-trans-heptenyl)-pyridine,
2-(4'-hydroxy-2'-fluorobiphenyl-4-yl)-5-(6-alkoxy-1-trans-heptenyl)-pyridine,
2-(4'-hydroxy-2'-fluorobiphenyl-4-yl)-5-(6-acyloxy-1-trans-heptenyl)-pyridine,
5-(4-hydroxy-2-fluorophenyl)-2-{4-(1-trans-alkenyl)-phenyl}-pyridine,
5-(4-hydroxy-2-fluorophenyl)-2-{4-(6-hydroxy-1-trans-heptenyl)-phenyl}-pyridine,
5-(4-hydroxy-2-fluorophenyl)-2-{4-(6-alkoxy-1-trans-heptenyl)-phenyl}-pyridine,
5-(4-hydroxy-2-fluorophenyl)-2-{4-(6-acyloxy-1-trans-heptenyl)-phenyl}-pyridine,
2-(4-hydroxy-2-fluorophenyl)-5-{4-(1-trans-alkenyl)-phenyl}-pyridine,
2-(4-hydroxy-2-fluorophenyl)-5-{4-(6-hydroxy-1-trans-heptenyl)-phenyl}-pyridine,
2-(4-hydroxy-2-fluorophenyl)-5-{4-(6-alkoxy-1-trans-heptenyl)-phenyl}-pyridine,
2-(4-hydroxy-2-fluorophenyl)-5-{4-(6-acyloxy-1-trans-heptenyl)-phenyl}-pyridine,
5-(4-hydroxyphenyl)-2-{4-(1-trans-alkenyl)-2-fluorophenyl}-pyridine,
5-(4-hydroxyphenyl)-2-{4-(6-hydroxy-1-trans-heptenyl)-2-fluorophenyl}-pyridine,
5-(4-hydroxyphenyl)-2-{4-(6-alkoxy-1-trans-heptenyl)-2-fluorophenyl}-pyridine,
5-(4-hydroxyphenyl)-2-{4-(6-acyloxy-1-trans-heptenyl)-2-fluorophenyl}-pyridine,
2-(4-hydroxyphenyl)-5-{4-(1-trans-alkenyl)-2-fluorophenyl}-pyridine,
2-(4-hydroxyphenyl)-5-{4-(6-hydroxy-1-trans-heptenyl)-2-fluorophenyl}-pyridine,
2-(4-hydroxyphenyl)-5-{4-(6-alkoxy-1-trans-heptenyl)-2-fluorophenyl}-pyridine,
2-(4-hydroxyphenyl)-5-{4-(6-acyloxy-1-trans-heptenyl)-2-fluorophenyl}-pyridine,
5-hydroxy-2-{4-(1-trans-alkenyl)-3-fluorophenyl}-pyridine,
5-hydroxy-2-{4-(6-hydroxy-1-trans-heptenyl)-3-fluorophenyl}-pyridine,
5-hydroxy-2-{4-(6-alkoxy-1-trans-heptenyl)-3-fluorophenyl}-pyridine,
5-hydroxy-2-{4-(6-acyloxy-1-trans-heptenyl)-3-fluorophenyl}-pyridine,
2-(4-hydroxy-3-fluorophenyl)-5-(1-trans-alkenyl)-pyridine,
2-(4-hydroxy-3-fluorophenyl)-5-(6-hydroxy-1-trans-heptenyl)-pyridine,
2-(4-hydroxy-3-fluorophenyl)-5-(6-alkoxy-1-trans-heptenyl)-pyridine,
2-(4-hydroxy-3-fluorophenyl)-5-(6-acyloxy-1-trans-heptenyl)-pyridine,
2-hydroxy-5-{4-(1-trans-alkenyl)-3-fluorophenyl}-pyridine,
2-hydroxy-5-{4-(6-hydroxy-1-trans-heptenyl)-3-fluorophenyl}-pyridine,
2-hydroxy-5-{4-(6-alkoxy-1-trans-heptenyl)-3-fluorophenyl}-pyridine,
2-hydroxy-5-{4-(6-acyloxy-1-trans-heptenyl)-3-fluorophenyl}-pyridine,
5-(4-hydroxy-3-fluorophenyl)-2-(1-trans-alkenyl)-pyridine,
5-(4-hydroxy-3-fluorophenyl)-2-(6-hydroxy-1-trans-heptenyl)-pyridine,
5-(4-hydroxy-3-fluorophenyl)-2-(6-alkoxy-1-trans-heptenyl)-pyridine,
5-(4-hydroxy-3-fluorophenyl)-2-(6-acyloxy-1-trans-heptenyl)-pyridine,
2-hydroxy-5-{4'-(1-trans-alkenyl)-3'-fluorobiphenyl-4-yl}-pyridine,
2-hydroxy-5-{4'-(6-hydroxy-1-trans-heptenyl)-3'-fluorobiphenyl-4-yl}-pyridine,
2-hydroxy-5-{4'-(6-alkoxy-1-trans-heptenyl)-3'-fluorobiphenyl-4-yl}-pyridine,
2-hydroxy-5-{4'-(6-acyloxy-1-trans-heptenyl)-3'-fluorobiphenyl-4-yl}-pyridine,
5-(4'-hydroxy-3'-fluorobiphenyl-4-yl)-2-(1-trans-alkenyl)-pyridine,
5-(4'-hydroxy-3'-fluorobiphenyl-4-yl)-2-(6-hydroxy-1-trans-heptenyl)-pyridine,
5-(4'-hydroxy-3'-fluorobiphenyl-4-yl)-2-(6-alkoxy-1-trans-heptenyl)-pyridine,
5-(4'-hydroxy-3'-fluorobiphenyl-4-yl)-2-(6-acyloxy-1-trans-heptenyl)-pyridine,
5-hydroxy-2-{4'-(1-trans-alkenyl)-3'-fluorobiphenyl-4-yl}-pyridine,
5-hydroxy-2-{4'-(6-hydroxy-1-trans-heptenyl)-3'-fluorobiphenyl-4-yl}-pyridine,
5-hydroxy-2-{4'-(6-alkoxy-1-trans-heptenyl)-3'-fluorobiphenyl-4-yl}-pyridine,
5-hydroxy-2-{4'-(6-acyloxy-1-trans-heptenyl)-3'-fluorobiphenyl-4-yl}-pyridine,
2-(4'-hydroxy-3'-fluorobiphenyl-4-yl)-5-(1-trans-alkenyl)-pyridine,
2-(4'-hydroxy-3'-fluorobiphenyl-4-yl)-5-(6-hydroxy-1-trans-heptenyl)-pyridine,
2-(4'-hydroxy-3'-fluorobiphenyl-4-yl)-5-(6-alkoxy-1-trans-heptenyl)-pyridine,
2-(4'-hydroxy-3'-fluorobiphenyl-4-yl)-5-(6-acyloxy-1-trans-heptenyl)-pyridine,
5-(4-hydroxy-3-fluorophenyl)-2-(4-(1-trans-alkenyl)-phenyl}-pyridine,
5-(4-hydroxy-3-fluorophenyl)-2-{4-(6-hydroxy-1-trans-heptenyl)-phenyl}-pyridine,
5-(4-hydroxy-3-fluorophenyl)-2-{4-(6-alkoxy-1-trans-heptenyl)-phenyl}-pyridine,
5-(4-hydroxy-3-fluorophenyl)-2-{4-(6-acyloxy-1-trans-heptenyl)-phenyl}-pyridine,
2-(4-hydroxy-3-fluorophenyl)-5-{4-(1-trans-alkenyl)-phenyl}-pyridine,
2-(4-hydroxy-3-fluorophenyl)-5-{4-(6-hydroxy-1-trans-heptenyl)-phenyl}-pyridine,
2-(4-hydroxy-3-fluorophenyl)-5-{4-(6-alkoxy-1-trans-heptenyl)-phenyl}-pyridine,
2-(4-hydroxy-3-fluorophenyl)-5-{4-(6-acyloxy-1-trans-heptenyl)-phenyl}-pyridine,
5-(4-hydroxyphenyl)-2-{4-(1-trans-alkenyl)-3-fluorophenyl}-pyridine,
5-(4-hydroxyphenyl)-2-{4-(6-hydroxy-1-trans-heptenyl)-3-fluorophenyl}-pyridine,
5-(4-hydroxyphenyl)-2-{4-(6-alkoxy-1-trans-heptenyl)-3-fluorophenyl}-pyridine,
5-(4-hydroxyphenyl)-2-{4-(6-acyloxy-1-trans-heptenyl)-3-fluorophenyl}-pyridine,
2-(4-hydroxyphenyl)-5-{4-(1-trans-alkenyl)-3-fluorophenyl}-pyridine,
2-(4-hydroxyphenyl)-5-{4-(6-hydroxy-1-trans-heptenyl)-3-fluorophenyl}-pyridine,
2-(4-hydroxyphenyl)-5-{4-(6-alkoxy-1-trans-heptenyl)-3-fluorophenyl}-pyridine,
2-(4-hydroxyphenyl)-5-{4-(6-acyloxy-1-trans-heptenyl)-3-fluorophenyl}-pyridine, 5-hydroxy-2-{4-(1-trans-alkenyl)-2-fluorophenyl}-pyrimidine,
5-hydroxy-2-{4-(6-hydroxy-1-trans-heptenyl)-2-fluorophenyl}-pyrimidine,
5-hydroxy-2-{4-(6-alkoxy-1-trans-heptenyl)-2-fluorophenyl}-pyrimidine,
5-hydroxy-2-{4-(6-acyloxy-1-trans-heptenyl)-2-fluorophenyl}-pyrimidine,
5-hydroxy-2-{4-(1-trans-alkenyl)-3-fluorophenyl}-pyrimidine,
5-hydroxy-2-{4-(6-hydroxy-1-trans-heptenyl)-3-fluorophenyl}-pyrimidine,
5-hydroxy-2-{4-(6-alkoxy-1-trans-heptenyl)-3-fluorophenyl}-pyrimidine, 5-hydroxy-2-{4-(6-acyloxy-1-trans-heptenyl)-3-fluorophenyl}-pyrimidine,
2-(4-hydroxy-2-fluorophenyl)-5-(1-trans-alkenyl)-pyrimidine,
2-(4-hydroxy-2-fluorophenyl)-5-(6-hydroxy-1-trans-heptenyl)-pyrimidine,
2-(4-hydroxy-2-fluorophenyl)-5-(6-alkoxy-1-trans-heptenyl)-pyrimidine,
2-(4-hydroxy-2-fluorophenyl)-5-(6-acyloxy-1-trans-heptenyl)-pyrimidine,
2-(4-hydroxy-3-fluorophenyl)-5-(1-trans-alkenyl)-pyrimidine,
2-(4-hydroxy-3-fluorophenyl)-5-(6-hydroxy-1-trans-heptenyl)-pyrimidine,
2-(4-hydroxy-3-fluorophenyl)-5-(6-alkoxy-1-trans-heptenyl)-pyrimidine,
2-(4-hydroxy-3-fluorophenyl)-5-(6-acyloxy-1-trans-heptenyl)-pyrimidine,
2-hydroxy-5-{4-(1-trans-alkenyl)-2-fluorophenyl}-pyrimidine,
2-hydroxy-5-{4-(6-hydroxy-1-trans-heptenyl)-2-fluorophenyl}-pyrimidine,
2-hydroxy-5-{4-(6-alkoxy-1-trans-heptenyl)-2-fluorophenyl}-pyrimidine,
2-hydroxy-5-{4-(6-acyloxy-1-trans-heptenyl)-2-fluorophenyl}-pyrimidine,
2-hydroxy-5-{4-(1-trans-alkenyl)-3-fluorophenyl}-pyrimidine,
2-hydroxy-5-{4-(6-hydroxy-1-trans-heptenyl)-3-fluorophenyl}-pyrimidine,
2-hydroxy-5-{4-(6-alkoxy-1-trans-heptenyl)-3-fluorophenyl}-pyrimidine,
2-hydroxy-5-{4-(6-acyloxy-1-trans-heptenyl)-3-fluorophenyl}-pyrimidine,
5-(4-hydroxy-2-fluorophenyl)-2-(1-trans-alkenyl)-pyrimidine,
5-(4-hydroxy-2-fluorophenyl)-2-(6-hydroxy-1-trans-heptenyl)-pyrimidine,
5(4-hydroxy-2-fluorophenyl)-2-(6-alkoxy-1-trans-heptenyl)-pyrimidine,
5-(4-hydroxy-2-fluorophenyl)-2-(6-acyloxy-1-trans-heptenyl)-pyrimidine,
5-(4-hydroxy-3-fluorophenyl)-2-(1-trans-alkenyl)-pyrimidine,
5-(4-hydroxy-3-fluorophenyl)-2-(6-hydroxy-1-trans-heptenyl)-pyrimidine,
5-(4-hydroxy-3-fluorophenyl)-2-(6-alkoxy-1-trans-heptenyl)-pyrimidine,
5-(4-hydroxy-3-fluorophenyl)-2-(6-acyloxy-1-trans-heptenyl)-pyrimidine,
6-hydroxy-3-{4-(1-trans-alkenyl)-2-fluorophenyl}-pyridazine,
6-hydroxy-3-{4-(6-hydroxy-1-trans-heptenyl)-2-fluorophenyl}-pyridazine,
6-hydroxy-3-{4-(6-alkoxy-1-trans-heptenyl)-2-fluorophenyl}-pyridazine,
6-hydroxy-3-{4-(6-acyloxy-1-trans-heptenyl)-2-fluorophenyl}-pyridazine,
6-(4-hydroxy-2-fluorophenyl)-3-(1-trans-alkenyl)-pyridazine,
6-(4-hydroxy-2-fluorophenyl)-3-(6-hydroxy-1-trans-heptenyl)-pyridazine,
6-(4-hydroxy-2-fluorophenyl)-3-(6-alkoxy-1-trans-heptenyl)-pyridazine,
6-(4-hydroxy-2-fluorophenyl)-3-(6-acyloxy-1-trans-heptenyl)-pyridazine,
6-hydroxy-3-{4-(1-trans-alkenyl)-3-fluorophenyl}-pyridazine,
6-hydroxy-3-{4-(6-hydroxy-1-trans-heptenyl)-3-fluorophenyl}-pyridazine,
6-hydroxy-3-{4-(6-alkoxy-1-trans-heptenyl)-3-fluorophenyl}-pyridazine,
6-hydroxy-3-{4-(6-acyloxy-1-trans-heptenyl)-3-fluorophenyl}-pyridazine,
6-(4-hydroxy-3-fluorophenyl)-3-(1-trans-alkenyl)-pyridazine,
6-(4-hydroxy-3-fluorophenyl)-3-(6-hydroxy-1-trans-heptenyl)-pyridazine,
6-(4-hydroxy-3-fluorophenyl)-3-(6-alkoxy-1-trans-heptenyl)-pyridazine,
6-(4-hydroxy-3-fluorophenyl)-3(6-acyloxy-1-trans-heptenyl)-pyridazine,
5-hydroxy-2-{4'-(1-trans-alkenyl)-2'-fluorobiphenyl-4yl}-pyrimidine,
5-hydroxy-2-{4'-(6-hydroxy-1-trans-heptenyl)-2'-fluorobiphenyl-4-yl}-pyrimidine,
5-hydroxy-2-{4'-(6-alkoxy-1-trans-heptenyl)-2'-fluorobiphenyl-4-yl}-pyrimidine,
5-hydroxy-2-{4'-(6-acyloxy-1-trans-heptenyl)-2'-fluorobiphenyl-4-yl}-pyrimidine,
2-(4'-hydroxy-2'-fluorobiphenyl-4yl)-5(1-trans-alkenyl)-pyrimidine,
2-(4'-hydroxy-2'-fluorobiphenyl-4yl)-5-(6-hydroxy-1-trans-heptenyl)-pyrimidine,
2-(4'-hydroxy-2'-fluorobiphenyl-4yl)-5-(6-alkoxy-1-trans-heptenyl)-pyrimidine,
2-(4'-hydroxy-2'-fluorobiphenyl-4yl)-5-(6-acyloxy-1-trans-heptenyl)-pyrimidine,
2-hydroxy-5-{4'-(1-trans-alkenyl)-2'-fluorobiphenyl-4-yl}-pyrimidine,
2-hydroxy-5-{4'-(6-hydroxy-1-trans-heptenyl)-2'-fluorobiphenyl-4-yl}-pyrimidine,
2-hydroxy-5-{4'-(6-alkoxy-1-trans-heptenyl)-2'-fluorobiphenyl-4-yl}-pyrimidine,
2-hydroxy-5-{4'-(6-acyloxy-1-trans-heptenyl)-2'-fluorobiphenyl-4-yl}-pyrimidine,
5-(4'-hydroxy-2'-fluorobiphenyl-4-yl)-2-(1-trans-alkenyl)-pyrimidine,
5-(4'-hydroxy-2'-fluorobiphenyl-4yl)-2-(6-hydroxy-1-trans-heptenyl)-pyrimidine,
5-(4'-hydroxy-2'-fluorobiphenyl-4yl)-2-(6-alkoxy-1-trans-heptenyl)-pyrimidine,
5-(4'-hydroxy-2'-fluorobiphenyl-4yl)-2-(6-acyloxy-1-trans-heptenyl)-pyrimidine,
5-(4-hydroxy-2-fluorophenyl)-2-{4-(1-trans-alkenyl)-phenyl}-pyrimidine,
5-(4-hydroxy-2-fluorophenyl)-2-{4-(6-hydroxy-1-trans-heptenyl)-phenyl)-pyrimidine,
5-(4-hydroxy-2-fluorophenyl)-2-{4-(6-alkoxy-1-trans-heptenyl)-phenyl}-pyrimidine,
5-(4-hydroxy-2-fluorophenyl)-2-{4-(6-acyloxy-1-trans-heptenyl)-phenyl}-pyrimidine, 2-(4-hydroxy-2-fluorophenyl)-5-{4-(1-trans-alkenyl)-phenyl}-pyrimidine,
2-(4-hydroxy-2-fluorophenyl)-5-{4-(6-hydroxy-1-trans-heptenyl)-phenyl}-pyrimidine,
2-(4-hydroxy-2-fluorophenyl)-5-{4-(6-alkoxy-1-trans-heptenyl)-phenyl}-pyrimidine,
2-(4-hydroxy-2-fluorophenyl)-5-{4-(6-acyloxy-1-trans-heptenyl)-phenyl}-pyrimidine,
5-(4-hydroxyphenyl)-2-{4-(1-trans-alkenyl)-2-fluorophenyl}-pyrimidine,
5-(4-hydroxyphenyl)-2-{4-(6-hydroxy-1-trans-heptenyl)-2-fluorophenyl}-pyrimidine,
5-(4-hydroxyphenyl)-2-{4-(6-alkoxy-1-trans-heptenyl)-2-fluorophenyl}-pyrimidine,
5-(4-hydroxyphenyl)-2-{4-(6-acyloxy-1-trans-heptenyl)-2-fluorophenyl}-pyrimidine,
2-(4-hydroxyphenyl)-5-{4-(1-trans-alkenyl)-2-fluorophenyl}-pyrimidine,
2-(4-hydroxyphenyl)-5-{4-(6-hydroxy-1-trans-heptenyl)-2-fluorophenyl}-pyrimidine,
2-(4-hydroxyphenyl)-5-{4-(6-alkoxy-1-trans-heptenyl)-2-fluorophenyl}-pyrimidine,
2-(4-hydroxyphenyl)-5-{4-(6-acyloxy-1-trans-heptenyl)-2-fluorophenyl}-pyrimidine,
5-hydroxy-2-{4'-(1-trans-alkenyl)-3'-fluorobiphenyl-4yl}-pyrimidine,
5-hydroxy-2-{4'-(6-hydroxy-1-trans-heptenyl)-3'-fluorobiphenyl-4-yl}-pyrimidine,
5-hydroxy-2-{4'-(6-alkoxy-1-trans-heptenyl)-3'-fluorobiphenyl-4yl}-pyrimidine,
5-hydroxy-2-{4'-(6-acyloxy-1-trans-heptenyl)-3'-fluorobiphenyl-4yl}-pyrimidine,
2-(4'-hydroxy-3'-fluorobiphenyl-4-yl)-5-(1-trans-alkenyl)-pyrimidine,
2-(4'-hydroxy-3'-fluorobiphenyl-4-yl)-5-(6-hydroxy-1-trans-heptenyl)-pyrimidine,
2(4'-hydroxy-3'-fluorobiphenyl-4-yl)-5-(6-alkoxy-1-trans-heptenyl)-pyrimidine,
2-(4'-hydroxy-3'-fluorobiphenyl-4-yl)-5-(6-acyloxy-1-trans-heptenyl)-pyrimidine,
2-hydroxy-5-{4'-(1-trans-alkenyl)-3'-fluorobiphenyl-4yl}-pyrimidine,
2-hydroxy-5-{4'-(6hydroxy-1-trans-heptenyl)-3'-fluorobiphenyl-4yl}-pyrimidine,
2-hydroxy-5-{4'-(6-alkoxy-1-trans-heptenyl)-3'-fluorobiphenyl-4yl}-pyrimidine,
2-hydroxy-5-{4-(6-acyloxy-1-trans-heptenyl)-3'-fluorobiphenyl-4-yl}-pyrimidine,
5-(4'-hydroxy-3'-fluorobiphenyl-4yl)-2-(1-trans-alkenyl)-pyrimidine,
5-(4'-hydroxy-3'-fluorobiphenyl-4-yl)-2-(6-hydroxy-1-trans-heptenyl)-pyrimidine,
5-(4'-hydroxy-3'-fluorobiphenyl-4-yl)-2-(6-alkoxy-1-trans-heptenyl)-pyrimidine,
5-(4'-hydroxy-3'-fluorobiphenyl-4yl)-2-(6-acyloxy-1-trans-heptenyl)-pyrimidine,
5-(4-hydroxy-3-fluorophenyl)-2-{4-(1-trans-alkenyl)-phenyl}-pyrimidine,
5-(4-hydroxy-3-fluorophenyl)-2-{4-(6-hydroxy-1-trans-heptenyl)-phenyl}-pyrimidine,
5-(4-hydroxy-3-fluorophenyl)-2-{4-(6-alkoxy-1-trans-heptenyl)-phenyl}-pyrimidine,
5-(4-hydroxy-3-fluorophenyl)-2-{4-(6-acyloxy-1-trans-heptenyl)-phenyl}-pyrimidine,
2-(4-hydroxy-3-fluorophenyl)-5-{4-(1-trans-alkenyl)-phenyl}-pyrimidine,
2-(4-hydroxy-3-fluorophenyl)-5-{4-(6-hydroxy-1-trans-heptenyl)-phenyl}-pyrimidine,
2-(4-hydroxy-3-fluorophenyl)-5-{4-(6-alkoxy-1-trans-heptenyl)-phenyl}-pyrimidine,
2-(4-hydroxy-3-fluorophenyl)-5-{4-(6-acyloxy-1-trans-heptenyl)-phenyl}-pyrimidine,
5-(4-hydroxyphenyl)-2-{4-(1-trans-alkenyl)-3-fluorophenyl}-pyrimidine,
5(4-hydroxyphenyl)-2-{4-(6-hydroxy-1-trans-heptenyl)-3-fluorophenyl}-pyrimidine,
5-(4-hydroxyphenyl)-2-{4-(6-alkoxy-1-trans-heptenyl)-3-fluorophenyl}-pyrimidine,
5-(4-hydroxyphenyl)-2-{4-(6-acyloxy-1-trans-heptenyl)-3-fluorophenyl}-pyrimidine,
2-(4-hydroxyphenyl)-5-{4-(1-trans-alkenyl)-2-fluorophenyl}-pyrimidine,
2-(4-hydroxyphenyl)-5-{4-(6-hydroxy-1-trans-heptenyl)-2-fluorophenyl}-pyrimidine,
2-(4-hydroxyphenyl)-5-{4-(6-alkoxy-1-trans-heptenyl)-2-fluorophenyl}-pyrimidine,
2-(4-hydroxyphenyl)-5-{4-(6-acyloxy-1-trans-heptenyl)-2-fluorophenyl}-pyrimidine,
7-hydroxy-3-{4-(1-trans-alkenyl)-2-fluorophenyl}-isoquinoline,
7-hydroxy-3-{4-(6-hydroxy-1-trans-heptenyl)-2-fluorophenyl}-isoquinoline,
7-hydroxy-3-{4-(6-alkoxy-1-trans-heptenyl)-2-fluorophenyl}-isoquinoline,
7-hydroxy-3-{4-(6-acyloxy-1-trans-heptenyl)-2-fluorophenyl}-isoquinoline,
3-(4-hydroxy-2-fluorophenyl)-7-(1-trans-alkenyl)-isoquinoline,
3-(4-hydroxy-2-fluorophenyl)-7-(6-hydroxy-1-trans-heptenyl)-isoquinoline,
3-(4-hydroxy-2-fluorophenyl)-7-(6-alkoxy-1-trans-heptenyl)-isoquinoline,
3-(4-hydroxy-2-fluorophenyl)-7-(6-acyloxy-1-trans-heptenyl)-isoquinoline,
7-hydroxy-3-{4-(1-trans-alkenyl)-3-fluorophenyl}-isoquinoline,
7-hydroxy-3-{4-(6-hydroxy-1-trans-heptenyl)-3-fluorophenyl}-isoquinoline,
7-hydroxy-3-{4-(6-alkoxy-1-trans-heptenyl)-3-fluorophenyl}-isoquinoline,
7-hydroxy-3-{4-(6-acyloxy-1-trans-heptenyl)-3-fluorophenyl}-isoquinoline,
3-(4-hydroxy-3-fluorophenyl)-7-(1-trans-alkenyl)-isoquinoline,
3-(4-hydroxy-3-fluorophenyl)-7-(6-hydroxy-1-trans-heptenyl)-isoquinoline,
3-(4-hydroxy-3-fluorophenyl)-7-(6-alkoxy-1-trans-heptenyl)-isoquinoline,
3-(4-hydroxy-3-fluorophenyl)-7-(6-acyloxy-1-trans-heptenyl)-isoquinoline,
6-hydroxy-2-{4-(1-trans-alkenyl)-2-fluorophenyl}-quinoline,
6-hydroxy-2-{4-(6-hydroxy-1-trans-heptenyl)-2-fluorophenyl}-quinoline,
6-hydroxy-2-{4-(6-alkoxy-1-trans-heptenyl)-2-fluorophenyl}-quinoline,
6-hydroxy-2-{4-(6-acyloxy-1-trans-heptenyl)-2-fluorophenyl}-quinoline,
2-(4-hydroxy-2-fluorophenyl)-6-(1-trans-alkenyl)-quinoline,
2-(4-hydroxy-2-fluorophenyl)-6-(6-hydroxy-1-trans-heptenyl)-quinoline,
2-(4-hydroxy-2-fluorophenyl)-6-(6-alkoxy-1-trans-heptenyl)-quinoline,
2-(4-hydroxy-2-fluorophenyl)-6-(6-acyloxy-1-trans-heptenyl)-quinoline, 6-hydroxy-2-{4-(1-trans-alkenyl)-3-fluorophenyl}-quinoline,
6-hydroxy-2-{4-(6-hydroxy-1-trans-heptenyl)-3-fluorophenyl}-quinoline,
6-hydroxy-2-{4-(6-alkoxy-1-trans-heptenyl)-3-fluorophenyl}-quinoline,
6-hydroxy-2-{4-(6-acyloxy-1-trans-heptenyl)-3-fluorophenyl}-quinoline,
2-(4-hydroxy-3-fluorophenyl)-6-(1-trans-alkenyl)-quinoline,
2-(4-hydroxy-3-fluorophenyl)-6-(6-hydroxy-1-trans-heptenyl)-quinoline,
2-(4-hydroxy-3-fluorophenyl)-6-(6-alkoxy-1-trans-heptenyl)-quinoline,
2-(4-hydroxy-3-fluorophenyl)-6-(6-acyloxy-1-trans-heptenyl)-quinoline,
2-hydroxy-6-{4-(1-trans-alkenyl)-2-fluorophenyl}-quinoxaline,
2-hydroxy-6-{4-(6-hydroxy-1-trans-heptenyl)-2-fluorophenyl}-quinoxaline,
2-hydroxy-6-{4-(6-alkoxy-1-trans-heptenyl)-2-fluorophenyl}-quinoxaline,
2-hydroxy-6-{4(6-acyloxy-1-trans-heptenyl)-2-fluorophenyl}-quinoxaline,
2-(1-trans-alkenyl)-6-(4-hydroxy-2-fluorophenyl)-quinoxaline,
2-(6-hydroxy-1-trans-heptenyl)-6-(4-hydroxy-2-fluorophenyl)-quinoxaline,
2-(6-alkoxy-1-trans-heptenyl)-6-(4-hydroxy-2-fluorophenyl)-quinoxaline,
2-(6-acyloxy-1-trans-heptenyl)-6-(4-hydroxy-2-fluorophenyl)-quinoxaline,
6-hydroxy-2-{4-(1-trans-alkenyl)-2-fluorophenyl}-quinoxaline,
6-hydroxy-2-{4-(6-hydroxy-1-trans-heptenyl)-2-fluorophenyl}-quinoxaline,
6-hydroxy-2-{4-(6-alkoxy-1-trans-heptenyl)-2-fluorophenyl}-quinoxaline,
6-hydroxy-2-{4-(6-acyloxy-1-trans-heptenyl)-2-fluorophenyl}-quinoxaline,
2-(4-hydroxy-2-fluorophenyl)-6-(1-trans-alkenyl)-quinoxaline,
2-(4-hydroxy-2-fluorophenyl)-6-(6-hydroxy-1-trans-heptenyl)-quinoxaline,
2-(4-hydroxy-2-fluorophenyl)-6-(6-alkoxy-1-trans-heptenyl)-quinoxaline,
2-(4-hydroxy-2-fluorophenyl)-6-(6-acyloxy-1-trans-heptenyl)-quinoxaline,
2-hydroxy-6-{4-(1-trans-alkenyl)-3-fluorophenyl}-quinoxaline,
2-hydroxy-6-{4-(6-hydroxy-1-trans-heptenyl)-3-fluorophenyl}-quinoxaline,
2-hydroxy-6-{4-(6-alkoxy-1-trans-heptenyl)-3-fluorophenyl}-quinoxaline,
2-hydroxy-6-{4-(6-acyloxy-1-trans-heptenyl)-3-fluorophenyl}-quinoxaline,
2(1-trans-alkenyl)-6-(4-hydroxy-3-fluorophenyl)-quinoxaline,
2-(6-hydroxy-1-trans-heptenyl)-6-(4-hydroxy-3-fluorophenyl)-quinoxaline,
2-(6-alkoxy-1-trans-heptenyl)-6-(4-hydroxy-3-fluorophenyl)-quinoxaline,
2-(6-acyloxy-1-trans-heptenyl)-6-(4-hydroxy-3-fluorophenyl)-quinoxaline,
6-hydroxy-2-{4-(1-trans-alkenyl)-3-fluorophenyl}-quinoxaline,
6-hydroxy-2-{4-(6-hydroxy-1-trans-heptenyl)-3-fluorophenyl}-quinoxaline,
6-hydroxy-2-{4-(6-alkoxy-1-trans-heptenyl)-3-fluorophenyl}-quinoxaline,
6-hydroxy-2-{4-(6-acyloxy-1-trans-heptenyl)-3-fluorophenyl}-quinoxaline,
2-(4-hydroxy-3-fluorophenyl)-6-(1-trans-alkenyl)-quinoxaline,
2(4-hydroxy-3-fluorophenyl)-6-(6-hydroxy-1-trans-heptenyl)-quinoxaline,
2-(4-hydroxy-3-fluorophenyl)-6-(6-alkoxy-1-trans-heptenyl)-quinoxaline,
2-(4-hydroxy-3-fluorophenyl)-6-(6-acyloxy-1-trans-heptenyl)-quinoxaline,
2-hydroxy-6-{4-(1-trans-alkenyl)-2-fluorophenyl}-quinazoline,
2-hydroxy-6-{4-(6-hydroxy-1-trans-heptenyl)-2-fluorophenyl}-quinazoline,
2-hydroxy-6-{4-(6-alkoxy-1-trans-heptenyl)-2-fluorophenyl}-quinazoline,
2-hydroxy-6-{4-(6-acyloxy-1-trans-heptenyl)-2-fluorophenyl}-quinazoline,
2-hydroxyoxy-6-{4-(1-trans-alkenyl)-2-fluorophenyl}-quinazoline,
2-(1-trans-alkenyl)-6-(4-hydroxy-2-fluorophenyl)-quinazoline,
2-(6-hydroxy-1-trans-heptenyl)-6-(4-hydroxy-2-fluorophenyl)-quinazoline,
2-(6-alkoxy-1-trans-heptenyl)-6-(4-hydroxy-2-fluorophenyl)-quinazoline,
2-(6-acyloxy-1-trans-heptenyl)-6-(4-hydroxy-2-fluorophenyl)-quinazoline,
2-hydroxy-6-{4-(1-trans-alkenyl)-3-fluorophenyl}-quinazoline,
2-hydroxy-6-{4-(6-hydroxy-1-trans-heptenyl)-3-fluorophenyl}-quinazoline,
2-hydroxy-6-{4-(6-alkoxy-1-trans-heptenyl)-3-fluorophenyl}-quinazoline,
2-hydroxy-6-{4-(6-acyloxy-1-trans-heptenyl)-3-fluorophenyl}-quinazoline,
2-(1-trans-alkenyl)-6-(4-hydroxy-3-fluorophenyl)-quinazoline,
2-(6-hydroxy-1-trans-heptenyl)-6-(4-hydroxy-3-fluorophenyl)-quinazoline,
2-(6-alkoxy-1-trans-heptenyl)-6-(4-hydroxy-3-fluorophenyl)-quinazoline,
2-(6-acyloxy-1-trans-heptenyl)-6-(4-hydroxy-3-fluorophenyl)-quinazoline,
4'-hydroxy-2,3-difluoro-4-(1-trans-alkenyl)-biphenyl,
4'-hydroxy-2,3-difluoro-4-(6-hydroxy-1-trans-heptenyl)-biphenyl,
4'-hydroxy-2,3-difluoro-4-(6-alkoxy-1-trans-heptenyl)-biphenyl,
4'-hydroxy-2,3-difluoro-4-(6-acyloxy-1-trans-heptenyl)-biphenyl,
4-hydroxy-2,3-difluoro-4'-(1-trans-alkenyl)-biphenyl,
4-hydroxy-2,3-difluoro-4'-(6-hydroxy-1-trans-heptenyl)-biphenyl,
4-hydroxy-2,3-difluoro-4'-(6-alkoxy-1-trans-heptenyl)-biphenyl,
4-hydroxy-2,3-difluoro-4'-(6-acyloxy-1-trans-heptenyl)-biphenyl,
2-hydroxy-6-{4-(1-trans-alkenyl)-2,3-difluorophenyl}-naphthalene,
2-hydroxy-6-{4-(6-hydroxy-1-trans-heptenyl)-2,3-difluorophenyl}-naphthalene,
2-hydroxy-6-{4-(6-alkoxy-1-trans-heptenyl)-2,3-difluorophenyl}-naphthalene,
2-hydroxy-6-{4-(6-acyloxy-1-trans-heptenyl)-2,3-difluorophenyl}-naphthalene, 2-{4-hydroxy-2,3-difluorophenyl}-6-(1-trans-alkenyl)-naphthalene,
2-{4-hydroxy-2,3-difluorophenyl}-6-(6-hydroxy-1-trans-heptenyl)-naphthalene,
2-{4-hydroxy-2,3-difluorophenyl}-6-(6-alkoxy-1-trans-heptenyl)-naphthalene,
2-{4-hydroxy-2,3-difluorophenyl}-6-(6-acyloxy-1-trans-heptenyl)-naphthalene,
4"-hydroxy-2,3-difluoro-4-(1-trans-alkenyl)-p-terphenyl,
4"-hydroxy-2,3-difluoro-4-(6-hydroxy-1-trans-heptenyl)-p-terphenyl,
4"-hydroxy-2,3-difluoro-4-(6-alkoxy-1-trans-heptenyl)-p-terphenyl,
4"-hydroxy-2,3-difluoro-4-(6-acyloxy-1-trans-heptenyl)-p-terphenyl,
4-hydroxy-2,3-difluoro-4"-(1-trans-alkenyl)-p-terphenyl,
4-hydroxy-2,3-difluoro-4"-(6-hydroxy-1-trans-heptenyl)-p-terphenyl,
4-hydroxy-2,3-difluoro-4"-(6-alkoxy-1-trans-heptenyl)-p-terphenyl,
4-hydroxy-2,3-difluoro-4"-(6-acyloxy-1-trans-heptenyl)-p-terphenyl,
4"-hydroxy-2',3'-difluoro-4-(1-trans-alkenyl)-p-terphenyl,
4"-hydroxy-2',3'-difluoro-4-(6-hydroxy-1-trans-heptenyl)-p-terphenyl,
4"-hydroxy-2',3'-difluoro-4-(6-alkoxy-1-trans-heptenyl)-p-terphenyl,
4"-hydroxy-2',3'-difluoro-4-(6-acyloxy-1-trans-heptenyl)-p-terphenyl,
5-hydroxy-2-{4-(1-trans-alkenyl)-2,3-difluorophenyl}-pyridine,
5-hydroxy-2-{4-(6-hydroxy-1-trans-heptenyl)-2,3-difluorophenyl}-pyridine,
5-hydroxy-2-{4-(6-alkoxy-1-trans-heptenyl)-2,3-difluorophenyl}-pyridine,
5-hydroxy-2-{4-(6-acyloxy-1-trans-heptenyl)-2,3-difluorophenyl}-pyridine,
2-(4-hydroxy-2,3-difluorophenyl)-5-(1-trans-alkenyl)-pyridine,
2-(4-hydroxy-2,3-difluorophenyl)-5(6-hydroxy-1-trans-heptenyl)-pyridine,
2-(4-hydroxy-2,3-difluorophenyl)-5-(6-alkoxy-1-trans-heptenyl)-pyridine,
2-(4-hydroxy-2,3-difluorophenyl)-5-(6-acyloxy-1-trans-heptenyl)-pyridine,
2-hydroxy-5-{4-(1-trans-alkenyl)-2,3-difluorophenyl}-pyridine,
2-hydroxy-5-{4-(6-hydroxy-1-trans-heptenyl)-2,3-difluorophenyl}-pyridine,
2-hydroxy-5-{4-(6-alkoxy-1-trans-heptenyl)-2,3-difluorophenyl}-pyridine,
2-hydroxy-5-{4-(6-acyloxy-1-trans-heptenyl)-2,3-difluorophenyl}-pyridine,
5-(4-hydroxy-2,3-difluorophenyl)-2-(1-trans-alkenyl)-pyridine,
5-(4-hydroxy-2,3-difluorophenyl)-2-(6-hydroxy-1-trans-heptenyl)-pyridine,
5-(4-hydroxy-2,3-difluorophenyl)-2-(6-alkoxy-1-trans-heptenyl)-pyridine,
5-(4-hydroxy-2,3-difluorophenyl)-2-(6-acyloxy-1-trans-heptenyl)-pyridine,
2-hydroxy-5-{4'-(1-trans-alkenyl)-2',3'-difluorobiphenyl-4}-pyridine,
2-hydroxy-5-{4'-(6-hydroxy-1-trans-heptenyl)-2',3'-difluorobiphenyl-4-yl}-pyridine,
2-hydroxy-5-{4'-(6-alkoxy-1-trans-heptenyl)-2',3'-difluorobiphenyl-4yl}-pyridine,
2-hydroxy-5-{4'-(6-acyloxy-1-trans-heptenyl)-2',3'-difluorobiphenyl-4yl}-pyridine,
5-(4'-hydroxy-2',3'-difluorobiphenyl-4yl)-2-(1-trans-alkenyl)-pyridine,
5-(4'-hydroxy-2',3'-difluorobiphenyl-4yl)-2-(6-hydroxy-1-trans-heptenyl)-pyridine,
5-(4'-hydroxy-2',3'-difluorobiphenyl-4yl)-2-(6-alkoxy-1-trans-heptenyl)-pyridine,
5-(4'-hydroxy-2',3'-difluorobiphenyl-4yl)-2-(6-acyloxy-1-trans-heptenyl)-pyridine,
5-hydroxy-2-{4'-(1-trans-alkenyl)-2',3'-difluorobiphenyl-4-yl}-pyridine,
5-hydroxy-2-{4'-(6-hydroxy-1-trans-heptenyl)-2',3'-difluorobiphenyl-4-yl}-pyridine,
5-hydroxy-2-{4'-(6-alkoxy-1-trans-heptenyl)-2',3'-difluorobiphenyl-4-yl}-pyridine,
5-hydroxy-2-{4'-(6-acyloxy-1-trans-heptenyl)-2',3'-difluorobiphenyl-4-yl}-pyridine,
2-(4'-hydroxy-2',3'-difluorobiphenyl-4-yl)-5-(1-trans-alkenyl)-pyridine,
2-(4'-hydroxy-2',3'-difluorobiphenyl-4yl)-5-(6-hydroxy-1-trans-heptenyl)-pyridine,
2-(4'-hydroxy-2',3'-difluorobiphenyl-4yl)-5-(6-alkoxy-1-trans-heptenyl)-pyridine,
2-(4'-hydroxy-2',3'-difluorobiphenyl-4-yl)-5-(6-acyloxy-1-trans-heptenyl)-pyridine,
5-(4-hydroxy-2,3-difluorophenyl)-2-{4-(1-trans-alkenyl)-phenyl}-pyridine,
5-(4-hydroxy-2,3-difluorophenyl)-2-{4-(6-hydroxy-1-trans-heptenyl)-phenyl}-pyridine,
5-(4-hydroxy-2,3-difluorophenyl)-2-{4-(6-alkoxy-1-trans-heptenyl)-phenyl}-pyridine,
5-(4-hydroxy-2,3-difluorophenyl)-2-{4-(6-acyloxy-1-trans-heptenyl)-phenyl}-pyridine,
2-(4-hydroxy-2,3-difluorophenyl)-5-{4-(1-trans-alkenyl)-phenyl}-pyridine,
2-(4-hydroxy-2,3-difluorophenyl)-5-{4-(6-hydroxy-1-trans-heptenyl)-phenyl}-pyridine,
2-(4-hydroxy-2,3-difluorophenyl)-5-{4-(6-alkoxy-1-trans-heptenyl)-phenyl}-pyridine,
2-(4-hydroxy-2,3-difluorophenyl)-5-{4-(6-acyloxy-1-trans-heptenyl)-phenyl}-pyridine,
5-(4-hydroxyphenyl)-2-{4-(1-trans-alkenyl)-2,3-difluorophenyl}-pyridine,
5-(4-hydroxyphenyl)-2-{4-(6-hydroxy-1-trans-heptenyl)-2,3-difluorophenyl}-pyridine,
5-(4-hydroxyphenyl)-2-{4-(6-alkoxy-1-trans-heptenyl)-2,3-difluorophenyl}-pyridine,
5-(4-hydroxyphenyl)-2-{4-(6-acyloxy-1-trans-heptenyl)-2,3-difluorophenyl}-pyridine,
2-(4-hydroxyphenyl)-5-{4-(1-trans-alkenyl)-2,3-difluorophenyl}-pyridine,
2-(4-hydroxyphenyl)-5-{4-(6-hydroxy-1-trans-heptenyl)-2,3-difluorophenyl}-pyridine,
2-(4-hydroxyphenyl)-5-{4-(6-alkoxy-1-trans-heptenyl)-2,3-difluorophenyl}-pyridine,
2-(4-hydroxyphenyl)-5-{4-(6-acyloxy-1-trans-heptenyl)-2,3-difluorophenyl}-pyridine,
5-hydroxy-2-{2,3-difluoro-4-(1-trans-alkenyl)-phenyl}-pyrimidine,
5-hydroxy-2-{2,3-difluoro-4-(6-hydroxy-1-trans-heptenyl)-phenyl}-pyrimidine,
5-hydroxy-2-{2,3-difluoro-4-(6-alkoxy-1-trans-heptenyl)-phenyl}-pyrimidine,
5-hydroxy-2-{2,3-difluoro-4-(6-acyloxy-1-trans-heptenyl)-phenyl}-pyrimidine,
2-(2,3-difluoro-4-hydroxyphenyl)-5(1-trans-alkenyl)-pyrimidine, 2-(2,3-difluoro-4-hydroxyphenyl)-5-(6-hydroxy-1-trans-heptenyl)-pyrimidine,
2-(2,3-difluoro-4-hydroxyphenyl)-5-(6-alkoxy-1-trans-heptenyl)-pyrimidine,
2-(2,3-difluoro-4-hydroxyphenyl)-5-(6-acyloxy-1-trans-heptenyl)-pyrimidine,
2-hydroxy-5-{4(1-trans-alkenyl)-2,3-difluorophenyl}-pyrimidine,
2-hydroxy-5-{4(6-hydroxy-1-trans-heptenyl)-2,3-difluorophenyl}-pyrimidine,
2-hydroxy-5-{4-(6-alkoxy-1-trans-heptenyl)-2,3-difluorophenyl}-pyrimidine,
2-hydroxy-5-{4-(6-acyloxy-1-trans-heptenyl)-2,3-difluorophenyl}-pyrimidine,
5-(4-hydroxy-2,3-difluorophenyl)-2-(1-trans-alkenyl)-pyrimidine,
5-(4-hydroxy-2,3-difluorophenyl)-2-(6-hydroxy-1-trans-heptenyl)-pyrimidine,
5-(4-hydroxy-2,3-difluorophenyl)-2-(6-alkoxy-1-trans-heptenyl)-pyrimidine,
5-(4-hydroxy-2,3-difluorophenyl)-2-(6-acyloxy-1-trans-heptenyl)-pyrimidine,
5-hydroxy-2-{4'-(1-trans-alkenyl)-2',3'-difluorobiphenyl-4yl}-pyrimidine,
5-hydroxy-2-{4'-(6-hydroxy-1-trans-heptenyl)-2',3'-difluorobiphenyl-4-yl}-pyrimidine,
5-hydroxy-2-{4'-(6-alkoxy-1-trans-heptenyl)-2',3'-difluorobiphenyl-4yl}-pyrimidine,
5-hydroxy-2-{4'-(6-acyloxy-1-trans-heptenyl)-2',3'-difluorobiphenyl-4-yl}-pyrimidine,
2-(4'-hydroxy-2',3'-difluorobiphenyl-4-yl)-5(1-trans-alkenyl)-pyrimidine,
2-(4'-hydroxy-2',3',-difluorobiphenyl-4-yl)-5(6-hydroxy-1-trans-heptenyl)-pyrimidine,
2-(4'-hydroxy-2',3'-difluorobiphenyl-4yl)-5-(6-alkoxy-1-trans-heptenyl)-pyrimidine,
2-(4'-hydroxy-2',3'-difluorobiphenyl-4-yl)-5-(6-acyloxy-1-trans-heptenyl)-pyrimidine,
2-hydroxy-5-{4-(1-trans-alkenyl)-2',3'-difluorobiphenyl-4yl}-pyrimidine,
2-hydroxy-5-{4'-(6-hydroxy-1-trans-heptenyl)-2',3'-difluorobiphenyl-4-yl}-pyrimidine,
2-hydroxy-5-{4'-(6-alkoxy-1-trans-heptenyl)-2',3'-difluorobiphenyl-4-yl}-pyrimidine,
2-hydroxy-5-{4-(6-acyloxy-1-trans-heptenyl)-2',3'-difluorobiphenyl-4-yl}-pyrimidine,
5-(4'-hydroxy-2',3'-difluorobiphenyl-4-yl)-2-(1-trans-alkenyl)-pyrimidine,
5-(4'-hydroxy-2',3'-difluorobiphenyl-4-yl)-2-(6-hydroxy-1-trans-heptenyl)-pyrimidine,
5-(4'-hydroxy-2',3'-difluorobiphenyl-4-yl)-2-(6-alkoxy-1-trans-heptenyl)-pyrimidine,
5-(4'-hydroxy-2',3'-difluorobiphenyl-4-yl)-2-(6-acyloxy-1-trans-heptenyl)-pyrimidine,
5-(4-hydroxy-2,3-difluorophenyl)-2-{4-(1-trans-alkenyl)-phenyl}-pyrimidine,
5-(4-hydroxy-2,3-difluorophenyl)-2-{4-(6-hydroxy-1-trans-heptenyl)-phenyl}-pyrimidine,
5-(4-hydroxy-2,3-difluorophenyl)-2-{4-(6-alkoxy-1-trans-heptenyl)-phenyl}-pyrimidine,
5-(4-hydroxy-2,3-difluorophenyl)-2-{4-(6-acyloxy-1-trans-heptenyl)-phenyl}-pyrimidine,
2-(4-hydroxy-2,3-difluorophenyl)-5-{4-(1-trans-alkenyl)-phenyl}-pyrimidine,
2-(4-hydroxy-2,3-difluorophenyl)-5-{4-(6-hydroxy-1-trans-heptenyl)-phenyl}-pyrimidine,
2-(4-hydroxy-2,3-difluorophenyl)-5-{4-(6-alkoxy-1-trans-heptenyl)-phenyl}-pyrimidine,
2-(4-hydroxy-2,3-difluorophenyl)-5-{4-(6-acyloxy-1-trans-heptenyl)-phenyl}-pyrimidine,
5-(4-hydroxyphenyl)-2-{4-(1-trans-alkenyl)-2,3-difluorophenyl}-pyrimidine,
5-(4-hydroxyphenyl)-2-{4-(6-hydroxy-1-trans-heptenyl)-2,3-difluorophenyl}-pyrimidine,
5-(4-hydroxyphenyl)-2-{4-(6-alkoxy-1-trans-heptenyl)-2,3-difluorophenyl}-pyrimidine,
5-(4-hydroxyphenyl)-2-{4-(6-acyloxy-1-trans-heptenyl)-2,3-difluorophenyl}-pyrimidine,
2-(4-hydroxyphenyl)-5-{4-(1-trans-alkenyl)-2,3-difluorophenyl}-pyrimidine,
2-(4-hydroxyphenyl)-5-{4-(6-hydroxy-1-trans-heptenyl)-2,3-difluorophenyl}-pyrimidine,
2-(4-hydroxyphenyl)-5-{4-(6-alkoxy-1-trans-heptenyl)-2,3-difluorophenyl}-pyrimidine,
2-(4-hydroxyphenyl)-5-{4-(6-acyloxy-1-trans-heptenyl)-2,3-difluorophenyl}-pyrimidine,
6-hydroxy-3-{4-(1-trans-alkenyl)-2,3-difluorophenyl}-pyridazine,
6-hydroxy-3-{4-(6-trans-heptenyl)-2,3-difluorophenyl}-pyridazine,
6-hydroxy-3-{4-(6-alkoxy-1-trans-heptenyl)-2,3-difluorophenyl}-pyridazine,
6-hydroxy-3-{4-(6-acyloxy-1-trans-heptenyl)-2,3-difluorophenyl}-pyridazine,
6-(4-hydroxy-2,3-difluorophenyl)-3-(1-trans-alkenyl)-pyridazine,
6-(4-hydroxy-2,3-difluorophenyl)-3-(6-hydroxy-1-trans-heptenyl)-pyridazine,
6-(4-hydroxy-2,3-difluorophenyl)-3-(6-alkoxy-1-trans-heptenyl)-pyridazine,
6-(4-hydroxy-2,3-difluorophenyl)-3-(6-acyloxy-1-trans-heptenyl)-pyridazine,
7-hydroxy-3-{4-(1-trans-alkenyl)-2,3-difluorophenyl}-isoquinoline,
7-hydroxy-3-{4-(6-hydroxy-1-trans-heptenyl)-2,3-difluorophenyl}-isoquinoline,
7-hydroxy-3-{4-(6-alkoxy-1-trans-heptenyl)-2,3-difluorophenyl}-isoquinoline,
7-hydroxy-3-{4-(6-acyloxy-1-trans-heptenyl)-2,3-difluorophenyl}-isoquinoline,
3-(4-hydroxy-2,3-difluorophenyl)-7-(1-trans-alkenyl)-isoquinoline,
3-(4-hydroxy-2,3-difluorophenyl)-7-(6-hydroxy-1-trans-heptenyl)-isoquinoline,
3-(4-hydroxy-2,3-difluorophenyl)-7-(6-alkoxy-1-trans-heptenyl)-isoquinoline,
3-(4-hydroxy-2,3-difluorophenyl)-7-(6-acyloxy-1-trans-heptenyl)-isoquinoline,
6-hydroxy-2-{4-(1-trans-alkenyl)-2,3-difluorophenyl}-quinoline,
6-hydroxy-2-{4-(6-hydroxy-1-trans-heptenyl)-2,3-difluorophenyl}-quinoline,
6-hydroxy-2-{4-(6-alkoxy-1-trans-heptenyl)-2,3-difluorophenyl}-quinoline,
6-hydroxy-2-{4-(6-acyloxy-1-trans-heptenyl)-2,3-difluorophenyl}-quinoline,
2-(4-hydroxy-2,3-difluorophenyl)-6-(1-trans-alkenyl)-quinoline,
2-(4-hydroxy-2,3-difluorophenyl)-6-(6-hydroxy-1-trans-heptenyl)-quinoline,
2-(4-hydroxy-2,3-difluorophenyl)-6-(6-alkoxy-1-trans-heptenyl)-quinoline,
2-(4-hydroxy-2,3-difluorophenyl)-6-(6-acyloxy-1-trans-heptenyl)-quinoline,
2-hydroxy-6-{4-(1-trans-alkenyl)-2,3-difluorophenyl}-quinoxaline, 2-hydroxy-6-{4-(6-hydroxy-1-trans-heptenyl)-2,3-difluorophenyl}-quinoxaline,
2-hydroxy-6-{4-(6-alkoxy-1-trans-heptenyl)-2,3-difluorophenyl}-quinoxaline,
2-hydroxy-6-{4-(6-acyloxy-1-trans-heptenyl)-2,3-difluorophenyl}-quinoxaline,
2-(1-trans-alkenyl)-6-(4-hydroxy-2,3-difluorophenyl)-quinoxaline,
2-(6-hydroxy-1-trans-heptenyl)-6-(4-hydroxy-2,3-difluorophenyl)-quinoxaline,
2-(6-alkoxy-1-trans-heptenyl)-6-(4-hydroxy-2,3-difluorophenyl)-quinoxaline,
2-(6-acyloxy-1-trans-heptenyl)-6-(4-hydroxy-2,3-difluorophenyl)-quinoxaline,
6-hydroxy-2-{4-(1-trans-alkenyl)-2,3-difluorophenyl}-quinoxaline,
6-hydroxy-2-{4-(6-hydroxy-1-trans-heptenyl)-2,3-difluorophenyl}-quinoxaline,
6-hydroxy-2-{4-(6-alkoxy-1-trans-heptenyl)-2,3-difluorophenyl}-quinoxaline,
6-hydroxy-2-{4-(6-acyloxy-1-trans-heptenyl)-2,3-difluorophenyl}-quinoxaline,
2-(4-hydroxy-2,3-difluorophenyl)-6-(1-trans-alkenyl)-quinoxaline,
2-(4-hydroxy-2,3-difluorophenyl)-6-(6-hydroxy-1-trans-heptenyl)-quinoxaline,
2-(4-hydroxy-2,3-difluorophenyl)-6-(6-alkoxy-1-trans-heptenyl)-quinoxaline,
2-(4-hydroxy-2,3-difluorophenyl)-6-(6-acyloxy-1-trans-heptenyl)-quinoxaline,
2-hydroxy-6-{4-(1-trans-alkenyl)-2,3-difluorophenyl}-quinazoline,
2-hydroxy-6-{4-(6-hydroxy-1-trans-heptenyl)-2,3-difluorophenyl}-quinazoline,
2-hydroxy-6-{4-(6-alkoxy-1-trans-heptenyl)-2,3-difluorophenyl}-quinazoline,
2-hydroxy-6-{4-(6-acyloxy-1-trans-heptenyl)-2,3-difluorophenyl}-quinazoline,
2-(1-trans-alkenyl)-6-(4-hydroxy-2,3-difluorophenyl)-quinazoline,
2-(6-hydroxy-1-trans-heptenyl)-6-(4-hydroxy-2,3-difluorophenyl)-quinazoline,
2-(6-alkoxy-1-trans-heptenyl)-6-(4-hydroxy-2,3-difluorophenyl)-quinazoline,
2-(6-acyloxy-1-trans-heptenyl)-6-(4-hydroxy-2,3-difluorophenyl)-quinazoline;

and the compounds in which the substituent (6-hydroxy-1-trans-heptenyl) group of the above-mentioned compounds is replaced by one of 3-hydroxy-1-trans-butenyl group, 4-hydroxy-1-trans-pentenyl group, 5-hydroxy-1-trans-hexenyl group, 6-hydroxy-1-trans-heptenyl group, 7-hydroxy-1-trans-octenyl group, 8-hydroxy-1-trans-nonenyl group, 9-hydroxy-1-trans-decenyl group, 10-hydroxy-1-trans-undecenyl group and 11-hydroxy-1-trans-dodecenyl group;

and the compounds in which the substituent (6-alkoxy-1-trans-heptenyl) group of the above-mentioned compounds is replaced by one of 3-alkoxy-1-trans-butenyl group, 4-alkoxy-1-trans-pentenyl group, 5-alkoxy-1-trans-hexenyl group, 6-alkoxy-1-trans-heptenyl group, 7-alkoxy-1-trans-octenyl group, 8-alkoxy-1-trans-nonenyl group, 9-alkoxy-1-trans-decenyl group, 10-alkoxy-1-trans-undecenyl group and 11-alkoxy-1-trans-dodecenyl group;

and the compounds in which the substituent (6-acyloxy-1-trans-heptenyl) group of the above-mentioned compounds is replaced by one of 3-acyloxy-1-trans-butenyl group, 4-acyloxy-1-trans-pentenyl group, 5-acyloxy-1-trans-hexenyl group, 6-acyloxy-1-trans-heptenyl group, 7-acyloxy-1-trans-octenyl group, 8-acyloxy-1-trans-nonenyl group, 9-acyloxy-1-trans-decenyl group, 10-acyloxy-1-trans-undecenyl group and 11-acyloxy-1-trans-dodecenyl group;

and the compounds in which the hydroxyl group of the hydroxyl group-carrying members of the above-mentioned compounds is protected by a protecting group;

and, as for optically active members among the above-mentioned compounds, the compounds in which the alkyl group and the alkyloxy group is replaced by, respectively, an alkenyl group and an alkenyloxy group;

provided that, in the compound names presented above, the terms alkyl, alkenyl and alkoxy mean those having 1–20 carbon atoms, and the term acyloxy group means those having 1–19 carbon atoms.

In preparing a liquid crystal composition from a trans-olefin compound represented by the general formula (1), the compound to be mixed may be any of optically inactive compound and the optically active compound. Either one of them or both of them may be mixed into the composition. Although the mixing ratio is not critical unless the liquid crystal phase is greatly deteriorated, a compound having no liquid crystal phase should preferably be mixed in an amount of 20% by mole or less, if such a compound is used.

Among the ingredients constituting the ferroelectric liquid crystal composition of the present invention, the optically inactive compounds to be mixed into the composition are, for example, as follows:

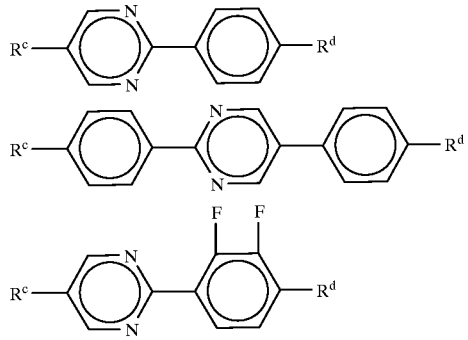

wherein $R^c$ and $R^d$ represent alkyl, alkoxy or alkoxyalkyl group having 1–20 carbon atoms, and the compounds represented by the general formula (A) wherein f=0.

As the optically active compounds, the compounds represented by the general formula (A) wherein f=1 can be referred to, in addition to which the compounds represented by the following formula can also be used:

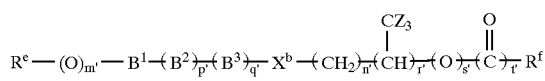

wherein $R^e$ represented alkyl group having 1–20 carbon atoms or alkoxyalkyl group having 2–20 carbon atoms, $R^f$ represents a saturated or unsaturated alkyl group having 1–20 carbon atoms which may optionally be substituted by halogen atom, a saturated or unsaturated alkoxyalkyl group having 2–20 carbon atoms which may optionally be substituted by halogen atom or a hydrogen atom, and $B^1$, $B^2$ and $B^3$ each represents the groups of the following formulas:

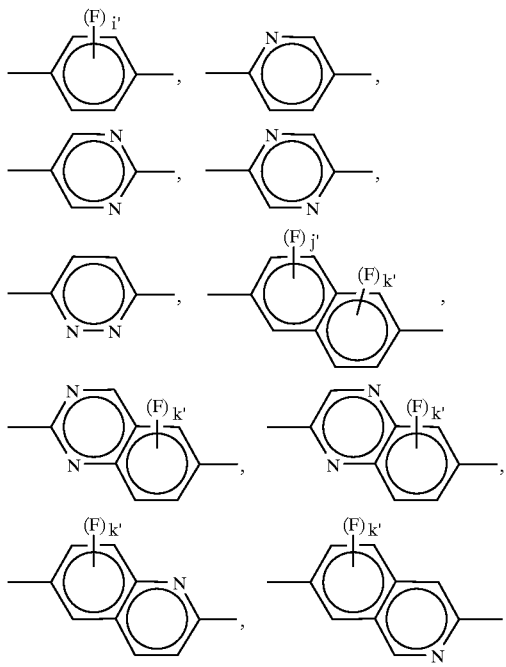

wherein i' is an integer of 0–4; j' and k' are each an integer of 0–3; and p' and q' are 0 or 1, provided that, when $B^1$ is a fused ring, p'+q'=0 or 1 and $B^2$, $B^3$ are single rings, and when $B^1$ is a single ring, p'+q'=1 or 2, provided that when p'+q'=2, $B^2$ and $B^3$ are both single rings; Z' represents hydrogen atom or fluorine atom; n' is an integer of 0–10; and m', r', s' and t' each represents 0 or 1.

Figure 1:
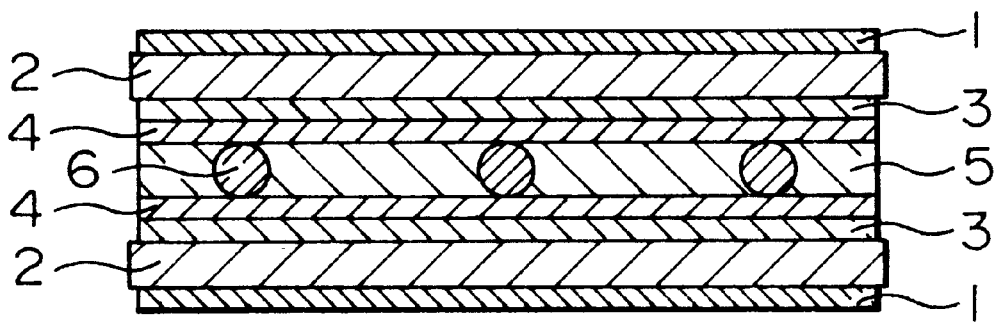

The liquid crystal element of the present invention can be utilized as various types of liquid crystal elements and display devices. Structure of the liquid crystal element of the invention is not particularly critical. FIG. 1 outlines one example of the ferroelectric liquid crystal element. In FIG. 1, 1 is polarizing plate, 2 is glass substrate, 3 is transparent electrode, 4 is electrically insulating, orientation-controlling film, 5 is ferroelectric liquid crystal, and 6 is spacer.

As an example of the liquid crystal element having a structure of FIG. 1, the surface-stabilization type ferroelectric liquid crystal displaying device can be referred to. This type of display is so constructed that two glass substrates 2 are placed in parallel with a very small gap to form a cell and a ferroelectric liquid crystal is filled into the gap so that the normal line of the smectic phase layer becomes parallel to the substrates.

Thickness of the ferroelectric liquid crystal layer 5 is dependent only on the gap between the two glass substrates 2 and the thicknesses of the transparent electrode 3 and insulating oriented film 4, both provided on the glass substrates in the direction of ferroelectric liquid crystal layer 5, and is usually in the range of from 0.5 to 20 μm, and preferably from 1 to 5 μm.

The transparent electrode 3 is placed so as to cover the glass substrate 2 of the liquid crystal layer side, and usually made of Indium—Tin Oxide, $In_2O_3$, $SnO_2$ or the like. On the liquid crystal layer side 5 of the transparent electrode 3, the insulating oriented film 4 is provided. Although the oriented film may be used in itself alone when the oriented film itself has a sufficient insulating property, an insulating film may be provided under the oriented films in order that both the films function as a whole as an insulating oriented film, if necessary.

As the oriented film, known film materials such as organic materials, inorganic materials, low molecular weight materials, high-polymeric materials and the like can be used. As the high-polymeric material, polyimide, polyamide, polyamide-imide, polyvinyl alcohol, polystyrene, polyester, polyester-imide, and a variety of photoresist materials may be used in accordance with need. When such a high-polymeric material is used as an oriented material, the orientation of liquid crystal molecules can additionally be promoted by a rubbing treatment, namely by rubbing the surface of the oriented film in one direction with cotton gauze, acetate-flocked cloth or the like, if desired.

As the insulating film, titanium oxide, aluminum oxide, zirconium oxide, silicon oxide, silicon nitride and the like can be used. The methods for forming these oriented film and insulating film may be selected in an optimum manner in accordance with the materials used.

For example, when a high-polymeric material is used, the polymeric material or a precursor thereof is dissolved in a solvent capable of dissolving these materials and then coated by the method of screen printing, spinner coating, dip coating, or the like. When an inorganic material is used, dipping method, vapor deposition method, slant vapor deposition method or the like may be adopted.

Although the thickness of said insulating oriented film is not particularly limited, it is usually in the range of 1 nm to 20000 nm, and preferably from 2 nm to 100 nm. The two glass substrates 3 carrying the insulating oriented film 4 and the transparent electrode 3 thereon are held at a prescribed distance through intermediation of spacer 6. As the spacer, a bead-form, fiber-form or film-form insulating material having a prescribed diameter or thickness and made of silica, alumina or a high-polymeric material can be used. After putting spacer 6 between two glass substrates 2 and sealing the circumference thereof with, for example, an epoxy type binder or the like, a ferroelectric liquid crystal can be sealed therein.

Outside the two glass substrates, one or two polarizing plates 1 are usually provided. FIG. 1 illustrates a case using two polarizing plates, in which the two polarizing plates are placed so that their polarization axes cross at a right angle, namely in the state of cross Nicol. The transparent electrode 3 is connected to the external driving circuit via an appropriate lead wire.

The compounds of the present invention represented by the general formula (1) have quite excellent properties as a liquid crystal material. Further, these compounds are useful as intermediate not only of liquid crystal materials but also of pesticides, medical drugs, etc. According to the process of the present invention, the objective trans-olefin compounds can be obtained in a high selectivity. The liquid crystal composition of the present invention are quite excellent in properties, for example in that they have a broad liquid crystal temperature range, and a liquid crystal element using said liquid crystal composition is successfully usable as a display element, optical shutter, and the like.

PREFERRED EMBODIMENTS OF THE INVENTION

Next, the present invention is illustrated in more detail with reference to the following non-limitative examples.

EXAMPLE 1

After replacing the inner atmosphere of a four-necked flask equipped with a stirring device and a thermometer with nitrogen gas, 3.85 g (40 mmol) of 1-n-heptyne was introduced, and 2.4 g (20 mmol) of catecholborane was dropwise added thereto. After vigorously stirring the content of the flask at room temperature for one hour, the content was reacted at 70° C. for 2 hours. The reaction mixture was cooled to ambient temperature and the 1-n-heptyne remaining unreacted was distilled off under reduced pressure to obtain E-1-heptenylcatecholborane.

Apart from the above, inner atmosphere of a four-necked flask equipped with a stirring device, a reflux condenser and a thermometer was replaced with nitrogen gas, and then the flask was charged with 5.0 g (13 mmol) of 5-decyloxy-2-(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained E-1-heptenylcatecholborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 4.5 g (yield 86%) of 5-decyloxy-2-{4-(1-trans-heptenyl)-phenyl}-pyrimidine.

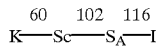

$^1$H-NMR revealed no presence of cis form at all.

EXAMPLE 2

After replacing the inner atmosphere of a four-necked flask equipped with a stirring device and a thermometer with nitrogen gas, 1.3 g (10 mmol) of 1-nonyne was introduced, and 0.6 g (5 mmol) of catecholborane was dropwise added thereto. After stirring the content of the flask at room temperature for one hour, the content was reacted at 70° C. for 2 hours. The reaction mixture was cooled to ambient temperature and the 1-nonyne remaining unreacted was distilled off under reduced pressure to obtain E-1-nonenylcatecholborane.

Apart from the above, inner atmosphere of a four-necked flask equipped with a stirring device, a reflux condenser and a thermometer was replaced with nitrogen gas, and then the flask was charged with 1.4 g (3.3 mmol) of 5-bromo-2-(4-decyloxy-2,3-difluorophenyl)-pyrimidine, 0.06 g (0.05 mmol) of tetrakis-triphenylphosphine-palladium, 0.6 g (15 mmol) of sodium hydroxide and 15 ml of tetrahydrofuran. Subsequently, 13 ml of a solution prepared by dissolving 5 mmol of the above-obtained E-1-nonenylcatecholborane in tetrahydrofuran was dropwise added thereto at room temperature. Then, the whole mixture was heated under reflux with stirring for 7 hours. After cooling the reaction mixture to room temperature, 3 ml of 10% aqueous solution of sodium hydroxide and 1 ml of 30% aqueous solution of hydrogen peroxide were added, and the resulting mixture was stirred for one hour. The mixture was extracted with ether, and the organic layer was twice washed with each 10 ml portion of saturated aqueous solution of sodium chloride and dried over anhydrous magnesium sulfate. The solvent was distilled off, and the residue was purified by silica gel column chromatography to obtain 1.2 g (yield 78%) of 2-(4-decyloxy-2,3-difluorophenyl)-5-(1-trans-nonenyl)-pyrimidine.

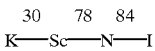

EXAMPLE 3

After replacing the inner atmosphere of a four-necked flask equipped with a stirring device and a thermometer with nitrogen gas, 1.3 g (10 mmol) of 1-nonyne was introduced, and 0.6 g (5 mmol) of catecholborane was dropwise added thereto. After stirring the content of the flask at room temperature for one hour, the content was reacted at 70° C. for 2 hours. The reaction mixture was cooled to ambient temperature and the 1-nonyne remaining unreacted was distilled off under reduced pressure to obtain E-1-nonenylcatecholborane.

Apart from the above, inner atmosphere of a four-necked flask equipped with a stirring device, a reflux condenser and a thermometer was replaced with nitrogen gas, and then the flask was charged with 1.6 g (3.3 mmol) of 5-decyl-2-(2,3-difluoro-4-trifluoromethylsulfonyloxyphenyl)-pyrimidine, 0.06 g (0.05 mmol) of tetrakis-triphenylphosphine-palladium, 0.6 g (15 mmol) of sodium hydroxide and 15 of tetrahydrofuran. Subsequently, 13 ml of a solution prepared by dissolving 5 mmol of the above-obtained E-1-nonenylcatecholborane in tetrahydrofuran was dropwise added thereto at room temperature. Then, the whole mixture was heated under reflux with stirring for 3 hours. After cooling the reaction mixture to room temperature, 3 ml of 10% aqueous solution of sodium hydroxide and 1 ml of 30% aqueous solution of hydrogen peroxide were added, and the resulting mixture was stirred for one hour. The mixture was extracted with ether, and the organic layer was twice washed with each 10 ml portion of saturated aqueous solution of sodium chloride and dried over anhydrous magnesium sulfate. The solvent was distilled off, and the residue was purified by silica gel column chromatography to obtain 1.2 g (yield 79%) of 5-decyl-2-{2,3-difluoro-4-(1-trans-nonenyl)-phenyl}-pyrimidine.

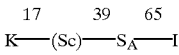

EXAMPLE 4

After replacing the inner atmosphere of a four-necked flask equipped with a stirring device and a thermometer with nitrogen gas, 2.3 g (20 mmol) of optically active 1-hydroxy-6-heptyne was introduced, and 4.8 g (40 mmol) of catecholborane was dropwise added thereto. After stirring the content of the flask at room temperature for one hour, the content was reacted at 70° C. for 2 hours. The reaction mixture was cooled to ambient temperature, 100 ml of water was added, the resulting mixture was stirred at 20° C. for 2 hours and cooled to 0° C., and the resulting precipitate was collected by filtration and twice washed with each 40 ml portion of water to obtain E-6-hydroxy-1-heptenyldihydroxyborane.

Apart from the above, inner atmosphere of a four-necked flask equipped with a stirring device, a reflux condenser and a thermometer was replaced with nitrogen gas, and then the flask was charged with 6.6 g (17 mmol) of 5-decyloxy-2-

(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained E-6-hydroxy-1-heptenyldihydroxyborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 5.9 g (yield 82%) of (−)-5-decyloxy-2-{4-(6-hydroxy-1-trans-heptenyl)-phenyl}-pyrimidine, $[\alpha]_D^{20}=-1.2$ (c=1.0, $CHCl_3$).

EXAMPLE 5

At room temperature, 1.7 g (4 mmol) of the optically active (−)-5-decyloxy-2-{4-(6-hydroxy-1-trans-heptenyl)-phenyl}pyrimidine obtained in Example 4, 20 ml of ethyl iodide and 2.8 g (12 mmol) of silver oxide were stirred for 60 hours, washed successively with 1 N hydrochloric acid and saturated aqueous solution of sodium chloride, and dried over anhydrous magnesium sulfate.

The reaction mixture thus obtained was concentrated under reduced pressure, and the residue was purified by silica gel column chromatography to obtain 0.92 g (Yield 50%) of (−)-5-decyloxy-2-{4-(6-ethoxy-1-trans-heptenyl)-phenyl}-pyrimidine, $[\alpha]_D^{20}=-1.79$ (c=1.0, $CHCl_3$).

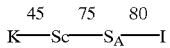

Phase series of the saturated product of the above-mentioned compound, namely (−)-5-decyloxy-2-{4-(6-ethoxyheptyl)-phenyl}-pyrimidine was as follows:

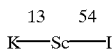

EXAMPLE 6

A reactor was charged with 1.7 g (4 mmol) of the optically active (−)-5-decyloxy-2-{4-(6-hydroxy-1-trans-heptenyl))-phenyl}-pyrimidine, 2 g of triethylamine and 30 g of dichloromethane. Then, 0.6 g (6 mmol) of propionyl chloride was dropwise added thereto at a temperature not exceeding 10° C., and the resulting mixture was reacted first at 0–10° C. for one hour and thereafter at 20–30° C. for two hours. After the reaction, the reaction mixture was poured into ice water and separated into two phases. The organic layer was washed successively with 5% hydrochloric acid, water, 5% aqueous solution of sodium bicarbonate and saturated aqueous solution of sodium chloride, then dried over magnesium sulfate, and concentrated under reduced pressure. Purification of the residue by silica gel column chromatography gave 1.7 g (yield 89%) of (+)-5-decyloxy-2-{4-(6-propionyloxy-1-trans-heptenyl)-phenyl}-pyrimidine, $[\alpha]_D^{20}=+1.1$ (c=1.0, $CHCl_3$).

EXAMPLE 7

After replacing the inner atmosphere of a four-necked flask equipped with a stirring device and a thermometer with nitrogen gas, 3.1 g (20 mmol) of optically active 1-acetoxy-6-heptyne was introduced, and 2.64 g (22 mmol) of catecholborane was dropwise added thereto. After stirring the content of the flask at room temperature for one hour, the content was reacted at 70° C. for 2 hours. The reaction mixture was cooled to ambient temperature, and the catecholborane remaining unreacted was distilled offer under reduced pressure. Thus, optically active E-6-acetoxy-1-heptenylcatecholborane was obtained.

Apart from the above, inner atmosphere of a four-necked flask equipped with a stirring device, a reflux condenser and a thermometer was replaced with nitrogen gas, and then the flask was charged with 6.6 g (17 mmol) of 5-decyloxy-2-(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained E-6-acetoxy-1-heptenylcatecholborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 6.5 g (yield 81%) of (+)-5-decyloxy-2-{4-(6-acetoxy-1-trans-heptenyl)-phenyl}-pyrimidine, $[\alpha]_D^{20}=+0.9$ (c=1.0, $CHCl_3$).

EXAMPLE 8

After replacing the inner atmosphere of a four-necked flask equipped with a stirring device and a thermometer with nitrogen gas, 3.1 g (20 mmol) of 1-acetoxy-6-heptyne was introduced, and 2.64 g (22 mmol) of catecholborane was dropwise added thereto. After stirring the content of the flask at room temperature for one hour, the content was reacted at 70° C. for 2 hours. The reaction mixture was cooled to ambient temperature, and the catecholborane remaining unreacted was distilled off under reduced pressure. Thus, E-6-acetoxy-1-heptenylcatecholborane was obtained.

Apart from the above, inner atmosphere of a four-necked flask equipped with a stirring device, a reflux condenser and a thermometer was replaced with nitrogen gas, and then the flask was charged with 6.2 g (17 mmol) of 5-octyloxy-2-(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained E-6-acetoxy-1-heptenylcatecholborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 6.0 g (yield 78%) of 5-octyloxy-2-{4-(6-acetoxy-1-trans-heptenyl)-phenyl}-pyrimidine.

EXAMPLE 9

A mixture of 4.5 g (10 mmol) of the 5-octyloxy-2-{4-(6-acetoxy-1-trans-heptenyl)-phenyl}-pyrimidine, 140 ml of 0.3 M phosphate buffer solution (pH 7.0), 2 ml of chloroform and 0.5 g of Genus Pseudomonas lipase was stirred at 30–35° C. for 40 hours. The mixture was then extracted with 100 ml of toluene, and the organic layer was washed with water and concentrated under reduced pressure. Separation of the residue thus obtained by silica gel column chromatography gave 1.8 g (yield 46%) of (−)-5-octyloxy-2-{4-(6-hydroxy-1-trans-heptenyl)-phenyl}pyrimidine ($[\alpha]_D^{20}$=−1.2 (c=1.0, CHCl$_3$)) and 2.3 g (yield 53%) of (−)-5-octyloxy-2-{(4-(6-acetoxy-1-trans-heptenyl)-phenyl}-pyrimidine.

EXAMPLE 10

At room temperature, 1.6 g (4 mmol) of the (−)-5-octyloxy-2-{4-(6-hydroxy-1-trans-heptenyl)-phenyl}-pyrimidine obtained in Example 9, 20 ml of ethyl iodide and 2.8 g (12 mmol) of silver oxide were stirred for 60 hours, washed successively with 1 N hydrochloric acid and saturated aqueous solution of sodium chloride, and dried over anhydrous magnesium sulfate. The reaction mixture thus obtained was concentrated under reduced pressure, and the residue was purified by silica gel column chromatography to obtain 0.76 g (yield 43%) of (−)-5-octyloxy-2-{4-(6-ethoxy-1-trans-heptenyl)-phenyl}-pyrimidine, $[\alpha]_D^{20}$=−1.2 (c=0.95, CHCl$_3$).

EXAMPLE 11

A reactor was charged with 1.6 g (4 mmol) of the (−)-5-octyloxy-2-{4-(6-hydroxy-heptyl)-phenyl}-pyrimidine obtained in Example 9, 2 g of triethylamine and 30 g of dichloromethane, to which was dropwise added 0.6 g (6 mmol) of propionyl chloride at a temperature not exceeding 10° C. The mixture was reacted first at 0–10° C. for one hour and thereafter at 20–30° C. for 2 hours. After the reaction, the reaction mixture was poured into ice water, and the mixture thus obtained was separated into two phases. The organic layer was washed successively with 5% hydrochloric acid, water, 5% aqueous solution of sodium bicarbonate and saturated aqueous solution of sodium chloride, dried over magnesium sulfate, and concentrated under reduced pressure. Purification of the residue by silica gel column chromatography gave 1.6 g (yield 85%) of (+)-5-octyloxy-2-{4-(6-propionyloxy-1-trans-heptenyl)-phenyl}-pyrimidine, $[\alpha]_D^{20}$=+0.96 (c=1.1, CHCl$_3$).

EXAMPLE 12

After replacing the inner atmosphere of a four-necked flask equipped with a stirring device and a thermometer with nitrogen gas, 2.3 g (20 mmol) of racemic 1-hydroxy-6-heptyne was introduced, and 4.8 g (40 mmol) of catecholborane was dropwise added thereto. After stirring the content of the flask at room temperature for one hour, the content was reacted at 70° C. for 2 hours. The reaction mixture was cooled to ambient temperature, 100 ml of water was added and the whole mixture was stirred at 20° C. for 2 hours, cooled to 0° C. and filtered. The product was washed twice with each 40 ml portion of water to obtain E-6-hydroxy-1-heptenyldihydroxyborane.

Apart from the above, inner atmosphere of a four-necked flask equipped with a stirring device, a reflux condenser and a thermometer was replaced with nitrogen gas, and then the flask was charged with 6.6 g (17 mmol) of 5-decyloxy-2-(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained E-6-hydroxy-1-heptenyldihydroxyborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 5.9 g (yield 82%) of 5-decyloxy-2-{4-(6-hydroxy-1-trans-heptenyl)-phenyl}-pyrimidine.

A reactor was charged with 1.7 g (4 mmol) of the 5-decyloxy-2-{4-(6-hydroxy-heptenyl))-phenyl}-pyrimidine obtained above, 2 g of triethylamine and 30 g of dichloromethane. Then, 0.5 g (6 mmol) of acetyl chloride was dropwise added thereto at a temperature not exceeding 10° C., and the resulting mixture was reacted first at 0–10° C. for one hour and thereafter at 20–30° C. for two hours. After the reaction, the reaction mixture was poured into ice water and separated into two phases. The organic layer was washed successively with 5% hydrochloric acid, water, 5% aqueous solution of sodium bicarbonate and saturated aqueous solution of sodium chloride, dried over magnesium sulfate, and concentrated under reduced pressure. Purification of the residue by silica gel column chromatography gave 1.8 g (yield 98%) of 5-decyloxy-2-{4-(6-acetoxy-1-trans-heptenyl)-phenyl}-pyrimidine.

Then, a mixture of 1.4 g (3 mmol) of the 5-decyloxy-2-{4-(6-acetoxy-1-trans-heptenyl)-phenyl}-pyrimidine obtained above, 400 ml of 0.3 M phosphate buffer solution (pH 7.0), 2 ml of chloroform and 0.3 g of Genus Pseudomonas lipase was stirred at 30–35° C. for 40 hours. The mixture was then extracted with 100 ml of toluene, and the organic layer was washed with water and concentrated under reduced pressure. Separation of the residue thus obtained by silica gel column chromatography gave 0.56 g (yield 44%) of (−)-5-decyloxy-2-{4-(6-hydroxy-1-trans-heptenyl)-phenyl}-pyrimidine and 0.77 g (yield 55%) of (−)-5l-decyloxy-2-{4-(6-acetoxy-1-trans-heptenyl)-phenyl}-pyrimidine.

Using the (−)-5-decyloxy-2-{4-(6-hydroxy-1-trans-heptenyl)-phenyl}-pyrimidine obtained above, the procedures of Examples 3 and 4 were repeated to obtain (−)-5-decyloxy-2-{4-(6-ethoxy-1-trans-heptenyl)-phenyl}-pyrimidine and (+)-5-decyloxy-2-{4-(6-acetoxy-1-trans-heptenyl)-phenyl}-pyrimidine, respectively.

EXAMPLE 13

After replacing the inner atmosphere of a four-necked flask equipped with a stirring device and a thermometer with nitrogen gas, 3.9 g (20 mmol) of optically active 6-(2-tetrahydropyranyloxy)-1-heptyne was introduced, and 2.9 g (24 mmol) of catecholborane was dropwise added thereto. After stirring the content of the flask at room temperature for one hour, the content was reacted at 70° C. for 2 hours. By distilling off the unreacted catecholborane, there was obtained optically active E-6-(2-tetrahydropyranyloxy)-1-heptenylcatecholborane.

Apart from the above, inner atmosphere of a four-necked flask equipped with a stirring device, a reflux condenser and a thermometer was replaced with nitrogen gas, and then the flask was charged with 6.8 g (17 mmol) of 5-undecyloxy-2-(4-bromophenyl)-pyrimidine, 0.23 g (0.2 mmol) of tetrakis-triphenylphosphine-palladium, 2.4 g (60 mmol) of sodium hydroxide and 60 ml of tetrahydrofuran. Subsequently, 50 ml of a solution prepared by dissolving 20 mmol of the above-obtained optically active E-6-(2-tetrahydropyranyloxy)-1-heptenyldihydroxyborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 7.1 g (yield 75%) of 5-undecyloxy-2-[4-{6-(2-tetrahydropyranyl-1-trans-heptenyl}-phenyl]-pyrimidine.

EXAMPLE 14

At 25° C., 6.7 g (12 mmol) of the 5-undecyloxy-2-[4-{6-(2-tetrahydropyranyl)-1-trans-heptenyl}-phenyl]-pyrimidine obtained in Example 13, 0.4 g (2 mmol) of p-toluenesulfonic acid hydrate, 50 ml of methanol and 5 ml of water were stirred for two hours. Then, water was added and the mixture was extracted with ether. The organic layer was washed with water and dried, the solvent was distilled off, and the residue was purified by silica gel column chromatography to obtain 4.7 g (yield 90%) of (−)-5-undecyloxy-2-{4-(6-hydroxy-1-trans-heptenyl)-phenyl}-pyrimidine, $[\alpha]_D^{20}=-1.1$ (c=1.3, $CHCl_3$).

EXAMPLE 15

At room temperature, 4.0 g (9 mmol) of the (−)-5-undecyloxy-2-{4-(6-hydroxy-1-trans-heptenyl)-phenyl}-pyrimidine obtained in Example 14, 40 ml of methyl iodide and 6.3 g (27 mmol) of silver oxide were stirred for 40 hours. Then, the reaction mixture was washed with 1 N hydrochloric acid and saturated aqueous solution of sodium chloride, dried over anhydrous magnesium sulfate, and concentrated under reduced pressure. Purification of the residue by silica gel column chromatography gave 2.1 g (yield 52%) of (−)-5-undecyloxy-2-{4-(6-methoxy-1-trans-heptenyl)-phenyl}-pyrimidine, $[\alpha]_D^{20}=-1.6$ (c=1.0, $CHCl_3$).

EXAMPLE 16

After replacing the inner atmosphere of a four-necked flask equipped with a stirring device and a thermometer with nitrogen gas, 1.2 g (10 mmol) of optically active 4-ethoxy-1-pentyne was introduced, and 1.4 g (12 mmol) of catecholborane was dropwise added thereto. After stirring the content of the flask at room temperature for one hour, the content was reacted at 70° C. for 2 hours. By distilling off the unreacted catecholborane under reduced pressure, there was obtained optically active E-4-ethoxy-1-pentenylcatecholborane.

Apart from the above, inner atmosphere of a four-necked flask equipped with a stirring device, a reflux condenser and a thermometer was replaced with nitrogen gas, and then the flask was charged with 2.4 g (8 mmol) of 2-(4-bromophenyl)-5-methoxymethylpyrimidine, 0.12 g (0.1 mmol) of tetrakis-triphenylphosphine-palladium, 1.2 g (30 mmol) of sodium hydroxide and 30 ml of tetrahydrofuran. Subsequently, 25 ml of a solution prepared by dissolving 10 mmol of the above-obtained optically active E-4-ethoxy-1-pentenylcatecholborane in tetrahydrofuran was dropwise added thereto at room temperature. Then, the whole mixture was heated under reflux with stirring for 6 hours. After cooling the reaction mixture to room temperature, 5 ml of 10% aqueous solution of sodium hydroxide and 2 ml of 30% aqueous solution of hydrogen peroxide were added, and the resulting mixture was stirred for one hour. The mixture was extracted with ether, and the organic layer was twice washed with each 20 ml portion of saturated aqueous solution of sodium chloride and dried over anhydrous magnesium sulfate. The solvent was distilled off, and the residue was purified by silica gel column chromatography to obtain 2.0 g (yield 81%) of (−)-5-methoxymethyl-2-[4-(4-ethoxy-1-trans-pentenyl)-phenyl]-pyrimidine.

A reactor was charged with 1.5 g (4.8 mmol) of the (−)-5-methoxymethyl-2-[4-(4-ethoxy-1-trans-pentenyl)-phenyl]-pyrimidine obtained above, 5 ml of 6 N-hydrochloric acid and 25 ml of tetrahydrofuran. After stirring the mixture at 50° C. for 6 hours, water was added. After extraction with ether, the organic layer was washed successively with aqueous solution of sodium bicarbonate and saturated aqueous solution of sodium chloride and dried, and the solvent was distilled off. Purification of the residue by silica gel column chromatography gave 1.0 g (yield 82%) of (−)-5-hydroxy-2-[4-(4-ethoxy-1-trans-pentenyl)-phenyl]-pyrimidine.

Then, a mixture of 0.9 g (3.4 mmol) of the (−)-5-hydroxy-2-[4-(4-ethoxy-1-trans-pentenyl)-phenyl]-pyrimidine obtained above, 1.24 g (6 mmol) of 1-bromononane, 1.24 g (9 mmol) of potassium carbonate and 15 ml of N,N-dimethylformamide was stirred at 100° C. for 4 hours. The mixture was washed successively with 1 N hydrochloric acid and saturated aqueous solution of sodium chloride and dried over anhydrous magnesium sulfate.

After concentration under reduced pressure, purification of the residue by silica gel column chromatography gave 1.3 g (yield 95%) of (−)-5-nonyloxy-2-[4-(4-ethoxy-1-trans-pentenyl)-phenyl]-pyrimidine, $[\alpha]_D^{20}=-1.2$ (c=0.8, $CHCl_3$).

EXAMPLE 17

After replacing inner atmosphere of a four-necked flask equipped with a stirring device and a thermometer with nitrogen gas, the flask was charged with 1.26 g (5 mmol) of 2-(4-bromophenyl)-5-hydroxy-pyrimidine, 0.01 g (0.008 mmol) of tetrakis-triphenylphosphine-palladium, 0.6 g (15 mmol) of sodium hydroxide and 20 ml of tetrahydrofuran. Then, 19.5 ml of a solution prepared by dissolving 7.5 mmol of E-1-nonenylcatecholborane, prepared in the same manner as in Example 2, in tetrahydrofuran was dropwise added at room temperature. The resulting mixture was heated under reflux with stirring for 7 hours. After cooling the mixture to room temperature, the mixture was extracted with 30 ml of toluene, and the organic layer was twice washed with each 10 ml portion of saturated aqueous solution of sodium chloride and dried over anhydrous magnesium sulfate. After distilling off the solvent, purification of the residue by silica gel column chromatography gave 1.16 g (yield 75%) of 2-{4-(1-decenyl)-phenyl}-5-hydroxypyrimidine.

A reactor was charged with 1.0g (2.67 mmol) of the 2-{4-(1-decenyl)-phenyl}-5-hydroxypyrimidine obtained above, 2 ml of pyridine, 0.01 g of 4-pyrrolidinopyridine and 20 ml of dichloromethane. While cooling the mixture to a temperature not higher than 0° C. in an atmosphere of nitrogen gas, 1.13 g (4 mmol) of trifluoromethanesulfonic acid anhydride was dropwise added and stirred for two hours. After extraction with water, the organic layer was washed successively with 1 N-hydrochloric acid and saturated aqueous solution of sodium chloride and dried over anhydrous magnesium sulfate. After distilling off the solvent, purification of the residue by silica gel column chromatography gave 1.06 g (yield 90%) of 2-{4-(1-decenyl)-phenyl}-5-trifluoromethylsulfonyloxypyrimidine.

After replacing the inner atmosphere of a four-necked flask equipped with a stirring device and a thermometer with nitrogen gas, the flask was charged with 1.0 g (2.26 mmol) of the 2-{4-(1-decenyl)-phenyl}-5-trifluoromethylsulfonyl-oxypyrimidine obtained above. Then, 0.01 g (0.008 mmol) of tetrakis-triphenylphosphine-palladium, 0.27 g (6.78 mmol) of sodium hydroxide and 20 ml of tetrahydrofuran were added thereto. Further, 19.5 ml of a solution prepared by dissolving 3.39 mmol of E-6-hydroxy-1-heptenyldihydroxyborane, prepared in the same manner as in Example 4, in tetrahydrofuran was dropwise added thereto at room temperature. The whole mixture was heated under reflux with stirring for 8 hours, and cooled to room temperature. After extraction with 30 ml of toluene, the organic layer was twice washed with each 10 ml portion of saturated aqueous solution of sodium chloride and dried over anhydrous magnesium sulfate. After distilling off the solvent, the residue was purified by silica gel column chromatography to obtain 0.63 g (yield 69%) of 2-{4-(1-decenyl)-phenyl}-5-(6-hydroxy-1-heptenyl)-pyrimidine.

A mixture of 0.5 g (1.23 mmol) of the 2-{4-(1-decenyl)-phenyl}-5-(6-hydroxy-1-heptenyl)-pyrimidine obtained above, 1.43 g (6.15 mmol) of silver oxide and 10 ml of ethyl iodide was stirred at room temperature for 70 hours. The reaction mixture was washed with 1N-hydrochloric acid and saturated aqueous solution of sodium chloride and dried over anhydrous magnesium sulfate. After distilling off the solvent, the residue was purified by silica gel column chromatography to obtain 0.26 g (yield 48%) of 2-{4-(1-decenyl)-phenyl}-5-(6-ethoxy-1-heptenyl)-pyrimidine, $[\alpha]_D^{20}=-1.12$ (c=1.0, CHCl$_3$).

EXAMPLES 18–109

The trans-olefin compounds (1) shown in Table 1 (1)–(13) were obtained by repeating the reaction of Example 1, except that the starting compounds shown in Table 1 (1)–(13) were used.

EXAMPLES 110–156

The trans-olefin compounds (1) shown in Table 2 (1)–(7) were obtained by repeating the reaction of Example 2, 3 and 4, except that the starting compounds shown in Table 2 (1)–(7) were used.

EXAMPLES 157–165

The trans-olefin compounds (1) shown in Table 3 (1)–(2) were obtained by repeating the reaction of Example 5, except that the starting compounds shown in Table 3 (1)–(2) were used.

EXAMPLES 166 and 167

The trans-olefin compounds (1) shown in Table 4 were obtained by repeating the reaction of Example 16, except that the starting compounds shown in Table 4 were used.

TABLE 1(1)

| | | | | Starting compounds | | | | | | | | | | |
|---|---|---|---|---|---|---|---|---|---|---|---|---|---|---|
| | | | | Halide (3) | | | | | Boron compound (2) | | | | | |
| Example | R$^1$ | m | A$^1$ | p | A$^2$ | q | A$^3$ | X | (R$^3$)$_2$ | n | r | s | t | R$^2$ |
| 18 | n-C$_{10}$H$_{21}$ | 0 | 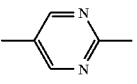 | 1 | 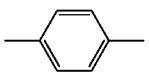 | 0 | — | Br | 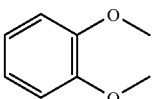 | 5 | 0 | 0 | 0 | H |
| 19 | n-C$_{10}$H$_{21}$ | 0 | 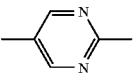 | 1 | 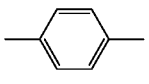 | 0 | — | Br | 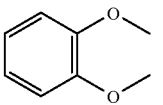 | 7 | 0 | 0 | 0 | H |
| 20 | n-C$_{10}$H$_{21}$ | 1 | 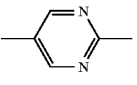 | 1 | 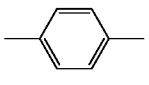 | 0 | — | Br | 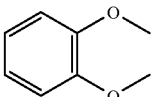 | 4 | 0 | 0 | 0 | H |
| 21 | n-C$_{10}$H$_{21}$ | 1 | 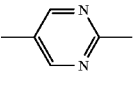 | 1 | 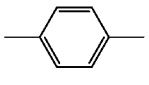 | 0 | — | Br | 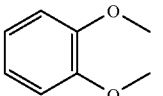 | 6 | 0 | 0 | 0 | H |

TABLE 1(1)-continued
| | | | | | | | | | | | | | |
|---|---|---|---|---|---|---|---|---|---|---|---|---|---|
| 22 | n-C₁₀H₂₁ | 1 | 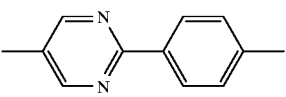 | 1 | 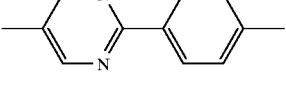 | 0 | — | Br | 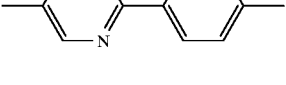 | 7 | 0 | 0 | 0 | H |
| 23 | n-C₉H₁₉ | 1 | 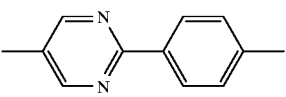 | 1 | 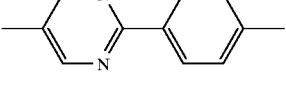 | 0 | — | Br | 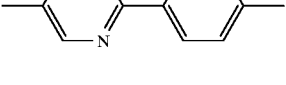 | 6 | 0 | 0 | 0 | H |
| 24 | n-C₉H₁₉ | 1 | 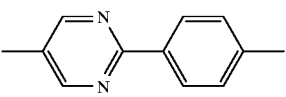 | 1 | 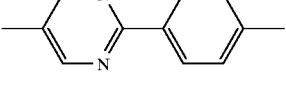 | 0 | — | Br | 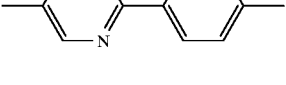 | 5 | 0 | 0 | 0 | H |
| 25 | n-C₁₀H₂₁ | 1 | 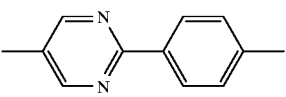 | 1 | 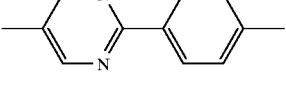 | 0 | — | I | 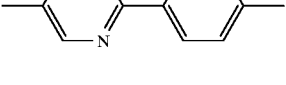 | 3 | 0 | 0 | 0 | H |
| | trans-Olefin compound (1) | | | | | Yield (%), Phase series |
|---|---|---|---|---|---|---|
| Example | $R^1$ | m | —$A^1$—$(A^2)_p$—$(A^3)_q$— | n | $R^2$ | (at elevated temp., ° C.) |
| 18 | n-C₁₀H₂₁ | 0 | 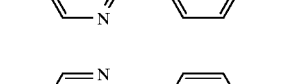 | 5 | H | 87 |
| 19 | n-C₁₀H₂₁ | 0 | 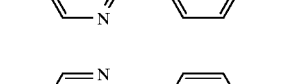 | 7 | H | 88 |
| 20 | n-C₁₀H₂₁ | 1 | 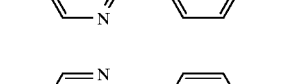 | 4 | H | 83  K—60—S_C—102—S_A—116—I |
| 21 | n-C₁₀H₂₁ | 1 | 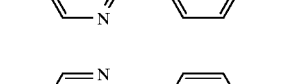 | 6 | H | 85  K—57—S_C—103—S_A—118—I |
| 22 | n-C₁₀H₂₁ | 1 | 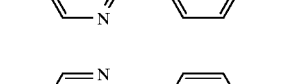 | 7 | H | 81 |
| 23 | n-C₉H₁₉ | 1 | 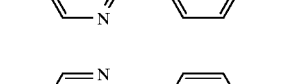 | 6 | H | 75 |
| 24 | n-C₉H₁₉ | 1 | 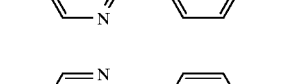 | 5 | H | 79 |
| 25 | n-C₁₀H₂₁ | 1 | 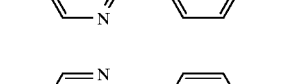 | 3 | H | 80 |

TABLE 1(2)
| | Starting compounds | | | | | | | | | | | | | |
|---|---|---|---|---|---|---|---|---|---|---|---|---|---|---|
| | Halide (3) | | | | | | | | Boron compound (2) | | | | | |
| Example | R¹ | m | A¹ | p | A² | q | A³ | X | (R³)₂ | n | r | s | t | R² |
| 26 | n-C₈H₁₇ | 1 | 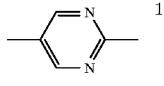 | 1 | 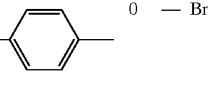 | 0 | — | Br | 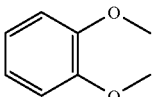 | 6 | 0 | 0 | 0 | H |
| 27 | n-C₈H₁₇ | 0 | 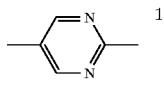 | 1 | 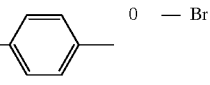 | 0 | — | Br | 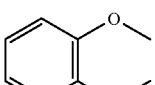 | 5 | 0 | 0 | 0 | H |
| 28 | n-C₇H₁₅ | 1 | 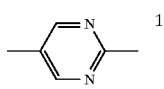 | 1 | 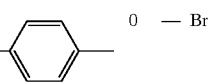 | 0 | — | Br | 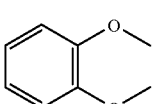 | 6 | 0 | 0 | 0 | H |
| 29 | n-C₆H₁₃ | 1 | 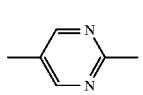 | 1 | 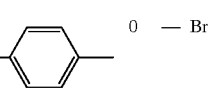 | 0 | — | Br | 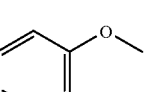 | 6 | 0 | 0 | 0 | H |
| 30 | n-C₄H₉ | 1 | 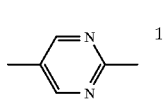 | 1 | 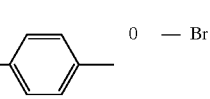 | 0 | — | Br | 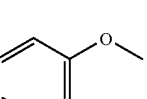 | 6 | 0 | 0 | 0 | H |
| 31 | n-C₁₀H₂₁ | 1 | 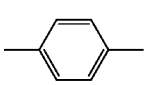 | 1 | 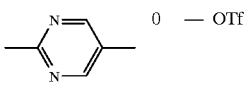 | 0 | — | OTf | 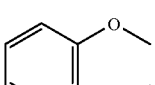 | 5 | 0 | 0 | 0 | H |
| 32 | n-C₁₀H₂₁ | 1 | 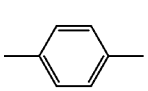 | 1 | 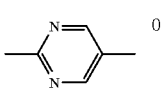 | 0 | — | OTf | 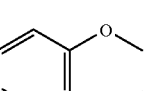 | 6 | 0 | 0 | 0 | H |
| 33 | n-C₁₀H₂₁ | 1 | 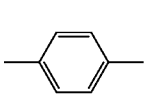 | 1 | 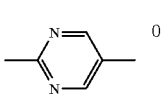 | 0 | — | OTf | 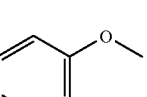 | 7 | 0 | 0 | 0 | H |
| | trans-Olefin compound (1) | | | | | Yield (%), Phase series |
|---|---|---|---|---|---|---|
| Example | R¹ | m | —A¹—(A²)ₚ—(A³)_q— | n | R² | (at elevated temp., °C.) |
| 26 | n-C₈H₁₇ | 1 | 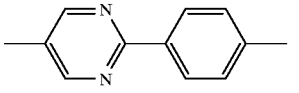 | 6 | H | 75  K —56— S_A —114— I |
| 27 | n-C₈H₁₇ | 0 | 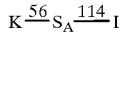 | 5 | H | 73 |
| 28 | n-C₇H₁₅ | 1 | 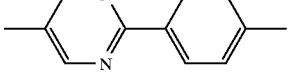 | 6 | H | 79 |

TABLE 1(2)-continued

| | | | | | | | | |
|---|---|---|---|---|---|---|---|---|
| 29 | n-C$_6$H$_{13}$ | 1 | 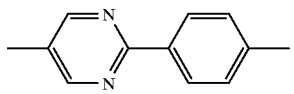 | | 6 | H | 80 | K $\frac{59}{}$ S$_A$ $\frac{107}{}$ I |
| 30 | n-C$_4$H$_9$ | 1 | 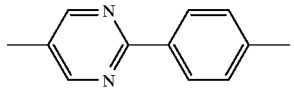 | | 6 | H | 82 | K $\frac{64}{}$ S$_C$ $\frac{78}{}$ N $\frac{104}{}$ I |
| 31 | n-C$_{10}$H$_{21}$ | 1 | 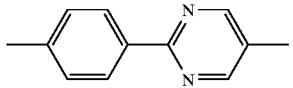 | | 5 | H | 80 | K $\frac{44}{}$ S$_C$ $\frac{75}{}$ N $\frac{105}{}$ I |
| 32 | n-C$_{10}$H$_{21}$ | 1 | 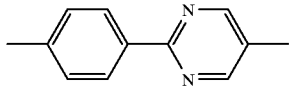 | | 6 | H | 85 | K $\frac{21}{}$ S$_C$ $\frac{71}{}$ N $\frac{94}{}$ I |
| 33 | n-C$_{10}$H$_{21}$ | 1 | 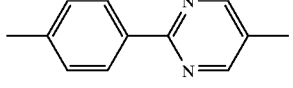 | | 7 | H | 83 | K $\frac{43}{}$ S$_C$ $\frac{84}{}$ S$_A$ $\frac{98}{}$ N $\frac{103}{}$ I |

*OTf: —OSO$_2$CF$_3$

TABLE 1(3)

| | Starting compounds | | | | | | | | | | | | |
|---|---|---|---|---|---|---|---|---|---|---|---|---|---|
| | Halide (3) | | | | | | | Boron compound (2) | | | | | |
| Example | R$^1$ | m | A$^1$ | p | A$^2$ | q | A$^3$ | X | (R$^3$)$_2$ | n | r | s | t | R$^2$ |
| 34 | n-C$_{12}$H$_{25}$ | 0 | 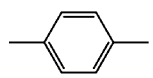 | 1 | 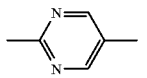 | 0 | — | OTf | 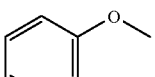 | 7 | 0 | 0 | 0 | H |
| 35 | n-C$_{10}$H$_{21}$ | 1 | 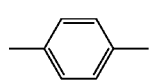 | 1 | 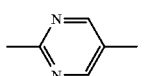 | 0 | — | OTf | 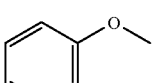 | 8 | 0 | 0 | 0 | H |
| 36 | n-C$_9$H$_{19}$ | 1 | 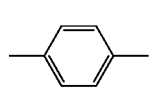 | 1 | 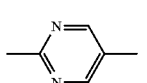 | 0 | — | OTf | 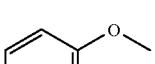 | 7 | 0 | 0 | 0 | H |
| 37 | n-C$_8$H$_{17}$ | 1 | 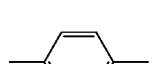 | 1 | 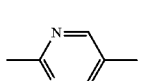 | 0 | — | OTf | 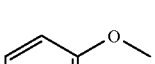 | 7 | 0 | 0 | 0 | H |
| 38 | n-C$_7$H$_{15}$ | 1 | 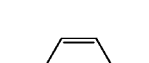 | 1 | 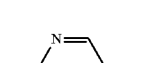 | 0 | — | OTf | 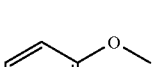 | 7 | 0 | 0 | 0 | H |
| 39 | n-C$_8$H$_{17}$ | 1 | 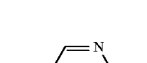 | 1 | 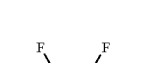 | 0 | — | OTf | 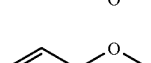 | 5 | 0 | 0 | 0 | H |

TABLE 1(3)-continued

| | | | | | | | | | | | | | |
|---|---|---|---|---|---|---|---|---|---|---|---|---|---|
| 40 | n-C₁₀H₂₁ | 1 | 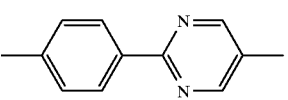 | 1 | 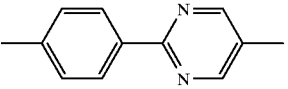 | 0 | — | OTf | 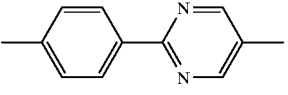 | 7 | 0 | 0 | 0 | H |
| 41 | n-C₁₂H₂₅ | 1 | 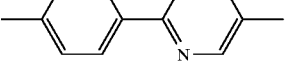 | 1 | 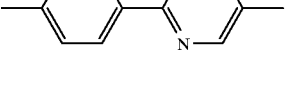 | 0 | — | OTf | 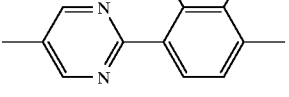 | 7 | 0 | 0 | 0 | H |

| | | trans-Olefin compound (1) | | | | Yield (%), Phase series |
|---|---|---|---|---|---|---|
| Example | $R^1$ | m | —$A^1$—($A^2$)$_p$—($A^3$)$_q$— | n | $R^2$ | (at elevated temp., °C.) |
| 34 | n-C₁₂H₂₅ | 0 | 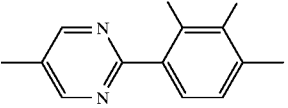 | 7 | H | 76 |
| 35 | n-C₁₀H₂₁ | 1 | | 8 | H | 70  K$\underline{\phantom{x}29\phantom{x}}$S$_C\underline{\phantom{x}89\phantom{x}}$S$_A\underline{\phantom{x}101\phantom{x}}$I |
| 36 | n-C₉H₁₉ | 1 | | 7 | H | 73 |
| 37 | n-C₈H₁₇ | 1 | | 7 | H | 81 |
| 38 | n-C₇H₁₅ | 1 | | 7 | H | 84 |
| 39 | n-C₈H₁₇ | 1 | 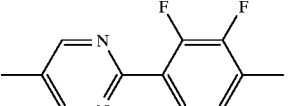 | 5 | H | 75 |
| 40 | n-C₁₀H₂₁ | 1 | | 7 | H | 78  K$\underline{\phantom{x}41\phantom{x}}$S$_C\underline{\phantom{x}79\phantom{x}}$S$_A\underline{\phantom{x}93\phantom{x}}$I |
| 41 | n-C₁₂H₂₅ | 1 | | 7 | H | 71 |

*OTf: —OSO₂CF₃

TABLE 1(4)
| | Starting compounds | | | | | | | | | | | | | |
|---|---|---|---|---|---|---|---|---|---|---|---|---|---|---|
| | Halide (3) | | | | | | | | Boron compound (2) | | | | | |
| Example | $R^1$ | m | $A^1$ | p | $A^2$ | q | $A^3$ | X | $(R^3)_2$ | n | r | s | t | $R^2$ |
| 42 | n-$C_{12}H_{25}$ | 0 | 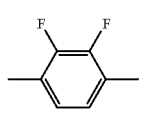 | 1 | 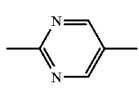 | 0 | — | Br | 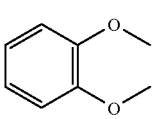 | 7 | 0 | 0 | 0 | H |
| 43 | n-$C_{10}H_{21}$ | 1 | 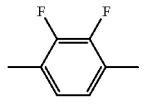 | 1 | 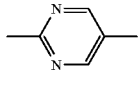 | 0 | — | Br | 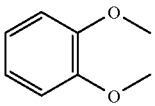 | 8 | 0 | 0 | 0 | H |
| 44 | n-$C_9H_{19}$ | 1 | 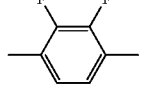 | 1 | 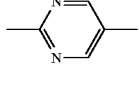 | 0 | — | Br | 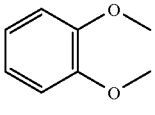 | 7 | 0 | 0 | 0 | H |
| 45 | n-$C_{10}H_{21}$ | 1 | 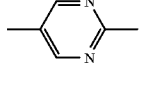 | 1 | 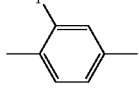 | 0 | — | OTf | 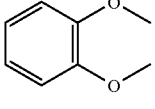 | 7 | 0 | 0 | 0 | H |
| 46 | n-$C_9H_{19}$ | 1 | 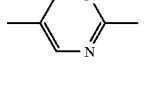 | 1 | 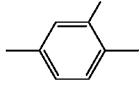 | 0 | — | OTf | 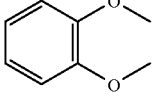 | 6 | 0 | 0 | 0 | H |
| 47 | n-$C_{11}H_{23}$ | 1 | 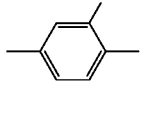 | 1 | 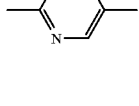 | 0 | — | Br | 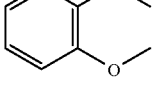 | 5 | 0 | 0 | 0 | $C_6H_{13}$ |
| 48 | n-$C_{10}H_{21}$ | 1 | 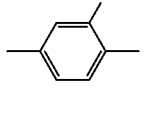 | 1 | 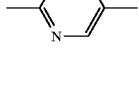 | 0 | — | Br | 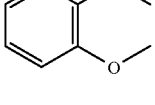 | 7 | 0 | 0 | 0 | H |
| 49 | n-$C_{10}H_{21}$ | 1 | 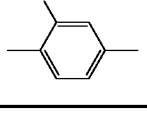 | 1 | 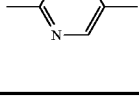 | 0 | — | Br | 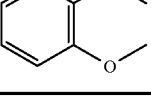 | 7 | 0 | 0 | 0 | H |
| | trans-Olefin compound (1) | | | | | Yield (%), Phase series |
|---|---|---|---|---|---|---|
| Example | $R^1$ | m | —$A^1$—$(A^2)_p$—$(A^3)_q$— | n | $R^2$ | (at elevated temp., ° C.) |
| 42 | n-$C_{12}H_{25}$ | 0 | 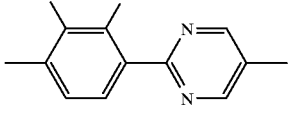 | 7 | H | 83 |
| 43 | n-$C_{10}H_{21}$ | 1 | 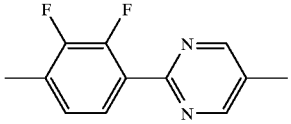 | 8 | H | 78   $K \xrightarrow{38} S_C \xrightarrow{81} N \xrightarrow{82} I$ |

TABLE 1(4)-continued

| Example | R¹ | m | A¹ | p | A² | q | A³ | X | (R³)₂ | n | r | s | t | R² | Phase transition |
|---|---|---|---|---|---|---|---|---|---|---|---|---|---|---|---|
| 44 | n-C₉H₁₉ | 1 | 2,3-difluoro-1,4-phenylene | | 5-pyrimidinyl (2-linked) | | | 7 | H | | | | | 79 | K —32— S_C —78— N —85— I |
| 45 | n-C₁₀H₂₁ | 1 | 2-fluoro-1,4-phenylene | | 5-pyrimidinyl (2-linked) | | | 7 | H | | | | | 74 | K —41— S_C —81— S_A —84— N —88— I |
| 46 | n-C₉H₁₉ | 1 | 2-fluoro-1,4-phenylene | | 5-pyrimidinyl (2-linked) | | | 6 | H | | | | | 82 | |
| 47 | n-C₁₁H₂₃ | 1 | 2-fluoro-1,4-phenylene | | 5-pyrimidinyl (2-linked) | | | 5 | C₆H₁₃ | | | | | 77 | |
| 48 | n-C₁₀H₂₁ | 1 | 2-fluoro-1,4-phenylene | | 5-pyrimidinyl (2-linked) | | | 7 | H | | | | | 84 | |
| 49 | n-C₁₀H₂₁ | 1 | 3-fluoro-1,4-phenylene | | 5-pyrimidinyl (2-linked) | | | 7 | H | | | | | 70 | K —33— S_C —69.5— S_A —90— I |

*OTf: —OSO₂CF₃

TABLE 1(5)

| | Starting compounds | | | | | | | | | | | | | |
|---|---|---|---|---|---|---|---|---|---|---|---|---|---|---|
| | Halide (3) | | | | | | | | Boron compound (2) | | | | | |
| Example | R¹ | m | A¹ | p | A² | q | A³ | X | (R³)₂ | n | r | s | t | R² |
| 50 | n-C₁₀H₂₁ | 1 | 1,4-phenylene | 1 | 1,4-phenylene | 0 | — | Br | 1,2-dimethoxyphenyl | 5 | 0 | 0 | 0 | H |
| 51 | n-C₁₀H₂₁ | 0 | 1,4-phenylene | 1 | 1,4-phenylene | 0 | — | Br | 1,2-dimethoxyphenyl | 4 | 0 | 0 | 0 | H |
| 52 | n-C₁₀H₂₁ | 1 | 2,3-difluoro-1,4-phenylene | 1 | 1,4-phenylene | 0 | — | Br | 1,2-dimethoxyphenyl | 7 | 0 | 0 | 0 | H |

TABLE 1(5)-continued
| | | | | | | | | | | | | | | |
|---|---|---|---|---|---|---|---|---|---|---|---|---|---|---|
| 53 | n-C$_9$H$_{19}$ | 1 | 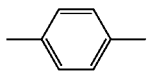 | 1 | 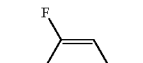 | 0 | — | OTf | 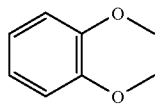 | 5 | 0 | 0 | 0 | C$_7$H$_{15}$ |
| 54 | n-C$_8$H$_{17}$ | 1 | 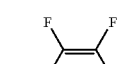 | 1 | 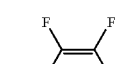 | 0 | — | OTf | 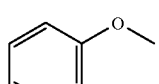 | 6 | 0 | 0 | 0 | H |
| 55 | n-C$_8$H$_{17}$ | 1 | 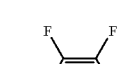 | 1 | 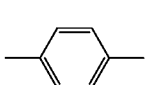 | 1 | 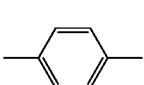 | Br | 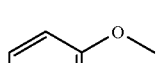 | 5 | 0 | 0 | 0 | H |
| 56 | n-C$_{10}$H$_{21}$ | 1 | 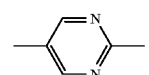 | 1 | 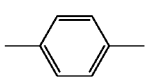 | 1 |  | OTf | 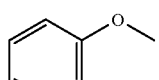 | 4 | 0 | 0 | 0 | H |
| 57 | n-C$_{12}$H$_{25}$ | 1 | 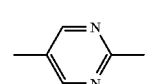 | 1 | 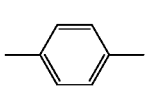 | 1 | 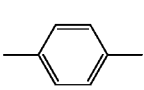 | OTf | 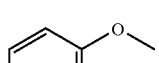 | 5 | 0 | 0 | 0 | H |
| | | trans-Olefin compound (1) | | | | Yield (%), Phase series |
|---|---|---|---|---|---|---|
| Example | R$^1$ | m | —A$^1$—(A$^2$)$_p$—(A$^3$)$_q$— | n | R$^2$ | (at elevated temp., ° C.) |
| 50 | n-C$_{10}$H$_{21}$ | 1 | 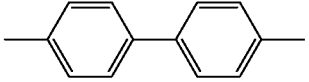 | 5 | H | 86 |
| 51 | n-C$_{10}$H$_{21}$ | 0 | 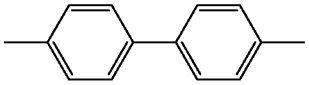 | 4 | H | 85 |
| 52 | n-C$_{10}$H$_{21}$ | 1 |  | 7 | H | 81 |
| 53 | n-C$_9$H$_{19}$ | 1 | 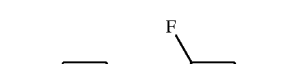 | 5 | C$_7$H$_{15}$ | 79 |
| 54 | n-C$_8$H$_{17}$ | 1 |  | 6 | H | 85 |
| 55 | n-C$_8$H$_{17}$ | 1 | 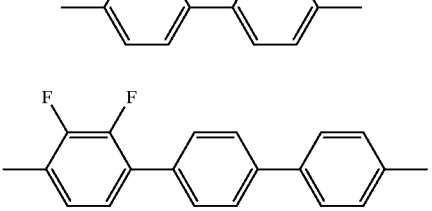 | 5 | H | 70 |

TABLE 1(5)-continued
| 56 | n-C₁₀H₂₁ | 1 | 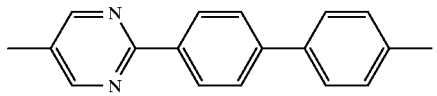 | 4 | H | 81 |
| 57 | n-C₁₂H₂₅ | 1 | 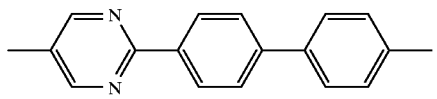 | 5 | H | 79 |
*OTf: —OSO₂CF₃
TABLE 1(6)
| | Starting compounds | | | | | | | | | | | | | |
|---|---|---|---|---|---|---|---|---|---|---|---|---|---|---|
| Example | Halide (3) | | | | | | | Boron compound (2) | | | | | | |
| | R¹ | m | A¹ | p | A² | q | A³ | X | (R³)₂ | n | r | s | t | R² |
| 58 | n-C₁₀H₂₁ | 1 |  | 1 |  | 1 |  | OTf |  | 7 | 0 | 0 | 0 | H |
| 59 | n-C₆H₁₃ | 0 |  | 1 |  | 1 |  | OTf |  | 8 | 0 | 0 | 0 | H |
| 60 | n-C₁₀H₂₁ | 1 |  | 1 |  | 1 |  | Br |  | 4 | 0 | 0 | 0 | H |
| 61 | n-C₁₀H₂₁ | 1 |  | 1 |  | 1 |  | Br |  | 5 | 0 | 0 | 0 | H |
| 62 | n-C₁₀H₂₁ | 1 |  | 1 |  | 1 |  | Br |  | 4 | 0 | 0 | 0 | H |
| 63 | n-C₆H₁₃ | 1 |  | 1 |  | 1 |  | Br |  | 8 | 0 | 0 | 0 | H |
| 64 | n-C₆H₁₃ | 1 |  | 1 |  | 1 |  | Br |  | 5 | 0 | 0 | 0 | H |
| 65 | n-C₇H₁₅ | 1 |  | 1 |  | 1 |  | OTf |  | 6 | 0 | 0 | 0 | H |
| Example | trans-Olefin compound (1) | | | | | Yield (%), Phase series |
|---|---|---|---|---|---|---|
| | R¹ | m | —A¹—(A²)ₚ—(A³)q— | n | R² | (at elevated temp., °C.) |
| 58 | n-C₁₀H₂₁ | 1 | 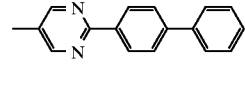 | 7 | H | 78 |
| 59 | n-C₆H₁₃ | 0 | 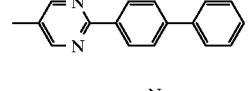 | 8 | H | 80 |
| 60 | n-C₁₀H₂₁ | 1 | 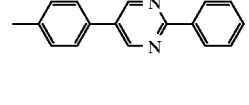 | 4 | H | 82 |

TABLE 1(6)-continued

| | | | | | | | |
|---|---|---|---|---|---|---|---|
| 61 | n-C₁₀H₂₁ | 1 | (phenyl-pyrimidine-phenyl) | | 5 | H | 81 |
| 62 | n-C₁₀H₂₁ | 1 | (phenyl-pyrimidine-phenyl) | | 4 | H | 83 |
| 63 | n-C₆H₁₃ | 1 | (phenyl-pyrimidine-phenyl) | | 8 | H | 82 |
| 64 | n-C₆H₁₃ | 1 | (phenyl-pyrimidine-phenyl) | | 5 | H | 79 |
| 65 | n-C₇H₁₅ | 1 | (pyrimidine-difluorophenyl-phenyl) | | 6 | H | 73 |

\*) OTf: —OSO₂CF₃

TABLE 1(7)

| | Starting compounds | | | | | | | | | | | | | |
|---|---|---|---|---|---|---|---|---|---|---|---|---|---|---|
| Exam- | | | Halide (3) | | | | | | Boron compound (2) | | | | | |
| ple | R¹ | m | A¹ | p | A² | q | A³ | X | (R³)₂ | n | r | s | t | R² |
| 66 | n-C₆H₁₃ | 1 | (phenyl) | 1 | (difluorophenyl) | 1 | (pyrimidine) | Br | (catechol borate) | 7 | 0 | 0 | 0 | H |
| 67 | n-C₈H₁₇ | 0 | (difluorophenyl) | 1 | (pyrimidine) | 1 | (phenyl) | Br | (catechol borate) | 8 | 0 | 0 | 0 | H |
| 68 | n-C₉H₁₉ | 1 | (phenyl) | 1 | (fluorophenyl) | 1 | (pyrimidine) | Br | (catechol borate) | 4 | 0 | 0 | 0 | H |
| 69 | n-C₁₀H₂₁ | 1 | (pyrimidine) | 1 | (phenyl) | 1 | (difluorophenyl) | OTf | (catechol borate) | 5 | 0 | 0 | 0 | H |
| 70 | n-C₁₀H₂₁ | 1 | (pyrimidine) | 1 | (fluorophenyl) | 1 | (phenyl) | Br | (catechol borate) | 4 | 0 | 0 | 0 | H |

| Exam- | trans-Olefin compound (1) | | | | | Yield (%), Phase series |
|---|---|---|---|---|---|---|
| ple | R¹ | m | —A¹—(A²)ₚ—(A³)_q— | n | R² | (at elevated temp., ° C.) |
| 66 | n-C₆H₁₃ | 1 | (phenyl-difluorophenyl-pyrimidine) | 7 | H | 81 |
| 67 | n-C₈H₁₇ | 0 | (difluorophenyl-pyrimidine-phenyl) | 8 | H | 71 |

TABLE 1(7)-continued

| | | | | | | |
|---|---|---|---|---|---|---|
| 68 | n-C$_9$H$_{19}$ | 1 | 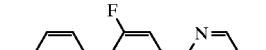 | 4 | H | 73 |
| 69 | n-C$_{10}$H$_{21}$ | 1 |  | 5 | H | 87 |
| 70 | n-C$_{10}$H$_{21}$ | 1 | 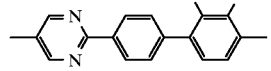 | 4 | H | 81 |

*) OTf: —OSO$_2$CF$_3$

TABLE 1(8)

| | Starting compounds | | | | | | | | | | | |
|---|---|---|---|---|---|---|---|---|---|---|---|---|
| | Halide (3) | | | | | | | Boron compound (2) | | | | |
| Example | R$^1$ | m | A$^1$ | p | A$^2$ | q | A$^3$ | X | (R$^3$)$_2$ | n | r | s | t | R$^2$ |
| 71 | n-C$_{10}$H$_{21}$ | 1 | 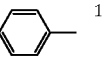 | 1 | 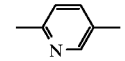 | 0 | — | Br | 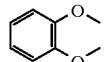 | 5 | 0 | 0 | 0 | H |
| 72 | n-C$_{10}$H$_{21}$ | 1 | 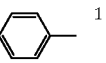 | 1 | 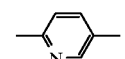 | 0 | — | Br | 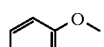 | 5 | 0 | 0 | 0 | H |
| 73 | n-C$_{10}$H$_{21}$ | 0 | 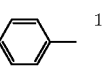 | 1 | 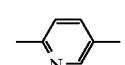 | 0 | — | Br | 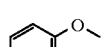 | 7 | 0 | 0 | 0 | H |
| 74 | n-C$_{10}$H$_{21}$ | 1 | 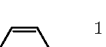 | 1 | 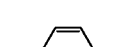 | 1 |  | OTf | 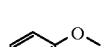 | 4 | 0 | 0 | 0 | H |
| 75 | n-C$_{10}$H$_{21}$ | 1 | 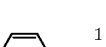 | 1 | 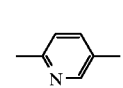 | 1 |  | Br | 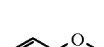 | 5 | 0 | 0 | 0 | H |
| 76 | n-C$_{10}$H$_{21}$ | 1 |  | 1 |  | 0 | — | Br | 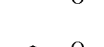 | 8 | 0 | 0 | 0 | H |
| 77 | n-C$_{10}$H$_{21}$ | 1 |  | 1 |  | 0 | — | Br | 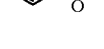 | 7 | 0 | 0 | 0 | H |
| 78 | n-C$_8$H$_{15}$ | 1 | 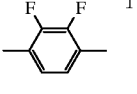 | 1 | 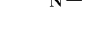 | 0 | — | Br | 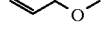 | 7 | 0 | 0 | 0 | H |

| Example | trans-Olefin compound (1) | | | | | Yield (%), Phase series |
|---|---|---|---|---|---|---|
| | R$^1$ | m | —A$^1$—(A$^2$)$_p$—(A$^3$)$_q$— | n | R$^2$ | (at elevated temp., ° C.) |
| 71 | n-C$_{10}$H$_{21}$ | 1 |  | 4 | H | 46   54   100   121<br>K—S$_2$—S$_1$—S$_0$—I |

TABLE 1(8)-continued

| | $R^1$ | m | A² (structure) | n | $R^2$ | Yield/Phase |
|---|---|---|---|---|---|---|
| 72 | n-$C_{10}H_{21}$ | 1 | phenyl-pyridine (2,5) | 5 | H | 81 |
| 73 | n-$C_{10}H_{21}$ | 0 | phenyl-pyridine (2,5) | 7 | H | 83 |
| 74 | n-$C_{10}H_{21}$ | 1 | phenyl-pyridine-phenyl (2,5) | 4 | H | 87 |
| 75 | n-$C_{10}H_{21}$ | 1 | phenyl-pyridine-phenyl | 5 | H | 79 |
| 76 | n-$C_{10}H_{21}$ | 1 | phenyl-pyridine (3,6) | 8 | H | 76 |
| 77 | n-$C_{10}H_{21}$ | 1 | difluorophenyl-pyridine | 7 | H | K—30—$S_0$—58—N—69—I |
| 78 | n-$C_8H_{15}$ | 1 | difluorophenyl-pyridine | 7 | H | 75 |

TABLE 1(9)

| | Starting compounds | | | | | | | | | | | | |
|---|---|---|---|---|---|---|---|---|---|---|---|---|---|
| | Halide (3) | | | | | | | Boron compound (2) | | | | | |
| Example | $R^1$ | m | $A^1$ | p | $A^2$ | q | $A^3$ | X | $(R^3)_2$ | n | r | s | t | $R^2$ |
| 79 | n-$C_{12}H_{25}$ | 1 | fluorophenyl | 1 | pyridine (2,5) | 0 | — | Br | catechol borate | 7 | 0 | 0 | 0 | H |
| 80 | n-$C_{10}H_{21}$ | 1 | phenyl | 1 | pyrazine | 0 | — | Br | catechol borate | 7 | 0 | 0 | 0 | H |
| 81 | n-$C_{10}H_{21}$ | 0 | phenyl | 1 | pyridazine | 0 | — | Br | catechol borate | 8 | 0 | 0 | 0 | H |
| 82 | n-$C_{10}H_{21}$ | 1 | difluorophenyl | 1 | pyridazine | 0 | — | Br | catechol borate | 6 | 0 | 0 | 0 | H |
| 83 | n-$C_{10}H_{21}$ | 1 | difluorophenyl | 1 | pyridazine | 1 | phenyl | Br | catechol borate | 8 | 0 | 0 | 0 | H |

| Example | $R^1$ | m | —$A^1$—$(A^2)_p$—$(A^3)_q$— | n | $R^2$ | Yield (%), Phase series (at elevated temp., °C.) |
|---|---|---|---|---|---|---|
| 79 | n-$C_{12}H_{25}$ | 1 | fluorophenyl-pyridine | 7 | H | 68 |

TABLE 1(9)-continued

| | | | | | | | |
|---|---|---|---|---|---|---|---|
| 80 | n-C$_{10}$H$_{21}$ | 1 | 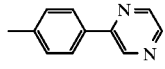 | | 7 | H | 62 |
| 81 | n-C$_{10}$H$_{21}$ | 0 | 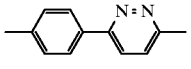 | | 8 | H | 55 |
| 82 | n-C$_{10}$H$_{21}$ | 1 | 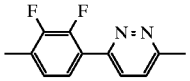 | | 6 | H | 59 |
| 83 | n-C$_{10}$H$_{21}$ | 1 | 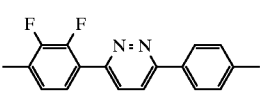 | | 8 | H | 75 |

*) OTf: —OSO$_2$CF$_3$

TABLE 1(10)

| Example | Starting compounds | | | | | | | | | | | | |
|---|---|---|---|---|---|---|---|---|---|---|---|---|---|
| | Halide (3) | | | | | | | Boron compound (2) | | | | | |
| | R$^1$ | m | A$^1$ | p | A$^2$ | q | A$^3$ | X | (R$^3$)$_2$ | n | r | s | t | R$^2$ |
| 84 | n-C$_{12}$H$_{15}$ | 1 | 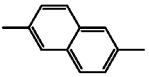 | 0 | — | 0 | — | Br | 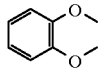 | 9 | 0 | 0 | 0 | C$_2$H$_5$ |
| 85 | n-C$_{10}$H$_{21}$ | 1 | 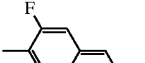 | 0 | — | 0 | — | Br | 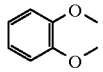 | 7 | 0 | 0 | 0 | H |
| 86 | n-C$_{10}$H$_{21}$ | 1 | 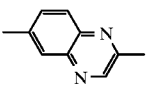 | 0 | — | 0 | — | Br | 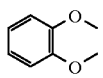 | 10 | 0 | 0 | 0 | H |
| 87 | n-C$_{10}$H$_{21}$ | 1 | 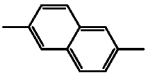 | 1 | 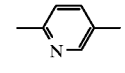 | 0 | — | Br | 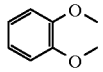 | 5 | 0 | 0 | 0 | H |
| 88 | n-C$_{10}$H$_{21}$ | 1 | 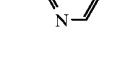 | 1 | 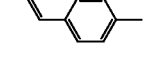 | 0 | — | OTf | 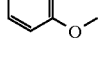 | 4 | 0 | 0 | 0 | H |
| 89 | n-C$_{10}$H$_{21}$ | 1 | 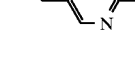 | 1 |  | 0 | — | Br | 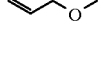 | 4 | 0 | 0 | 0 | H |
| 90 | n-C$_{10}$H$_{21}$ | 1 | 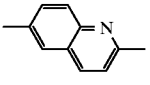 | 1 | 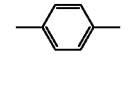 | 0 | — | OTf | 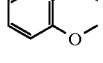 | 4 | 0 | 0 | 0 | H |

| Example | trans-Olefin compound (1) | | | | | Yield (%), Phase series (at elevated temp., ° C.) |
|---|---|---|---|---|---|---|
| | R$^1$ | m | —A$^1$—(A$^2$)$_p$—(A$^3$)$_q$— | n | R$^2$ | |
| 84 | n-C$_{12}$H$_{15}$ | 1 | 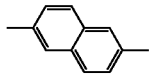 | 9 | C$_2$H$_5$ | 74 |

TABLE 1(10)-continued
| | | | | | | |
|---|---|---|---|---|---|---|
| 85 | n-C$_{10}$H$_{21}$ | 1 | 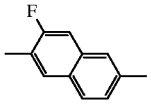 | 7 | H | 69 |
| 86 | n-C$_{10}$H$_{21}$ | 1 | 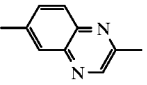 | 10 | H | 71 |
| 87 | n-C$_{10}$H$_{21}$ | 1 | 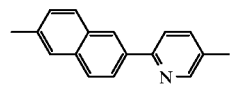 | 5 | H | 70 |
| 88 | n-C$_{10}$H$_{21}$ | 1 | 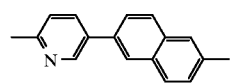 | 4 | H | 67 |
| 89 | n-C$_{10}$H$_{21}$ | 1 | 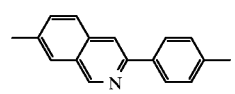 | 4 | H | 65 |
| 90 | n-C$_{10}$H$_{21}$ | 1 | 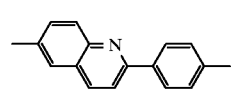 | 4 | H | 76 |
*) OTf: —OSO$_2$CF$_3$
TABLE 1(11)
| | Starting Compounds | | | | | | | | | | | | |
|---|---|---|---|---|---|---|---|---|---|---|---|---|---|
| | Halide (3) | | | | | | | Boron compound (2) | | | | | |
| Example | R$^1$ | m | A$^1$ | p | A$^2$ | q | A$^3$ | X | (R$^3$)$_2$ | n | r | s | t | R$^2$ |
| 91 | n-C$_{10}$H$_{21}$ | 1 | 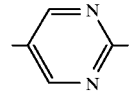 | 1 | 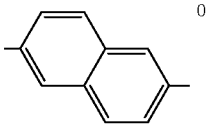 | 0 | — | OTf | 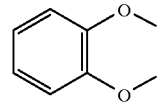 | 4 | 0 | 0 | 0 | H |
| 92 | n-C$_{10}$H$_{21}$ | 1 | 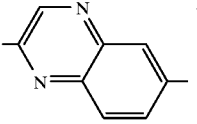 | 1 | 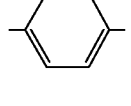 | 0 | — | OTf | 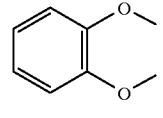 | 4 | 0 | 0 | 0 | H |
| 93 | n-C$_{10}$H$_{21}$ | 1 | 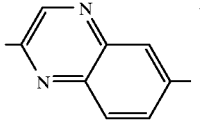 | 1 | 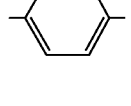 | 0 | — | OTf | 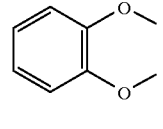 | 5 | 0 | 0 | 0 | H |
| 94 | n-C$_8$H$_{17}$ | 1 | 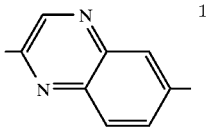 | 1 | 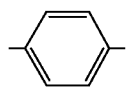 | 0 | — | OTf | 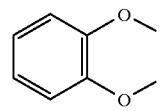 | 5 | 0 | 0 | 0 | H |

TABLE 1(11)-continued
| | | | | | | | | | | | | | |
|---|---|---|---|---|---|---|---|---|---|---|---|---|---|
| 95 | n-C$_7$H$_{15}$ | 1 | 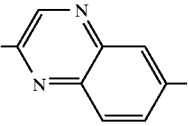 | 1 |  | 0 | — | OTf | 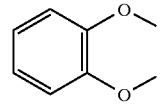 | 5 | 0 | 0 | 0 | H |
| 96 | n-C$_6$H$_{13}$ | 1 | 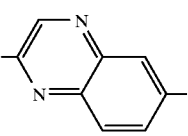 | 1 | 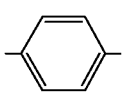 | 0 | — | OTf | 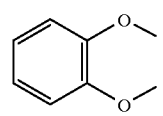 | 8 | 0 | 0 | 0 | H |
| 97 | n-C$_6$H$_{13}$ | 1 | 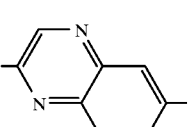 | 1 | 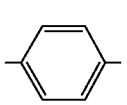 | 0 | — | OTf | 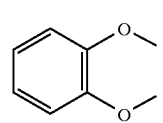 | 4 | 0 | 0 | 0 | H |
| Example | trans-Olefin compound (1) | | | | | Yield (%), Phase series |
|---|---|---|---|---|---|---|
| | R$^1$ | m | —A$^1$—(A$^2$)$_p$—(A$^3$)$_q$— | n | R$^2$ | (at elevated temp., °C.) |
| 91 | n-C$_{10}$H$_{21}$ | 1 | 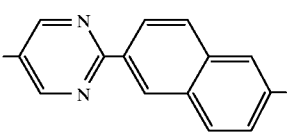 | 4 | H | 83 |
| 92 | n-C$_{10}$H$_{21}$ | 1 | 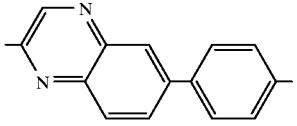 | 4 | H | 75 |
| 93 | n-C$_{10}$H$_{21}$ | 1 | 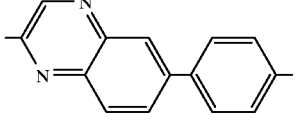 | 5 | H | 80 |
| 94 | n-C$_8$H$_{17}$ | 1 | 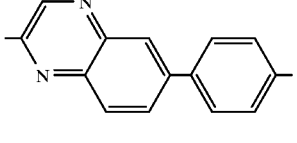 | 5 | H | 82 |
| 95 | n-C$_7$H$_{15}$ | 1 | 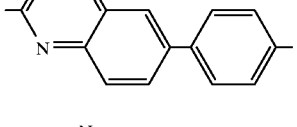 | 5 | H | 80 |
| 96 | n-C$_6$H$_{13}$ | 1 | 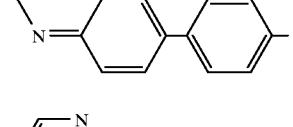 | 8 | H | 79 |
| 97 | n-C$_6$H$_{13}$ | 1 | 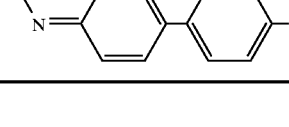 | 4 | H | 83 |
*) OTf: —OSO$_2$CF$_3$ TABLE 1(12)
| Example | Starting compounds | | | | | | | | | | | | | |
|---|---|---|---|---|---|---|---|---|---|---|---|---|---|---|
| | Halide (3) | | | | | | | | Boron compound (2) | | | | | |
| | $R^1$ | m | $A^1$ | p | $A^2$ | q | $A^3$ | X | $(R^3)$ | n | r | s | t | $R^2$ |
| 98 | n-$C_{10}H_{21}$ | 1 | 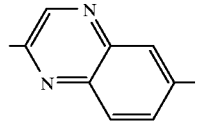 | 1 | 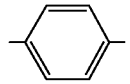 | 0 | — | OTf | 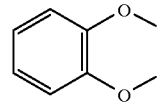 | 4 | 0 | 0 | 0 | H |
| 99 | n-$C_{10}H_{21}$ | 1 | 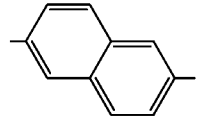 | 1 | 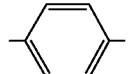 | 0 | — | OTf | 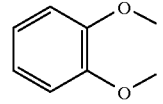 | 8 | 0 | 0 | 0 | H |
| 100 | n-$C_9H_{19}$ | 1 | 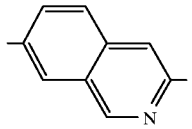 | 1 | 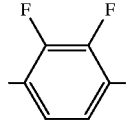 | 0 | — | OTf | 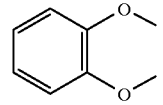 | 4 | 0 | 0 | 0 | H |
| 101 | n-$C_8H_{17}$ | 1 | 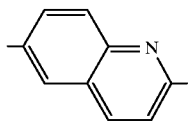 | 1 | 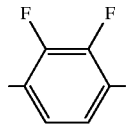 | 0 | — | OTf | 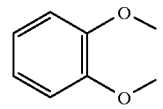 | 5 | 0 | 0 | 0 | H |
| 102 | n-$C_{10}H_{21}$ | 1 | 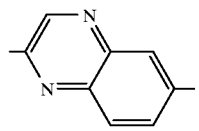 | 1 | 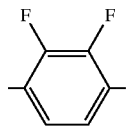 | 0 | — | OTf | 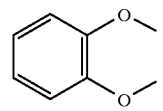 | 4 | 0 | 0 | 0 | H |
| 103 | n-$C_6H_{13}$ | 1 | 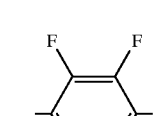 | 1 | 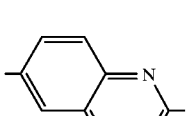 | 0 | — | OTf | 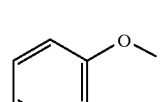 | 8 | 0 | 0 | 0 | H |
| 104 | n-$C_{10}H_{21}$ | 1 | 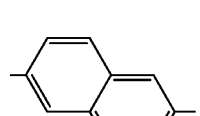 | 1 | 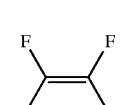 | 0 | — | OTf | 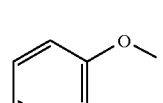 | 8 | 0 | 0 | 0 | H |
| 105 | n-$C_8H_{17}$ | 1 | 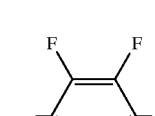 | 1 | 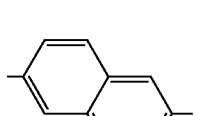 | 0 | — | OTf | 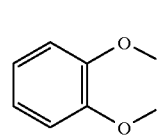 | 7 | 0 | 0 | 0 | H |
| Example | trans-Olefin compound (1) | | | | | Yield (%), Phase series |
|---|---|---|---|---|---|---|
| | $R^1$ | m | —$A^1$—$(A^2)_p$—$(A^3)_q$— | n | $R^2$ | (at elevated temp., °C.) |
| 98 | n-$C_{10}H_{21}$ | 1 | 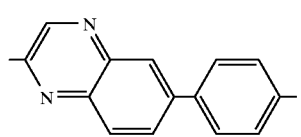 | 4 | H | 75 |

TABLE 1(12)-continued
| | | | | | | |
|---|---|---|---|---|---|---|
| 99 | n-C$_{10}$H$_{21}$ | 1 | 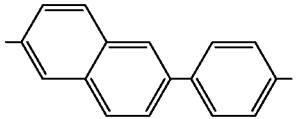 | 8 | H | 84 |
| 100 | n-C$_9$H$_{19}$ | 1 | 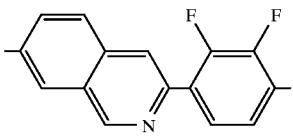 | 4 | H | 83 |
| 101 | n-C$_8$H$_{17}$ | 1 | 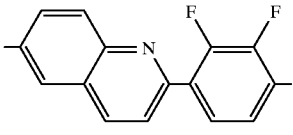 | 5 | H | 85 |
| 102 | n-C$_{10}$H$_{21}$ | 1 | 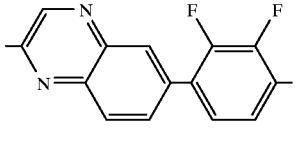 | 4 | H | 83 |
| 103 | n-C$_6$H$_{13}$ | 1 | 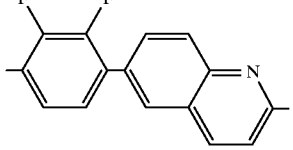 | 8 | H | 79 |
| 104 | n-C$_{10}$H$_{21}$ | 1 | 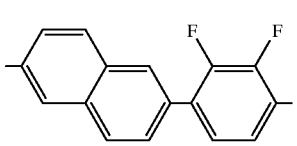 | 8 | H | 81 |
| 105 | n-C$_8$H$_{17}$ | 1 | 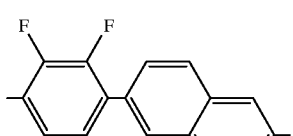 | 7 | H | 75 |
*) OTf: —OSO$_2$CF$_3$
TABLE 1(13)
| Example | Starting compounds | | | | | | | | | | | |
|---|---|---|---|---|---|---|---|---|---|---|---|---|
| | Hailde (3) | | | | | | Boron compound (2) | | | | | |
| | R$^1$ | m | A$^1$ | p | A$^2$ | q | X | (R$^3$)$_2$ | n | r | s | t | R$^2$ |
| 106 | 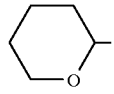 | 1 | 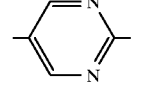 | 1 |  | 0 | OTf | 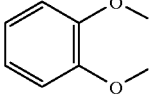 | 4 | 0 | 0 | 0 | H |
| 107 | CH$_3$OCH$_2$— | 1 | 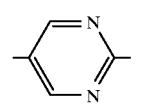 | 1 |  | 0 | OTf | 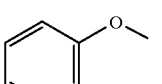 | 8 | 0 | 0 | 0 | H |

TABLE 1(13)-continued

| | | | | | | | | | | | | | |
|---|---|---|---|---|---|---|---|---|---|---|---|---|---|
| 108 | tBu(CH$_3$)$_2$Si— | 1 | 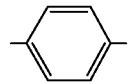 | 1 | 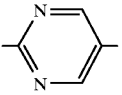 | 0 | OTf | 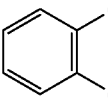 | 7 | 0 | 0 | 0 | H |
| 109 | 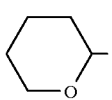 | 1 | 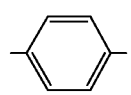 | 1 | 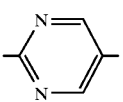 | 1 | OTf | 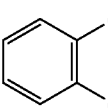 | 5 | 0 | 0 | 0 | H |

A$^3$: 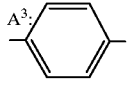

| Example | trans-Olefin compound (1) | | | | | Yield (%), Phase series |
|---|---|---|---|---|---|---|
| | R$^1$ | m | —A$^1$—(A$^2$)$_p$—(A$^3$)$_q$— | n | R$^2$ | (at elevated temp., °C.) |
| 106 | 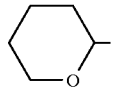 | 1 | 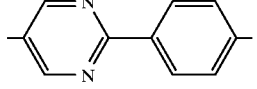 | 4 | H | 71 |
| 107 | CH$_3$OCH$_2$— | 1 | 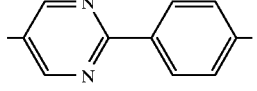 | 8 | H | 68 |
| 108 | tBu(CH$_3$)$_2$Si— | 1 | 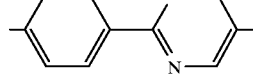 | 7 | H | 65 |
| 109 | 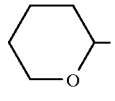 | 1 | 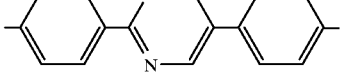 | 5 | H | 73 |

*) OTf: —OSO$_2$CF$_3$

TABLE 2(1)

| | Starting compounds | | | | | | | | | | | | | |
|---|---|---|---|---|---|---|---|---|---|---|---|---|---|---|
| Example | Halide (3) | | | | | | | | Boron compound (2) | | | | | |
| | R$^1$ | m | A$^1$ | p | A$^2$ | q | A$^3$ | X | (R$^3$)$_2$ | n | r | s | t | Z | R$^2$ |
| 110 | n-C$_8$H$_{17}$ | 1 | 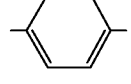 | 1 | 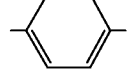 | 0 | — | Br | (HO)$_2$ | 1 | 0 | 1 | 0 | — | H |
| 111 | n-C$_{10}$H$_{21}$ | 1 | 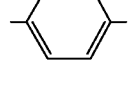 | 1 | 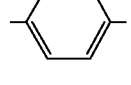 | 0 | — | Br | (HO)$_2$ | 3 | 0 | 1 | 0 | — | H |
| 112 | n-C$_{10}$H$_{21}$ | 1 | 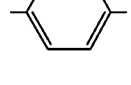 | 1 | 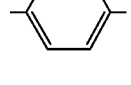 | 0 | — | Br | (HO)$_2$ | 3 | 1 | 1 | 0 | F | H |
| 113 | n-C$_{10}$H$_{21}$ | 1 | 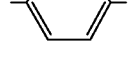 | 1 | 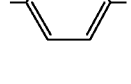 | 1 | 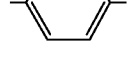 | Br | (HO)$_2$ | 3 | 1 | 1 | 0 | H | H |

TABLE 2(1)-continued

| | | | | | | | | | | | | | | | | |
|---|---|---|---|---|---|---|---|---|---|---|---|---|---|---|---|---|
| 114 | n-C$_8$H$_{17}$ | 1 | 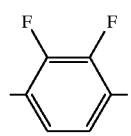 (2,3-difluorophenyl) | 1 | 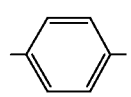 | 1 | 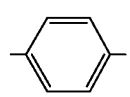 | Br | (HO)$_2$ | 2 | 1 | 1 | 0 | H | H | |
| 115 | n-C$_8$H$_{17}$ | 1 | 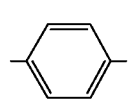 | 1 | 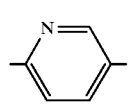 (pyridine) | 1 | 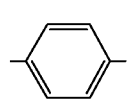 | OTf | (HO)$_2$ | 3 | 1 | 1 | 0 | H | H | |
| 116 | n-C$_{10}$H$_{21}$ | 1 | 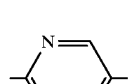 (pyridine) | 1 | 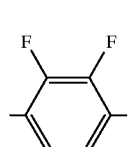 (2,3-difluorophenyl) | 0 | — | OTf | (HO)$_2$ | 1 | 1 | 1 | 0 | H | H | |
| 117 | n-C$_{12}$H$_{25}$ | 1 | 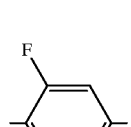 (fluorophenyl) | 1 | 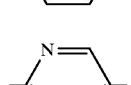 (pyridine) | 0 | — | OTf | (HO)$_2$ | 1 | 1 | 1 | 0 | H | H | |

| Example | Carboxylic acid (4) or alkylating agent (5) | trans-Olefin compound (1) | | | | | | | | | | | | Optical rotation |
|---|---|---|---|---|---|---|---|---|---|---|---|---|---|---|
| | | R$^1$ | m | A$^1$ | p | A$^2$ | q | A$^3$ | n | r | s | t | Z | R$^2$ | $[\alpha]_D^{20}$ |
| 110 | C$_4$H$_9$I | n-C$_8$H$_{17}$ | 1 |  | 1 | 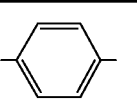 | 0 | — | 1 | 0 | 1 | 0 | — | C$_4$H$_9$ | — |
| 111 | C$_4$H$_9$I | n-C$_{10}$H$_{21}$ | 1 | 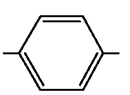 | 1 | 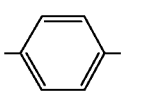 | 0 | — | 3 | 0 | 1 | 0 | — | C$_4$H$_9$ | — |
| 112 | C$_2$H$_5$I | n-C$_{10}$H$_{21}$ | 1 | 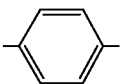 | 1 | 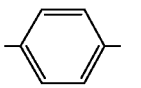 | 0 | — | 3 | 1 | 1 | 0 | F | C$_2$H$_5$ | -1.26° (C = 1.43, CHCl$_3$) |
| 113 | C$_2$H$_5$I | n-C$_{10}$H$_{21}$ | 1 |  | 1 | 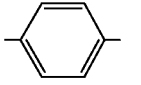 | 1 | 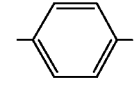 | 3 | 1 | 1 | 0 | H | C$_2$H$_5$ | -1.02° (C = 1.0, CHCl$_3$) |
| 114 | C$_2$H$_5$I | n-C$_8$H$_{17}$ | 1 | 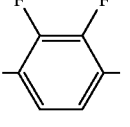 | 1 | 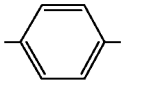 | 1 | 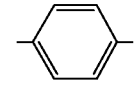 | 2 | 1 | 1 | 0 | H | C$_2$H$_5$ | — |
| 115 | C$_2$H$_5$I | n-C$_8$H$_{17}$ | 1 | 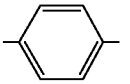 | 1 | 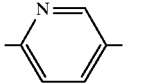 | 1 | 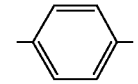 | 3 | 1 | 1 | 0 | H | C$_2$H$_5$ | -1.1° (C = 1.21, CHCl$_3$) |
| 116 | C$_4$H$_9$I | n-C$_{10}$H$_{21}$ | 1 | 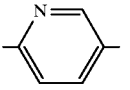 | 1 | 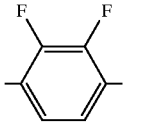 | 0 | — | 1 | 1 | 1 | 0 | H | C$_4$H$_9$ | -1.3° (C = 1.0, CHCl$_3$) |

TABLE 2(1)-continued

| 117 | C$_4$H$_9$I | n-C$_{12}$H$_{25}$ | 1 | (3-F-phenylene) | 1 | (pyridine-2,5-diyl) | 0 | — | 1 | 1 | 1 | 0 | H | C$_4$H$_9$ | — |

*) OTf: —OSO$_2$CF$_3$

TABLE 2(2)

| Example | Starting compounds |||||||| |||||||
|---|---|---|---|---|---|---|---|---|---|---|---|---|---|---|---|
| | Halide (3) |||||||| Boron compound (2) ||||||
| | R$^1$ | m | A$^1$ | p | A$^2$ | q | A$^3$ | X | (R$^3$)$_2$ | n | r | s | t | Z | R$^2$ |
| 118 | n-C$_8$H$_{17}$ | 1 | (pyrimidine-2,5-diyl) | 1 | (1,4-phenylene) | 0 | — | Br | (HO)$_2$ | 1 | 0 | 1 | 0 | — | H |
| 119 | n-C$_8$H$_{17}$ | 1 | (pyrimidine-2,5-diyl) | 1 | (1,4-phenylene) | 0 | — | Br | (HO)$_2$ | 3 | 0 | 1 | 0 | — | H |
| 120 | n-C$_{11}$H$_{23}$ | 1 | (pyrimidine-2,5-diyl) | 1 | (1,4-phenylene) | 0 | — | Br | (HO)$_2$ | 3 | 0 | 1 | 0 | — | H |
| 121 | n-C$_{10}$H$_{21}$ | 1 | (pyrimidine-2,5-diyl) | 1 | (1,4-phenylene) | 0 | — | Br | (HO)$_2$ | 2 | 1 | 1 | 0 | H | H |
| 122 | n-C$_{10}$H$_{21}$ | 1 | (1,4-phenylene) | 1 | (pyrimidine-2,5-diyl) | 0 | — | OTf | (HO)$_2$ | 3 | 1 | 1 | 0 | H | H |
| 123 | n-C$_{12}$H$_{25}$ | 1 | (1,4-phenylene) | 1 | (pyrimidine-2,5-diyl) | 1 | (1,4-phenylene) | Br | (HO)$_2$ | 1 | 1 | 1 | 0 | H | H |
| 124 | n-C$_8$H$_{17}$ | 0 | (2,3-difluoro-1,4-phenylene) | 1 | (pyrimidine-2,5-diyl) | 0 | — | Br | (HO)$_2$ | 5 | 1 | 1 | 0 | H | H |
| 125 | n-C$_8$H$_{17}$ | 0 | (pyrimidine-2,5-diyl) | 1 | (3-F-phenylene) | 0 | — | OTf | (HO)$_2$ | 5 | 1 | 1 | 0 | F | H |

TABLE 2(2)-continued

| Example | Carboxylic acid (4) or alkylating agent (5) | trans-Olefin compound (1) | | | | | | | | | | | | Optical rotation |
|---|---|---|---|---|---|---|---|---|---|---|---|---|---|---|
| | | $R^1$ | m | $A^1$ | p | $A^2$ | q | $A^3$ | n | r | s | t | Z | $R^2$ | $[\alpha]_D^{20}$ |
| 118 | $C_4H_9I$ | n-$C_8H_{17}$ | 1 | 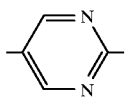 | 1 | 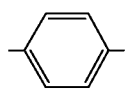 | 0 | — | 1 | 0 | 1 | 0 | — | $C_4H_9$ | — |
| 119 | $C_4H_9I$ | n-$C_8H_{17}$ | 1 | 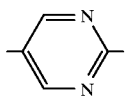 | 1 | 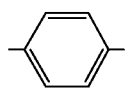 | 0 | — | 3 | 0 | 1 | 0 | — | $C_4H_9$ | — |
| 120 | $C_4H_9I$ | n-$C_{11}H_{23}$ | 1 | 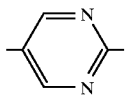 | 1 | 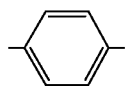 | 0 | — | 3 | 0 | 1 | 0 | — | $C_4H_9$ | — |
| 121 | $CH_3I$ | n-$C_{10}H_{21}$ | 1 | 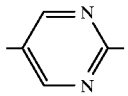 | 1 | 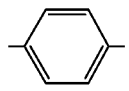 | 0 | — | 2 | 1 | 1 | 0 | H | $CH_3$ | −1.7° (C = 1.0, $CHCl_3$) |
| 122 | $(CH_3CO)_2O$ | n-$C_{10}H_{21}$ | 1 | 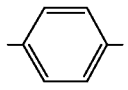 | 1 | 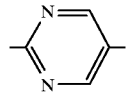 | 0 | — | 3 | 1 | 1 | 1 | H | $CH_3$ | −1.2° (C = 1.0, $CHCl_3$) |
| 123 | $C_2H_5I$ | n-$C_{12}H_{25}$ | 1 | 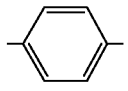 | 1 | 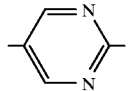 | 1 | 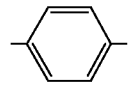 | 1 | 1 | 1 | 0 | H | $C_2H_5$ | −2.1° (C = 1.2, $CHCl_3$) |
| 124 | $C_3H_7O$ | n-$C_8H_{17}$ | 0 |  | 1 | 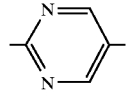 | 0 | — | 5 | 1 | 1 | 0 | H | $C_3H_7$ | −1.2° (C = 0.8, $CHCl_3$) |
| 125 | $CH_3COCl$ | n-$C_8H_{17}$ | 0 | 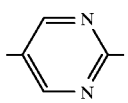 | 1 | 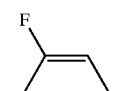 | 0 | — | 5 | 1 | 1 | 1 | F | $CH_3$ | — |

*) OTf: —$OSO_2CF_3$

TABLE 2(3)

| Example | Starting compounds | | | | | | | | | | | | | |
|---|---|---|---|---|---|---|---|---|---|---|---|---|---|---|
| | Halide (3) | | | | | | | | Boron compound (2) | | | | | |
| | $R^1$ | m | $A^1$ | p | $A^2$ | q | $A^3$ | X | $(R^3)_2$ | n | r | s | t | Z | $R^2$ |
| 126 | n-$C_5H_{11}$ | 1 |  | 1 |  | 0 | — | Br | $(HO)_2$ | 3 | 1 | 1 | 0 | H | H |
| 127 | n-$C_{10}H_{21}$ | 1 |  | 1 |  | 1 | 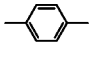 | Br | $(HO)_2$ | 3 | 1 | 1 | 0 | H | H |

TABLE 2(3)-continued

| Example | R¹ | m | A¹ | p | A² | q | A³ | n | r | s | t | Z | R² |
|---|---|---|---|---|---|---|---|---|---|---|---|---|---|
| 128 | n-C₁₀H₂₁ | 1 | phenyl | 1 | pyrimidine | 1 | phenyl | Br | (HO)₂ | 3 | 1 | 1 | 0 | H | H |
| 129 | n-C₁₀H₂₁ | 1 | pyrimidine | 1 | phenyl | 1 | pyrimidine | Br | (HO)₂ | 3 | 1 | 1 | 0 | H | H |
| 130 | n-C₁₀H₂₁ | 1 | phenyl | 1 | pyrimidine | 1 | phenyl | Br | (HO)₂ | 5 | 1 | 1 | 0 | H | H |
| 131 | n-C₁₀H₂₁ | 1 | F-phenyl | 1 | pyrimidine | 1 | phenyl | Br | (HO)₂ | 3 | 1 | 1 | 0 | H | H |
| 132 | n-C₁₀H₂₁ | 1 | pyrimidine | 1 | F-phenyl | 1 | phenyl | Br | (HO)₂ | 3 | 1 | 1 | 0 | H | H |
| 133 | n-C₁₀H₂₁ | 1 | pyrimidine | 1 | phenyl | 1 | phenyl | Br | (HO)₂ | 3 | 1 | 1 | 0 | F | H |

| Example | Carboxylic acid (4) or alkylating agent (5) | trans-Olefin compound (1) | | | | | | | | | | | | Optical rotation [α]_D^20 |
|---|---|---|---|---|---|---|---|---|---|---|---|---|---|---|
| | | R¹ | m | A¹ | p | A² | q | A³ | n | r | s | t | Z | R² | |
| 126 | C₄H₉I | n-C₅H₁₁ | 1 | F-phenyl | 1 | pyrimidine | 0 | — | 3 | 1 | 1 | 0 | H | C₄H₉ | — |
| 127 | CH₃I | n-C₁₀H₂₁ | 1 | phenyl | 1 | pyrimidine | 1 | phenyl | 3 | 1 | 1 | 0 | H | CH₃ | −1.2° (C = 1.0, CHCl₃) |
| 128 | C₂H₅I | n-C₁₀H₂₁ | 1 | phenyl | 1 | pyrimidine | 1 | phenyl | 3 | 1 | 1 | 0 | H | C₂H₅ | −1.3° (C = 1.0, CHCl₃) |
| 129 | CH₃I | n-C₁₀H₂₁ | 1 | pyrimidine | 1 | phenyl | 1 | pyrimidine | 3 | 1 | 1 | 0 | H | CH₃ | −0.8° (C = 0.9 CHCl₃) |
| 130 | C₂H₅I | n-C₁₀H₂₁ | 1 | phenyl | 1 | pyrimidine | 1 | phenyl | 5 | 1 | 1 | 0 | H | C₂H₅ | −1.3° (C = 1.3, CHCl₃) |
| 131 | C₂H₅OT_s *) | n-C₁₀H₂₁ | 1 | F-phenyl | 1 | pyrimidine | 1 | phenyl | 3 | 1 | 1 | 0 | H | C₂H₅ | — |
| 132 | C₂H₅I | n-C₁₀H₂₁ | 1 | pyrimidine | 1 | F-phenyl | 1 | phenyl | 3 | 1 | 1 | 0 | H | C₂H₅ | −0.8° (C = 1.1, CHCl₃) |
| 133 | C₃H₇COCl | n-C₁₀H₂₁ | 1 | pyrimidine | 1 | phenyl | 1 | phenyl | 3 | 1 | 1 | 1 | F | C₃H₇ | — |

*) OTf: —OSO₂CF₃
*) OTs: —OSO₂—⌬—CH₃

TABLE 2(4)

| Example | Starting compounds | | | | | | | | | | | | | |
|---|---|---|---|---|---|---|---|---|---|---|---|---|---|---|
| | Halide (3) | | | | | | | | Boron compound (2) | | | | | |
| | R¹ | m | A¹ | p | A² | q | A³ | X | (R³)₂ | n | r | s | t | Z | R² |
| 134 | n-$C_{10}H_{21}$ | 1 |  | 1 | 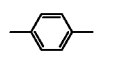 | 1 | 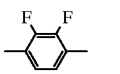 | OTf | (HO)₂ | 3 | 1 | 1 | 0 | H | H |
| 135 | n-$C_8H_{17}$ | 0 | 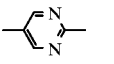 | 1 | 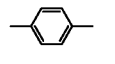 | 1 | 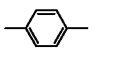 | Br | (HO)₂ | 1 | 1 | 1 | 0 | F | H |
| 136 | n-$C_{10}H_{21}$ | 1 | 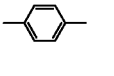 | 1 | 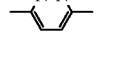 | 0 | — | Cl | (HO)₂ | 2 | 1 | 1 | 0 | H | H |
| 137 | n-$C_{10}H_{21}$ | 1 | 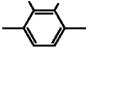 | 1 |  | 0 | — | Cl | (HO)₂ | 1 | 1 | 1 | 0 | H | H |
| 138 | n-$C_9H_{19}$ | 1 |  | 1 |  | 1 |  | Br | (HO)₂ | 3 | 1 | 1 | 0 | H | H |
| 139 | n-$C_{10}H_{21}$ | 1 | 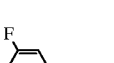 | 1 |  | 1 | 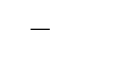 | Br | (HO)₂ | 3 | 1 | 1 | 0 | H | H |
| 140 | n-$C_{10}H_{21}$ | 1 | 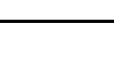 | 0 | — | 0 | — | Br | (HO)₂ | 4 | 1 | 1 | 0 | H | H |

| Example | Carboxylic acid (4) or alkylating agent (5) | trans-Olefin compound (1) | | | | | | | | | | | | | Optical rotation |
|---|---|---|---|---|---|---|---|---|---|---|---|---|---|---|---|---|
| | | R¹ | m | A¹ | p | A² | q | A³ | n | r | s | t | Z | R² | $[\alpha]_D^{20}$ |
| 134 | CH₃I | n-$C_{10}H_{21}$ | 1 | 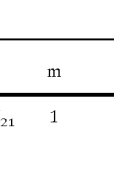 | 1 | 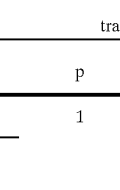 | 1 | 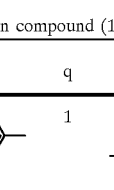 | 3 | 1 | 1 | 0 | H | CH₃ | −0.8 (C = 0.9, CHCl₃) |
| 135 | (CH₃CO)₂O | n-$C_8H_{17}$ | 0 |  | 1 |  | 1 |  | 1 | 1 | 1 | 1 | F | CH₃ | — |
| 136 | $C_2H_5$I | n-$C_{10}H_{21}$ | 1 |  | 1 |  | 0 | — | 2 | 1 | 1 | 0 | H | $C_2H_5$ | — |
| 137 | $C_5H_{11}$I | n-$C_{10}H_{21}$ | 1 | 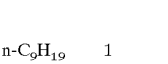 | 1 | 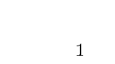 | 0 | — | 1 | 1 | 1 | 0 | H | $C_5H_{11}$ | −1.3° (C = 0.9, CHCl₃) |
| 138 | $C_2H_5$I | n-$C_9H_{19}$ | 1 |  | 1 |  | 1 | 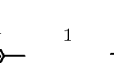 | 3 | 1 | 1 | 0 | H | $C_2H_5$ | −1.1° (C = 1.0, CHCl₃) |
| 139 | $C_2H_5$I | n-$C_{10}H_{21}$ | 1 | 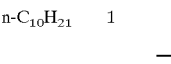 | 1 | 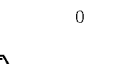 | 1 | 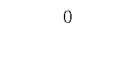 | 3 | 1 | 1 | 0 | H | $C_2H_5$ | −0.9° (C = 0.7 CHCl₃) |
| 140 | $C_4H_9$I | n-$C_{10}H_{21}$ | 1 | 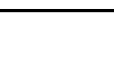 | 0 | — | 0 | — | 4 | 1 | 1 | 0 | H | $C_4H_9$ | — |

*) OTf: —$OSO_2CF_3$

TABLE 2(5)

| Example | Starting compounds | | | | | | | | | | | | | |
|---|---|---|---|---|---|---|---|---|---|---|---|---|---|---|
| | Halide (3) | | | | | | | Boron compound (2) | | | | | | |
| | $R^1$ | m | $A^1$ | p | $A^2$ | q | $A^3$ | X | $(R^3)_2$ | n | r | s | t | Z | $R^2$ |
| 141 | n-$C_{10}H_{21}$ | 1 | 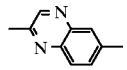 | 1 |  | 0 | — | OTf | $(HO)_2$ | 3 | 1 | 1 | 0 | H | H |
| 142 | n-$C_{10}H_{21}$ | 1 | 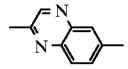 | 1 |  | 0 | — | OTf | $(HO)_2$ | 3 | 1 | 1 | 0 | H | H |
| 143 | n-$C_8H_{17}$ | 1 | 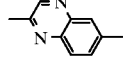 | 1 |  | 0 | — | OTf | $(HO)_2$ | 1 | 1 | 1 | 0 | H | H |
| 144 | n-$C_{10}H_{21}$ | 1 | 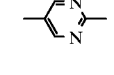 | 1 |  | 0 | — | Br | $(HO)_2$ | 3 | 1 | 1 | 0 | H | H |
| 145 | n-$C_6H_{13}$ | 1 | 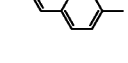 | 1 |  | 0 | — | Br | $(HO)_2$ | 3 | 1 | 1 | 0 | H | H |
| 146 | n-$C_6H_{13}$ | 1 | 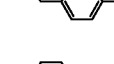 | 1 |  | 0 | — | OTf | $(HO)_2$ | 3 | 1 | 1 | 0 | H | H |
| 147 | n-$C_{10}H_{21}$ | 1 | 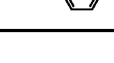 | 1 |  | 0 | — | OTf | $(HO)_2$ | 3 | 1 | 1 | 0 | H | H |

| Example | Carboxylic acid (4) or alkylating agent (5) | trans-Olefin compound (1) | | | | | | | | | | | | | Optical rotation |
|---|---|---|---|---|---|---|---|---|---|---|---|---|---|---|---|
| | | $R^1$ | m | $A^1$ | p | $A^2$ | q | $A^3$ | n | r | s | t | Z | $R^2$ | $[\alpha]_D^{20}$ |
| 141 | $C_4H_9I$ | n-$C_{10}H_{21}$ | 1 | 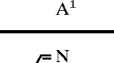 | 1 |  | 0 | — | 3 | 1 | 1 | 0 | H | $C_4H_9$ | |
| 142 | $C_2H_5I$ | n-$C_{10}H_{21}$ | 1 | 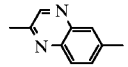 | 1 |  | 0 | — | 3 | 1 | 1 | 0 | H | $C_2H_5$ | |
| 143 | $C_2H_5I$ | n-$C_8H_{17}$ | 1 | 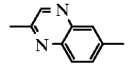 | 1 |  | 0 | — | 1 | 1 | 1 | 0 | H | $C_2H_5$ | |
| 144 | $C_2H_5I$ | n-$C_{10}H_{21}$ | 1 | 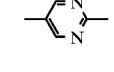 | 1 |  | 0 | — | 3 | 1 | 1 | 0 | H | $C_2H_5$ | |
| 145 | $CH_3I$ | n-$C_6H_{13}$ | 1 | 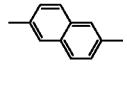 | 1 |  | 0 | — | 3 | 1 | 1 | 0 | H | $CH_3$ | |
| 146 | $C_2H_5I$ | n-$C_6H_{13}$ | 1 | 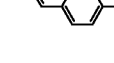 | 1 |  | 0 | — | 3 | 1 | 1 | 0 | H | $C_2H_5$ | |
| 147 | $C_2H_5I$ | n-$C_{10}H_{21}$ | 1 | 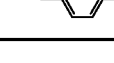 | 1 |  | 0 | — | 3 | 1 | 1 | 0 | H | $C_2H_5$ | |

*) OTf: —$OSO_2CF_3$

TABLE 2(6)

| | Starting compounds | | | | | | | | | | | | | |
|---|---|---|---|---|---|---|---|---|---|---|---|---|---|---|
| | Halide (3) | | | | | | | | Boron compound (2) | | | | | |
| Example | $R^1$ | m | $A^1$ | p | $A^2$ | q | $A^3$ | X | $(R^3)_2$ | n | r | s | t | Z | $R^2$ |
| 148 | n-$C_{10}H_{21}$ | 1 | 2-F-naphthalene-2,6-diyl | 1 | pyrimidine-2,5-diyl | 0 | — | Br | $(HO)_2$ | 2 | 1 | 1 | 0 | H | H |
| 149 | n-$C_{12}H_{25}$ | 1 | 2,3-diF-phenylene | 1 | naphthalene-2,6-diyl | 0 | — | Br | $(HO)_2$ | 4 | 1 | 1 | 0 | H | H |
| 150 | n-$C_6H_{13}$ | 1 | 2,3-diF-phenylene | 1 | benzimidazole-2,5-diyl | 0 | — | Br | $(HO)_2$ | 1 | 1 | 1 | 0 | H | H |
| 151 | n-$C_{10}H_{21}$ | 1 | 2-F-naphthalene-2,6-diyl | 1 | pyridine-2,5-diyl | 0 | — | Br | $(HO)_2$ | 3 | 1 | 1 | 0 | H | H |
| 152 | n-$C_8H_{17}$ | 1 | 2-F-phenylene | 1 | quinoline-2,6-diyl | 0 | — | Br | $(HO)_2$ | 1 | 1 | 1 | 0 | H | H |

| | Carboxylic acid (4) or alkylating | trans-Olefin compound (1) | | | | | | | | | | | | Optical rotation |
|---|---|---|---|---|---|---|---|---|---|---|---|---|---|---|
| Example | agent (5) | $R^1$ | m | $A^1$ | p | $A^2$ | q | $A^3$ | n | r | s | t | Z | $R^2$ | $[\alpha]_D^{20}$ |
| 148 | $C_2H_5I$ | n-$C_{10}H_{21}$ | 1 | 2-F-naphthalene-2,6-diyl | 1 | pyrimidine-2,5-diyl | 0 | — | 2 | 1 | 1 | 0 | H | $C_2H_5$ | — |
| 149 | $CH_3I$ | n-$C_{12}H_{25}$ | 1 | 2,3-diF-phenylene | 1 | naphthalene-2,6-diyl | 0 | — | 4 | 1 | 1 | 0 | H | $CH_3$ | −1.5° (C = 1.1, $CHCl_3$) |
| 150 | $C_2H_5I$ | n-$C_6H_{13}$ | 1 | 2,3-diF-phenylene | 1 | quinoline-2,6-diyl | 0 | — | 1 | 1 | 1 | 0 | H | $C_2H_5$ | −1.2° (C = 0.6, $CHCl_3$) |
| 151 | $C_5H_{11}OT_s$ *) | n-$C_{10}H_{21}$ | 1 | 2-F-naphthalene-2,6-diyl | 1 | pyridine-2,5-diyl | 0 | — | 3 | 1 | 1 | 0 | H | $C_5H_{11}$ | — |
| 152 | $C_3H_7COCl$ | n-$C_8H_{17}$ | 1 | 2-F-phenylene | 1 | quinoline-2,6-diyl | 0 | — | 1 | 1 | 1 | 1 | H | $C_3H_7$ | — |

*) OTf: —$OSO_2CF_3$

*) OTs: 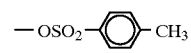

TABLE 2(7)

| | Starting compounds | | | | | | | | | | | | | | |
|---|---|---|---|---|---|---|---|---|---|---|---|---|---|---|---|
| | Halide (3) | | | | | | | | Boron compound (2) | | | | | | |
| Example | $R^1$ | m | $A^1$ | p | $A^2$ | q | $A^3$ | X | $(R^3)_2$ | n | r | s | t | Z | $R^2$ |
| 153 | H,CH₂— / n-C₇H₁₅,H (trans-olefin) | 1 | pyrimidine | 1 | phenylene | 0 | — | OTf | (HO)₂ | 3 | 1 | 1 | 0 | H | H |
| 154 | H,CH₂— / n-C₃H₇,H | 1 | pyrimidine | 1 | phenylene | 0 | — | OTf | (HO)₂ | 3 | 1 | 1 | 0 | H | H |
| 155 | H,CH₂— / n-C₇H₁₅,H | 0 | phenylene | 1 | pyrimidine | 0 | — | OTf | (HO)₂ | 3 | 1 | 1 | 0 | H | H |
| 156 | H,CH₂— / n-C₇H₁₅,H | 1 | phenylene | 1 | pyrimidine | 1 | phenylene | Br | (HO)₂ | 3 | 1 | 1 | 0 | H | H |

| Example | Carboxylic acid (4) or alkylating agent (5) | trans-Olefin compound (1) | | | | | | | | | | | | Optical rotation $[\alpha]_D^{20}$ |
|---|---|---|---|---|---|---|---|---|---|---|---|---|---|---|
| | | $R^1$ | m | $A^1$ | p | $A^2$ | q | $A^3$ | n | r | s | t | Z | $R^2$ | |
| 153 | CH₃I | H,CH₂—/n-C₇H₁₅,H | 1 | pyrimidine | 1 | phenylene | 0 | — | 3 | 1 | 1 | 0 | H | CH₃ | −1.3° (C = 1.1, CHCl₃) |
| 154 | CH₃I | H,CH₂—/n-C₃H₇,H | 1 | pyrimidine | 1 | phenylene | 0 | — | 3 | 1 | 1 | 0 | H | CH₃ | −1.2° (C = 1.1, CHCl₃) |
| 155 | C₂H₅I | H,CH₂—/n-C₇H₁₅,H | 0 | phenylene | 1 | pyrimidine | 0 | — | 3 | 1 | 1 | 0 | H | C₂H₅ | −1.3° (C = 1.0, CHCl₃) |
| 156 | C₂H₅I | H,CH₂—/n-C₇H₁₅,H | 1 | phenylene | 1 | pyrimidine | 1 | phenylene | 3 | 1 | 1 | 0 | H | C₂H₅ | −0.9° (C = 1.2, CHCl₃) |

*) OTf: —OSO₂CF₃

TABLE 3(1)

| | Starting compounds | | | | | | | | | | | | | | |
|---|---|---|---|---|---|---|---|---|---|---|---|---|---|---|---|
| | Halide (3) | | | | | | | | Boron compound (2) | | | | | | |
| Example | $R^1$ | m | $A^1$ | p | $A^2$ | q | $A^3$ | X | $(R^3)_2$ | n | r | s | t | Z | $R^2$ |
| 157 | n-C₁₀H₂₁ | 1 | pyrimidine | 1 | phenylene | 0 | — | Br | catecholboronate | 1 | 1 | 1 | 1 | H | CH₃ |
| 158 | n-C₁₀H₂₁ | 1 | pyridazine | 1 | phenylene | 0 | — | Br | catecholboronate | 1 | 1 | 1 | 1 | H | CH₃ |
| 159 | n-C₁₀H₂₁ | 1 | pyrimidine | 1 | phenylene | 0 | — | Br | catecholboronate | 1 | 1 | 1 | 1 | H | CH₃ |
| 160 | n-C₁₀H₂₁ | 1 | phenylene | 1 | pyrimidine | 0 | — | OTf | catecholboronate | 3 | 1 | 1 | 1 | H | CH₃ |

TABLE 3(1)-continued

| | | | | | | | | | | | | | | | | | |
|---|---|---|---|---|---|---|---|---|---|---|---|---|---|---|---|---|---|
| 161 | n-$C_{11}H_{23}$ | 1 | (phenyl) | 1 | (pyrimidinyl) | 0 | — | OTf | (benzodioxole) | 2 | 1 | 1 | 1 | H | $CH_3$ | | |
| 162 | n-$C_{12}H_{25}$ | 1 | (phenyl) | 1 | (pyrimidinyl) | 0 | — | OTf | (benzodioxole) | 3 | 1 | 1 | 0 | H | $CH_3$ | | |

| Example | Carboxylic acid (4) or alkylating agent (5) | trans-Olefin compound (1) | | | | | | | | | | | | Optical rotation $[\alpha]_D^{20}$ |
|---|---|---|---|---|---|---|---|---|---|---|---|---|---|---|
| | | $R^1$ | m | $A^1$ | p | $A^2$ | q | $A^3$ | n | r | s | t | Z | $R^2$ | |
| 157 | $C_2H_5I$ | n-$C_{10}H_{21}$ | 1 | (pyrimidinyl) | 1 | (phenyl) | 0 | — | 1 | 1 | 1 | 0 | H | $C_2H_5$ | −3.2° (C = 1.0, $CHCl_3$) |
| 158 | $CH_3I$ | n-$C_{10}H_{21}$ | 1 | (pyrimidinyl) | 1 | (phenyl) | 0 | — | 1 | 1 | 1 | 0 | H | $CH_3$ | −2.5° (C = 1.2, $CHCl_3$) |
| 159 | $C_2H_5I$ | n-$C_{10}H_{21}$ | 1 | (pyrimidinyl) | 1 | (phenyl) | 0 | — | 1 | 1 | 1 | 0 | H | $C_2H_5$ | −2.1° (C = 1.1, $CHCl_3$) |
| 160 | $C_2H_5I$ | n-$C_{10}H_{21}$ | 1 | (phenyl) | 1 | (pyrimidinyl) | 0 | — | 3 | 1 | 1 | 0 | H | $C_2H_5$ | −1.1° (C = 1.0, $CHCl_3$) |
| 161 | $C_2H_5I$ | n-$C_{11}H_{23}$ | 1 | (phenyl) | 1 | (pyrimidinyl) | 0 | — | 2 | 1 | 1 | 0 | H | $C_2H_5$ | −1.5° (C = 1.0, $CHCl_3$) |
| 162 | $C_2H_5I$ | n-$C_{12}H_{25}$ | 1 | (phenyl) | 1 | (pyrimidinyl) | 0 | — | 3 | 1 | 1 | 0 | H | $C_5H_{11}$ | −1.0° (C = 1.0, $CHCl_3$) |

*) OTf: —$OSO_2CF_3$

TABLE 3(2)

| | Starting compounds | | | | | | | | | | | | | |
|---|---|---|---|---|---|---|---|---|---|---|---|---|---|---|
| Example | Halide (3) | | | | | | | | Boron compound (2) | | | | | |
| | $R^1$ | m | $A^1$ | p | $A^2$ | q | $A^3$ | X | $(R^3)_2$ | n | r | s | t | Z | $R^2$ |
| 163 | n-$C_{10}H_{21}$ | 1 | (phenyl) | 1 | (phenyl) | 1 | (phenyl) | Br | (benzodioxole) | 3 | 1 | 1 | 1 | H | $CH_3$ |
| 164 | n-$C_{10}H_{21}$ | 1 | (phenyl) | 1 | (phenyl) | 0 | — | Br | (benzodioxole) | 5 | 1 | 1 | 1 | H | $CH_3$ |
| 165 | n-$C_{10}H_{21}$ | 1 | (phenyl) | 1 | (pyridyl) | 0 | — | Br | (benzodioxole) | 1 | 1 | 1 | 1 | H | $CH_3$ |

| Example | Carboxylic acid (4) or alkylating agent (5) | trans-Olefin compound (1) | | | | | | | | | | | | Optical rotation $[\alpha]_D^{20}$ |
|---|---|---|---|---|---|---|---|---|---|---|---|---|---|---|
| | | $R^1$ | m | $A^1$ | p | $A^2$ | q | $A^3$ | n | r | s | t | Z | $R^2$ | |
| 163 | $CH_3I$ | n-$C_{10}H_{21}$ | 1 | (phenyl) | 1 | (phenyl) | 1 | (phenyl) | 3 | 1 | 1 | 0 | H | $CH_3$ | −1.2° (C = 1.3, $CHCl_3$) |
| 164 | $C_2H_5I$ | n-$C_{10}H_{21}$ | 1 | (phenyl) | 1 | (phenyl) | 0 | — | 5 | 1 | 1 | 0 | H | $C_2H_5$ | −1.1° (C = 1.0, $CHCl_3$) |

TABLE 3(2)-continued

| 165 | C$_2$H$_5$I | n-C$_{10}$H$_{21}$ | 1 | ⟨phenylene⟩ | 1 | ⟨pyridine⟩ | 0 | — | 1 | 1 | 1 | 0 | H | C$_2$H$_5$ | −1.0° (C = 0.9, CHCl$_3$) |

*) OTf: —OSO$_2$CF$_3$

TABLE 4

| | Starting compounds | | | | | | | | | | | | | |
|---|---|---|---|---|---|---|---|---|---|---|---|---|---|---|
| Example | Halide (3) | | | | | | | Boron compound (2) | | | | | | |
| | R$^1$ | m | A$^1$ | p | A$^2$ | q | A$^3$ | X | (R$^3$)$_2$ | n | r | s | t | Z | R$^2$ |
| 166 | HO | 1 | pyrimidine | 1 | phenylene | 0 | — | Br | veratryl | 7 | 0 | 0 | 0 | — | H |
| 167 | HO | 1 | 2,3-difluorophenylene | 1 | pyrimidine | 0 | — | Br | veratryl | 7 | 0 | 0 | 0 | — | H |

| Example | trans-Olefin compound (1) | | | | | Yield (%), Phase series |
|---|---|---|---|---|---|---|
| | R$^1$ | m | —A$^1$—(A$^2$)$_p$—(A$^3$)$_q$— | n | R$^2$ | (at elevated temp., °C.) |
| 166 | HO | 1 | pyrimidine-phenylene | 7 | H | 71 |
| 167 | HO | 1 | 2,3-difluorophenylene-pyrimidine | 7 | H | 63 |

| | Starting compounds | | | | | | | | | | | | | |
|---|---|---|---|---|---|---|---|---|---|---|---|---|---|---|
| Example | Halide (3) | | | | | | | Boron compound (2) | | | | | | |
| | R$^1$ | m | A$^1$ | p | A$^2$ | q | A$^3$ | X | (R$^3$)$_2$ | n | r | s | t | Z | R$^2$ |
| 166 | C$_7$H$_{15}$-CH=CH- | 0 | phenylene | 1 | pyrimidine | 0 | — | OTf | veratryl | 1 | 1 | 1 | 0 | H | H |
| 167 | C$_7$H$_{15}$-CH=CH- | 0 | pyrimidine | 1 | 2,3-difluorophenylene | 0 | — | OTf | veratryl | 3 | 1 | 1 | 0 | H | H |

| Example | Carboxylic acid (4) or alkylating agent (5) | trans-Olefin compound (1) | | | | | | | | | | | | Optical rotation |
|---|---|---|---|---|---|---|---|---|---|---|---|---|---|---|
| | | R$^1$ | m | A$^1$ | p | A$^2$ | q | A$^3$ | n | r | s | t | Z | R$^2$ | [α]$_D^{20}$ |
| 166 | C$_2$H$_5$I | C$_7$H$_{15}$-CH=CH- | 0 | phenylene | 1 | pyrimidine | 0 | — | 1 | 1 | 1 | 0 | H | C$_2$H$_5$ | |

TABLE 4-continued

| 167 | C₂H₅I | C₇H₁₅—CH=CH— | 0 | pyrimidine | 1 | 2,3-difluorophenyl | 0 | — | 3 | 1 | 1 | 0 | H | C₂H₅ |

*) OTf: —OSO₂CF₃

EXAMPLE 168

Liquid crystal parent composition (1-a) was prepared by mixing together the following compounds at the compounding ratio mentioned below.

TABLE 5

Constituents and compounding ratio of parent composition (1-a)

| Compound used | Ratio (mol %) |
|---|---|
| C₄H₉O—(pyrimidine)—(phenyl)—CH=CH—C₆H₁₃ | 25 |
| C₁₀H₂₁O—(phenyl)—(pyrimidine)—CH=CH—C₅H₁₁ | 25 |
| C₁₀H₂₁O—(phenyl)—(pyrimidine)—CH=CH—C₇H₁₅ | 50 |

(All the double bonds are trans-form.)

The composition was put between two glass substrates carrying their respective transparent electrodes and oriented polyimide films. The gap between the two glass substrates were adjusted to 2 μm with a spacer. Two polarizing plates having 90°-rotated planes of polarization were provided outside the two glass substrates to prepare a liquid crystal element. The axis of polarization in the incident side was made to coincide with the direction of rubbing of the oriented polyimide films.

COMPARATIVE EXAMPLE 1

Liquid crystal composition (1-b) was prepared by the use of phenylpyrimidine compounds represented by the following general formula:

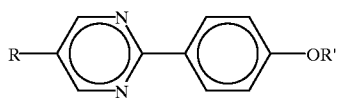

wherein R and R' each represents an alkyl group, which are generally used as ingredient of parent composition.

TABLE 6

Constituents and compounding ratio of parent composition (1-b)

| Compound used | Ratio (mol %) |
|---|---|
| C₈H₁₇—(pyrimidine)—(phenyl)—OC₉H₁₉ | 14 |
| C₈H₁₇—(pyrimidine)—(phenyl)—OC₁₀H₂₁ | 14 |
| C₈H₁₇—(pyrimidine)—(phenyl)—OC₈H₁₇ | 29 |
| C₈H₁₇—(pyrimidine)—(phenyl)—OC₆H₁₃ | 43 |

Next, phase series of these liquid crystal elements were measured.

Phase series were determined by heating a liquid crystal element to a liquid state, thereafter cooling the liquid crystal element at a rate of 2.5° C. per minute, and observing the texture by means of polarizing microscope. Table 7 lists the results obtained in Example 168 and Comparative Example 1, wherein the unit is °C.

TABLE 7

| | Comparison of phase series | |
|---|---|---|
| | Parent composition (1-a) | Parent composition (1-b) |
| Phase series | -13  58  87  96<br>K—S_C—S_A—N—I | 1   46  59  66<br>K—S_C—S_A—N—I |
| Temp. range of Sc phase | 71 | 45 |

It is apparent from Table 7 that a parent composition constituted from a trans-olefin compound has a phase series necessary for acquiring a good orientation, namely liquid phase→nematic phase→smectic A phase→smectic C phase, and the temperature range of smectic C phase is broader than that of composition (1-b) constituted from a compound having no trans bond and the upper limit of the temperature range is higher than that of composition (1-b). Accordingly, parent compositions constituted of trans-olefin compounds are superior to those constituted of compounds having no trans bond.

EXAMPLE 169

Next, a ferroelectric liquid crystal composition (2a) was prepared by mixing the parent composition (1-a) of Example 168 with the following optically active compound at the compounding ratio mentioned below.

TABLE 8

| Constituents and compounding ratio of ferroelectric liquid crystal composition (2-a) | |
|---|---|
| Compound used | Ratio (mol %) |
| Composition (1-a) | 90 |
| 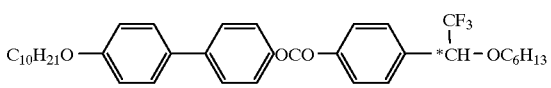 | 10 |

COMPARATIVE EXAMPLE 2

Ferroelectric liquid crystal composition (2-b) was prepared by mixing the same optically active compound as used in the preparation of (2-a) into the parent composition (1-b) of Comparative Example 1.

TABLE 9

| Constituents and compounding ratio of ferroelectric liquid crystal composition (2-b) | |
|---|---|
| Compound used | Ratio (mol %) |
| Composition (1-b) | 90 |
| 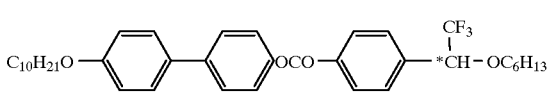 | 10 |

Next, phase series, spontaneous polarizations, tilt angles and response times of these liquid crystal elements were measured.

Spontaneous polarization was calculated according to the triangular wave method mentioned in Japanese Journal of Applied Physics, Vol. 22, part 2, Pages L661–663 (1993).

Tilt angle was determined by placing a liquid crystal element on a sample table, applying a rectangular wave voltage of 10 V/$\mu$m thereto, measuring the angles $\theta 1$ and $\theta 2$ of the extinction positions with regard to electric field and polarization while rotating the sample table, and taking one halves of the angles as tilt angles.

Response time was determined by projecting light to a liquid crystal element, inputting a rectangular wave of ±10 V/$\mu$m, and measuring the period of time required for changing the light transmittance of liquid crystal element from 10% to 90% at the time of inversion of polarity.

Results of Examples 169 and Comparative Example 2 are summarized in the following table, wherein the unit is °C.

TABLE 10

| Comparison of characteristic properties | | |
|---|---|---|
| | Ferroelectric liquid crystal composition (2-a) | Ferroelectric liquid crystal composition (2-b) |
| Phase series | 53  96  98<br>$S_C*$ — $S_A$ — N — I | 37  60  98<br>$S_C*$ — $S_A$ — N — I |
| Magnitud of spontaneous polarization | 2 nC/cm$^2$ [1] | 0.1 nC/cm$^2$ under[1] |
| Tilt angle | 17° [1] | 14° [1] |
| Response time | 244 $\mu$s[2] | 696 $\mu$s[2] |

[1] Measured at a temperature 17° lower than $S_A$—$S_C*$ transition.
[2] Measured at 20° C.

It is apparent from Table 10 that the composition (2-a) containing a trans-olefin compound has a phase series necessary for acquiring a good orientation, namely liquid phase→cholesteric phase→smectic A phase→chiral smectic C phase, and upper limit temperature of the chiral smectic C phase was higher than that of the composition (2-b) containing a compound having no trans bond. Further, liquid crystal composition (2-a) was greater than composition (2-b) in induced spontaneous polarization and tilt angle. Accordingly, the amount of optically active compound could be made smaller in the case of trans-olefin compound than in the case of a compound having no trans bond.

Table 10 also demonstrates that composition (2-a) is smaller than composition (2-b) in response time at 20° C. That is, a composition using trans-olefin compound is superior to a composition using a compound having no trans bond in high-speed response property.

It can be concluded from the above that a composition using a trans-olefin compound is superior to a composition using a compound having no trans bond.

EXAMPLE 170

Liquid crystal parent composition (3-a) was prepared by mixing the following compounds at the following compounding ratio. Using the composition, a liquid crystal element was prepared in the same manner as in Example 168.

TABLE 11

| Constituents and compounding ratio of parent composition (3-a) | |
|---|---|
| Compound used | Ratio (mol %) |
| [structure: F,F-substituted pyrimidine with $C_{10}H_{21}$ and $C_7H_{15}$ vinyl] | 40 |
| [structure: F,F-substituted pyrimidine with $C_9H_{19}O$ and $C_7H_{15}$ vinyl] | 60 |

COMPARATIVE EXAMPLE 3

For comparison with Example 170, liquid crystal composition (3-b) was prepared from a bicyclic phenylpyrimidine compound having no trans-olefin structure on its side chain, from which a liquid crystal element was prepared in the same manner as in Example 170.

TABLE 12

| Constituents and compounding ratio of parent composition (3-b) | |
|---|---|
| Compound used | Ratio (mol %) |
| [structure: F,F-substituted pyrimidine with $C_9H_{19}O$ and $C_9H_{19}$] | 27 |

TABLE 12-continued

| Constituents and compounding ratio of parent composition (3-b) | |
|---|---|
| Compound used | Ratio (mol %) |
| [structure: F,F-substituted pyrimidine with $C_8H_{17}O$ and $C_9H_{19}$] | 34 |
| [structure: F,F-substituted pyrimidine with $C_7H_{15}O$ and $C_9H_{19}$] | 39 |

Next, phase series of these liquid crystal elements were measured. Phase series was determined by heating a liquid crystal element to a liquid state, cooling the liquid crystal element at a rate of 2.5° C. per minute, and identifying the phase a series while observing the texture by means of polarizing microscope. Table 13 summarizes the results of Example 170 and Comparative Example 3. The data shown in Table 13 are those obtained by cooling the sample from liquid state until crystallization and thereafter elevating the temperature at the same rate. The unit is °C.

TABLE 13

| | Comparison of phase series | |
|---|---|---|
| Example | Parent composition | Phase series |
| 170 | (3-a) | $K \xrightarrow{18} S_C \xrightarrow{65} S_A \xrightarrow{67} N \xrightarrow{75} I$ |
| Comparative Example | (3-b) | $K \xrightarrow{33} S_C \xrightarrow{51} I$ |

Unit: ° C.

It is apparent from Table 13 that a liquid crystal parent composition constituted of a trans-olefin compound has a phase series necessary for acquiring a good orientation, namely a phase series of changing from isotropic phase, passing nematic phase and smectic A phase and reaching smectic C phase when cooled slowly, while composition (3-b) constituted of a compound having no trans-olefin structure exhibits only smectic C phase as a liquid crystal phase.

Further, as to the temperature range of smectic C phase, liquid crystal parent composition (3-a) is broader than liquid crystal parent composition (3-b) in both upper and lower limits. Accordingly, a liquid crystal parent composition constituted of a trans-olefin compound is superior to that constituted of a compound having no trans-olefin structure.

EXAMPLE 171

Next, ferroelectric liquid crystal composition (4-a) was prepared by mixing the liquid crystal parent composition (3-a) with the following optically active composition at the following compounding ratio.

TABLE 14

Constituents and compounding ratio of
ferroelectric liquid crystal composition (4-a)

| Compound used | Ratio (mol %) |
|---|---|
| Composition (3-a) | 95 |
| $C_{10}H_{21}O$—[pyrimidine]—[phenyl]—*CHOCOC$_5H_{11}$ with CH$_3$ | 5 |

COMPARATIVE EXAMPLE 4

Ferroelectric liquid crystal composition (4-b) was prepared by mixing the same optically active compound as in the preparation of ferroelectric liquid crystal composition (4-a) into the liquid crystal parent composition (3-b) shown in Comparative Example 3 at the same compounding ratio.

TABLE 15

Constituents and compounding ratio of
ferroelectric liquid crystal composition (4-b)

| Compound used | Ratio (mol %) |
|---|---|
| Composition (3-b) | 95 |
| $C_{10}H_{21}O$—[pyrimidine]—[phenyl]—*CHOCOC$_5H_{11}$ with CH$_3$ | 5 |

Next, liquid crystal elements similar to that of Example 168 were prepared from these ferroelectric liquid crystal compositions, and phase series were evaluated. The data shown in Table 16 are those obtained at the time of cooling the samples from liquid state at a rate of 2.5° C. per minute.

TABLE 16

Comparison of phase series

| Example | Ferroelectric liquid crystal composition | Phase series |
|---|---|---|
| 171 | (4-a) | Sc*$\xrightarrow{62}$S$_A\xrightarrow{71}$Ch$\xrightarrow{72}$I |
| Comparative Example | (4-b) | Sc*$\xrightarrow{48}$I |

It is apparent from Table 16 that the ferroelectric liquid crystal composition (4-a) constituted of a trans-olefin compound has a phase series necessary for acquiring a good orientation, namely a phase series which, at the time of slow cooling from isotropic phase, changing via cholesteric phase and smectic A phase to chiral smectic C phase, while the composition (4-b) constituted of a compound having no trans-olefin structure changed directly to chiral smectic C phase simultaneously with slow cooling from isotropic phase, without exhibiting neither cholesteric phase nor smectic A phase.

Further, the ferroelectric liquid crystal composition (4-a) was higher than (4-b) in the upper limit of the temperature range of chiral smectic C phase.

The ferroelectric liquid crystal composition (4-a) constituted of a trans-olefin compound had a phase series necessary for acquiring a good orientation. Thus, the electric field dependence of response time (τ-V character-istic) was measured to evaluate the performance as inverse mode type liquid crystal material. The "response time" herein referred to means a minimum pulse width giving a good switching state at the time of inputting monopolar pulse.

τ-V characteristics were evaluated in the following manner. A monopolar pulse having a duty ratio of 1:400, as shown in FIG. 2, was input to cause switching, and the change in the quantity of transmitting light was detected by means of photomultiplier. After current-voltage conversion, the change was input into oscilloscope and visually examined.

The minimum pulse width giving a good switching state, namely the minimum pulse width retaining a memorial property, at an electric field was taken as the minimum pulse width at that electric field. As used herein, the term "not retaining memorial property" means that the contrast ratio between two stable states decreases. By plotting the minimum value of pulse width, a τ-V characteristic curve was obtained. Minimum value of input electric field in the τ-V curve was expressed by Emin, and the pulse width at this point was expressed by τmin FIG. 3 illustrates the τ-V characteristic curve of Example 171 at 25° C. The ferroelectric liquid crystal composition (4-a) had Emin value of 14 V/μm and τmin value of 148 μs, demonstrating its excellence as a liquid crystal material for inverse mode.

EXAMPLE 172

Ferroelectric liquid crystal composition 5 was prepared by mixing a compound represented by general formula (1) and other compounds at a compounding ratio shown in Table 17 (% by mol, hereinafter the same).

TABLE 17

| Structural formula | Ratio (mol %) |
|---|---|
| $C_{10}H_{21}$—[pyrimidine]—[phenyl(F,F)]—CH=CH—$C_7H_5$ | 15 |
| $C_9H_{19}$—[pyrimidine]—[phenyl(F,F)]—OC$_7H_{15}$ | 2 |
| $C_9H_{19}$—[pyrimidine]—[phenyl(F,F)]—OC$_8H_{17}$ | 3 |
| $C_9H_{19}$—[pyrimidine]—[phenyl(F,F)]—OC$_9H_{19}$ | 3 |
| $C_7H_{15}O$—[phenyl]—[phenyl]—COO—[phenyl(F)]—C$_5H_{11}$ | 6 |

TABLE 17-continued

| Structural formula | Ratio (mol %) |
|---|---|
| 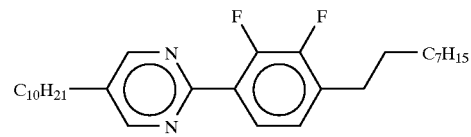 | 24 |
| 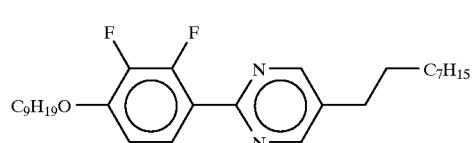 | 4 |
| 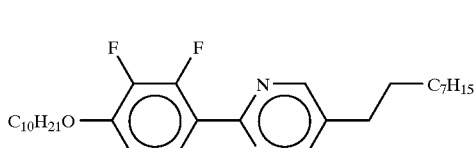 | 10.5 |
| 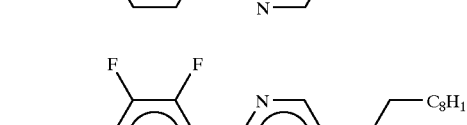 | 10.5 |
| 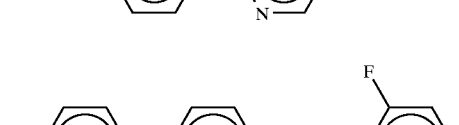 | 11 |
| C$_6$H$_{13}$O–(pyrimidine)–(phenyl)–OC$_6$H$_{13}$ | 11 |

Using this liquid crystal composition, a liquid crystal element was prepared in the same manner as in Example 168.

Next, electric field dependence (τ-V characteristic curve) of the minimum pulse width of this liquid crystal composition was measured in the following manner. Thus, a monopolar pulse having a duty ratio of 1:400 was input to the liquid crystal element, and the change in the quantity of transmitting light was detected by means of photomultiplier. After current-voltage conversion, the change was input into oscilloscope and visually examined. The minimum pulse width retaining a memorial property at a voltage was taken as the minimum pulse width at that voltage. As used herein, the term "not retaining memorial property" means that the contrast ratio between two stable states decreases. FIG. 4 illustrates the τ-V characteristic at 25° C. In FIG. 4, the minimum pulse width capable of retaining memorial property is defined as τmin, and the electric field at that time is defined as Emin. The composition of this example had τmin value 94 μs and Emin value of 20 V/μm. The τ-V characteristic curve of FIG. 4 demonstrates that this liquid crystal composition 5 can be used as a composition for τ-Vmin mode.

EXAMPLE 173

Ferroelectric liquid crystal composition 6 was prepared by mixing a compound represented by the general formula (1) and other compounds at the compounding ratio shown in Table 18.

TABLE 18

| Structural formula | Ratio (mol %) |
|---|---|
| C$_{10}$H$_{21}$–(pyrimidine)–(difluorophenyl)–C$_7$H$_{15}$ | 20 |
| C$_9$H$_{19}$O–(difluorophenyl)–(pyrimidine)–C$_7$H$_{15}$ | 12 |
| C$_{10}$H$_{21}$O–(difluorophenyl)–(pyrimidine)–C$_7$H$_{15}$ | 17 |
| C$_{10}$H$_{21}$O–(difluorophenyl)–(pyrimidine)–C$_8$H$_{17}$ | 17 |
| C$_7$H$_{15}$O–(phenyl)–(phenyl)–COO–(fluorophenyl)–C$_5$H$_{11}$ | 9 |

TABLE 18-continued

| Structural formula | Ratio (mol %) |
|---|---|
| 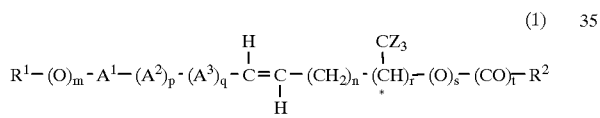 | 10 |
| 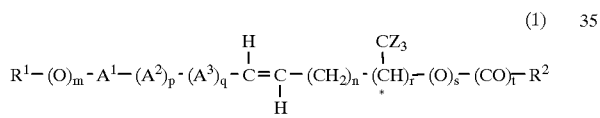 | 10 |
| 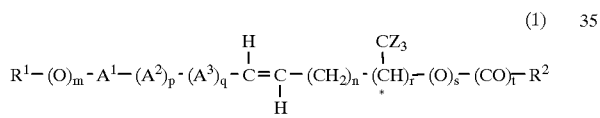 | 5 |

FIG. 5 illustrates the τ-V characteristics measured in the same manner as in Example 172. In this liquid crystal composition 6, τmin was 167 μs and Emin was 18 V/μm. It is apparent from FIG. 5 that this liquid crystal composition 6 can be used as a composition for τ-Vmin mode.

What is claimed is:

1. A trans-olefin compound represented by the formula (1):

$$R^1-(O)_m-A^1-(A^2)_p-(A^3)_q-\overset{H}{\underset{H}{C}}=\overset{CZ_3}{\underset{*}{C}}-(CH_2)_n-(CH)_r-(O)_s-(CO)_t-R^2 \quad (1)$$

wherein n in an integer of 0–10; m represents 0 or 1; r, s and t are 0; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided that when m=1, $R^1$ may also be a protecting group as hereinafter defined; $R^2$ is hydrogen atom, saturated or unsaturated alkyl group having 1–20 carbon atoms optionally substituted by halogen atom, or saturated or unsaturated alkoxyalkyl group having 2–20 carbon atoms optionally substituted by halogen atom, wherein the protecting group of $R^1$ is selected from the group consisting of aliphatic acyl group which may optionally be substituted by halogen atom or by alkoxy group; benzoyl group which may optionally be substituted by halogen atom, or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and triaralkylsilyl group, provided that the phenyl and aralkyl groups in the above-mentioned groups may optionally be substituted by halogen atom, alkyl group, alkoxy group; and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

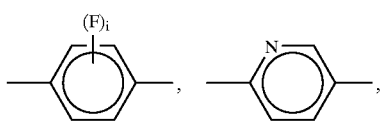

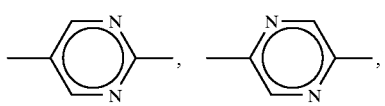

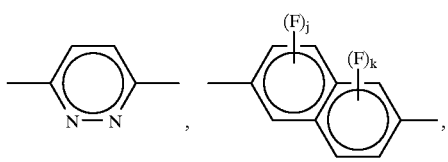

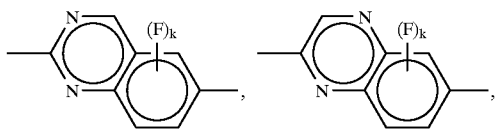

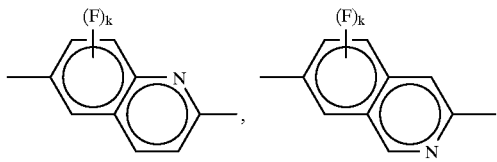

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings, provided that at least one of $A^1$, $A^2$ and $A^3$ is a group of

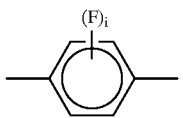

wherein i is an integer of 1–4, or a group of

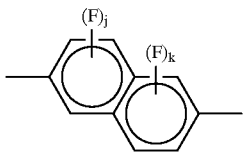

wherein j is an integer of 1–3 or k is an integer of 1–3.

2. A trans-olefin compound according to claim 1, wherein one of the rings $A^1$, $A^2$ and $A^3$ is 2,3-difluorophenylene group.

3. A liquid crystal composition containing at least one trans-olefin compound according to claim 2 and at least one compound represented by formula (A):

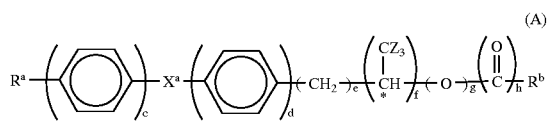

wherein $R^a$ represents alkyl, alkoxy or alkoxyalkyl group having 5–15 carbon atoms connected by single, double, or triple bonds; $R^b$ represents an alkyl or alkoxy group having 1–10 carbon atoms connected with single, double, or triple bonds optionally substituted by halogen atom, or an alkoxyalkyl group having 2–10 carbon atoms connected by single, double, or triple bonds optionally substituted by halogen atom; c and d independently represent an integer of 1 or greater, provided that c+d is equal to 3; e is an integer of 0–10, f, g, and h are independently 0 or 1; $X^a$ is —COO— or —OCO—; the hydrogen atoms of the benzene rings may optionally be substituted by fluorine atom; the mark * signifies an asymmetric carbon atom; and Z represents hydrogen atom or fluorine atom, as indispensable ingredients; and provided that, when none of the compounds of the general formula (1) and the general formula (A) are optically active, said ferroelectric liquid crystal composition contains another optically active compound.

4. A trans-olefin compound represented by formula (1):

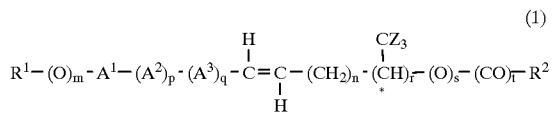

wherein n is an integer of 0–10; m, r, s and t each represents 0 or 1; Z is hydrogen atom to fluorine atom; $R^1$ is hydrogen, saturated or unsaturated alkyl group having 1–20 carbon atoms, or saturated or unsaturated alkoxyalkyl group having 2–20 carbon atoms, provided that when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom, or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom, or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and triaralkylsilyl group, provided that the phenyl and aralkyl groups in the above-mentioned groups may optionally be substituted by halogen atom, alkyl group, alkoxy group; and tetrahydropyranyl group, tetrahydrofuranyl group and 1-(alkoxy)-alkyl groups, which may optionally be substituted by halogen atoms or alkoxy group; $A^1$, $A^2$ and $A^3$ each represents one of the following groups:

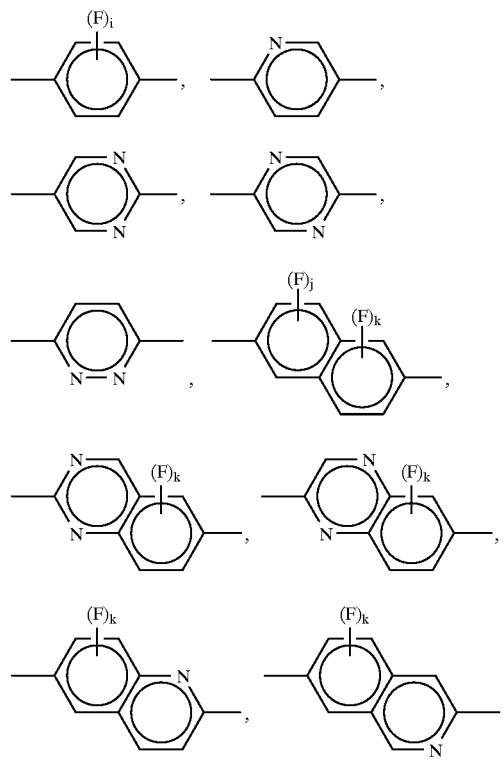

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings, provided that at least one of $A^1$, $A^2$ and $A^3$ is a group of

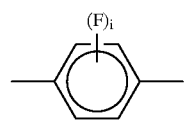

wherein i is an integer of 1–4, or a group of

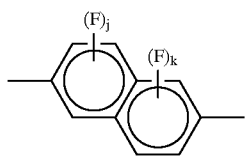

wherein j is an integer of 1–3 or k is an integer of 1–3; wherein one of the rings $A^1$, $A^2$ and $A^3$ is 2,3-difluorophenylene group.

5. A trans-olefin compound represented by formula (1):

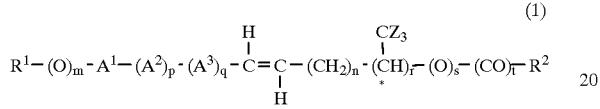

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom; or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

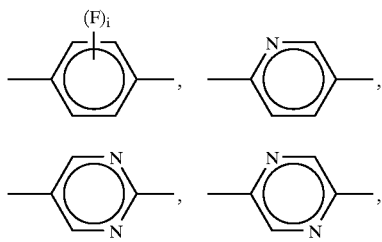

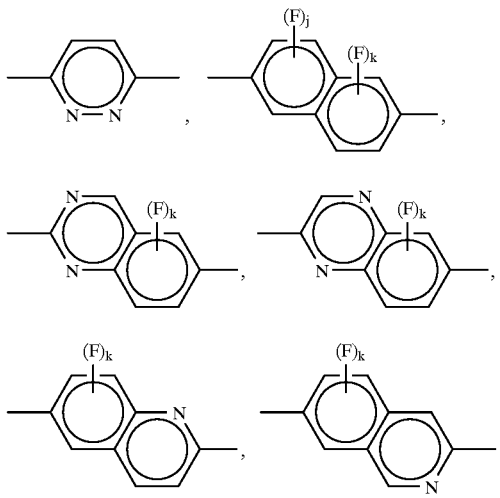

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

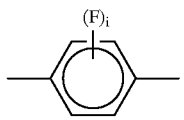

wherein i is an integer of 1–4, or a group of

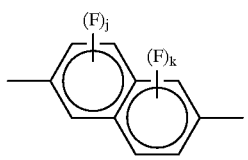

wherein j is an integer of 1–3 or k is an integer of 1–3, wherein, when r=1, p+q=1 and $A^1$ is a pyrimidine-2,5-diyl group, $A^2$ and $A^3$ each represents one of the following groups:

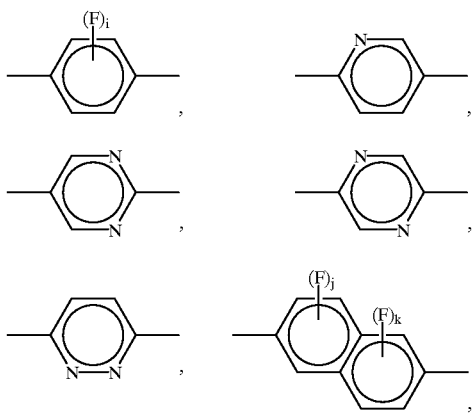

-continued

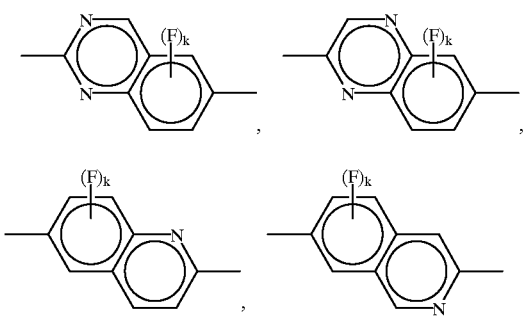

an i is an integer of 1–4 and j and k are each an integer of 0–3, and when r=1, p+q=1 and $A^2$ and $A^3$ represents pyrimidine-2,5-diyl group, $A^1$ represents one of the following groups:

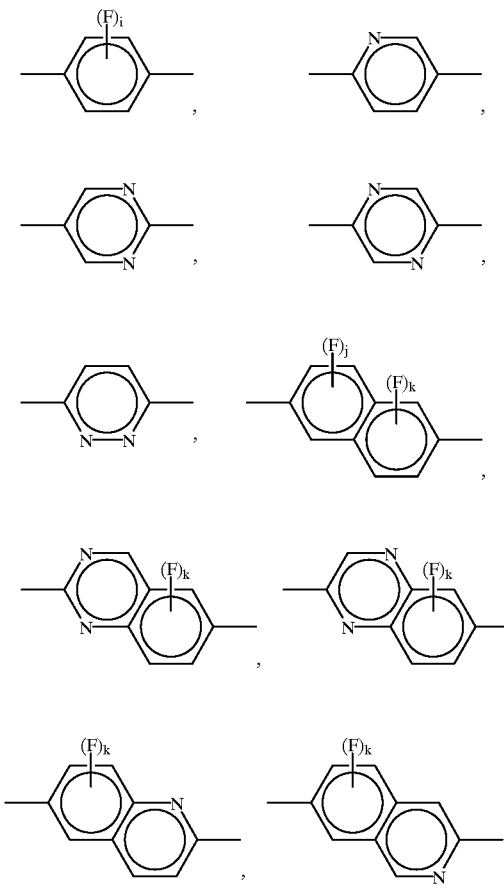

and i is an integer of 1–4 and j and k are each an integer of 0–3.

6. A method for producing a trans-olefin compound represented by formula (1):

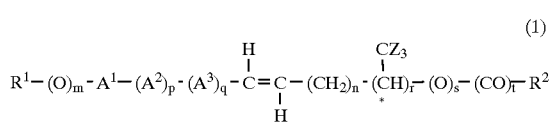

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom, or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

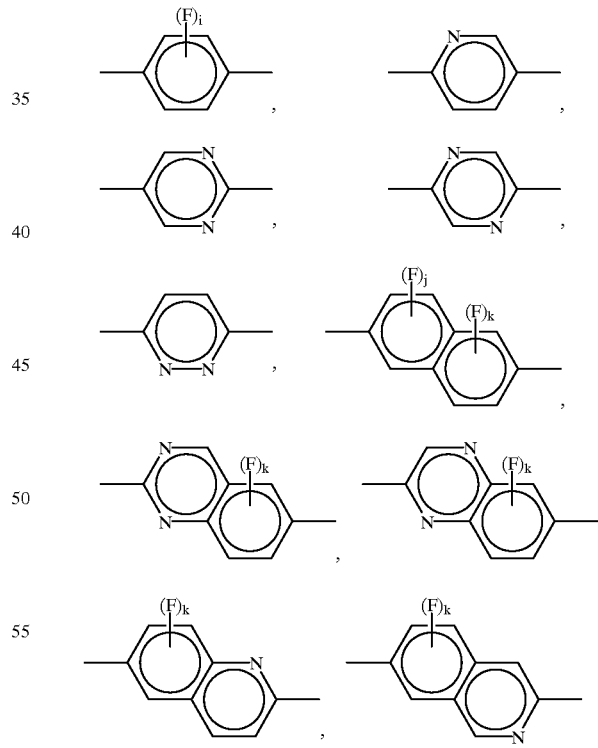

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

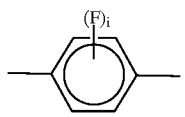

wherein i is an integer of 1–4, or a group of

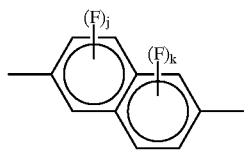

wherein j is an integer of 1–3 or k is an integer of 1–3; wherein, which comprises reacting a boron compound represented by formula (2);

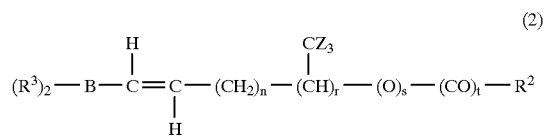

wherein n is an integer of 0–10; and m, r, s and t each represents 0 or 1; Z is hydrogen atom or fluorine atom; $R^2$ is hydrogen atom, saturated or unsaturated alkyl group having 1–20 carbon atoms optionally substituted by halogen atom, or saturated or unsaturated alkoxyalkyl group having 2–20 carbon atoms optionally substituted by halogen atom, provided that when s=1 and t=0, $R^2$ may also be a protecting group, and $R^3$ represents a hydroxyl group, a straight chain, branched chain or cyclic alkyl group or a straight chain, branched chain or cyclic alkoxy group, provided that the two $R^3$, taken individually, may join together to form a ring, or the two R groups, taken conjointly, may represent an optionally substituted benzodioxy group, with a compound represented by formula (3)

wherein m, p and q are 0 or 1; $R^1$ is hydrogen, saturated or unsaturated alkyl group having 1–20 carbon atoms, or saturated or unsaturated alkoxyalkyl group having 2–20 carbon atoms, provided that when m=1, $R^1$ may also be a protecting group; X represents a halogen atom, or —$OSO_2R'$ in which R' is an alkyl group having 1–5 carbon atoms optionally substituted by a fluorine atom or phenyl group optionally substituted by $C_1$–$C_5$ alkyl group, $C_1$–$C_5$ alkoxy group or halogen atom, in the presence of a palladium catalyst and a basic substance.

7. A method for obtaining an optically active trans-olefin compound according to claim 6, wherein s and t each represent 0 or 1, and r=1.

8. A fluorine containing trans-olefin type liquid crystal composition containing at least one trans-olefin compound represented by formula (1):

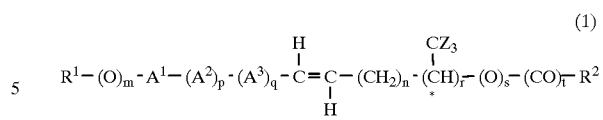

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom, or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

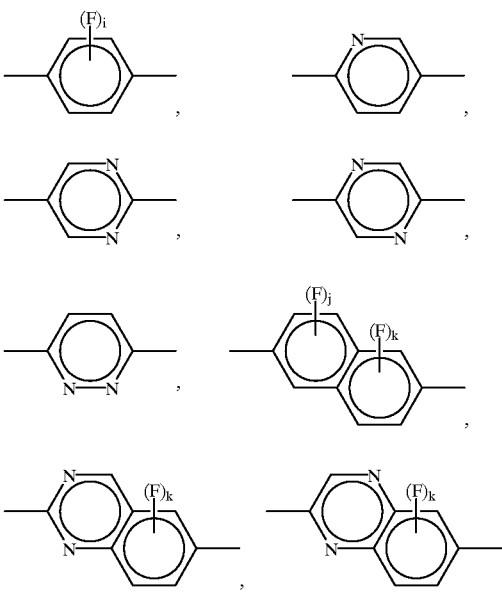

-continued

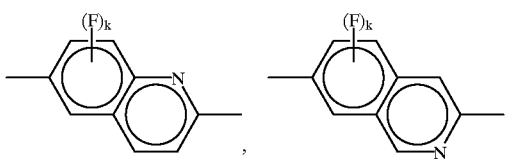

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

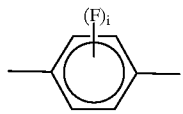

wherein i is an integer of 1–4, or a group of

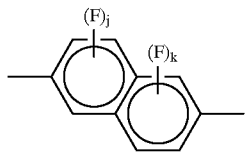

wherein j is an integer of 1–3 or k is an integer of 1–3.

9. A ferroelectric liquid crystal composition containing at least one trans-olefin compound represented by the formula (1):

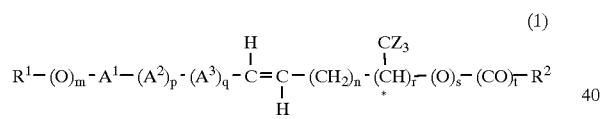

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom; or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

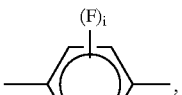

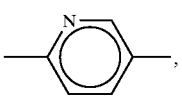

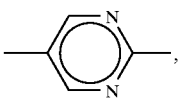

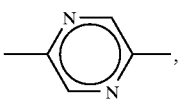

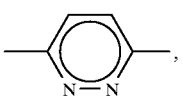

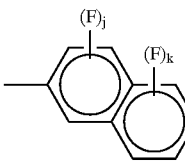

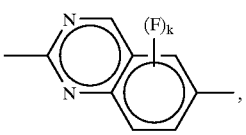

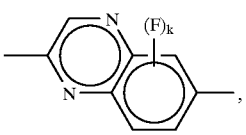

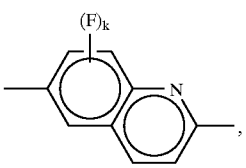

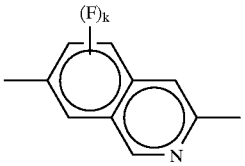

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

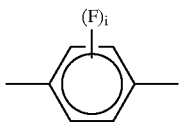

wherein i is an integer of 1–4, or a group of

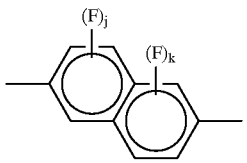

wherein j is an integer of 1–3 or k is an integer of 1–3; and at least one compound represented by formula (A):

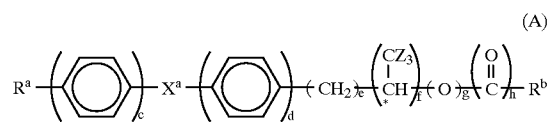

(A)

wherein $R^a$ represents alkyl, alkoxy or alkoxyalkyl group having 5–15 carbon atoms, and single bond of methylene chain in said alkyl, alkoxy or alkoxyalkyl group may optionally be substituted by double bond or triple bond; $R^b$ represents an alkyl or alkoxy group having 1–10 carbon atoms optionally substituted by halogen atom, or an alkoxyalkyl group having 2–10 carbon atoms optionally substituted by halogen atom, and at least one single bond of methylene chain in said alkyl, alkoxy or alkoxyalkyl group may optionally be substituted by double bond or triple bond; c and d independently represent an integer of 1 or greater, provided that c+d is equal to 3; e is an integer of 0–10; f, g and h are independently 0 or 1; $X^a$ is —COO— or —OCO—; the hydrogen atoms of the benzene rings may optionally be substituted by fluorine atom; the mark * signifies an asymmetric carbon atom; and Z represents hydrogen atom or fluorine atom, as indispensable ingredients; provided that, when none of the compounds of the general formula (1) and the general formula (A) are optically active, said ferroelectric liquid crystal composition contains another optically active compound.

10. A liquid crystal element, wherein a liquid crystal composition, containing a trans-olefin compound represented by formula (1) as an active ingredient, is held between a pair of electrode substrates:

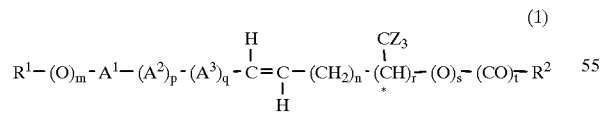

(1)

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom; or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

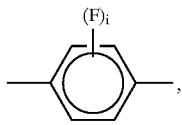

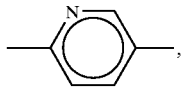

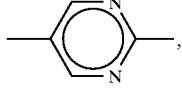

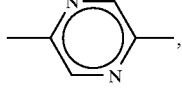

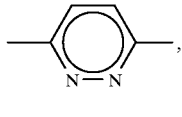

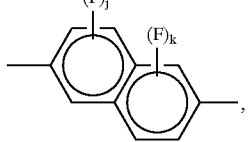

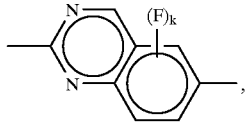

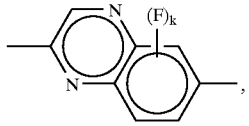

-continued

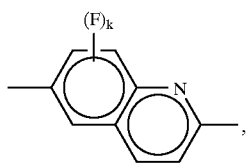

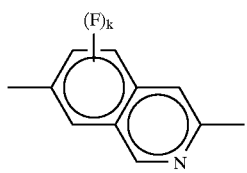

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

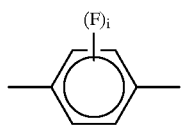

wherein i is an integer of 1–4, or a group of

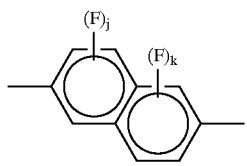

wherein j is an integer of 1–3 or k is an integer of 1–3.

11. A trans-olefin compound represented by formula (1):

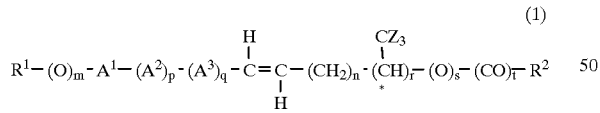

wherein $R^1$ is —$C_{10}H_{21}$, $R^2$ is hydrogen atom, m is 1, n is 7, r, s and t each represent 0 or 1, Z is hydrogen atom or fluorine atom, and -$A^1$-$(A^2)_p$-$(A^3)_q$- is

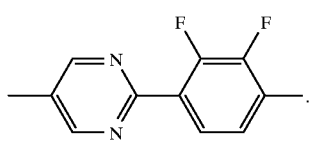

12. A trans-olefin compound represented by formula (1):

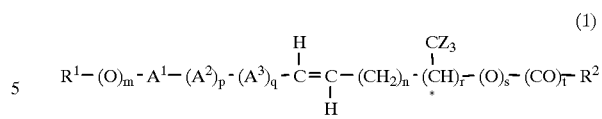

wherein n is an integer of 0–10; m, r, s and t each represents 0 or 1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined and when r=0, s=0, and t=0, $R^1$ cannot be an unsaturated alkyl group; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, provided that when s=1 and t=0, $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom; or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group; and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

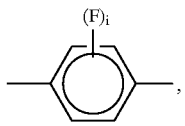

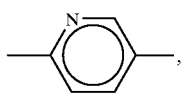

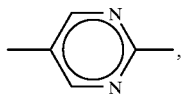

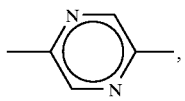

-continued

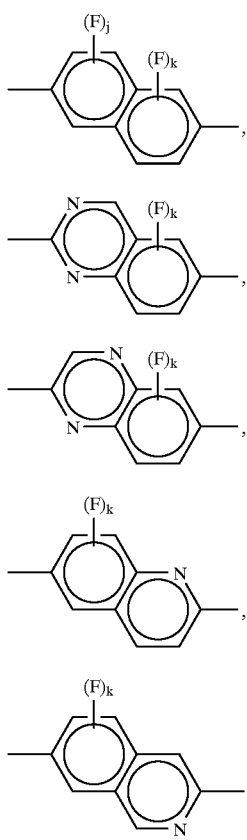

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings, wherein at least one of $A^1$, $A^2$ and $A^3$ is a group of

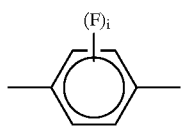

in which i is an integer of 1–4.

13. A method for producing a trans-olefin compound represented by the general formula (1):

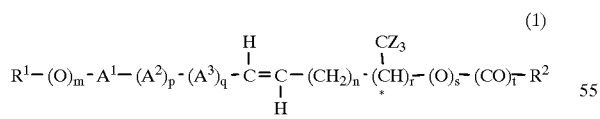 (1)

wherein n is an integer of 0–10; m and r each represents 0 or 1; s=1 and t=1; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, wherein the protecting group of $R^1$ is selected from the group consisting of aliphatic acyl group which may optionally be substituted by halogen atom or by alkoxy group; benzoyl group which may optionally be substituted by halogen atom; or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

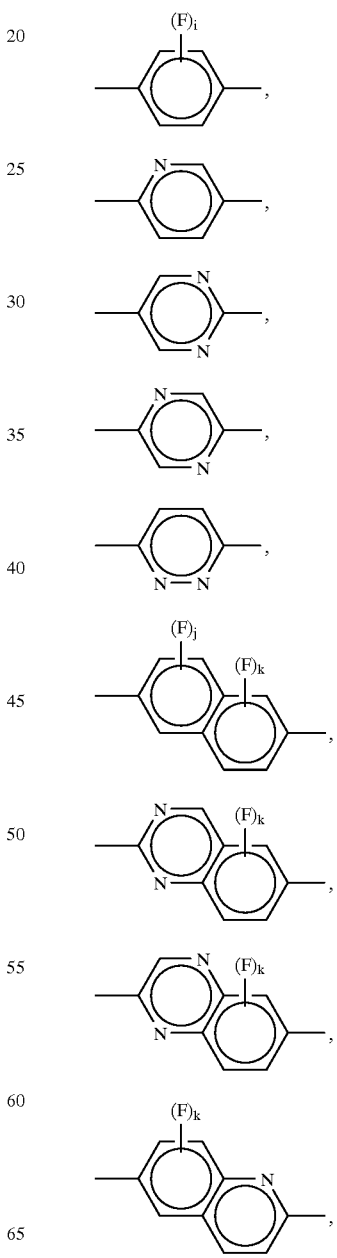

-continued

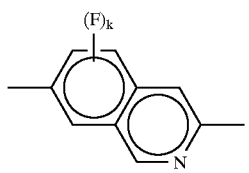

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings provided that at least one of $A^1$, $A^2$ and $A^3$ is a group of

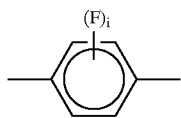

wherein i is an integer of 1–4, or a group of

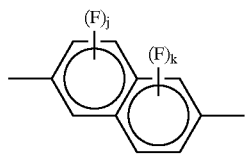

wherein j is an integer of 1–3 or k is an integer of 1–3, which method comprises reacting a boron compound represented by formula (2'):

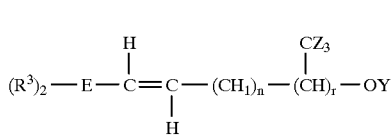

wherein Y represents a hydrogen atom or $(R^3)_2B$ and $R^3$ represents a hydroxyl group, a straight chain, branched chain or cyclic alkyl group or a straight chain, branched chain or cyclic alkoxy group provided that the two $R^3$, taken individually, may join together to form a ring may represent an optionally substituted benzodioxy group, with a compound of the formula (3):

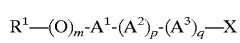

wherein m, p and q are 0 or 1; $R^1$ is hydrogen, saturated or unsaturated alkyl group having 1–20 carbon atoms, or saturated or unsaturated alkoxyalkyl group having 2–20 carbon atoms, provided that when m=1, $R^1$ may also be a protecting group, X represents halogen atom, or —$OSO_2R^1$ in which $R^1$ is an alkyl group having 1–5 carbon atoms optionally substituted by a fluorine atom or phenyl group optionally substituted by $C_1$–$C_5$ alkoxy group or halogen atom, to obtain a compound represented by general formula (1''):

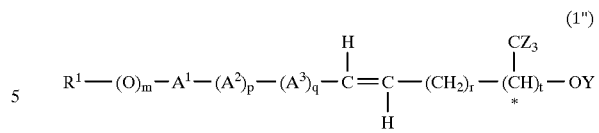

followed by reacting the compound (1'') with a carboxylic acid compound represented by formula (4):

$$R^2COR'' \qquad (4)$$

wherein R'' represents a hydroxyl group, halogen atom or —$OCOR^2$.

14. A method for producing a trans-olefin compound represented by the formula (1):

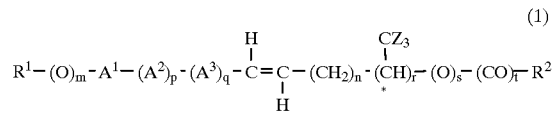

wherein n is an integer of 0–10; m and r each represents 0 or 1; s=1 and t=0; Z is hydrogen atom or fluorine atom; $R^1$ is hydrogen, saturated or unsaturated alkyl group having 1–20 carbon atoms, or saturated or unsaturated alkoxyalkyl group having 2–20 carbon atoms, provided than when m=1, $R^1$ may also be a protecting group as hereinafter defined; $R^2$ is hydrogen atom, saturated or unsaturated alkyl group having 1–20 carbon atoms optionally substituted by halogen atom; or saturated or unsaturated alkoxyalkyl group having 2–20 carbon atoms optionally substituted by halogen atom, and $R^2$ may also be a protecting group as hereinafter defined, wherein the protecting group of $R^1$ and $R^2$, which may be the same or different, is selected from the group consisting of aliphatic acyl group which may optionally be substituted by halogen atom or by alkoxy group; benzoyl group which may optionally be substituted by halogen atom, or by alkyl group, or by alkoxy group, or by nitro group, or by cyano group; benzyl group which may optionally be substituted by halogen atom, or by alkyl group, or by alkoxy group, or by nitro group, or by cyano group; trialkylsilyl group, dialkylphenylsilyl group, alkyldiphenylsilyl group, triphenylsilyl group, aralkyldialkylsilyl group, diaralkylalkylsilyl group and trialkylsilyl group, provided that the phenyl and aralkyl groups in the above-mentioned groups may optionally be substituted by halogen atom, alkyl group, alkoxy group, and tetrahydropyranyl group, tetrahydrofuranyl group and 1-(alkoxy)-alkyl groups, which may optionally be substituted by halogen atom or alkoxy group; $A^1$, $A^2$ and $A^3$ each represents one of the following groups:

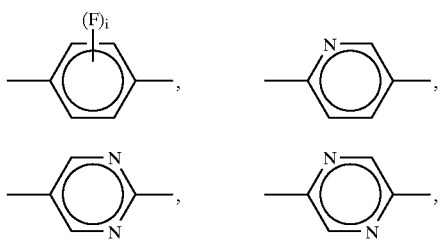

-continued

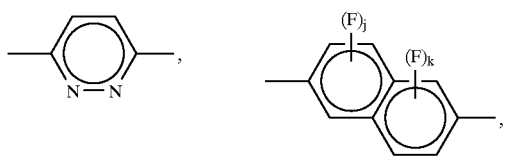

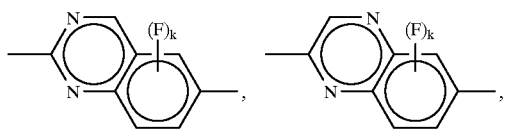

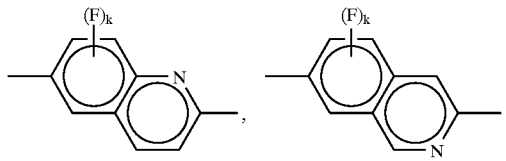

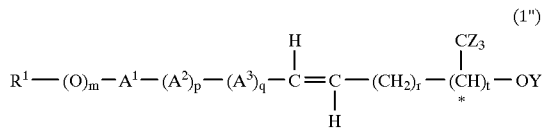

wherein j is an integer of 1–3 or k is an integer of 1–3, which method comprises reacting a compound represented by the formula (1"):

(1")

in which i is an integer of 0–4; j and k are each an integer of 0–3; and p and q are 0 or 1, provided that when $A^1$ is a fused ring, p+q=0 or 1 and $A^2$ and $A^3$ are single rings, and when $A^1$ is a single ring, p+q=1 or 2, provided that when p+q=2, $A^2$ and $A^3$ are both single rings, provided that at least one of $A^1$, $A^2$ and $A^3$ is a group of

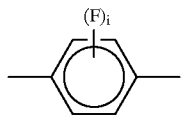

wherein i is an integer of 1–4, or a group of with an alkylating agent represented by formula (5):

$$R^2X \quad (5)$$

wherein X represents a halogen atom, or —$OSO_2R'$ in which R' in which R' is an alkyl group having 1–5 carbon atoms optionally substituted by a fluorine atom or phenyl group optionally substituted by $C_1$–$C_5$ alkoxy group or halogen atom, and $R^1$ is the same as defined above.

* * * * *